(12) United States Patent
Grauert et al.

(10) Patent No.: US 8,889,677 B2
(45) Date of Patent: *Nov. 18, 2014

(54) SUBSTITUTED TRIAZOLES USEFUL AS MGLU5 RECEPTOR MODULATORS

(71) Applicants: Matthias Grauert, Biberach an der Riss (DE); Daniel Bischoff, Biberach an der Riss (DE); Georg Dahmann, Warthausen-Birkenhard (DE); Raimund Kuelzer, Mittelbiberach (DE); Klaus Rudolf, Warthausen (DE)

(72) Inventors: Matthias Grauert, Biberach an der Riss (DE); Daniel Bischoff, Biberach an der Riss (DE); Georg Dahmann, Warthausen-Birkenhard (DE); Raimund Kuelzer, Mittelbiberach (DE); Klaus Rudolf, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 30 days.

This patent is subject to a terminal disclaimer.

(21) Appl. No.: 13/739,059

(22) Filed: Jan. 11, 2013

(65) Prior Publication Data

US 2013/0184248 A1    Jul. 18, 2013

(30) Foreign Application Priority Data

Jan. 17, 2012 (EP) .................... 12151331

(51) Int. Cl.

| | |
|---|---|
| *A61K 31/496* | (2006.01) |
| *A61K 31/506* | (2006.01) |
| *A61K 31/52* | (2006.01) |
| *A61K 31/53* | (2006.01) |
| *A61K 31/5377* | (2006.01) |
| *C07D 401/12* | (2006.01) |
| *C07D 401/14* | (2006.01) |
| *C07D 403/12* | (2006.01) |
| *C07D 403/14* | (2006.01) |
| *C07D 405/14* | (2006.01) |
| *C07D 473/34* | (2006.01) |
| *C07D 249/08* | (2006.01) |

(52) U.S. Cl.
CPC ........... *C07D 249/08* (2013.01); *C07D 401/14* (2013.01); *C07D 403/14* (2013.01); *C07D 401/12* (2013.01); *C07D 403/12* (2013.01); *C07D 405/14* (2013.01)
USPC .............. 514/236.2; 514/241; 514/252.02; 514/252.19; 514/252.11; 514/253.06; 514/253.09; 514/254.05; 514/252.16; 544/121; 544/219; 544/238; 544/295; 544/357; 544/277; 544/363; 544/364; 544/366

(58) Field of Classification Search
None
See application file for complete search history.

(56) References Cited

U.S. PATENT DOCUMENTS

| | | | |
|---|---|---|---|
| 6,166,008 A | 12/2000 | Johnson et al. | |
| 7,582,635 B2 | 9/2009 | Sun et al. | |
| 8,008,300 B2 | 8/2011 | Sun et al. | |
| 8,048,890 B2 | 11/2011 | Buschmann et al. | |
| 8,642,774 B2 * | 2/2014 | Grauert et al. ............. | 546/272.4 |
| 2003/0055085 A1 | 3/2003 | Wagenen et al. | |
| 2004/0186111 A1 | 9/2004 | Sun et al. | |
| 2005/0256130 A1 | 11/2005 | Pennell et al. | |
| 2007/0154428 A1 | 7/2007 | Sato et al. | |
| 2010/0004254 A1 | 1/2010 | Sun et al. | |
| 2010/0216787 A1 | 8/2010 | Sato et al. | |
| 2012/0004217 A1 | 1/2012 | Sun et al. | |
| 2012/0015954 A1 | 1/2012 | Sun et al. | |
| 2013/0137688 A1 | 5/2013 | Grauert et al. | |
| 2013/0143870 A1 | 6/2013 | Grauert et al. | |
| 2013/0150341 A1 | 6/2013 | Grauert et al. | |
| 2013/0150347 A1 | 6/2013 | Rudolf et al. | |
| 2013/0150355 A1 | 6/2013 | Rudolf et al. | |
| 2013/0158011 A1 | 6/2013 | Rudolf et al. | |
| 2013/0158038 A1 | 6/2013 | Rudolf et al. | |
| 2013/0184248 A1 | 7/2013 | Grauert et al. | |

FOREIGN PATENT DOCUMENTS

| | | |
|---|---|---|
| CA | 2476031 A1 | 9/2003 |
| EP | 0307145 A1 | 3/1989 |
| EP | 0919232 A1 | 6/1999 |
| WO | 9749395 | 12/1997 |
| WO | 0206288 A1 | 1/2002 |
| WO | 03051833 A2 | 6/2003 |
| WO | 03053922 A2 | 7/2003 |
| WO | 03076432 A1 | 9/2003 |

(Continued)

OTHER PUBLICATIONS

CA Registry No. 1317767-98-8, entered into CA Registry File on Aug. 15, 2011, supplied by FCH Group.*

(Continued)

*Primary Examiner* — Emily Bernhardt
(74) *Attorney, Agent, or Firm* — Michael P. Morris; Anthony P. Bottino

(57) ABSTRACT

This invention relates to compounds of formula I

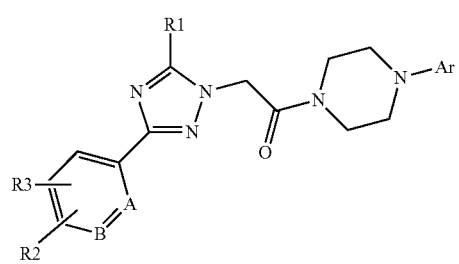

their use as positive allosteric modulators of mGlu5 receptor activity, pharmaceutical compositions containing the same, and methods of using the same as agents for treatment and/or prevention of neurological and psychiatric disorders associated with glutamate dysfunction such as schizophrenia or cognitive decline such as dementia or cognitive impairment. A, B, Ar, $R^1$, $R^2$, $R^3$ have meanings given in the description.

10 Claims, No Drawings

(56) References Cited

FOREIGN PATENT DOCUMENTS

| WO | 03105853 A1 | 12/2003 |
|---|---|---|
| WO | 2004058754 A1 | 7/2004 |
| WO | 2005030128 A2 | 4/2005 |
| WO | 2005056015 A1 | 6/2005 |
| WO | 2007021573 A1 | 2/2007 |
| WO | 2007087135 A2 | 8/2007 |
| WO | 2008112440 A1 | 9/2008 |
| WO | 2008145616 A1 | 12/2008 |
| WO | 2008148840 A1 | 12/2008 |
| WO | 2008156580 A1 | 12/2008 |
| WO | 2009143404 A1 | 11/2009 |
| WO | 2010124055 A1 | 10/2010 |
| WO | 2010126811 A1 | 11/2010 |
| WO | 2011002067 A1 | 1/2011 |
| WO | 2011082010 A1 | 7/2011 |

OTHER PUBLICATIONS

CA Registry No. 1316344-84-9, entered into CA Registry File on Aug. 12, 2011, supplied by FCH Group.*
FCH Group Product Guide, 1 page, retrieved from the Internet at http://fchgroup.net/products.php on Apr. 5, 2014.*
Abstract in English for WO2011002067, Publication Date: Jan. 1, 2011.
Adams, C.E. et al., "Chlorpromazine Versus Placebo for Schizophrenia (Review)." The Cochrane Library, 2009, pp. 1-3.
Chemcats: Accession No. 0046382561, Oct. 14, 2011.
Dorwald, F. Z. "Side Reactions in Organic Synthesis: A Guide to Successful Synthesis Design." Wiley-VCH Verlag GmbH & Co. KGaA, 2005, pp. 1-390.
European Search Report for EP 11193380.0 mailed Mar. 14, 2012.
International Search Report and Written Opinion for PCT/EP2012/075312 mailed Feb. 7, 2013.
International Search Report and Written Opinion for PCT/EP2012/075313 mailed Feb. 7, 2013.
Lindsley, C.W., et al., "Discovery of Positive Allosteric Modulators for the Metabotropic Glutamate Receptor Subtype-5 from a Series of N-(1,3-Diphenyl-1H-pyrazol-5-yl) benzamides that Potentiate Receptor Function in Vivo", J. Med. Chem, 2004, 47, pp. 5825-5828.
Shasheva. E. Y. et al., "Reactions of Hydroxyphenyl-substituted 1,2,4-Triazoles with Electrophylic Reagents", Russian Journal of General Chemistry, 2009, vol. 79, No. 10, pp. 2234-2243.
Wermuth, Camille G. "Practice of Medicinal Chemistry, Third Edition." Elsevier Ltd., 2008, Ch. 6, 15, 18, and 20. pp. 125-143 and 282-335.

* cited by examiner

SUBSTITUTED TRIAZOLES USEFUL AS MGLU5 RECEPTOR MODULATORS

FIELD OF THE INVENTION

This invention relates to substituted triazoles and their use as positive allosteric modulators of mGlu5 receptor activity, pharmaceutical compositions containing the same, and methods of using the same as agents for treatment and/or prevention of neurological and psychiatric disorders associated with glutamate dysfunction such as schizophrenia or cognitive decline such as dementia or cognitive impairment.

BACKGROUND OF THE INVENTION

Glutamate is the primary excitatory amino acid in the mammalian central nervous system. Neurotransmission mediated by glutamate has been demonstrated to be critical in many physiological processes, such as synaptic plasticity, long term potentiation involved in both learning and memory as well as sensory perception (Riedel et al., Behav. Brain Res. 2003, 140:1-47). Furthermore, it has been demonstrated that an imbalance of glutamate neurotransmission plays a critical role in the pathophysiology of various neurological and psychiatric diseases.

The excitatory neurotransmission of glutamate is mediated through at least two different classes of receptors, the ionotropic glutamate receptors (NMDA, AMPA and kainate) and the metabotropic glutamate receptors (mGluR). The ionotropic receptors are ligand gated ion channels and are thought to be responsible for the regulating rapid neuronal transmission between two neurons. The metabotropic glutamate receptors are G-protein coupled receptors (GPCRs) which appear to mediate not only synaptic transmission, but also to regulate the extent of neurotransmitter release as well as post synaptic receptor activation.

Dysregulation in glutamatergic neurotransmission, for example through altered glutamate release or post-synaptic receptor activation, has been demonstrated in a variety of neurological ans well as psychiatric disorders. Hypofunction of the NMDA receptor has not only been demonstrated in Alzheimer's patients, but is increasingly accepted as the putative cause of schizophrenia (Farber et al., Prog. Brain Res., 1998, 116: 421-437, Coyle et al., Cell. and Mol. Neurobiol. 2006, 26: 365-384). This is supported by clinical studies showing that antagonists of the NMDA receptor induce symptoms indistinguishable to those suffered by schizophrenia patients (Javitt et al., Am J. Psychiatry, 1991, 148: 1301-1308). Therefore, approaches that could potentiate or normalize NMDA receptor signaling have the potential to treat neurological and psychiatric disorders. mGluR5 belongs to a superfamily of currently eight identified Type III GPCRs, which are unique in that the glutamate ligand binds to a large extracelullar amino-terminal protein domain. This superfamily is further divided into three gropus (Group I, II and III) based on amino acid homology as well as the intracellular signalling cascades they regulate (Schoepp et al., Neuropharma, 1999, 38:1431-1476). mGluR5 belongs to group I and is coupled to the phospholipase C signalling cascade which regulates intracellular calcium mobilization. In the CNS, mGluR5 has been demonstrated to be expressed mainly in the cortex, hippocampus, nucleus accumbens and the caudate-putamen. These brain regions are known to be involved in memory formation and cognitive function as well as emotional response. mGluR5 has been shown to be localized post-synaptically, adjacent to the post-synaptic density (Lujan et al., Eur. J. Neurosci. 1996, 8: 1488-1500). A functional interaction between mGluR5 and the NMDA receptor has also been demonstrated, where activation of mGluR5 potentiates the activation state of the NMDA receptor (Mannaioni et al, NeuroSci., 2001, 21:5925-5924, Rosenbrock et al., Eur. J. Pharma., 2010, 639:40-46). Furthermore, activation of mGluR5 has been demonstrated in pre-clinical in vivo models to rescue cognitive impairment as well as psychotic disturbance induced by NMDA receptor antagonists (Chan et al., Psychopharma. 2008, 198:141-148). Therefore, activation of mGluR5, and thereby potentiation or normalization of the NMDA receptor signaling, is a potential mechanism for the treatment of psychiatric and neurological disorders. Most agonists of mGluR5 bind the orthosteric glutamate binding site. Since the glutamate binding site between the mGluR family members is highly conserved, it has been challenging to develop selective mGluR5 agonists which have acceptable CNS penetration and demonstrate in vivo activity. An alternative approach to achieve selectivity between the mGluR family members is to develop compounds which bind to an allosteric site, which is not as highly conserved between the family members. These allosteric binding compounds would not interfere with the natural glutamate binding and signaling, but modulate the receptor activation state.

Positive allosteric modulators of mGluR5 have recently been identified (O'Brien et al., Mol. Pharma. 2003, 64: 731-740, Lindsley et al., J. Med. Chem. 2004, 47: 5825-5828). These compounds potentiate mGluR5 activity in the presence of bound glutamate. In the absence of bound glutamate, the mGluR5 positive modulators do not demonstrate intrinsic activity. Therefore, these compounds potentiate the natural signaling of mGluR5 as opposed to agonists which activate the receptor in a permanent, unnatural manner. mGluR5 positive allosteric modulators therefore represent an approach to potentiate mGluR5 signaling which in turn potentiates and normalizes the NMDA receptor hypofunction detected in neurological and psychiatric disorders.

WO 2003/105853 and WO 2005/056015 disclose substituted pyrazoles that are said to be CCR1 receptor antagonists and to be useful for the treatment of inflammation and immune disorders. Quite surprisingly, according to the present invention, some selected triazole derivatives show positive modulatory activity on the mGluR5 receptor without having an inhibitory effect on the CCR1 receptor. Such compounds are useful for the treatment of psychotic disorders, cognitive disorders and dementias.

DETAILED DESCRIPTION OF THE INVENTION

The present invention is directed to compounds of formula I:

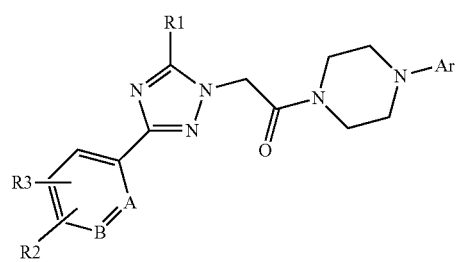

in which

A and B independently represent CH or N;

R$^1$ represents phenylethynyl, C$_{3-6}$cycloalkylethynyl, C$_{2-5}$alkenyl, C$_{5-7}$cycloalkenyl, aryl, heteroaryl, C$_{1-8}$alkyl, C$_{3-7}$cycloalkyl, —O—C$_{1-8}$alkyl which latter five groups are optionally substituted with one or more substituents selected from halogen, cyano, C$_{1-3}$alkyl, C$_{3-6}$cycloalkyl, —O—C$_{1-3}$alkyl, —CH$_2$—O—CH$_3$, —CH$_2$-morpholine, —CH$_2$CN which latter six substituents are optionally substituted with one or more fluorine atoms;

R$^2$ and R$^3$ independently represent —H, halogen, —CN, —COO—C$_{1-4}$alkyl, C$_{1-5}$alkyl, C$_{3-5}$cycloalkyl, —O—C$_{1-5}$alkyl which latter four groups are optionally substituted with one or more fluorine atoms;

Ar represents phenyl,

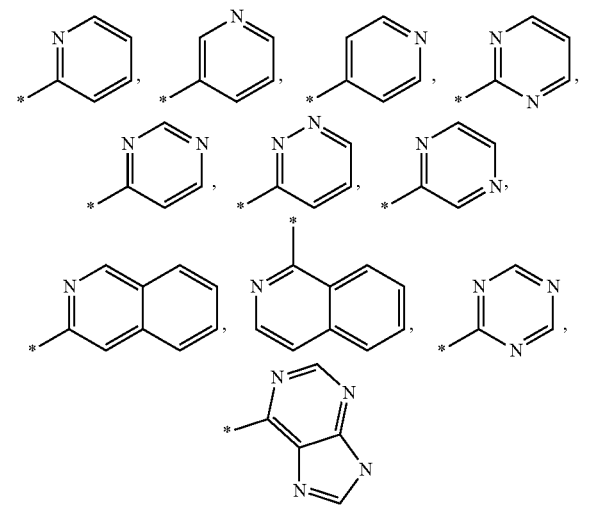

which latter twelve groups are optionally substituted with one or more substituents selected from fluoro, chloro, bromo, cyano, —OH, —O—C$_{1-3}$alkyl-NMe-C$_{1-3}$alkyl-OH, —O-tetrahydrofuranyl, —O-tetrahydropyranyl, —O—(N-acetyl-piperidinyl), —COO—C$_{1-4}$alkyl, —NH$_2$, —NH—C$_{1-5}$alkyl, —N(C$_{1-5}$alkyl)$_2$, —CONH$_2$, C$_{1-3}$alkyl, —O—C$_{1-4}$alkyl, 5-6 membered heterocyclyl which latter seven groups are optionally substituted with one or more substituents selected from fluoro, —OH, —NMe$_2$, C$_{3-6}$cycloalkyl, —C$_{1-3}$alkyl-O—C$_{1-3}$alkyl, —O—C$_{1-3}$alkyl, —O—C$_{1-3}$alkyl-OH, —O—C$_{1-3}$alkyl-O—C$_{1-3}$alkyl-OH, —O—C$_{1-3}$alkyl-O—C$_{1-3}$alkyl, 2-pyridyl, 3-imidazolyl, 5-6 membered heterocyclyl optionally substituted with keto, —OH, methyl;

or a salt thereof, particularly a physiologically acceptable salt thereof.

In a second embodiment, in the general formula I, A, B, Ar, R$^2$, R$^3$ have the same meaning as defined in any of the preceding embodiments, and R$^1$ represents phenylethynyl, cyclohexylethynyl, C$_{2-4}$alkenyl, C$_{5-6}$cycloalkenyl, phenyl, furyl, C$_{1-5}$alkyl, C$_{3-6}$cycloalkyl which latter four groups are optionally substituted with one or more substituents selected from fluoro, chloro, cyano, —CH$_2$-morpholine, —CH$_2$—O—CH$_3$, —CH$_2$CN, C$_{1-3}$alkyl, C$_{3-6}$cycloalkyl, —O—C$_{1-3}$alkyl which latter three substituents are optionally substituted with one or more fluorine atoms.

In another embodiment, in the general formula I, A, B, Ar, R$^2$, R$^3$ have the same meaning as defined in any of the preceding embodiments, and Ar represents phenyl,

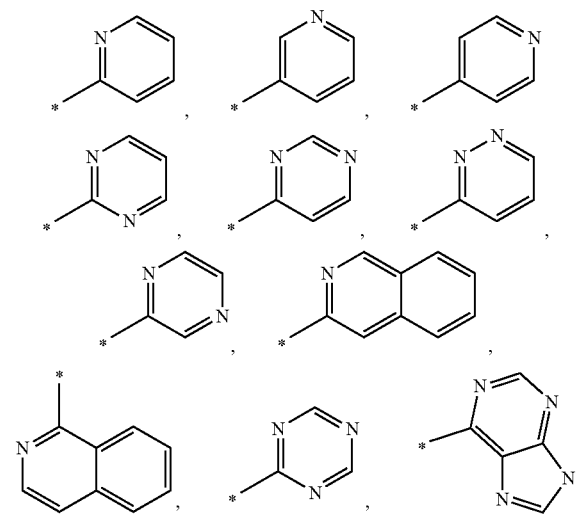

which latter twelve groups are optionally substituted with one or more substituents selected from fluoro, chloro, bromo, cyano, —OH, methyl, ethyl, methoxy, ethoxy, iso-propoxy, —NH$_2$, —NMe$_2$, —NHMe, —NHEt, —CONH$_2$, —COOEt,

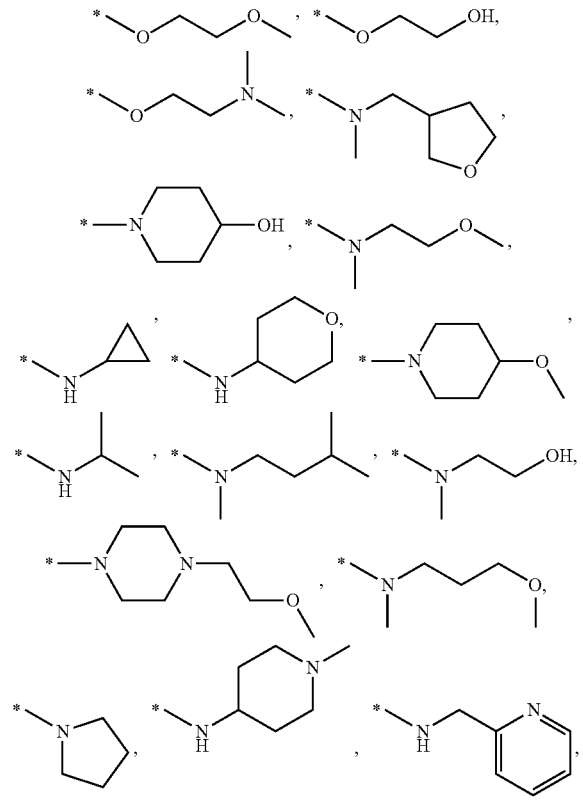

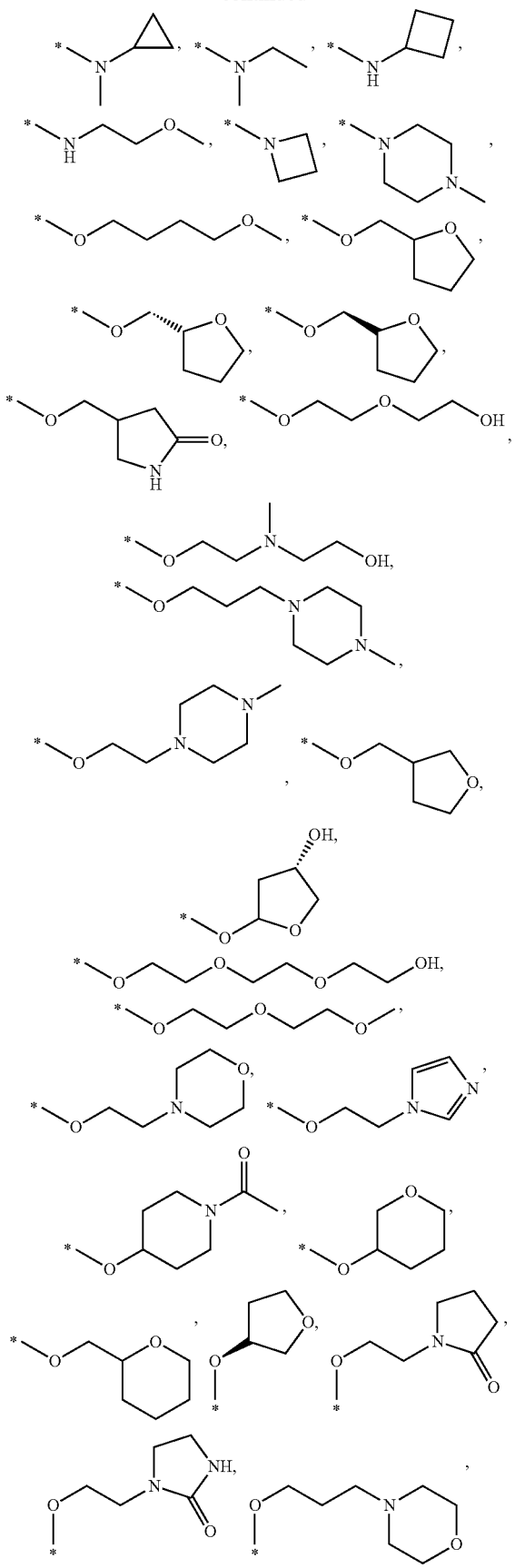

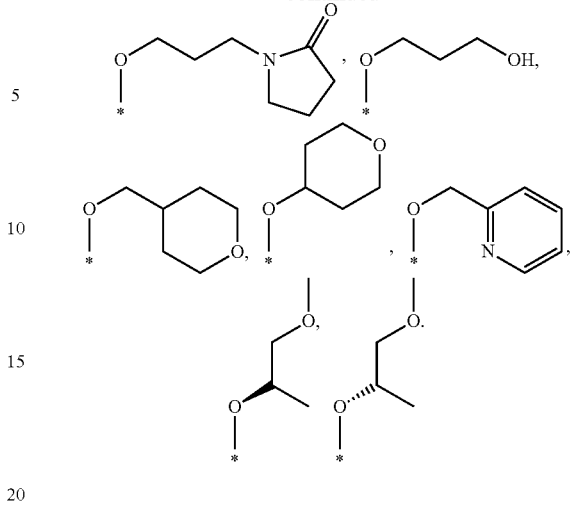

In another embodiment, in the general formula I, Ar, $R^1$ have the same meaning as defined in any of the preceding embodiments, and A represents N or CH;
B represents CH.

In another embodiment, in the general formula I, Ar, $R^1$ have the same meaning as defined in any of the preceding embodiments, and the group

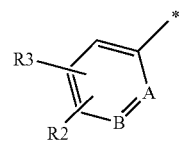

represents
phenyl, 2-pyridyl which latter two groups are optionally substituted with one or two substituents selected from fluoro, chloro, bromo, —CN, $C_{1-3}$alkyl optionally substituted with one or more fluorine atoms.

A further embodiment of the present invention comprises compounds of formula I in which $R^1$ represents phenylethynyl, cyclohexylethynyl, $C_{2-4}$alkenyl, $C_{5-6}$cycloalkenyl, phenyl, furyl, $C_{1-5}$alkyl, $C_{3-6}$cycloalkyl which latter four groups are optionally substituted with one or more substituents selected from fluoro, chloro, cyano, —$CH_2$-morpholine, —$CH_2$—O—$CH_3$, —$CH_2CN$, $C_{1-3}$alkyl, $C_{3-6}$cycloalkyl, —O—$C_{1-3}$alkyl which latter three substituents are optionally substituted with one or more fluorine atoms;

Ar represents phenyl,

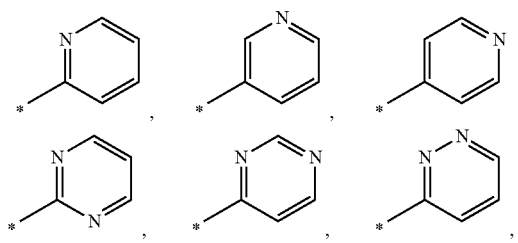

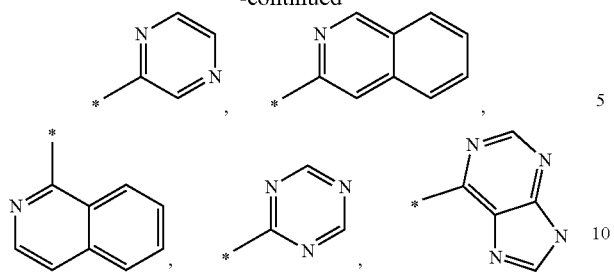
which latter twelve groups are optionally substituted with one or more substituents selected from fluoro, chloro, bromo, cyano, —OH, methyl, ethyl, methoxy, ethoxy, iso-propoxy,
—NH$_2$, —NMe$_2$, —NHMe, —NHEt, —CONH$_2$, —COOEt,
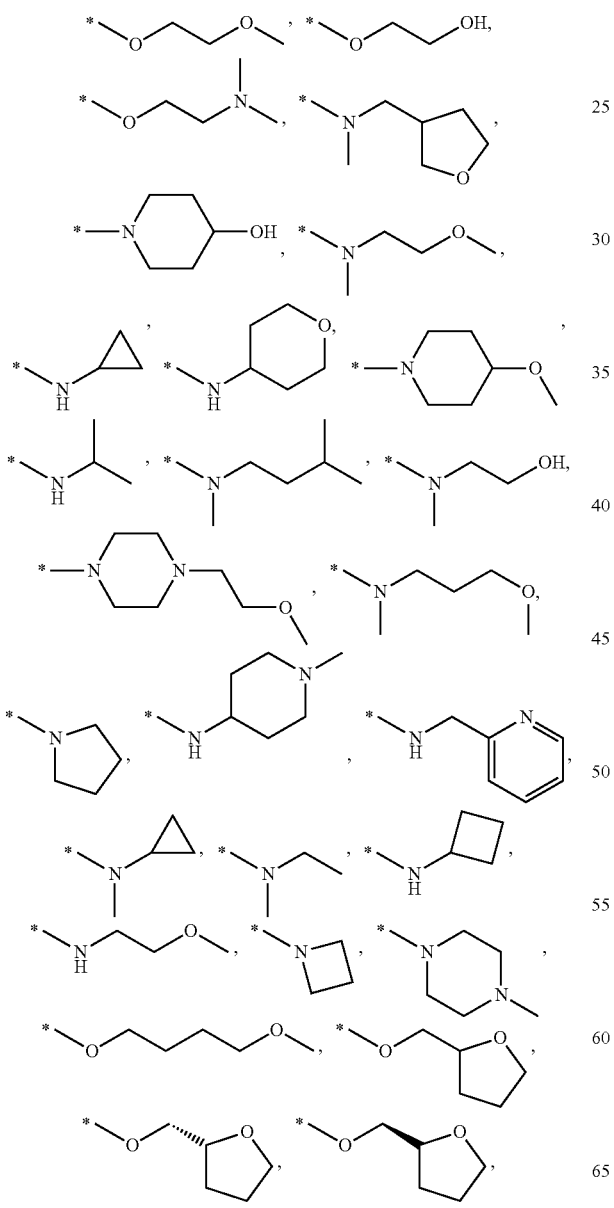
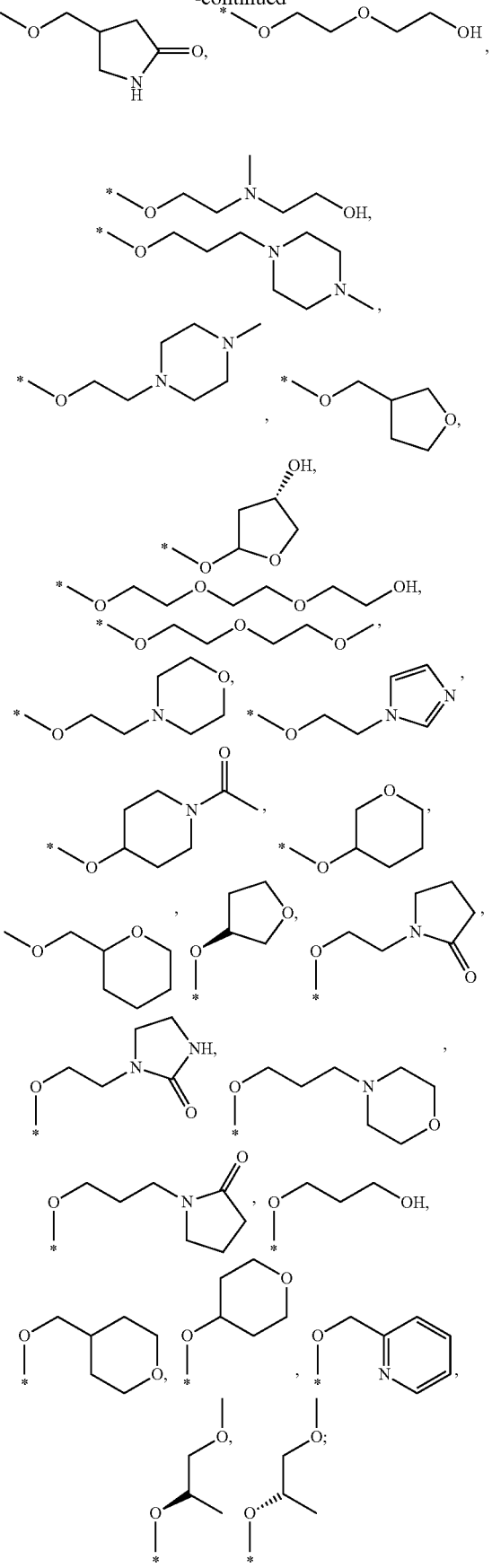

and the group

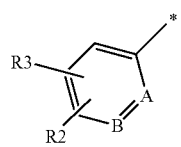

represents phenyl, 2-pyridyl which latter two groups are optionally substituted with one or two substituents selected from fluoro, chloro, bromo, —CN, $C_{1-3}$alkyl optionally substituted with one or more fluorine atoms;

or a salt thereof, particularly a physiologically acceptable salt thereof.

In another embodiment, in the general formula I, A, B, Ar, $R^2$, $R^3$ have the same meaning as defined in any of the preceding embodiments, and $R^1$ represents phenyl, methyl, ethyl, propyl, iso-propyl, n-butyl, n-pentyl, cyclopentyl, cyclohexyl,

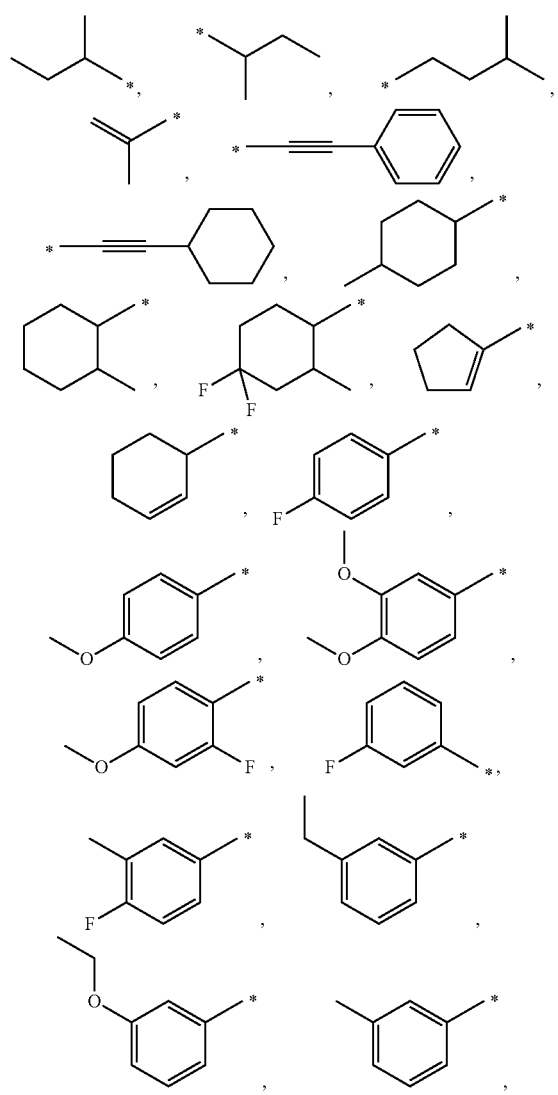

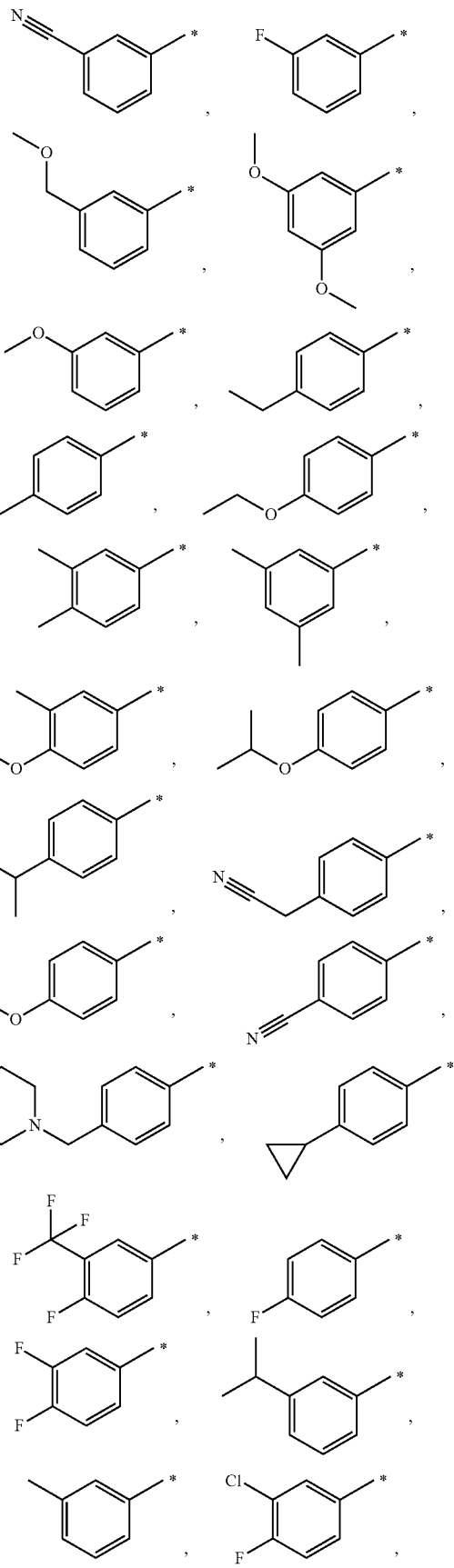

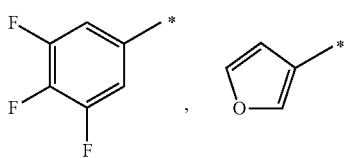
In another embodiment, in the general formula I, A, B, $R^1$, $R^2$, $R^3$ have the same meaning as defined in any of the preceding embodiments, and
Ar represents
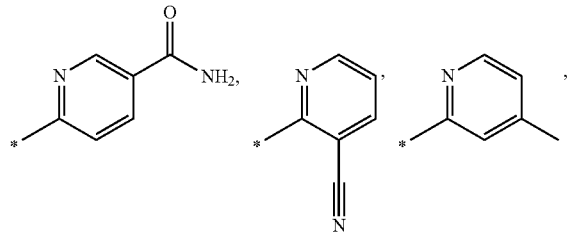
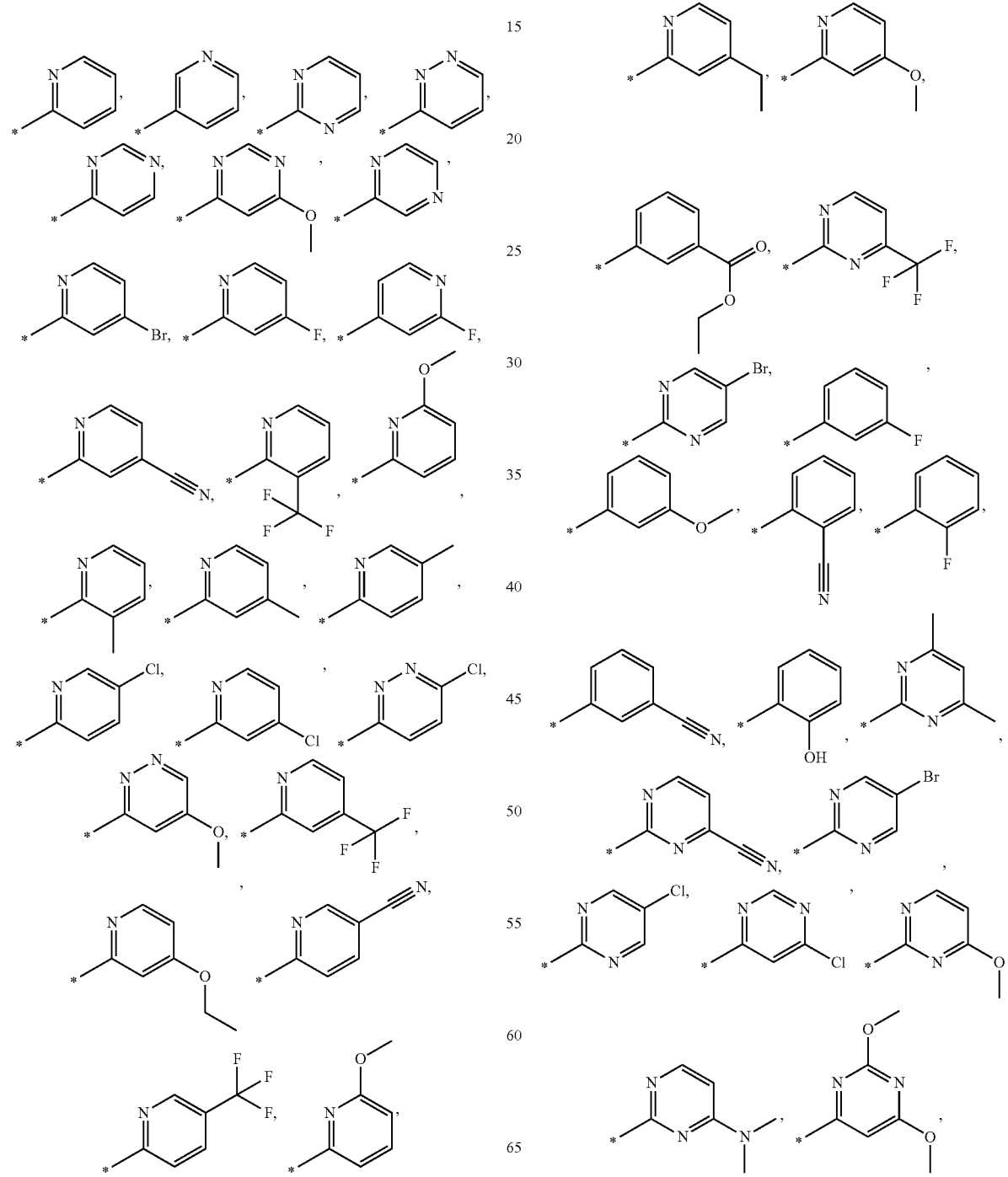

-continued
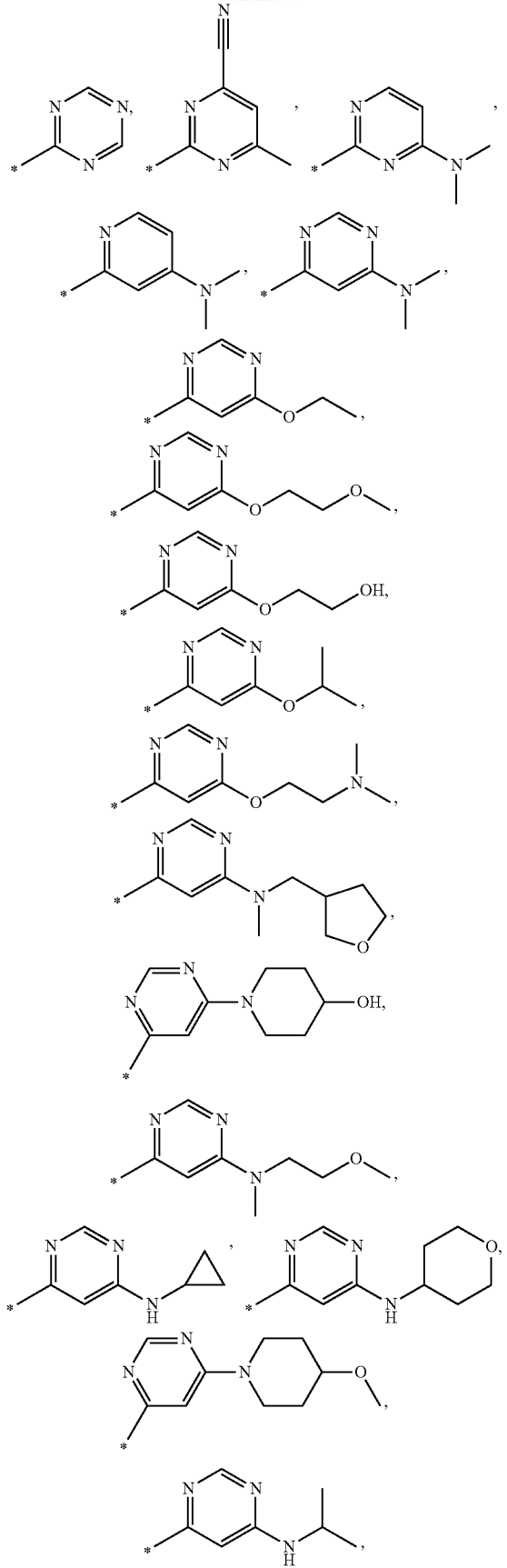
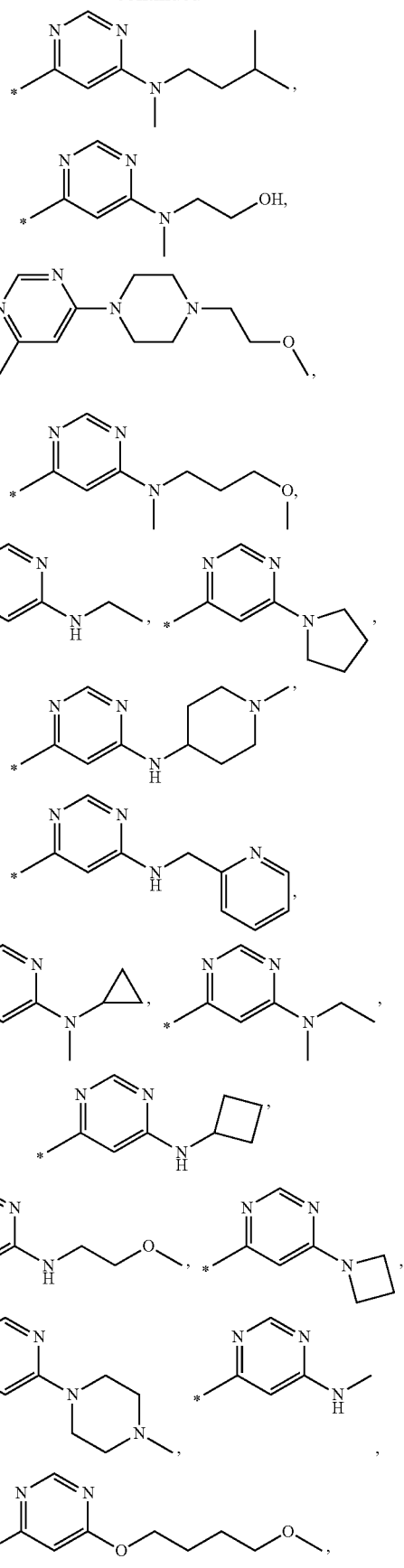

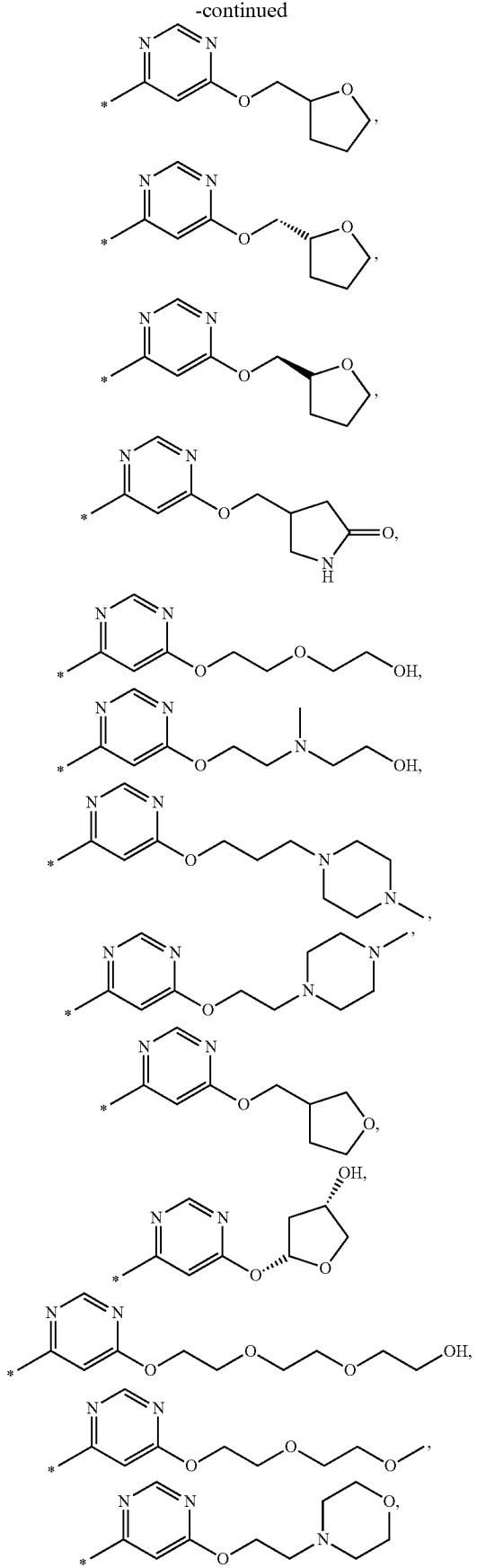
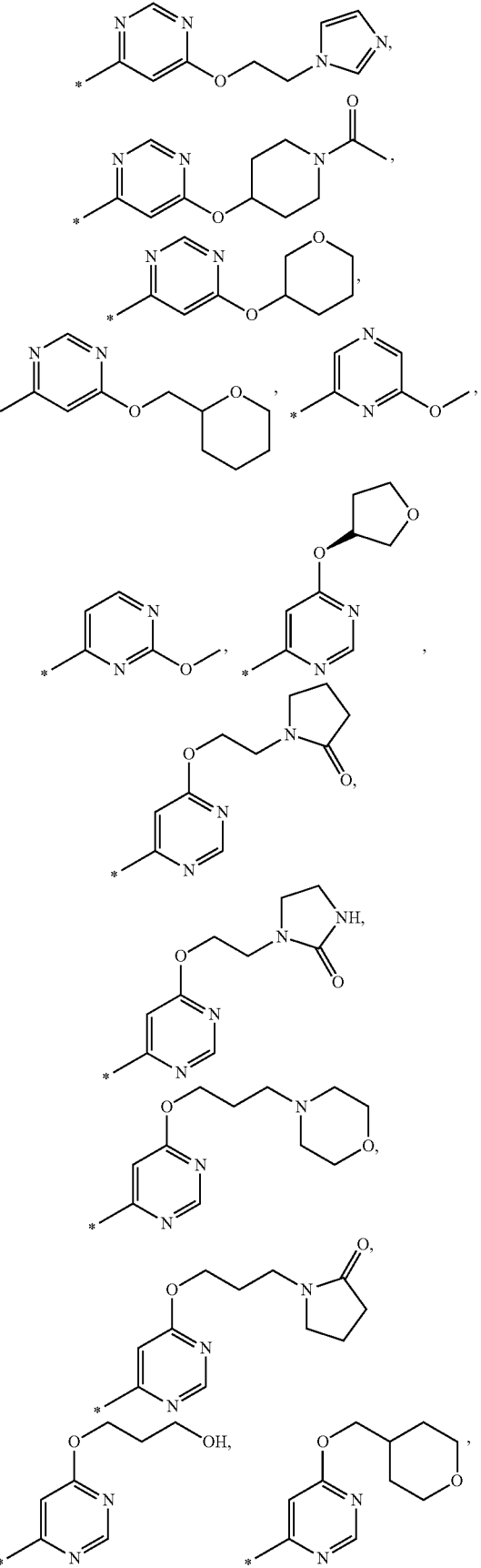

-continued
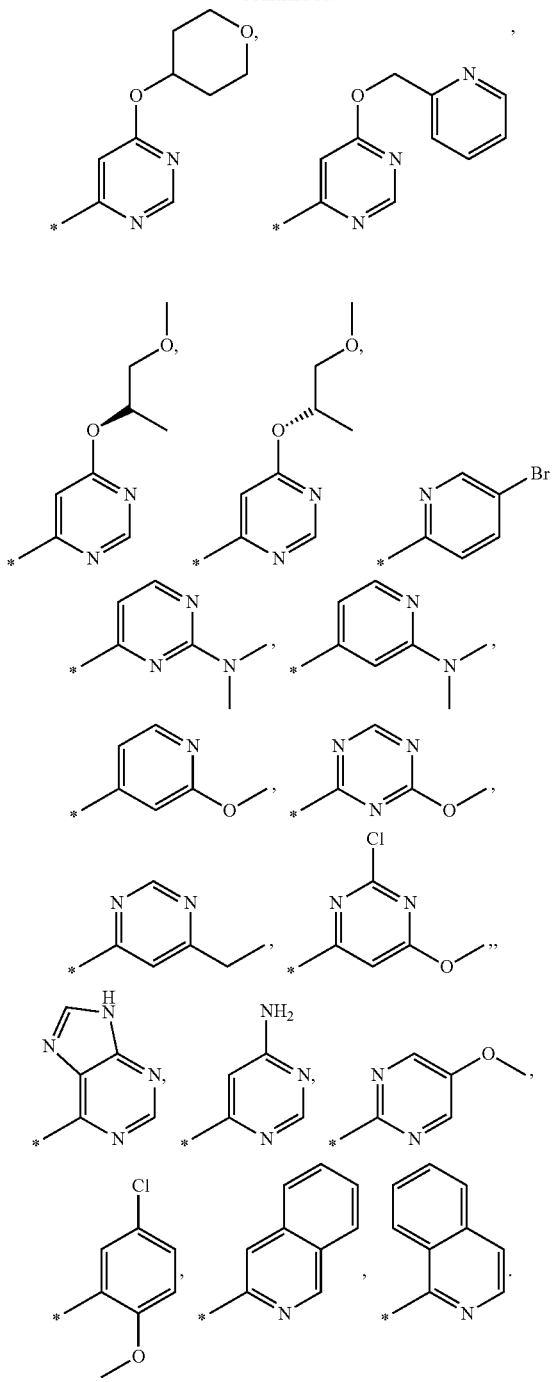
In another embodiment, in the general formula I, Ar, R¹ have the same meaning as defined in any of the preceding embodiments, and the group
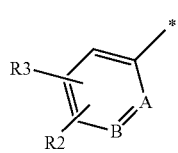
represents
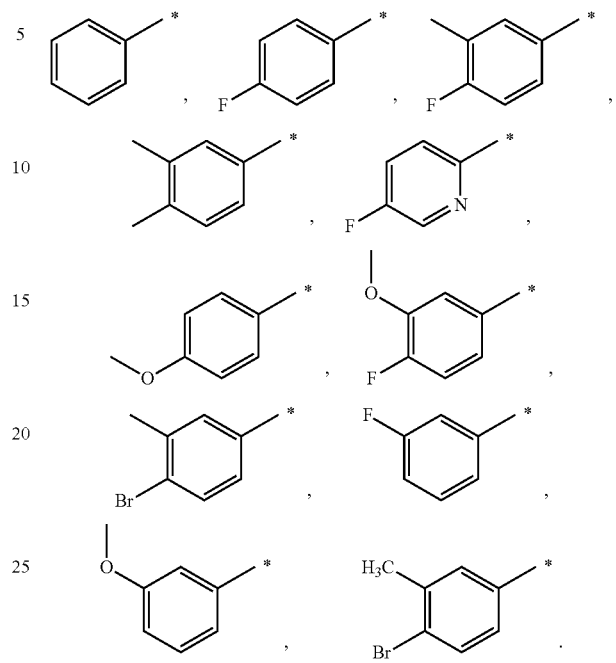
A further embodiment of the present invention comprises compounds of formula I in which
R¹ represents phenyl, methyl, ethyl, propyl, iso-propyl, n-butyl, n-pentyl, cyclopentyl, cyclohexyl,
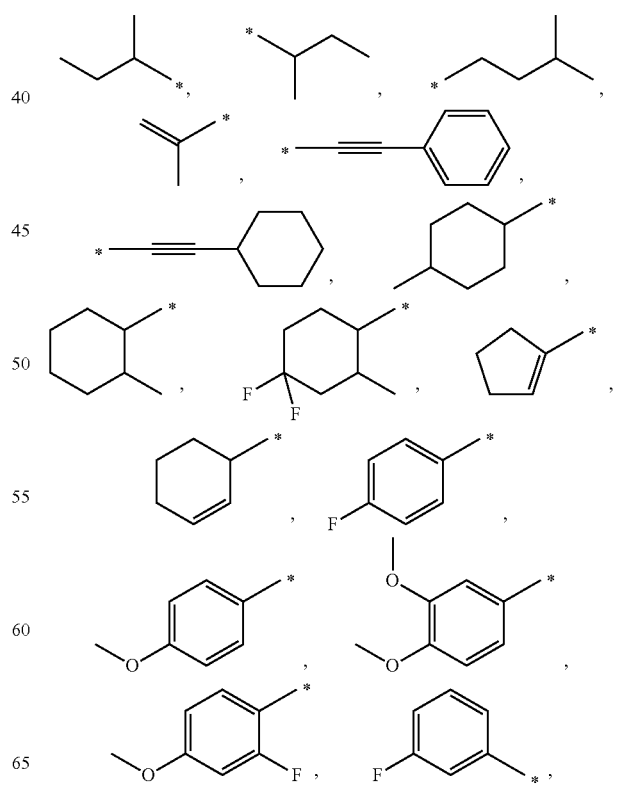

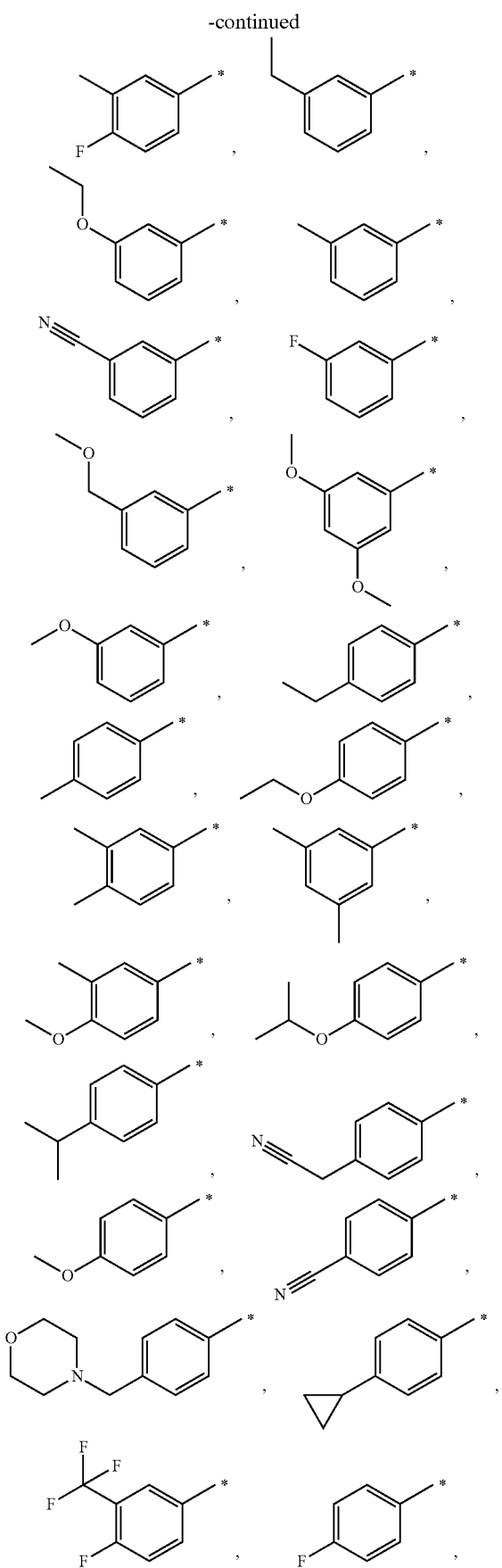
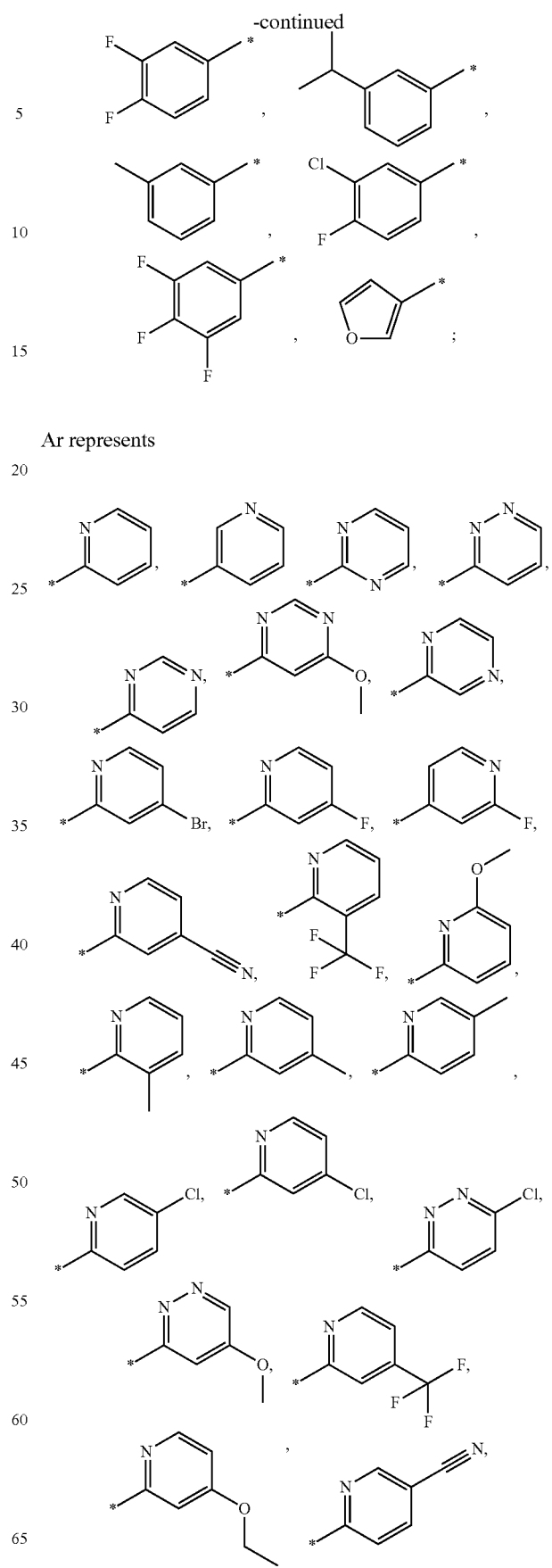
Ar represents

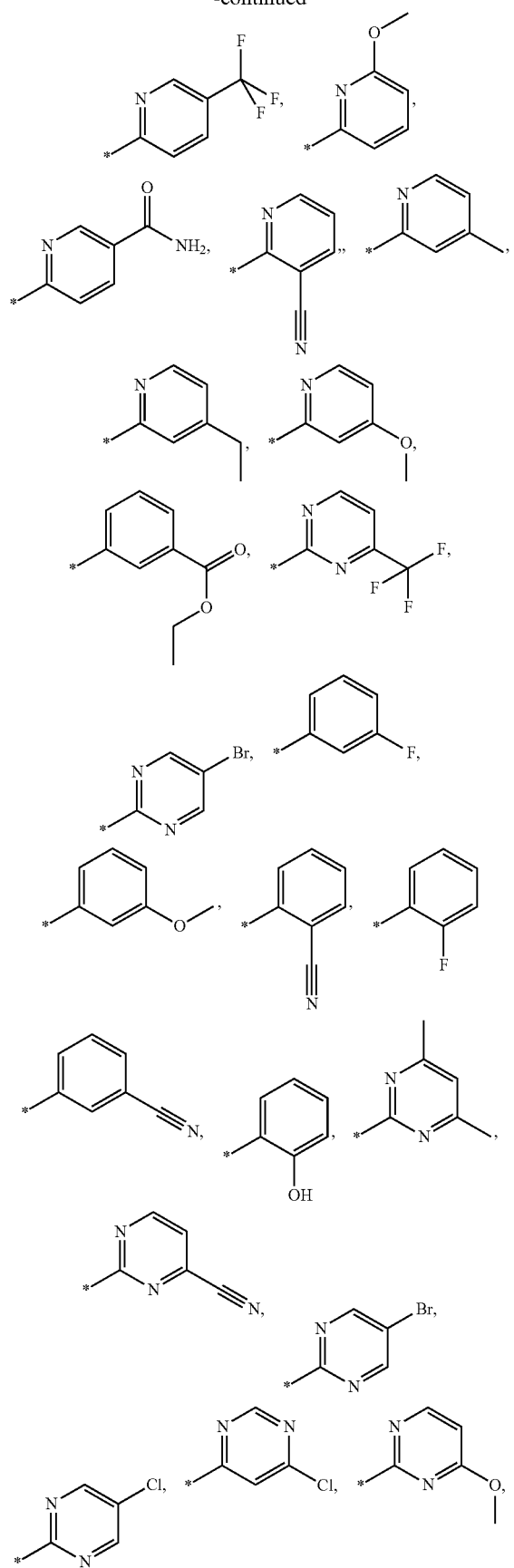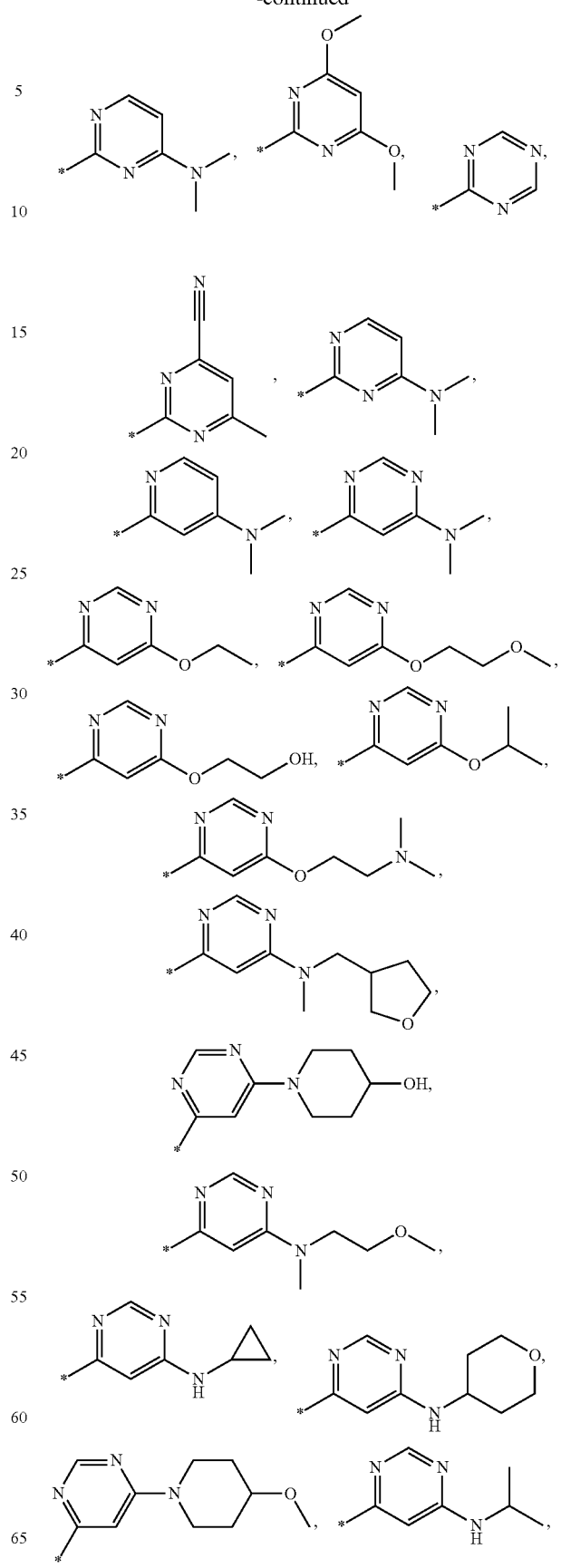

-continued
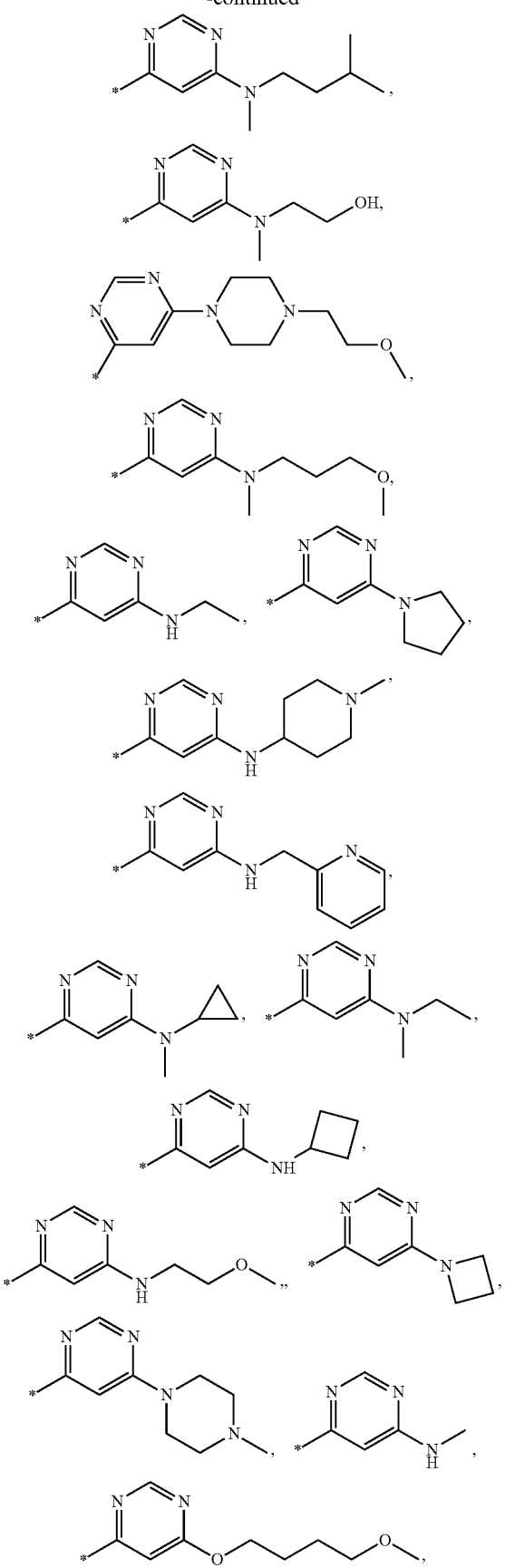
-continued
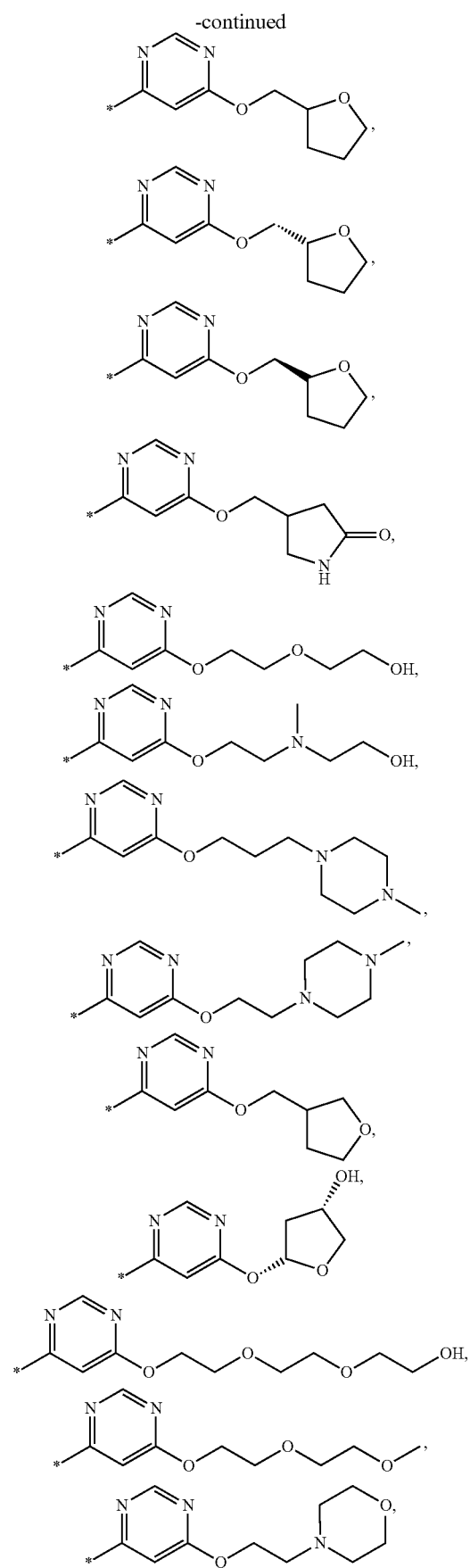

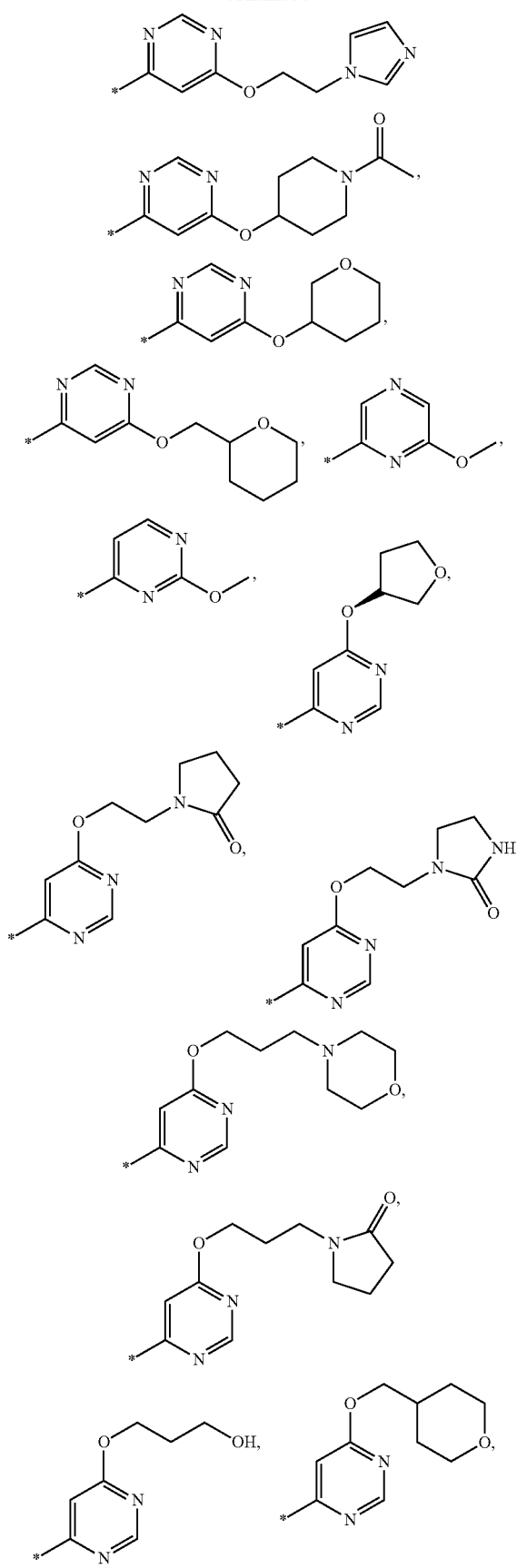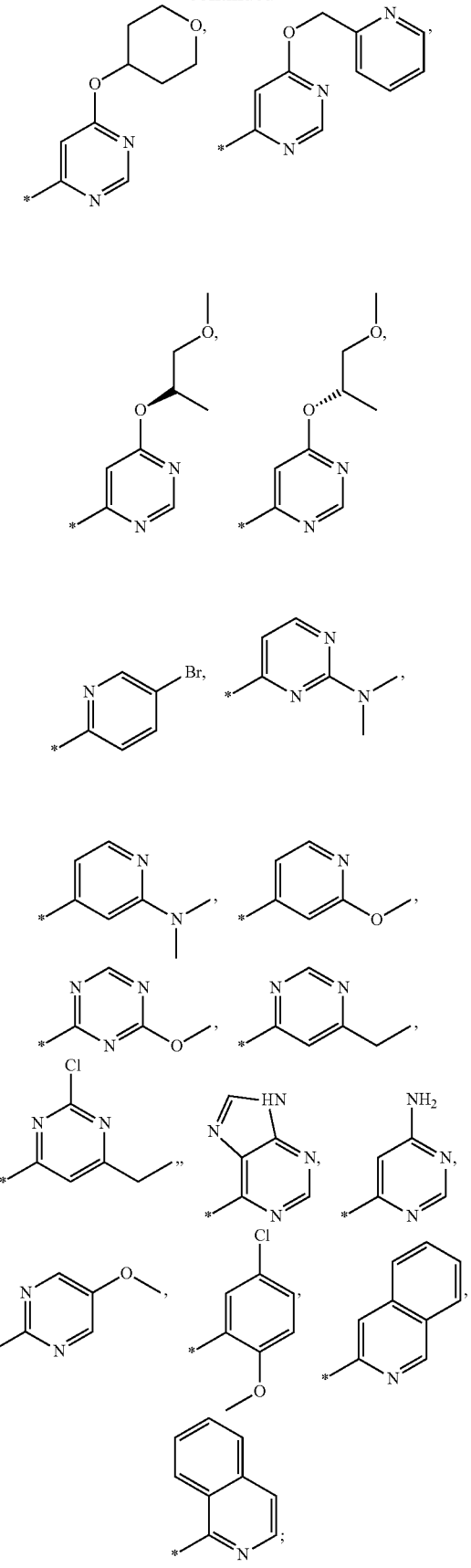

the group

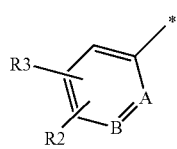

represents

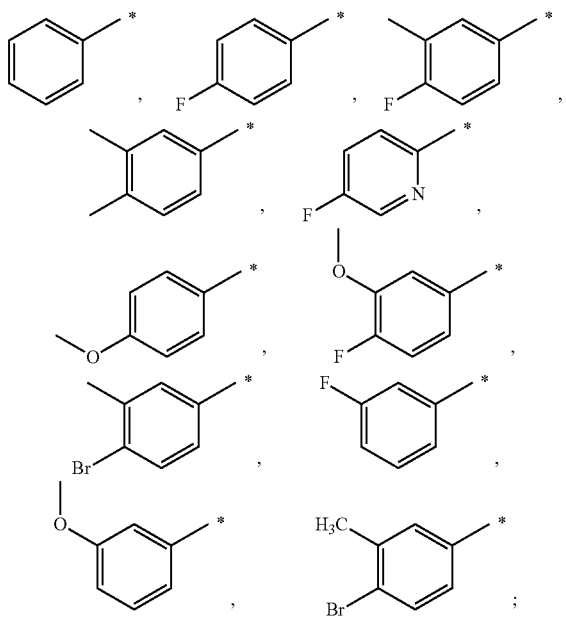

or a salt thereof, particularly a physiologically acceptable salt thereof.

Terms And Definitions Used

General Definitions:

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

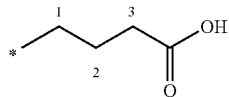

wherein the carboxy group is attached to the third carbon atom of the propyl group. The terms "1-methylpropyl-", "2,2-dimethylpropyl-" or "cyclopropylmethyl-" group represent the following groups:

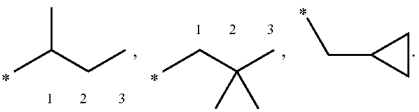

The asterisk may be used in sub-formulas to indicate the bond which is connected to the core molecule as defined.

Stereochemistry/Solvates/Hydrates:

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine(2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine(2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoro acetate salts,) also comprise a part of the invention.

Halogen:

The term halogen generally denotes fluorine, chlorine, bromine and iodine.

Alkyl:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Alkenyl:

The term "$C_{2-n}$-alkenyl", is used for a group as defined in the definition for "$C_{1-n}$-alkyl" with at least two carbon atoms, if at least two of those carbon atoms of said group are bonded to each other by a double bond.

Alkynyl:

The term "$C_{2-n}$-alkynyl", is used for a group as defined in the definition for "$C_{1-n}$-alkyl" with at least two carbon atoms, if at least two of those carbon atoms of said group are bonded to each other by a triple bond.

Cycloalkyl:

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

Cycloalkenyl:

The term "$C_{3-n}$-cycloalkenyl", wherein n is an integer 3 to n, either alone or in combination with another radical, denotes an cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl cycloheptadienyl and cycloheptatrienyl.

Aryl:

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

Heterocyclyl:

The term "heterocyclyl" means a saturated or unsaturated mono- or polycyclic-ring systems including aromatic ring system containing one or more heteroatoms selected from N, O or S(O)$_r$, wherein r=0, 1 or 2, consisting of 3 to 14 ring atoms wherein none of the heteroatoms is part of the aromatic ring. The term "heterocycle" is intended to include all the possible isomeric forms. Thus, the term "heterocyclyl" includes the following exemplary structures which are not depicted as radicals as each form may be attached through a covalent bond to any atom so long as appropriate valences are maintained:

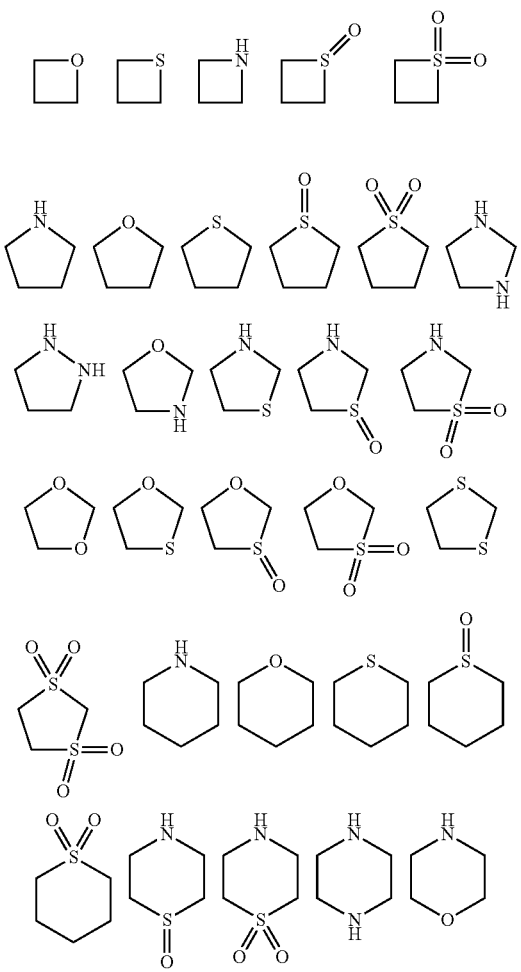

31
-continued
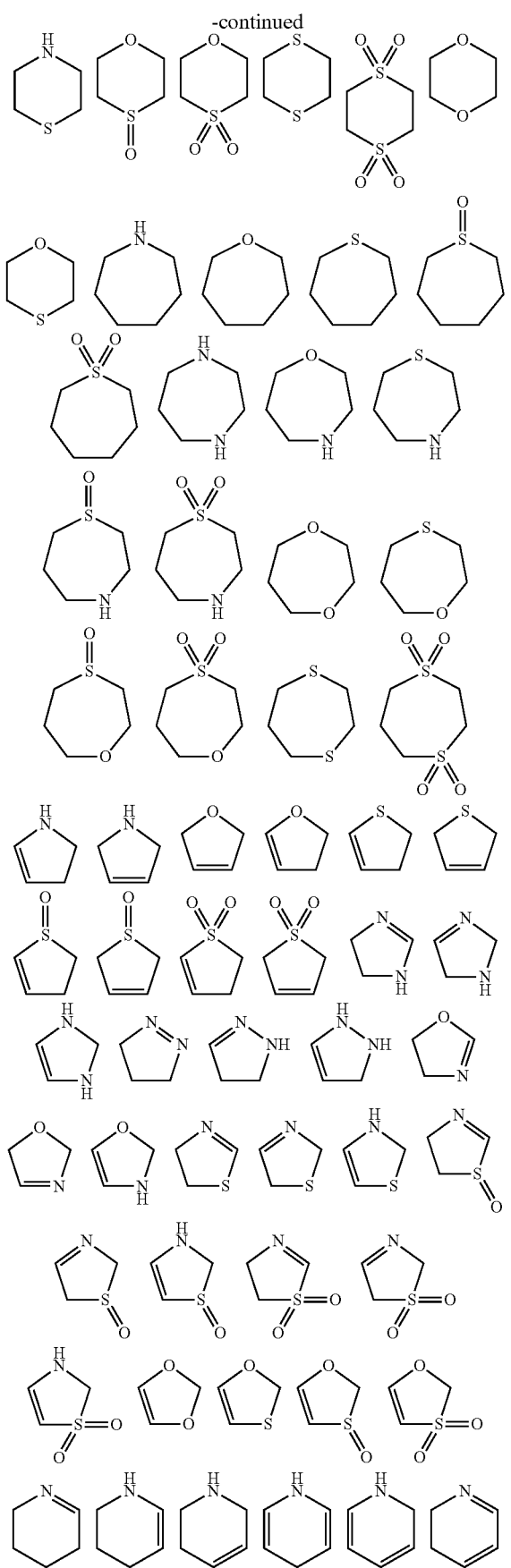
32
-continued
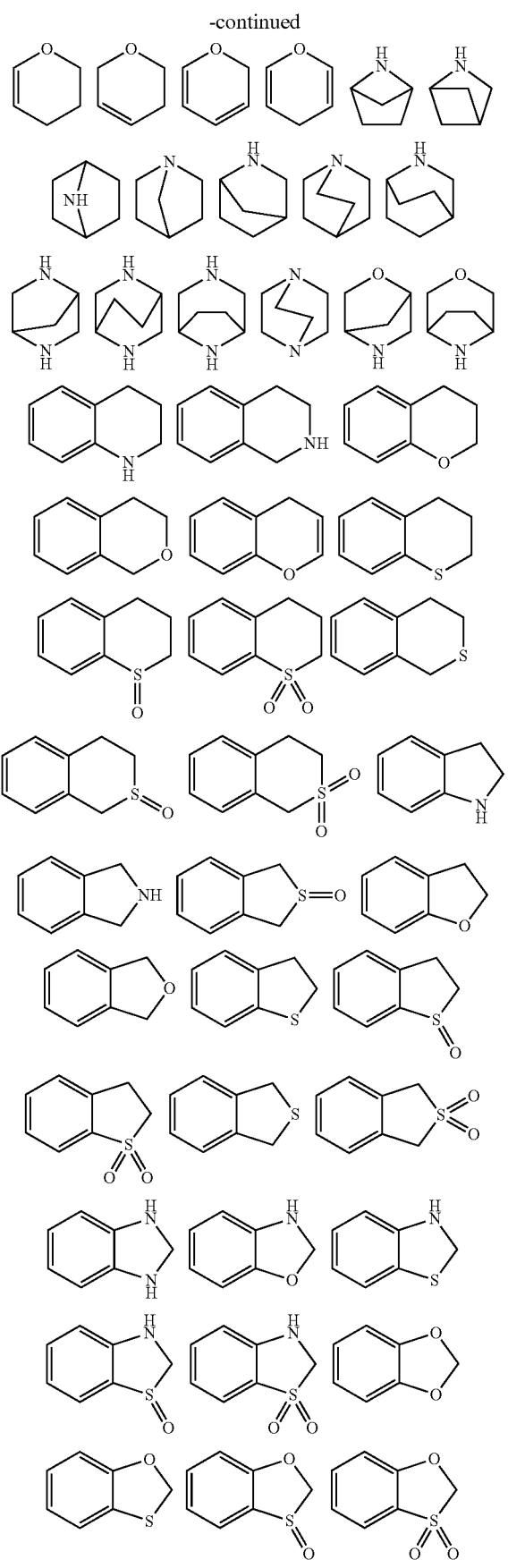

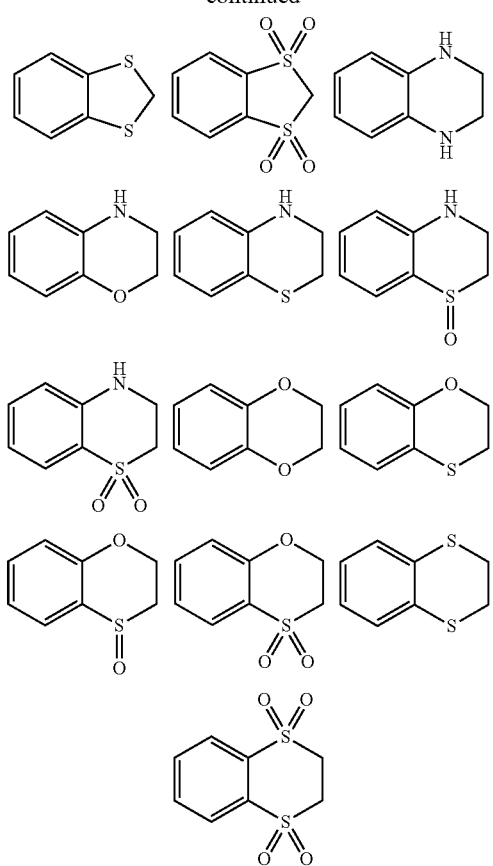

Heteroaryl:

The term "heteroaryl" means a mono- or polycyclic-ring systems containing one or more heteroatoms selected from N, O or S(O)$_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

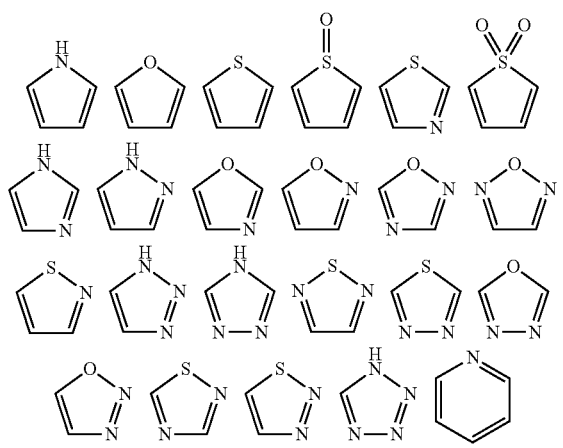

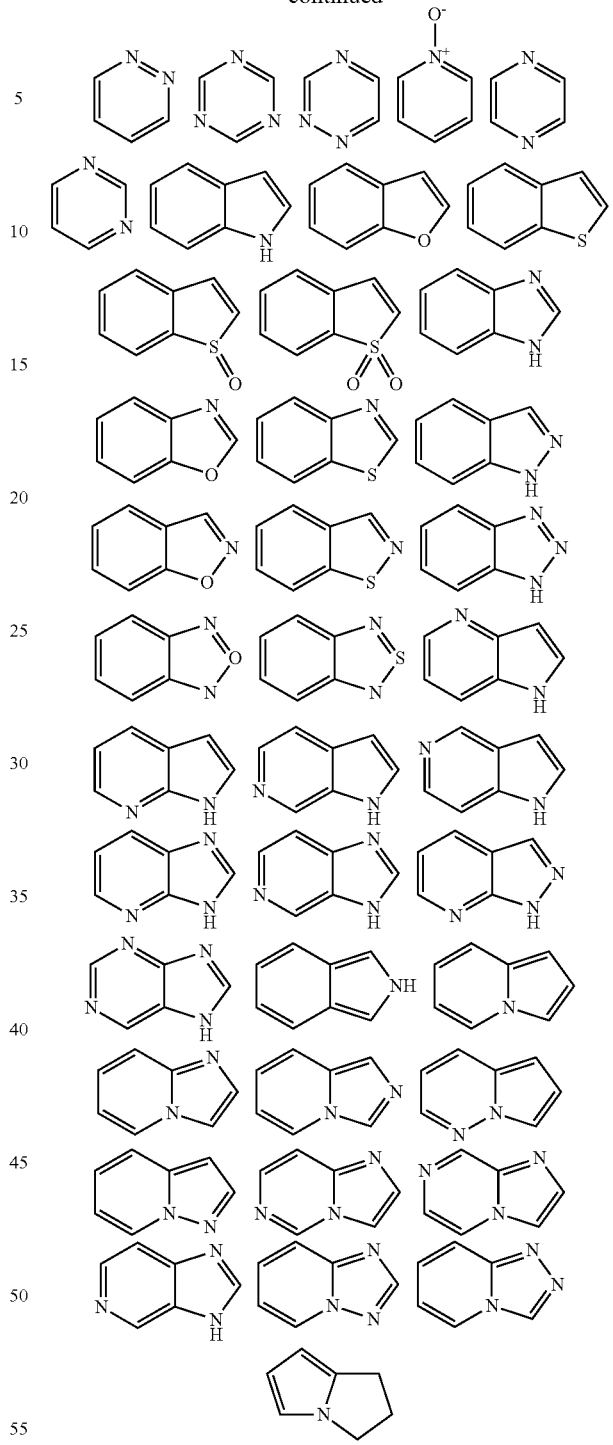

Many of the terms given above may be used repeatedly in the definition of a formula or group and in each case have one of the meanings given above, independently of one another.

General Method of Preparation

Compounds of the present invention can be prepared in accordance with techniques that are well known to those skilled in the art.

Compounds of the present invention can be synthesized according to scheme 1.

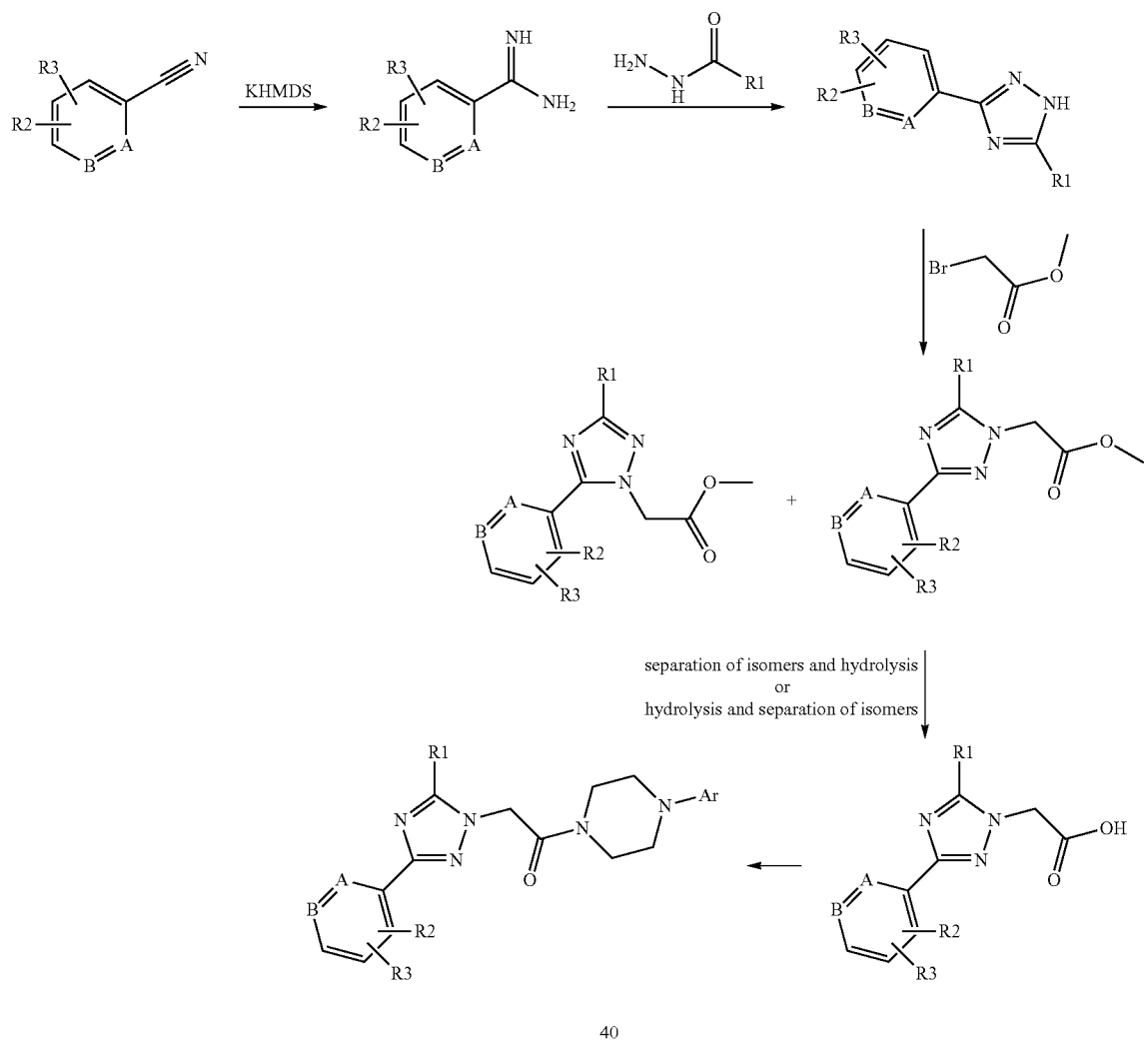

Nitriles were reacted with LiHMDS or KHMDS to benzamidines which were converted to triazole by melting with hydrazides. The triazoles were coupled with 2-bromoacetic acid methyl ester under basic conditions to give the desired triazole-1-yl-acetic acid methyl ester together with different quantities of the isomeric systhem. The triazole-1-yl-acetic acid methyl ester was hydrolyzed with LiOH to the coresponding acid. The isomeres were either seperated before ore after hydrolysis of the ester. Finally, the triazole-1-yl-acetic acides were coupled with aryl substituted piperazines to the desired products.

A subseries of compounds can be synthesized according to scheme 2 starting from the acid-intermediate of scheme 1:

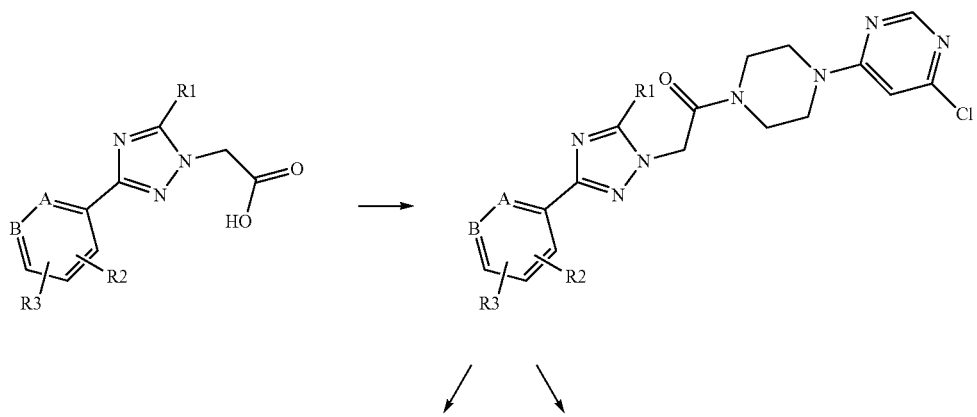

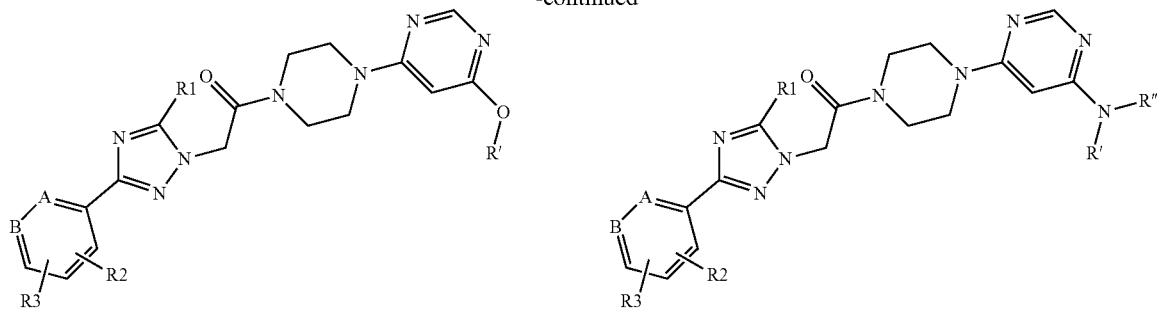

The triazole-1-yl-acetic acides were coupled with chloro-pyrimidin-4-yl)-(piperazine to form the corresponding triazole-(chloro-pyrimidin-4-yl)-(piperazine-1yl)-ethanone derivates. These derivatives were coupled with amines and triethylamines or with alcohols under basic conditions and at high temperature to the desired products.

A subseries of compounds can be synthesized according to scheme 3 starting from the acid-intermediate of scheme 1

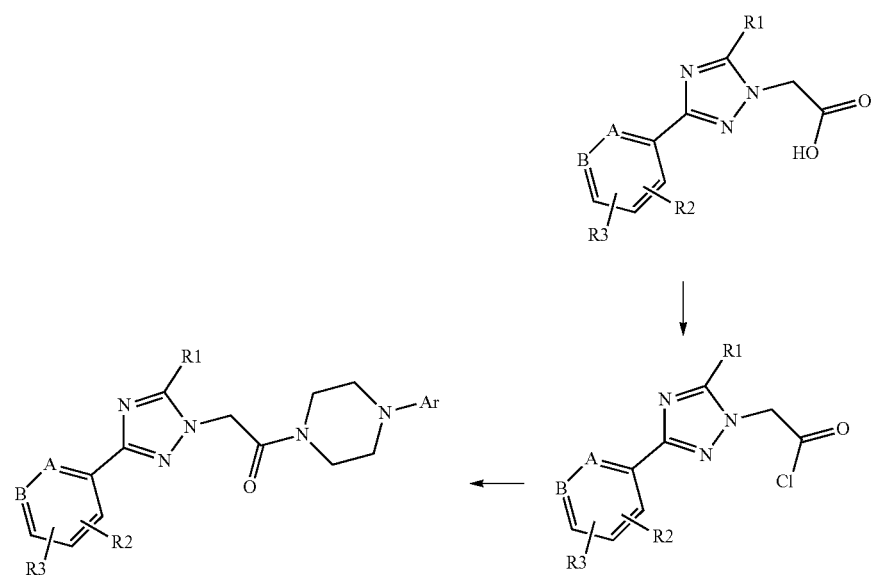

The acid clorides were formed from the triazole-1-yl-acetic acides with thionylchloride and were directly coupled with aryl substituted piperazines to the desired products.

A subseries of compounds can be synthesized according to scheme 4:

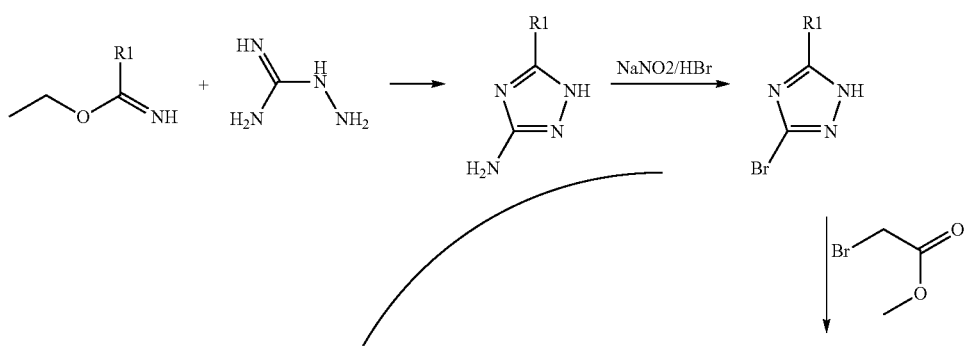

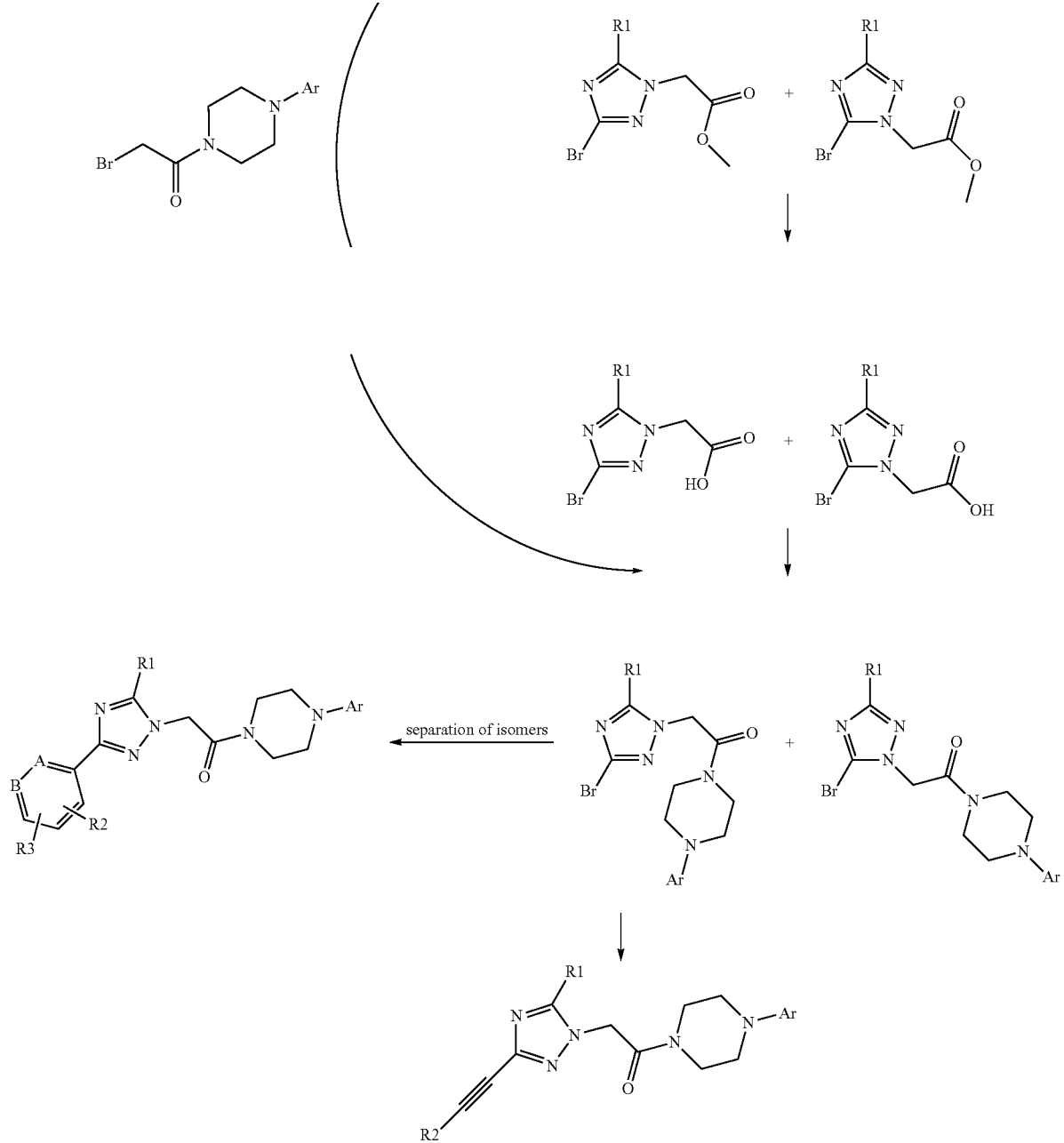

Imidic acid esters were reacted with aminoguanidines to triazole-3-yl-amine derivates to form triazole-3-yl-amines. These were converted in a Sandmeyer reaction with sodium-nitrite and bromine hydro acid to the 3-bromo-1H-triazole derivates. Accordingly to scheme 1, the triazoles were coupled with 2-bromoacetic acid methyl ester, hydrolyzed to the corresponding acid and coupled with aryl substituted piperazines. Finally, the desired products were obtained by a Suzzuki or a Sonogashira reaction of the bromine-compound. Alternatively, the 3-bromo-1H-triazole derivates can be directly coupled with pyrimidin-2-yl-piperazin-1-yl ethanes.

As an additional altrenative, the compounds of invention can be synthesized according to scheme 5:

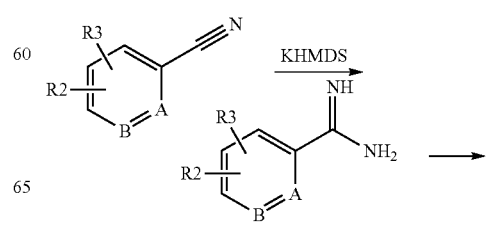

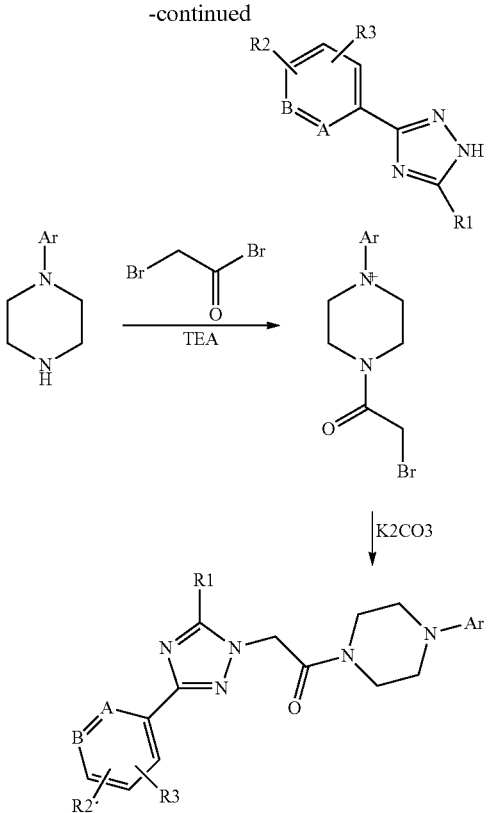

The triazole-systems were formed following the same strategy as illustrated in scheme 1. However, in this case the aryl piperazines were first coupled with bromacetylbromide under basic conditions. Subsequently, the bromo-arylpiperazinyl-ethanon derivates were coupled with the triazoles to the desired products.

Biological Assay

The positive modulation of mGluR5 is measured in a HEK 293 cell line expressing human recombinant mGluR5 and is detected with calcium based FLIPR assay. The cells are cultured with DMEM supplemented with 10% FCS, 2 µg/mL tetracycline, 100 µg/mL hygromycin and 500 µg/mL gneticin. The cell culture media is exchanged for tetracycline-free cell culture media 3-7 days before the assay. One day before the assay the cell culture medium is exchanged to DMEM without glutamine and phenol red and supplemented with 10% FCS, 100 µg/mL hygromycin and 500 µg/mL geneticin. On the assay day, the medium of the subconfluent cultures is removed and the cells are detached by addition of 2.5 ml EDTA (0.02%) per 175 cm2 culture flask for 1 minute. The cells are resuspend in Ringer solution (140 mM NaCl, 5 mM KCl, 2.5 mM CaCl2, 1.5 mM MgCl2, 5 mM Glucose, 10 mM Hepes; adjusted to pH 7.4 with NaOH), pooled and Ringer solution added to adjust the volume to 50 mL. The cell suspension is centrifuged for 5 mM at 1500 U/min (425 g). The supernatant is removed and the cells washed a second time with 50 ml fresh Ringer solution and centrifuged again as before. The supernatant is again removed and the pellet resuspended in Ringer solution to 1,000,000 cells/ml (1×10^6 cells/mL). The cells are plated onto BD BioCoat Poly-D-Lysine 384 well plates (20.000 cells/well; 20 µl/well). The lid covered plates are then incubated until use at 37° C./10% $CO_2$. For dye loading, 20 µl of Calcium-4 assay kit solution (prepared according to the manufacturer's description in Ringer solution) are added to the cells and the plates are incubated for 80 min 37° C. and then 10 min at room temperature.

Controls, Compound Dilution and Assay Execution:

Each assay plate contained wells with "high" and "low" controls:

Low controls 1% DMSO/ringer solution+basal glutamate activation (defined as 100% CTL).

High controls 10 µM CDPPB+basal glutamate activation (defined as 200% CTL).

Test compounds are dissolved and diluted in DMSO to 100-fold the desired concentrations. In a second step, the compounds are diluted in Ringer solution such that the compounds are 4-fold more concentrated than the desired final assay concentration. The final DMSO concentration was 1%.

20 µl of each compound solution are then transferred to the assay plate and the Ca2+ kinetic is measured to determine any intrinsic compound activity. After 5 min incubation in the FLIPR device, the second stimulation with 20 µl of glutamate in Ringer solution (glutamate concentration adjusted to approximately 5% basal stimulation of the maximal possible glutamate effect) is added and the kinetic Ca2+ response of the wells was measured for the modulation effect.

Analysis:

The peak height of the Ca release related fluorescence signal (9-66) is used for the EC50. The EC50 of the modulation is calculated over a nonlinear regression with GraphPad Prism (Table 1).

TABLE 1

| Example | EC50 [nM] | Example | EC50 [nM] | Example | EC50 [nM] | Example | EC50 [nM] |
|---|---|---|---|---|---|---|---|
| 07.01.01. | 24 | 07.04.023. | 370 | 07.04.107. | 500 | 07.08.18. | 455 |
| 07.01.02. | 56 | 07.04.024. | 945 | 07.04.108. | 317 | 07.08.19. | 208 |
| 07.01.03. | 80 | 07.04.025. | 868 | 07.04.109. | 824 | 07.08.20. | 155 |
| 07.01.04. | 82 | 07.04.026. | 236 | 07.04.11. | 1570 | 07.08.21. | 201 |
| 07.01.05. | 399 | 07.04.027. | 38 | 07.04.110. | 409 | 07.08.22. | 280 |
| 07.01.06. | 13 | 07.04.028. | 30 | 07.04.111. | 131 | 07.08.23. | 1593 |
| 07.01.07. | 66 | 07.04.029. | 1564 | 07.04.112. | 311 | 07.08.24. | 191 |
| 07.02.01. | 190 | 07.04.030. | 1416 | 07.04.113. | 263 | 07.09.01. | 68 |
| 07.02.02. | 474 | 07.04.031. | 661 | 07.04.114. | 495 | 07.09.02. | 59 |
| 07.02.03. | 220 | 07.04.032. | 39 | 07.04.115. | 208 | 07.09.03. | 58 |
| 07.02.04. | 1065 | 07.04.033. | 37 | 07.04.116. | 697 | 07.09.04. | 64 |
| 07.02.05. | 44 | 07.04.034. | 52 | 07.04.117. | 390 | 07.09.05. | 41 |
| 07.02.06. | 155 | 07.04.035. | 40 | 07.04.118. | 255 | 07.09.06. | 130 |
| 07.02.07. | 217 | 07.04.036. | 32 | 07.04.119. | 298 | 07.09.07. | 110 |
| 07.02.08. | 36 | 07.04.037. | 114 | 07.04.12. | 176 | 07.09.08. | 74 |
| 07.02.09. | 61 | 07.04.038. | 23 | 07.04.120. | 153 | 07.09.09. | 109 |

TABLE 1-continued

| Example | EC50 [nM] | Example | EC50 [nM] | Example | EC50 [nM] | Example | EC50 [nM] |
|---|---|---|---|---|---|---|---|
| 07.02.10. | 83 | 07.04.039. | 30 | 07.04.121. | 209 | 07.09.10. | 52 |
| 07.02.11. | 375 | 07.04.040. | 33 | 07.04.122. | 140 | 07.09.11. | 56 |
| 07.02.12. | 328 | 07.04.041. | 113 | 07.04.123. | 92 | 07.09.12. | 170 |
| 07.02.13. | 1293 | 07.04.042. | 148 | 07.04.124. | 125 | 07.09.13. | 47 |
| 07.02.14. | 1054 | 07.04.043. | 334 | 07.04.125. | 109 | 07.09.14. | 38 |
| 07.02.15. | 675 | 07.04.044. | 88 | 07.04.126. | 110 | 07.09.15. | 224 |
| 07.02.16. | 266 | 07.04.045. | 80 | 07.04.127. | 64 | 07.09.16. | 173 |
| 07.02.17. | 644 | 07.04.046. | 586 | 07.04.128. | 485 | 07.09.17. | 106 |
| 07.02.18. | 227 | 07.04.047. | 1380 | 07.04.129. | 1325 | 07.09.18. | 103 |
| 07.02.19. | 494 | 07.04.048. | 591 | 07.04.13. | 1208 | 07.09.19. | 200 |
| 07.02.20. | 162 | 07.04.049. | 37 | 07.04.130. | 848 | 07.09.20. | 65 |
| 07.02.21. | 451 | 07.04.050. | 459 | 07.04.131. | 1001 | 07.09.21. | 79 |
| 07.02.22. | 681 | 07.04.051. | 997 | 07.04.132. | 960 | 07.09.22. | 39 |
| 07.02.23. | 1905 | 07.04.052. | 898 | 07.04.133. | 1082 | 07.09.23. | 62 |
| 07.02.24. | 229 | 07.04.053. | 1153 | 07.04.134. | 1030 | 07.09.24. | 101 |
| 07.02.25. | 424 | 07.04.054. | 100 | 07.04.135. | 392 | 07.09.25. | 301 |
| 07.02.26. | 252 | 07.04.055. | 101 | 07.04.136. | 1222 | 07.09.26. | 252 |
| 07.02.27. | 353 | 07.04.056. | 64 | 07.04.137. | 1049 | 07.09.27. | 86 |
| 07.02.28. | 243 | 07.04.057. | 75 | 07.04.138. | 1008 | 07.09.28. | 523 |
| 07.03.01. | 88 | 07.04.058. | 25 | 07.04.139. | 809 | 07.09.29. | 44 |
| 07.03.02. | 1283 | 07.04.059. | 160 | 07.04.140. | 320 | 07.09.30. | 75 |
| 07.03.03. | 595 | 07.04.060. | 55 | 07.04.141. | 932 | 07.10.01. | 11 |
| 07.03.04. | 50 | 07.04.061. | 67 | 07.04.142. | 434 | 07.10.02. | 37 |
| 07.03.05. | 469 | 07.04.062. | 57 | 07.04.143. | 783 | 07.10.03. | 15 |
| 07.03.06. | 350 | 07.04.063. | 61 | 07.04.144. | 1267 | 07.10.04. | 43 |
| 07.03.07. | 610 | 07.04.064. | 192 | 07.04.145. | 373 | 07.10.05. | 17 |
| 07.03.08. | 124 | 07.04.065. | 296 | 07.04.146. | 1337 | 07.10.06. | 164 |
| 07.03.09. | 121 | 07.04.066. | 101 | 07.04.147. | 713 | 07.10.07. | 189 |
| 07.03.10. | 67 | 07.04.067. | 207 | 07.04.148. | 918 | 07.10.08. | 181 |
| 07.03.11. | 283 | 07.04.068. | 246 | 07.04.149. | 869 | 07.10.09. | 553 |
| 07.03.12. | 134 | 07.04.069. | 229 | 07.04.150. | 323 | 07.10.10. | 50 |
| 07.03.13. | 224 | 07.04.070. | 318 | 07.04.151. | 560 | 07.10.11. | 22 |
| 07.03.14. | 85 | 07.04.071. | 347 | 07.04.152. | 174 | 07.10.12. | 23 |
| 07.03.15. | 574 | 07.04.072. | 257 | 07.04.153. | 22 | 07.10.13. | 77 |
| 07.03.16. | 66 | 07.04.073. | 87 | 07.04.154. | 54 | 07.10.14. | 33 |
| 07.03.17. | 601 | 07.04.074. | 325 | 07.04.155. | 59 | 07.10.15. | 24 |
| 07.03.18. | 179 | 07.04.075. | 657 | 07.04.156. | 18 | 07.10.16. | 31 |
| 07.03.19. | 440 | 07.04.076. | 220 | 07.04.157. | 36 | 07.10.17. | 43 |
| 07.03.20. | 467 | 07.04.077. | 244 | 07.04.158. | 27 | 07.10.18. | 1051 |
| 07.03.21. | 278 | 07.04.078. | 679 | 07.04.159. | 282 | 07.10.19. | 233 |
| 07.03.22. | 476 | 07.04.079. | 1329 | 07.04.160. | 80 | 07.10.20. | 35 |
| 07.03.23. | 1010 | 07.04.080. | 771 | 07.04.161. | 1517 | 07.10.21. | 1498 |
| 07.03.24. | 254 | 07.04.081. | 353 | 07.05.01. | 50 | 07.10.22. | 87 |
| 07.03.25. | 75 | 07.04.082. | 306 | 07.05.02. | 43 | 07.10.23. | 459 |
| 07.03.26. | 177 | 07.04.083. | 497 | 07.06.01. | 167 | 07.10.24. | 300 |
| 07.03.27. | 1212 | 07.04.084. | 1600 | 07.06.02. | 70 | 07.10.25. | 639 |
| 07.03.28. | 319 | 07.04.085. | 379 | 07.06.03. | 101 | 07.10.26. | 543 |
| 07.04.001. | 25 | 07.04.086. | 1169 | 07.06.04. | 153 | 07.10.27. | 1469 |
| 07.04.002. | 1997 | 07.04.087. | 904 | 07.07.01. | 165 | 07.10.28. | 804 |
| 07.04.003. | 259 | 07.04.088. | 896 | 07.07.02. | 988 | 07.10.29. | 219 |
| 07.04.004. | 600 | 07.04.089. | 340 | 07.08.01. | 201 | 07.10.30. | 50 |
| 07.04.005. | 400 | 07.04.090. | 1163 | 07.08.02. | 284 | 07.10.31. | 270 |
| 07.04.006. | 899 | 07.04.091. | 1090 | 07.08.03. | 238 | 07.10.32. | 225 |
| 07.04.007. | 1348 | 07.04.092. | 654 | 07.08.04. | 430 | 07.10.33. | 359 |
| 07.04.008. | 117 | 07.04.093. | 1733 | 07.08.05. | 510 | 07.10.34. | 157 |
| 07.04.009. | 166 | 07.04.094. | 991 | 07.08.06. | 259 | 07.10.35. | 98 |
| 07.04.010. | 1196 | 07.04.095. | 1657 | 07.08.07. | 151 | 07.10.36. | 121 |
| 07.04.0100. | 670 | 07.04.096. | 1523 | 07.08.08. | 359 | 07.10.37. | 101 |
| 07.04.014. | 467 | 07.04.097. | 1190 | 07.08.09. | 332 | 07.10.38. | 622 |
| 07.04.015. | 364 | 07.04.098. | 738 | 07.08.10. | 1033 | 07.10.39. | 389 |
| 07.04.016. | 62 | 07.04.099. | 499 | 07.08.11. | 293 | 07.10.40. | 128 |
| 07.04.017. | 421 | 07.04.101. | 294 | 07.08.12. | 210 | 07.10.41. | 182 |
| 07.04.018. | 200 | 07.04.102. | 998 | 07.08.13. | 343 | 07.10.42. | 81 |
| 07.04.019. | 1094 | 07.04.103. | 748 | 07.08.14. | 822 | 07.10.43. | 571 |
| 07.04.020. | 388 | 07.04.104. | 1852 | 07.08.15. | 205 | 07.11.01. | 98 |
| 07.04.021. | 647 | 07.04.105. | 382 | 07.08.16. | 1157 | 07.11.02. | 416 |
| 07.04.022. | 1039 | 07.04.106. | 387 | 07.08.17. | 286 | 7.04.168 | 249 |
| 7.04.162 | 19 | 7.04.164 | 22 | 7.04.166 | 431 | 7.04.169 | 928 |
| 7.04.163 | 850 | 7.04.165 | 13 | 7.04.167 | 527 | | |

Method of Treatment

The present invention is directed to compounds of general formula I which are useful in the treatment of a disease and/or condition wherein the activity of an mGluR5 positive modulator is of therapeutic benefit, including but not limited to the treatment of psychotic disorders, cognitive disorders and dementias.

The compounds of general formula I are useful for the treatment of psychotic disorders including schizophrenia, schizoaffective disorder and substance induced psychotic disorder; cognitive disorders and dementias including age-associated learning and memory impairments or losses, post stroke dementia, deficits in concentration, mild cognitive impairment, the cognitive dysfunction in Alzheimers disease, and the cognitive dysfunction of schizophrenia. Therefore, the present invention also relates to a compound of general formula I as a medicament.

A further aspect of the present invention relates to the use of a compound of general formula I for the treatment of a disease and/or condition wherein the activity of mGluR5 positive modulator is of therapeutic benefit.

Furthermore, the present invention relates to the use of a compound of general formula I for the treatment of psychotic disorders, cognitive disorders and dementias.

Furthermore, the present invention relates to the use of a compound of general formula I for the treatment of psychotic disorders including schizophrenia, schizoaffective disorder and substance induced psychotic disorder; cognitive disorders and dementias including age-associated learning and memory impairments or losses, post stroke dementia, deficits in concentration, mild cognitive impairment, the cognitive dysfunction in Alzheimers disease, and the cognitive dysfunction of schizophrenia.

In a further aspect of the present invention the present invention relates to methods for the treatment or prevention of above mentioned diseases and conditions, which method comprises the administration of an effective amount of a compound of general formula I to a human being.

Dosage

The dose range of the compounds of general formula I applicable per day is usually from 0.1 to 5000 mg, preferably from 0.1 to 1000 mg, more preferably from 5 to 500 mg, most preferably, 10 or 100 mg. Each dosage unit may conveniently contain from 0.1 to 500 mg, preferably 10 to 100 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Compositions

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 1 to 99 wt.-%, preferably 10 to 90 wt.-%, more preferably 20 to 70 wt.-%, of the composition as a whole. Suitable tablets may be obtained, for example, by mixing one or more compounds according to formula I with known excipients, for example inert diluents, carriers, disintegrants, adjuvants, surfactants, binders and/or lubricants. The tablets may also consist of several layers. A further aspect of the invention is a pharmaceutical formulation including a compound of formula I in admixture with a pharmaceutically acceptable adjuvant, diluent or carrier.

Combination Therapy

In another aspect the present invention relates to a combination therapy in which an active compound according to the present invention is administered together with another active compound. Accordingly, the invention also refers to pharmaceutical formulations that provide such a combination of active ingredients, whereby one of which is an active compound of the present invention. Such combinations may be fixed dose combinations (the active ingredients that are to be combined are subject of the same pharmaceutical formulation) or free dose combinations (active ingredients are in separate pharmaceutical formulations).

Consequently, a further aspect of the present invention refers to a combination of each of the active compounds of the present invention, preferably at least one active compound according to the present invention, with another active compound for example selected from the group of antipsychotics such as haloperidol, clozapine, risperidone, quetiapine, aripripazole, and olanzapine; antidepressants such as selective serotonin re-uptake inhibitors and dual serotonin/noradrenaline re-uptake inhibitors; mood stabilizers such as lithium valproate and lamotrigine; beta-secretase inhibitors; gamma-secretase inhibitors; gamma-secretase modulators; amyloid aggregation inhibitors such as e.g. scyllo-inositol; directly or indirectly acting neuroprotective and/or disease-modifying substances; anti-oxidants, such as e.g. vitamin E, ginko biloba or ginkolide; anti-inflammatory substances, such as e.g. Cox inhibitors, NSAIDs additionally or exclusively having Aβ (Abeta) lowering properties; HMG-CoA reductase inhibitors, such as statins; acetylcholine esterase inhibitors, such as donepezil, rivastigmine, tacrine, galantamine; NMDA receptor antagonists such as e.g. memantine; AMPA receptor agonists; AMPA receptor positive modulators, AMPkines, glycine transporter 1 inhibitors; monoamine receptor reuptake inhibitors; substances modulating the concentration or release of neurotransmitters; substances inducing the secretion of growth hormone such as ibutamoren mesylate and capromorelin; CB-1 receptor antagonists or inverse agonists; antibiotics such as minocyclin or rifampicin; PDE1, PDE2, PDE4, PDE5, PDE9 or PDE10 inhibitors, GABAA receptor inverse agonists; GABAA alpha5 receptor inverse agonists; GABAA receptor antagonists; nicotinic receptor agonists or partial agonists or positive modulators; alpha4beta2 nicotinic receptor agonists or partial agonists or positive modulators; alpha7 nicotinic receptor agonists or partial agonists; histamine receptor H3 antagonists; 5-HT4 receptor agonists or partial agonists; 5-HT6 receptor antagonists; alpha2-adrenoreceptor antagonists, calcium antagonists; muscarinic receptor M1 agonists or partial agonists or positive modulators; muscarinic receptor M2 antagonists; muscarinic receptor M4 antagonists; muscarinic receptor M4 positive allosteric modulators; metabotropic glutamate receptor 5 positive allosteric modulators; metabotropic glutamate receptor 2 antagonists; metabotropic glutamate receptor 2/3 agonists; metabotropic glutamate receptor 2 positive allosteric modulators and other substances that modulate receptors or enzymes in a manner such that the efficacy and/or safety of the active compounds according to the invention is increased and/or unwanted side effects are reduced.

The active compounds according to the invention may also be used in combination with immunotherapies such as e.g. active immunisation with Abeta or parts thereof or passive immunisation with humanised anti-Abeta antibodies, nanobodies or antibody fragments for the treatment of the above mentioned diseases and conditions.

The active compounds according to the invention also may be combined with antipsychotics like haloperidol, flupentixol, fluspirilene, chlorprothixene, prothipendyl, levomepromazine, clozapine, olanzapine, quetiapine, risperidone, paliperidone, amisulpride, ziprasidone, aripiprazol, sulpiride, zotepine, sertindole, fluphenazine, perphenazine, perazine, promazine, chlorpromazine, levomepromazine, benperidol, bromperidol, pimozid, melperone, pipamperone, iloperidone, asenapine, perospirone, blonanserin, lurasidone.

The active compounds according to the invention also may be combined with antidepressants like amitriptyline imipramine hydrochloride, imipramine maleate, lofepramine, desipramine, doxepin, trimipramine.

Or the active compounds according to the invention also may be combined with serotonin (5-HT) reuptake inhibitors such as alaproclate, citalopram escitalopram, clomipramine, duloxetine, femoxetine, fenfluramine, norfenfluramine, fluoxetine, fluvoxamine, indalpine, milnacipran, paroxetine, sertraline, trazodone, venlafaxine, zimelidine, bicifadine, desvenlafaxine, brasofensme and tesofensine.

The combinations according to the present invention may be provided simultaneously in one and the same dosage form, i.e. in form of a combination preparation, for example the two components may be incorporated in one tablet, e.g. in different layers of said tablet. The combination may be also provided separately, in form of a free combination, i.e. the active compounds of the present invention are provided in one dosage form and one or more of the above mentioned combination partners is provided in another dosage form. These two dosage forms may be equal dosage forms, for example a co-administration of two tablets, one containing a therapeutically effective amount of the active compound of the present invention and one containing a therapeutically effective amount of the above mentioned combination partner. It is also possible to combine different administration forms, if desired. Any type of suitable administration forms may be provided.

The active compound according to the invention, or a physiologically acceptable salt thereof, in combination with another active substance may be used simultaneously or at staggered times, but particularly close together in time. If administered simultaneously, the two active substances are given to the patient together; if administered at staggered times the two active substances are given to the patient successively within a period of less than or equal to 12, particularly less than or equal to 6 hours.

The dosage or administration forms are not limited, in the frame of the present invention any suitable dosage form may be used. Exemplarily the dosage forms may be selected from solid preparations such as patches, tablets, capsules, pills, pellets, dragees, powders, troches, suppositories, liquid preparations such as solutions, suspensions, emulsions, drops, syrups, elixirs, or gaseous preparations such as aerosols, sprays and the like.

The dosage forms are advantageously formulated in dosage units, each dosage unit being adapted to supply a single dose of each active component being present. Depending from the administration route and dosage form the ingredients are selected accordingly.

The dosage for the above-mentioned combination partners may be expediently 1/5 of the normally recommended lowest dose up to 1/1 of the normally recommended dose.

The dosage forms are administered to the patient for example 1, 2, 3, or 4 times daily depending on the nature of the formulation. In case of retarding or extended release formulations or other pharmaceutical formulations, the same may be applied differently (e.g. once weekly or monthly etc.). It is preferred that the active compounds of the invention be administered either three or fewer times, more preferably once or twice daily.

Experimental Section

Preparation of Examples for Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:

Abbreviations

RT: room temperature
THF: tetrahydrofuran
KOtBu: kalium tert butoxide
PFTU: pentafluorphenol-tetramethyluronium hexafluorophosphat
ACN: acetonitrile
MeOH: methanol
DIPEA: diisopropylamine
DEA: diethylamine
EtOAC: ethyl acetate
DMF: dimethylformamide
TBTU: [(Benzotriazol-1-yloxy)-dimethylamino-methylene]-dimethyl-ammonium; tetrafluoro borate
HATU: (O-(7-Azobenzotriazol-1-yl)-1,1,3,3-Tetramethyluronium hexafluorophosphate)
conc.: concentrated
min.: minutes
DCM: dichlormethane
LiHMDS: lithium bis(trimethylsilyl)amide
HCl: hydrochlorid acid
BINAP: 2,2'-bis(diphenylphosphino)-1,1'-binaphzhyl
BYBOP: benzotriazole-1-yl-oxy-trispyrrolidinophosphonium hexafluorophosphate Analytical Methods All compounds specified in the examples below gave the correct mass spectra matching the theoretical isotope pattern. For practical reasons, only one of the major isotope peaks is given as representative data for the mass spectrum.

List of Analytical HPLC-Methods:

Method A:

Waters ZMD, Alliance 2690/2695 HPLC, Waters 996/2996 diodenarraydetector

Eluent:

A: water with 0.10% TFA
B: acetonitril with 0.10% TFA

Gradient:

| time in min | % A | % B | flow in ml/min |
| --- | --- | --- | --- |
| 0.00 | 95 | 5 | 2.80 |
| 0.30 | 95 | 5 | 2.80 |
| 1.60 | 2 | 98 | 2.80 |
| 1.90 | 2 | 98 | 2.80 |
| 2.00 | 95 | 5 | 2.50 |

Column: Merck Chromolith™ Flash RP-18e, 3 mm×100 mm (temperature: isocratic 25° C.)
Method B:
  Waters ZQ MS, Alliance 2690/2695 HPLC, Waters 996/2996 diodenarraydetector
Eluent:
A: water with 0.10% TFA
D: methanol
Gradient:

| time in min | % A | % D | flow in ml/min |
|---|---|---|---|
| 0.00 | 95 | 5 | 4.00 |
| 0.20 | 95 | 5 | 4.00 |
| 1.60 | 0 | 100 | 4.00 |
| 2.10 | 0 | 100 | 4.00 |

Column: Waters XBridge™ C18 3.5 µm, 4.6×20 mm IS™ (temperature: isocratic 40° C.).
Diodenarray Detection: 210-400 nm.
Method C:
  Waters ZQ 2000MS, Agilent HP100, binäre pumps
Eluent:
A: water with 0.10% TFA
B: methanol
Gradient:

| time in min | % A | % B | flow in ml/min |
|---|---|---|---|
| 0.00 | 80 | 20 | 2.00 |
| 1.70 | 0 | 100 | 2.00 |
| 2.50 | 0 | 100 | 2.00 |
| 2.60 | 80 | 20 | 2.00 |

Column: Sunfire C18, 4.6×50 mm, 3.5 µm (temperature: isocratic 60° C.).
Diodenarray Detection: 210-500 nm
Method D:
  Waters ZQ 2000MS, Agilent HP100, binäre pumps
Eluent:
A: water with 0.10% TFA
B: methanol
Gradient:

| time in min | % A | % B | flow in ml/min |
|---|---|---|---|
| 0.00 | 95 | 5 | 1.50 |
| 1.30 | 0 | 100 | 1.50 |
| 2.50 | 0 | 100 | 1.50 |
| 2.60 | 95 | 5 | 1.50 |

Column: Sunfire C18, 4.6×50 mm, 3.5 µm (temperature: isocratic 40° C.).
Diodenarray Detection: 210-400 nm
Method E:
  Waters Acquity with diodenarraydetector and massdetector
Eluent:
A: water with 0.1% TFA
B: methanol
Gradient:

| time in min | % A | % B | flow in ml/min |
|---|---|---|---|
| 0.00 | 99 | 1 | 1.50 |
| 0.05 | 99 | 1 | 1.50 |
| 1.05 | 0 | 100 | 1.50 |
| 1.20 | 0 | 100 | 1.50 |

Column: Xbridge BEH C18, 2.1×30 mm, 1.7 µm (temperature: isocratic 60° C.).
Diodenarray Detektion: 210-400 nm.
Method F:
  Waters Alliance with diodenarraydetector and massdetector
Eluent:
A: water with 0.10% TFA
B: methanol
Gradient:

| time in min | % A | % B | flow in ml/min |
|---|---|---|---|
| 0.00 | 95 | 5 | 4.90 |
| 1.60 | 0 | 100 | 4.90 |
| 2.20 | 95 | 5 | 4.90 |

Column: XBridge C18, 4.6×30 mm, 3.5 µm (temperature: isocratic 60° C.).
Method G:
  Agilent 1200 System
Eluent:
A: water with 0.10% formicacid
B: acetonitril 0.10% formicacid
Gradient:

| time in min | % A | % B | flow in ml/min |
|---|---|---|---|
| 0.00 | 95 | 5 | 1.60 |
| 0.10 | 95 | 5 | 1.60 |
| 1.75 | 5 | 95 | 1.60 |
| 1.90 | 5 | 95 | 1.60 |
| 1.95 | 95 | 5 | 1.60 |
| 2.00 | 95 | 5 | 1.60 |

Column: Zorbax StableBond C18, 3.0×30 mm, 1.8 µm (temperature: isocratic 25° C.).
Detection: 254 nm
Method H:
  Waters ZQ 2000MS, Agilent HP100, binäre pumps
Eluent:
A: water with 0.032% ammonia
B: methanol
Gradient:

| time in min | % A | % B | flow in ml/min |
|---|---|---|---|
| 0.00 | 5 | 95 | 1.50 |
| 2.00 | 0 | 100 | 1.50 |

Column: waters C18, 4.6×50 mm, 3.5 µm (temperature: isocratic 40° C.).
Diodenarray Detection: 210-500 nm
Method I:
  Waters ZQ 2000MS, Agilent HP100, binäre pumps
Eluent:
A: water with 0.1% TFA
B: methanol Gradient:

| time in min | % A | % B | flow in ml/min |
|---|---|---|---|
| 0.00 | 95 | 5 | 1.50 |
| 1.30 | 0 | 100 | 1.50 |
| 3.00 | 0 | 100 | 1.50 |
| 3.40 | 95 | 5 | 1.50 |

Column: Sunfire C18, 4.6×50 mm, 3.5 µm (temperature: isocratic 40° C.).
Diodenarray Detection: 210-500 nm
Method J:
    Waters ZQ 2000MS, Agilent HP100, binäre pumps
Eluent:
A: water with 0.1% TFA
B: methanol
Gradient:

| time in min | % A | % B | flow in ml/min |
|---|---|---|---|
| 0.00 | 80 | 20 | 2.00 |
| 1.70 | 0 | 100 | 2.00 |
| 2.50 | 0 | 100 | 2.00 |
| 2.60 | 80 | 20 | 2.00 |

Column: Sunfire C18, 4.6×50 mm, 3.5 µm (temperature: isocratic 60° C.).
Diodenarray Detection: 210-500 nm
Method K:
    Waters ZQ 2000MS, Agilent HP100, binäre pumps
Eluent:
A: water with 0.1% ammonia
B: methanol
Gradient:

| time in min | % A | % B | flow in ml/min |
|---|---|---|---|
| 0.00 | 95 | 0 | 1.50 |
| 2.00 | 0 | 100 | 1.50 |

Column: Xbridge C18, 4.6×50 mm, 3.5 µm (temperature: isocratic 40° C.).
Diodenarray Detection: 210-500 nm
Method L:
    Waters ZQ 2000MS, Agilent HP100, binäre pumps
Eluent:
A: water with 0.15% formicacid
B: methanol
Gradient:

| time in min | % A | % B | flowin ml/min |
|---|---|---|---|
| 0.00 | 95 | 0 | 1.50 |
| 2.00 | 0 | 100 | 1.50 |

Column: Xbridge C18, 4.6×50 mm, 3.5 µm (temperature: isocratic 40° C.).
Diodenarray Detection: 210-500 nm
Method M:
    Waters ZQ 2000MS, Agilent HP100, binäre pumps
Eluent:
A: water with 0.1% ammonia
B: acetonitrile
Gradient:

| time in min | % A | % B | flow in ml/min |
|---|---|---|---|
| 0.00 | 95 | 0 | 1.50 |
| 2.00 | 0 | 100 | 1.50 |

Column: Xbridge C18, 4.6×50 mm, 3.5 µm (temperature: isocratic 40° C.).
Diodenarray Detection: 210-500 nm.
Method N:
    Waters ZQ 2000MS, Agilent HP100, binäre pumps
Eluent:
A: water with 0.032% ammonia
B: acetonitrile
Gradient:

| time in min | % A | % B | flow in ml/min |
|---|---|---|---|
| 0.00 | 95 | 0 | 1.50 |
| 2.00 | 0 | 100 | 1.50 |

Column: Xbridge C18, 4.6×50 mm, 3.5 µm (temperature: isocratic 40° C.).
Diodenarray Detection: 210-500 nm
Method O:
    Waters ZQ 2000MS, Agilent HP100, binäre pumps
Eluent:
A: water with 0.15% formicacid
B: methanol
Gradient:

| time in min | % A | % B | flow in ml/min |
|---|---|---|---|
| 0.00 | 95 | 0 | 1.50 |
| 2.00 | 0 | 100 | 1.50 |

Column: Xbridge C18, 4.6×50 mm, 3.5 µm (temperature: isocratic 40° C.).
Diodenarray Detection: 210-500 nm
Method P:
    Waters Alliance with diodenarraydetector and massdetector
Eluent:
A: water with 0.10% TFA
B: methanol
Gradient:

| time in min | % A | % B | flow in ml/min |
|---|---|---|---|
| 0.00 | 95 | 5 | 4.00 |
| 1.60 | 0 | 100 | 4.00 |
| 1.85 | 0 | 100 | 4.00 |
| 1.90 | 95 | 5 | 4.00 |

Column: Sunfire C18, 4.6×30 mm, 3.5 µm (temperature: isocratic 60° C.).
Method Q:
    Waters ZQ 2000MS, Agilent HP100, binäre pumps
Eluent:
A: water with 0.1% TFA
B: acetonitrile with 0.08% TFA Gradient:

| time in min | % A | % B | flow in ml/min |
|---|---|---|---|
| 0.00 | 95 | 5 | 1.50 |
| 2.00 | 0 | 100 | 1.50 |
| 2.50 | 0 | 100 | 1.50 |
| 2.60 | 95 | 5 | 1.50 |

Column: Sunfire C18, 4.6×50 mm, 3.5 μm (temperature: isocratic 40° C.).
Diodenarray Detection: 210-500 nm
Method R:
  Agilent 1200
Eluent:
A: 4 L water with 1.5 mL TFA
B: 4 L acetonitrile with 1.5 mL TFA
Gradient:

| time in min | % A | % B | flow in ml/min |
|---|---|---|---|
| 0.00 | 90 | 10 | 1.00 |
| 2.00 | 20 | 80 | 1.00 |
| 2.48 | 20 | 80 | 1.00 |
| 2.50 | 90 | 10 | 1.20 |
| 3.00 | 90 | 10 | 1.20 |

Column: Venusil XBP-C18 2.1×50 mm, 5 μm (temperature: isocratic 50° C.).
Wave Length: 220 nm
Method S:
  Aquility MS, diodenarraydetector, UPLC LG 500
Eluent:
A: water with 0.13% TFA
B: methanol with 0.08% TFA
Gradient:

| time in min | % A | % B | flow in ml/min |
|---|---|---|---|
| 0.00 | 99 | 1 | 1.30 |
| 0.05 | 99 | 1 | 1.30 |
| 0.35 | 0 | 100 | 1.30 |
| 0.50 | 0 | 100 | 1.30 |

Column: XBridgeBEH C18 2.1×30 mm, 1.7 μm (temperature: isocratic 60° C.).
Wave Length: 210-400 nm.
Method T:
  Waters Acquity with diodenarraydetector and massdetector
Eluent:
A: water with 0.13% TFA
B: methanol 0.05% TFA
Gradient:

| time in min | % A | % B | flow in ml/min |
|---|---|---|---|
| 0.00 | 99 | 1 | 1.30 |
| 0.05 | 99 | 1 | 1.30 |
| 1.05 | 0 | 100 | 1.30 |
| 1.20 | 0 | 100 | 1.30 |

Column: Xbridge BEH C18, 2.1×30 mm, 1.7 μm (temperature: isocratic 60° C.).
Diodenarray Detektion: 210-400 nm.
Method U:
  Waters Alliance with diodenarraydetector and massdetector
Eluent:
A: water with 0.10% TFA
B: methanol with 0.10% TFA
Gradient:

| time in min | % A | % B | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 |
| 1.85 | 95 | 5 | 4.00 |

Column: XBridge C18, 4.6×30 mm, 3.5 μm (temperature: isocratic 60° C.).
Method V:
  Waters Alliance with diodenarraydetector and massdetector
Eluent:
A: water with 0.1% ammonia
B: methanol with 0.1% ammonia
Gradient:

| time in min | % A | % B | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 |

Column: XBridge C18, 4.6×30 mm, 3.5 μm (temperature: isocratic 60° C.).
Method W:
  Waters Acquity with diodenarraydetector and massdetector
Eluent:
A: water with 0.1% TFA
B: methanol
Gradient:

| time in min | % A | % B | flow in ml/min |
|---|---|---|---|
| 0.00 | 99 | 1 | 1.40 |
| 0.05 | 99 | 1 | 1.40 |
| 1.00 | 0 | 100 | 1.40 |
| 1.10 | 0 | 100 | 1.40 |

Column: Xbridge BEH C18, 2.1×30 mm, 1.7 μm (temperature: isocratic 60° C.).
Diodenarray Detektion: 210-400 nm.
Method X:
  Waters Alliance with diodenarraydetector and massdetector
Eluent:
A: water with 0.1% TFA
B: methanol Gradient:

| time in min | % A | % B | flow in ml/min |
| --- | --- | --- | --- |
| 0.00 | 95 | 5 | 4.80 |
| 1.60 | 95 | 5 | 4.80 |
| 1.85 | 0 | 100 | 4.80 |
| 1.90 | 95 | 5 | 4.80 |

Column: XBridge C18, 4.6×30 mm, 3.5 μm (temperature: isocratic 60° C.).#

Method Y:

Waters Alliance with diodenarraydetector and massdetector

Eluent:

A: water with 0.1% TFA

B: methanol

Gradient:

| time in min | % A | % B | flow in ml/min |
| --- | --- | --- | --- |
| 0.00 | 95 | 5 | 4.00 |
| 0.20 | 95 | 5 | 4.00 |
| 1.50 | 0 | 100 | 4.00 |
| 1.75 | 0 | 100 | 4.00 |
| 1.85 | 95 | 5 | 4.00 |

Column:
XBridge C18, 4.6×30 mm, 3.5 μm (temperature: isocratic 60° C.).

Synthesis of Intermediates 6.01. Synthesis of Building Blocks 6.01.01 2-Bromo-1-(4-pyrimidin-2-yl-piperazin-1-yl)-ethanon

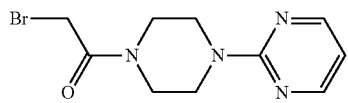

20.2 g bromacetylbromide was dropped to 16.5 g 1-pyrimidin-2-yl-piperazin and 10.2 g triethylamine in 250 mL THF. The reaction was stirred over night at RT and evaporated. The residue was extracted with DCM and water. The organic layer was evaporated and the residue was crystallized with petrolether and then purified by chromatography on silica gel (DCM/MeOH:95/5) to yield 36 mg of the desired compound.

$R_t$: 1.09 min (method A), $(M+H)^+$: 286

By using the same synthesis strategy as for 2-bromo-1-(4-pyrimidin-2-yl-piperazin-1-yl)-ethanon the following compounds were obtained:

| Examples | Starting material | Product | MS m/z [M + H]+ | HPLC Method | Rt min |
| --- | --- | --- | --- | --- | --- |
| 6.01.02 | | | 284 | method A | 0.89 |

6.01.03 1-(4-methoxy-pyridin-2-yl)-piperazine

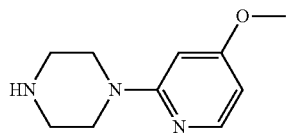

46 mg 2-chloro-4-methoxy-pyridine and 277 mg piperazine in 2 mL n-methyl-2-pyrrolidinone were stirred 45 min at 140° C. and 30 min at 200° C. under microwave conditions. The reaction was diluted with water and purified by HPLC to give 10 mg desired product.

By using the same synthesis strategy as for 2-bromo-1-(4-pyrimidin-2-yl-piperazin-1-yl)-ethanon the following compounds were obtained:

| Examples | Starting material | Product | MS m/z [M + H]⁺ | HPLC Method | Rt min |
|---|---|---|---|---|---|
| 6.01.04 | | | 208 | method I | 2.13 |
| 6.01.05 | | | 195 | method H | 1.54 |
| 6.01.06 | | | 207 | method H | 2.57 |
| 6.01.07 | | | 194 | method H | 1.89 |

6.01.06.01 2,4-diiodo-pyridine

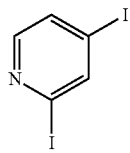

61 g Sodiumhydride and 19.2 mL acetylchloride were added to 20 g 2,4-dichloro-pyridine in 250 mL acetonitrile and was refluxed over night. The reaction was diluted with dichlormethane washed with 10% potassiumdicarbonate solution, 5% sodiumhydrosulffit solution and evaporated. The residue was purified chromatography on silica gel (petrolether/EtOAC (5+1)) to yield 16.2 g of the desired compound. $R_f$: 0.5 (petrolether: ethylacetate/5:1)

6.01.06.02 (2-iodo-pyridin-4-yl)-dimethyl-amine and (4-iodo-pyridin-2-yl)-dimethyl-amine isomeres Mixture

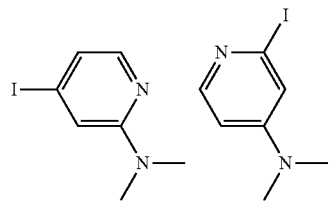

500 mg 2,4-diiodo-pyridine and 5 mL dimethylamine in 10 mL DMF were stirred 10.5 h. at 120° C. under microwave conditions. The mixture was evaporated to give 348 mg as a mixture of isomeres. $R_t$: 2.27 min/2.57 min (method H), (M+H)$^+$: 248/49

By using the same synthesis strategy as for 2-methoxy-4-piperazin-1-yl-pyrimidine hydrochloride
the following compounds were obtained:

| Examples | Product | MS m/z [M + H]$^+$ | HPLC Method | Rt min |
|---|---|---|---|---|
| 6.01.07.01 | 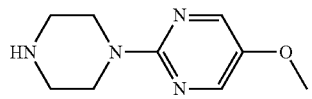 | 235/36 | method H | 2.57 + 2.52 |

6.01.08 5-methoxy-2-piperazin-1-yl-pyrimidine hydrochlorid

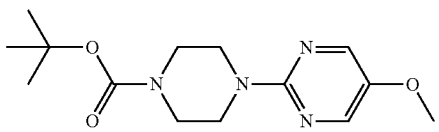 [SMILES: COc1cnc(N2CCN(C(=O)OC(C)(C)C)CC2)nc1]

6.02.08.01 4-(5-methoxy-pyrimidin-2-yl)-piperazine-1-carboxylic acid tert-butyl ester 1.5 g piperazine-1-carboxylic acid tert-butyl ester was added to 1.2 g 2-chlor-5-methoxy-pyrimidine and 2.2 mL triethylamine in 30 mL DMF. The reaction was stirred 6 days at 60° C. The solvent was removed and the residue was dissolved in dichlormethane and extracted with water. The organic layer was washed with a saturated sodium chloride solution and evaporated to give 957 mg desired product. $R_t$: 0.82 min (method E), (M+H)$^+$: 295

By using the same synthesis strategy as for 4-(5-methoxy-pyrimidin-2-yl)-piperazine-1-carboxylic acid tert-butyl ester the following compounds were obtained:

| Examples | Product | MS m/z [M + H]$^+$ | HPLC Method | Rt min |
|---|---|---|---|---|
| 6.01.09.01 | 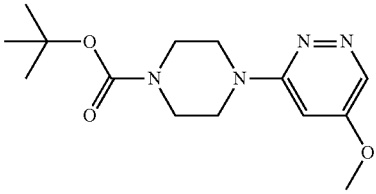 [SMILES: COc1cnnc(N2CCN(C(=O)OC(C)(C)C)CC2)c1] | 295 | | |
| 6.01.10.01 | 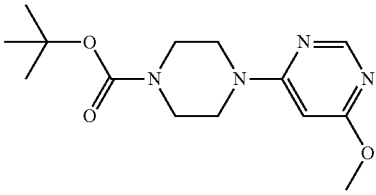 [SMILES: COc1cc(N2CCN(C(=O)OC(C)(C)C)CC2)ncn1] | 295 | method B | 1.12 |

6.01.08.02 5-methoxy-2-piperazin-1-yl-pyrimidine hydrochloride

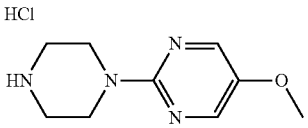

953 mg 4-(5-methoxy-pyrimidin-2-yl)-piperazine-1-carboxylic acid tert-butyl ester was stirred in 16 mL 4 mol/L HCl solution in dioxane for 45 min The precipitate was filtered, washed with dioxane and dried to yield 723 mg of the desired compound. $R_t$: 0.46 min (method F), (M+H)$^+$: 195

By using the same synthesis strategy as for 5-methoxy-2-piperazin-1-yl-pyrimidine hydrochloride the following compounds were obtained:

| Examples | Product | MS m/z [M + H]+ | HPLC Method | Rt min |
|---|---|---|---|---|
| 6.01.09 | | 195 | | |
| 6.01.10 | | 195 | | Rf: 0.75 Cyclohexane: ethylacetate + ammonia (3:1) |

6.01.11 4-piperazin-1-yl-benzoic acid ethyl ester hydrobromide 26 g bis-(2-chlor-ethyl)-amine hydrochloride and 25 g ethyl 3-aminobezoate in 20 mL diethylene glycol monomethyl ether were stirred 7.5 h at 156° C. The mixture was cooled to RT, diluted with EtOAc and conc. Ammonia was added until pH=4. The layers were seperated and the aqueous layer was extracted with EtOAc. The combined extracts were washed with brine and treated with hydrobromide 33% in acetic acid. The mixture was stirred 45 min and the precipitate was filtered and crystallized with ethanol to give 15.2 g of the desired product.

$R_f$: 0.19 min (dichlormethane: cyclohexane: methanol: ethylacetate:ammonia/720:57:57:195:7.5) (M+H)+: 235

6.01.12 2-methoxy-4-piperazin-1-yl-pyrimidine hydrochloride

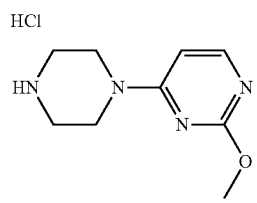

6.01.12.01 4-(2-methoxy-pyrimidin-4-yl)-piperazine-1-carboxylic acid tert-butyl ester 1.3 g piperazine-1-carboxylic acid tert-butyl ester and 1.42 mL DIPEA were added to 1 g 2,4-dichlor-pyrimidine in 10 mL dichlormethane. The reaction was stirred over night at RT. The solvent was removed and the residue was purified by chromatography on silica gel (cyclohexane/ethylacetate) to yield 1.6 g of the desired compound.

$R_f$: 2.10 min (method I), (M+H)+: 299

By using the same synthesis strategy as for 4-(2-methoxy-pyrimidin-4-yl)-piperazine-1-carboxylic acid tert-butyl ester the following compounds were obtained:

| Examples | Product | MS m/z [M + H]+ | HPLC Method | Rt min |
|---|---|---|---|---|
| 6.01.13.01. | | 299 | method I | 2.10 |
| 6.01.14.01 | | 300 | method C | 2.15 |

6.01.12.02 2-methoxy-4-piperazin-1-yl-pyrimidine hydrochloride

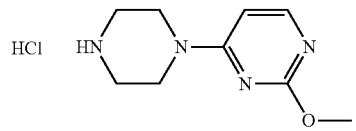

400 mg 4-(2-methoxy-pyrimidin-4-yl)-piperazine-1-carboxylic acid tert-butyl ester and 747 mg sodium methanolate in 5 mL methanol were stirred 45 min at 120° C. under microwave conditions. The mixture was evaporated and cleanded by HPLC. The residue was stirred over night in 10 mL HCl in dioxane and evaporated to give 120 mg of the desired product.

By using the same synthesis strategy as for 2-methoxy-4-piperazin-1-yl-pyrimidine hydrochloride the following compounds were obtained:

| Examples | Product | MS m/z [M + H]$^+$ | HPLC Method | Rt min |
|---|---|---|---|---|
| 6.01.13 | | 208 | | |
| 6.01.14 | | 208 | method C | 2.00 |

6.01.15 4-ethyl-6-piperazin-1-yl-pyrimidine trifluoracetate

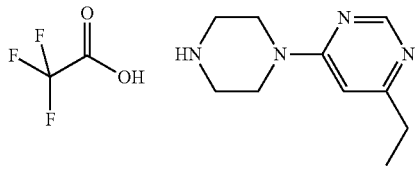

6.01.15.01 4-(6-ethyl-pyrimidin-4-yl)-piperazine-1-carboxylic acid tert-butyl ester 4 mL DIPEA and 3 g PYBOP was added to 2.9 g 6-ethyl-3H-pyrimidin-4-one in 10 mL DMF. The reaction was stirred 5 min at ambient temperature and 1.1 g piperazine-1-carboxylic acid tert-butyl ester was added. The reaction was stirred overnight at RT. The solvent was removed and the residue was purified by HPLC to give 1 g of the desired compound.

$R_t$: 1.82 min (method L), (M+H)$^+$: 293

6.01.15.02 4-ethyl-6-piperazin-1-yl-pyrimidine trifluoracetate

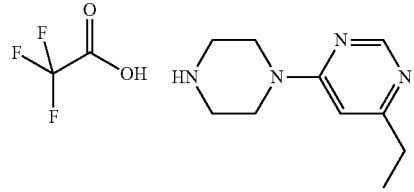

1 g 4-(6-ethyl-pyrimidin-4-yl)-piperazine-1-carboxylic acid tert-butyl ester and 20 mL trifluor acetic acid were stirred in 20 mL dichlormethane for 24 h. The solvent was removed to yield 4.5 g of the desired compound. (M+H)$^+$: 193

By using the same synthesis strategy as for 4-ethyl-6-piperazin-1-yl-pyrimidine trifluoracetate the following compounds were obtained:

| Examples | Product | MS m/z [M + H]$^+$ | HPLC Method | Rt min |
|---|---|---|---|---|
| 6.01.16 | | 227/29 | method H | 2.04 |

6.01.16.01 4-(2-chloro-6-ethyl-pyrimidin-4-yl)-piperazine-1-carboxylic acid tert-butyl ester

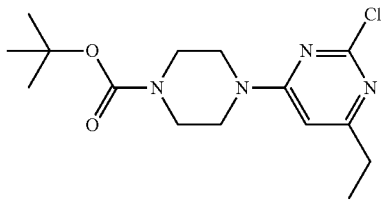 [SMILES: CCc1cc(N2CCN(C(=O)OC(C)(C)C)CC2)nc(Cl)n1]

200 mg palladium charcoal was added to 200 mg 4-(2-chloro-6,7-dihydro-thieno[3,2-d]pyrimidin-4-yl)-piperazine-1-carboxylic acid tert-butyl ester in 10 mL THF and 0.08 mL triethylamine. Raney-nickel and 5 mL ethanol was added and the reaction was stirred 24 h at 50° C. and 3 bar hydrogen. The mixture was filtered. The filtrate was evaporated and the residue was purified by HPLC to give 20 mg desired product.

$R_t$: 2.02 min (method J), $(M+H)^+$: 327/29

6.01.17 R-(tetrahydrofuran-2-yl)-methanol

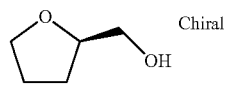

20 g R-tetrahydrofuran-2-carboxylic acid in 60 mL THF was dropped to 6.6 g lithium aluminium hydride in 140 mL THF. The reaction was refluxed until gas formation was stopped. The reaction was coolded with an ice bath and 20 mL water and 10 mL 15N sodiunhydroxide was added. The reaction was stirred 20 min, diluted with 100 mL THF, filltered over magnesiumsulfate and the filtrate was evaporated to give 16.1 g desired product. (M+Na)+: 124 1H-NMR (400 MHZ): 4.6 (1H OH), 3.8; 3.6; 3.3 (5H, CH$_2$, CH, CH$_2$); 1.8; 1.55 (m, 4H, CH$_2$, CH$_2$).

By using the same synthesis strategy as for R-(tetrahydrofuran-2-yl)-methanol the following compound was obtained:

| Examples | Product | IR | Rf |
|---|---|---|---|
| 6.01.18 | 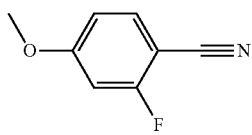 | 3413, 2872, 1047 cm$^{-1}$ | 0.4 Dichloromethane: ethanol (20:1) |

6.01.19.01 2-fluoro-4-methoxy-benzonitrile

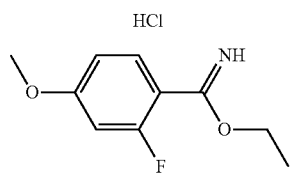

2.59 mL bromine was added to 7 g 3-fluoroanisole in 50 ml chloroform at RT. The reaction mixture was stirred 7 h at 60° C. and concentrated in vacuo. The resulting material was dissolved in 30 ml DMF and treated with 5.9 g cupper cyanide. After refluxing overnight, the reaction was partitioned between ethylacetate and acidic ferric chloride solution (19.2 g of ferric chloride hexa hydrate, 44.8 mL of hydrochloric acid, and 48 ml of water). The organic phase was washed with brine, dried over sodiumsulfate, and concentrated in vacuo. The resulting mixture was purified by chromatography on silica gel to give 7.8 g of the desired product.

6.01.19.01 2-fluoro-4-methoxy-benzimidic acid ethyl ester hydrochloride

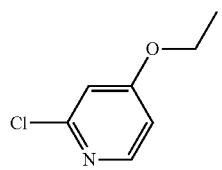

HCl gas was passed through a solution of 10 g 2-fluoro-4-methoxy-benzonitrile in 200 mL ethanol at 0° C. for 90 min and the reaction mixture was stirred at RT for 4 h. The solvent was removed in vacuo. Diethylether was added to the residue. The suspension was stirred for 15 min and filtered. The filtrate was concentrated in vacuo to give 12 g of the desired product.

By using the same synthesis strategy as for 4-bromo-3-methyl-benzoyl chloride the following compounds were obtained:

| Examples | Product | MS m/z $[M + H]^+$ | HPLC Method | Rt min |
|---|---|---|---|---|
| 6.01.20 | ![structure] | | | |
| 6.01.21 | ![structure] | 182 | method U | 0.99 |

6.01.22.01 2-chloro-4-ethoxy-pyridine 33 ml sodium ethoxide was added to 19.2 g 2-chloro-4-iodopyridine in 150 mL ethanol. The reaction was refluxed overnight. Then water was added and extracted with tert-butyl-methylether. The organic layer was evaporated and the residue cleanded by chromatography on silica gel (petrolether/EtOAC:9/1) to yield 5 g of the desired compound.

$R_f$: 0.3 (petrolether/EtOAC:4/1), $(M+H)^+$: 158

6.01.22.02 1-(4-ethoxy-pyridin-2-yl)-piperazine hydrochloride

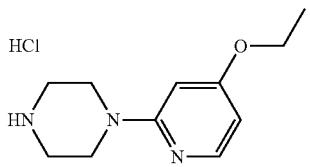

860 mg piperazine was added to 350 mg 2-chloro-4-ethoxy-pyridine in 3.5 mL n-butanol. The reaction was stirred 1.5 days at 115° C. The reaction was filtered and the filtrate was washed with water and evaporated. 1N HCl was added to the residue and the precpipate was filtered to give 238 mg of the desired product. $R_t$: 0.3 min (method B), $(M+H)^+$: 208

6.01.23.01 4-bromo-3-methyl-benzoyl chloride

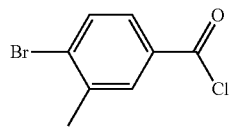

1 g 4-bromo-3-methyl-benzoic acid in 20 g thionylchloride was refluxed 1 h. The reaction was evaporated to give 1.1 g desired product.

By using the same synthesis strategy as for 4-bromo-3-methyl-benzoyl chloride the following compounds were obtained:

| Examples | Product |
|---|---|
| 6.01.23.02 | (F, methyl benzoyl chloride) |
| 6.01.23.03 | (F, methoxy benzoyl chloride) |
| 6.01.23.04 | (methyl cyclohexanecarbonyl chloride) |
| 6.01.23.05 | (methyl cyclohexanecarbonyl chloride) |
| 6.01.23.06 | (difluoro cyclohexanecarbonyl chloride) |
| 6.01.23.07 | (methyl cyclohexanecarbonyl chloride) |

6.02. Synthesis of triazole-1yl-acids 6.02.01.01 N'-(4-bromo-3-methyl-benzoyl)-hydrazinecarboxylic acid tert-butyl ester

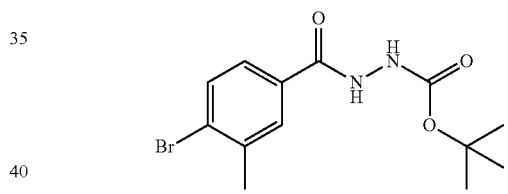

54.3 g 4-bromo-3-methyl-benzoyl chloride was added to 23.3 g triethylamine and 30.4 g hydrazinecarboxylic acid tert-butyl ester in 1 L dichlormethane. The reaction was stirred 1 h at RT and extracted with water. The organic layer was evaporated and the residue was crystallized with diisopropylether to give 70 g desired product.

$R_t$: 1.32 min (method B), $(M+H)^+$: 329/31

By using the same synthesis strategy as for N'-(4-bromo-3-methyl-benzoyl)-hydrazinecarboxylic acid tert-butyl ester the following compounds were obtained:

| Examples | Product | MS m/z [M + H]+ | HPLC Method | Rt min |
|---|---|---|---|---|
| 6.02.01.02 | (structure) | 269 | method B | 1.22 |

| Examples | Product | MS m/z [M + H]+ | HPLC Method | Rt min |
|---|---|---|---|---|
| 6.02.01.03 | (4-fluoro-3-methoxy-benzoyl hydrazinecarboxylic acid tert-butyl ester) | 285 | method B | 1.14 |
| 6.02.02.04 | (4-methyl-cyclohexanecarbonyl hydrazinecarboxylic acid tert-butyl ester) | 257 | method T | 0.88 |
| 6.02.02.05 | (2-methyl-cyclohexanecarbonyl hydrazinecarboxylic acid tert-butyl ester) | 257 | method T | 0.86 |
| 6.02.02.06 | (4,4-difluoro-cyclohexanecarbonyl hydrazinecarboxylic acid tert-butyl ester) | 279 | method T | 0.75 |
| 6.02.02.07 | (3-methyl-cyclohexanecarbonyl hydrazinecarboxylic acid tert-butyl ester) | 257 | method T | 0.87 |

6.02.02.01 4-bromo-3-methyl-benzoic acid hydrazide

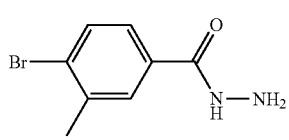

500 mL trifluor acetic acid was added to 70 g N'-(4-bromo-3-methyl-benzoyl)-hydrazinecarboxylic acid tert-butyl ester in 1 L dichlormethane. The reaction was stirred 1 h at RT and evaporated. The residue was basicfied with 1N sodiumhydroxide and extracted with saturated sodiumchloride solution and tetrahyrofuran. The organic layer was evaporated and the residue crystallized with ethyl acetate to give 25 g desired product.

$R_t$: 1.02 min (method B), (M+H)+: 329/31

By using the same synthesis strategy as for N'-(4-bromo-3-methyl-benzoyl)-hydrazinecarboxylic acid tert-butyl ester the following compounds were obtained:

| Examples | Product | MS m/z [M + H]+ | HPLC Method | Rt min |
|---|---|---|---|---|
| 6.02.02.02 | (4-fluoro-3-methyl-benzoic acid hydrazide) | 169 | method B | 0.80 |
| 6.02.02.03 | (4-fluoro-3-methoxy-benzoic acid hydrazide) | 185 | method B | 0.67 |

| Examples | Product | MS m/z [M + H]+ | HPLC Method | Rt min |
|---|---|---|---|---|
| 6.02.02.04 | 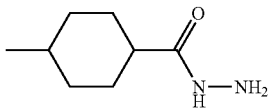 | 157 | method T | 0.63 |
| 6.02.02.05 | | 157 | method T | 0.61 |
| 6.02.02.06 | | 179 | method T | 0.51 |

| Examples | Product | MS m/z [M + H]+ | HPLC Method | Rt min |
|---|---|---|---|---|
| 6.02.02.07 | 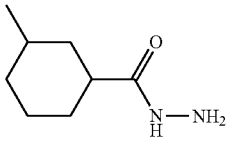 | 157 | method T | 0.63 |

6.02.03.01 4-fluoro-benzamidine

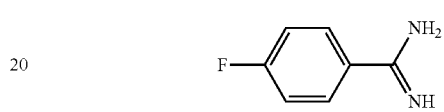

380 mL 1N LiHMDS-solution in n-hexane was added to 20 g 4-fluoro-benzonitrile in 1 L diethylether. The reaction was stirred 2 h at RT and 4N HCL solution was added at 0° C. until pH=12. The water layer was extracted with chloroform. The organic layer was dried and evaporated to give 6.64 g of the desired product. $R_t$: 2.28 min (method K), (M+H)+: 139

By using the same synthesis strategy as for 4-fluoro-benzamidine the following compounds were obtained:

| Examples | Product | MS m/z [M + H]+ | HPLC Method | Rt min |
|---|---|---|---|---|
| 6.02.03.02 | | 151 | method A | 0.60 |
| 6.02.03.03 | | 121 | method B | 0.24 |
| 6.02.03.04 | | 151 | $R_f$ = 0.05 (dichlormethane/methanol:95/5) | |
| 6.02.03.05 | | 139 | $R_f$ = 0.05 (dichlormethane) | |
| 6.02.03.06 | | 153 | method | 0.64 |
| 6.02.03.07 | | 140 | $R_f$ = 0.05 (dichlormethane) | |

6.02.03.09 1-fluoro-3-methoxy-benzenecarboximidic acid hydrazide

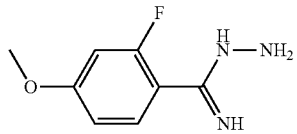

4.4 g hydrazine hydrate was added to 16 g 2-fluoro-4-methoxy-benzimidic acid ethyl ester hydrochloride in 250 mL ethanol at 0° C. Then the mixture was stirred at this temperature 2 h and then the solvent was removed. The residue was recrystallized from dichlormetane to give 10 g of the desired product.

By using the same synthesis strategy as for 1-fluoro-3-methoxy-benzenecarboximidic acid hydrazide the following compounds was obtained:

| Examples | Product | MS m/z [M + H]$^+$ | HPLC Method | Rt min |
|---|---|---|---|---|
| 6.02.03.10 | 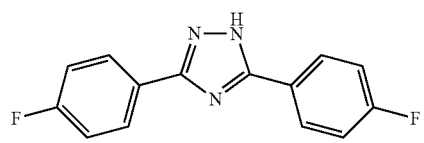 [SMILES: Fc1ccc(-c2n[nH]c(-c3ccc(F)cc3)n2)cc1] | 154 | | |

6.02.04.01
3,5-bis-(4-fluoro-phenyl)-1H-(1,2,4)triazole 4 g 4-fluoro-benzamidine was added to 4.5 g 4-fluoro-benzoic acid hydrazide and this mixture was melted. This mixture was crystallized with ethyl acetate to give 5.3 g of the desired compound. R$_t$: 1.55 min (method A), (M+H)$^+$: 258

By using the same synthesis strategy as for 3,5-bis-(4-fluoro-phenyl)-1H-(1,2,4)triazole the following compounds were obtained:

| Examples | Product | MS m/z [M + H]$^+$ | HPLC Method | Rt min |
|---|---|---|---|---|
| 6.02.04.02 | | 282 | method A | 1.38 |
| 6.02.04.03 | | 282 | method B | 1.25 |
| 6.02.04.04 | | 258 | method B | 1.22 |
| 6.02.04.05 | | 222 | method B | 1.30 |
| 6.02.04.06 | | 258 | method B | 1.44 |

| Examples | Product | MS m/z [M + H]+ | HPLC Method | Rt min |
|---|---|---|---|---|
| 6.02.04.07 | 3-(4-fluorophenyl)-5-(3-methoxyphenyl)-1H-1,2,4-triazole | 270 | method B | 1.35 |
| 6.02.04.08 | 3-cyclohexyl-5-(4-fluorophenyl)-1H-1,2,4-triazole | 246 | method B | 1.33 |
| 6.02.04.09 | 3-(4-fluorophenyl)-5-(4-methoxyphenyl)-1H-1,2,4-triazole | 270 | method A | 1.34 |
| 6.02.04.10 | 3-cyclopentyl-5-(4-fluorophenyl)-1H-1,2,4-triazole | 231 | method B | 1.23 |
| 6.02.04.11 | 3-cyclohexyl-5-(3-methoxyphenyl)-1H-1,2,4-triazole | 258 | method B | 1.30 |
| 6.02.04.12 | 3-(4-methoxyphenyl)-5-phenyl-1H-1,2,4-triazole | 252 | method B | 1.29 |
| 6.02.04.13 | 3-(4-bromo-3-methylphenyl)-5-phenyl-1H-1,2,4-triazole | 314/316 | method B | 1.54 |
| 6.02.04.14 | 3-(4-fluoro-3-methylphenyl)-5-phenyl-1H-1,2,4-triazole | 254 | method B | 1.45 |

-continued
| Examples | Product | MS m/z [M + H]+ | HPLC Method | Rt min |
|---|---|---|---|---|
| 6.02.04.15 | 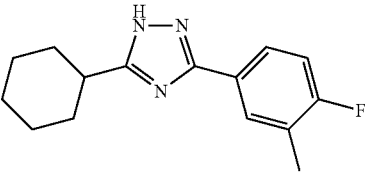 [SMILES: Cc1cc(-c2n[nH]c(C3CCCCC3)n2)ccc1F] | 260 | method B | 1.40 |
| 6.02.04.16 | 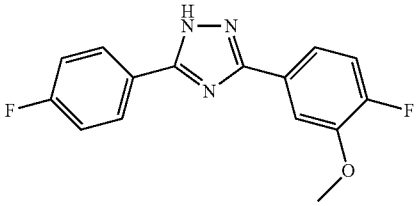 [SMILES: COc1cc(-c2n[nH]c(-c3ccc(F)cc3)n2)ccc1F] | 288 | method B | 1.42 |
| 6.02.04.17 | 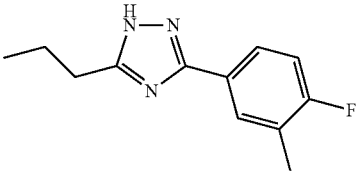 [SMILES: CCCc1nc(-c2ccc(F)c(C)c2)n[nH]1] | 220 | method U | 1.25 |
| 6.02.04.18 | 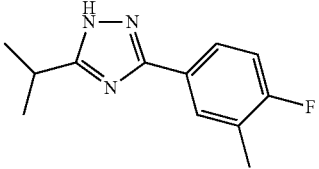 [SMILES: Cc1cc(-c2n[nH]c(C(C)C)n2)ccc1F] | 220 | method U | 1.23 |
| 6.02.04.19 | 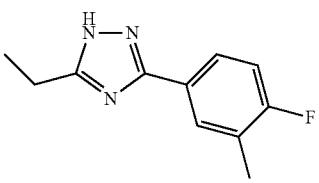 | 206 | method T | 0.66 |
| 6.02.04.20 | 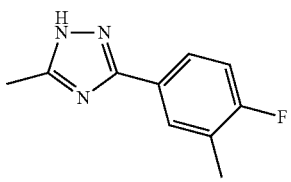 | 192 | method V | 1.16 |
| 6.02.04.21 | 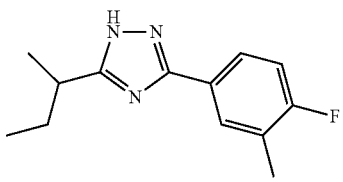 [SMILES: CCC(C)c1nc(-c2ccc(F)c(C)c2)n[nH]1] | 234 | method T | 0.79 |
| 6.02.04.22 | 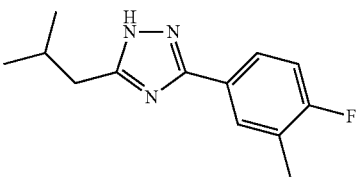 [SMILES: Cc1cc(-c2n[nH]c(CC(C)C)n2)ccc1F] | 234 | method U | 1.35 |

-continued

| Examples | Product | MS m/z [M + H]+ | HPLC Method | Rt min |
|---|---|---|---|---|
| 6.02.04.23 | | 246 | method T | 0.81 |
| 6.02.04.24 | | 234 | method U | 1.23 |
| 6.02.04.25 | | 248 | method T | 0.87 |
| 6.02.04.26 | | 248 | method T | 0.83 |
| 6.02.04.27 | | 274 | method T | 0.98 |
| 6.02.04.28 | | 274 | method T | 1.00 |
| 6.02.04.29 | | 259 | method X | 1.19 |
| 6.02.04.30 | | 296 | method E | 0.86 |

-continued

| Examples | Product | MS m/z [M + H]⁺ | HPLC Method | Rt min |
|---|---|---|---|---|
| 6.02.04.31 | | 274 | method E | 0.91 |
| 6.02.04.32 | | 286 | method T | 0.94 |
| 6.02.04.33 | | 288 | method B | 1.42 |
| 6.02.04.34 | | 217 | method B | 1.08 |
| 6.02.04.35 | | 288 | method L | 0.87 |
| 6.02.04.36 | | 240 | method L | 0.69 |
| 6.02.04.37 | | 254 | method L | 0.76 |

6.02.04.35 3-cyclohexyl-5-(2-fluoro-4-methoxy-phenyl)-1H-(1,2,4)triazole

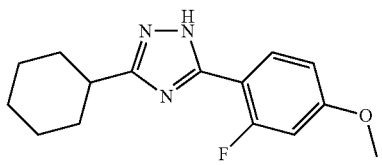 [SMILES: COc1ccc(-c2nc(C3CCCCC3)n[nH]2)c(F)c1]

8.4 g cyclohexanecarbonyl chloride in 30 mL tetrahydrofuran was dropped to 10 g 1-fluoro-3-methoxy-benzenecarboximidic acid hydrazide and 11.1 g triethylamine 200 mL tetrahydrofuran at 0° C. The reaction was finished after the addition of the chloride and then the solvent was removed. 150 mL acetic acid/DMF (1/1) was added to the residue and the mixture was stirred at 80° C. overnight. The acetic acid was removed and ethyl acetate was added. The organic layer was washed with water sodiumhydrogencarbonate, water and brine, dried over sodium sulfate and concentrated to give 7 g of the desired product.

By using the same synthesis strategy as for 3-cyclohexyl-5-(2-fluoro-4-methoxy-phenyl)-1H-(1,2,4)triazole the following compound was obtained:

| Examples | Product | MS m/z [M + H]$^+$ | HPLC Method | Rt min |
|---|---|---|---|---|
| 6.02.04.36 | 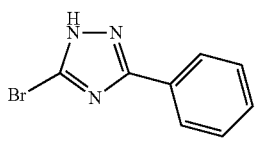 [SMILES: Brc1nc(-c2ccccc2)n[nH]1] | 268 | | |

6.02.04.37 5-bromo-3-phenyl-1H-(1,2,4)triazole

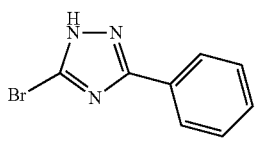 [SMILES: Brc1nc(-c2ccccc2)n[nH]1]

115 mL bromine hydro acid was added to 9.5 g 5-phenyl-2H-(1,2,4)triazol-3-ylamine and 12.3 g sodiumnitrite at −5°C. The reaction was warmed to RT and refluxed for 20 min. Then the mixture was cooled and basicfied with sodiumdicarbonate and extracted with ethyl acetate. The organic layer was dried and evaporated to give 11 g of the desired product.

R$_t$: 1.07 min (method B), (M+H)$^+$: 223/225

By using the same synthesis strategy as for 5-bromo-3-phenyl-1H-(1,2,4)triazole the following compound was obtained:

| Examples | Product | MS m/z [M + H]$^+$ | HPLC Method | Rt min |
|---|---|---|---|---|
| 6.02.04.38 | 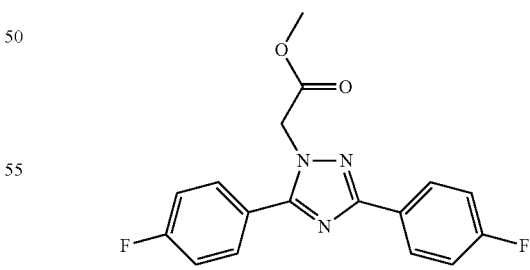 | 242/ 244 | method B | 1.14 |

6.02.05.01 (3,5-bis-(4-fluoro-phenyl)-(1,2,4)triazol-1-yl)-acetic acid methyl ester

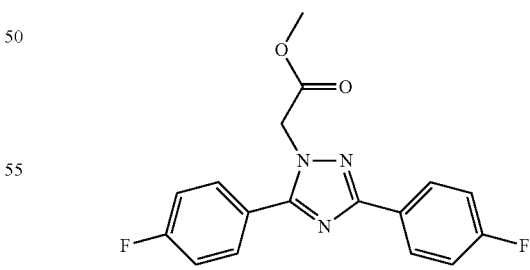

26.5 g 3,5-bis-(4-fluoro-phenyl)-1H-(1,2,4)triazole, 62.6 g K$_2$CO$_3$ and 15.7 g 2-bromoacetic acid methyl ester were dissolved in 1 L acetone and stirred for 24 h under reflux. K$_2$CO$_3$ was filtered and the solvent was removed to yield 30.8 g of the desired product.

R$_t$: 1.35 min (method B)
(M+H)$^+$: 330

By using the same synthesis strategy as for (3,5-bis-(4-fluoro-phenyl)-(1,2,4)triazol-1-yl)-acetic acid methyl ester the following compounds were obtained:

| Examples | Product | MS m/z [M + H]+ | HPLC Method | Rt min |
|---|---|---|---|---|
| 6.02.05.02 | (structure) | 354 | method A | 1.54 |
| 6.02.05.03 | (structure) | 354 | method B | 1.24 |
| 6.02.05.04 | (structure) | 330 | method B | 1.34 |
| 6.02.05.05 | (structure) | 294 | method B | 1.31 |
| 6.02.05.06 | (structure) | 330 | method B | 1.39 |

-continued

| Examples | Product | MS m/z [M + H]+ | HPLC Method | Rt min |
|---|---|---|---|---|
| 6.02.05.07 | | 342 | method B | 1.33 |
| 6.02.05.08 | | 342 | method B | 1.37 |
| 6.02.05.09 | | 318 | method B | 1.35/ 1.41 |
| 6.02.05.10 | | 342 | method A | 1.32 |
| 6.02.05.11 | | 342 | method A | 1.36 |

-continued

| Examples | Product | MS m/z [M + H]⁺ | HPLC Method | Rt min |
| --- | --- | --- | --- | --- |
| 6.02.05.12 | | 304 | method B | 1.30 |
| 6.02.05.13 | | 330 | method B | 1.34 |
| 6.02.05.14 | | 324 | method B | 1.37 |
| 6.02.05.15 | | 386/388 | method B | 1.52 |
| 6.02.05.16 | | 326 | method B | 1.43 |

-continued

| Examples | Product | MS m/z [M + H]+ | HPLC Method | Rt min |
|---|---|---|---|---|
| 6.02.05.17 | | 332 | method B | 1.50 |
| 6.02.05.18 | | 326 | method B | 1.43 |
| 6.02.05.19 | | 360 | method B | 1.37 |
| 6.02.05.20 | | 292 | method U | 1.38 |
| 6.02.05.21 | | 292 | method U | 1.36 |

-continued

| Examples | Product | MS m/z [M + H]+ | HPLC Method | Rt min |
|---|---|---|---|---|
| 6.02.05.22 | | 278 | method T | 0.78 |
| 6.02.05.23 | | 264 | method V | 1.26 |
| 6.02.05.24 | | 306 | method T | 0.88 |
| 6.02.05.25 | | 306 | method U | 1.43 |
| 6.02.05.26 | | 304 | method T | 0.85 |

-continued
| Examples | Product | MS m/z [M + H]+ | HPLC Method | Rt min |
|---|---|---|---|---|
| 6.02.05.27 | 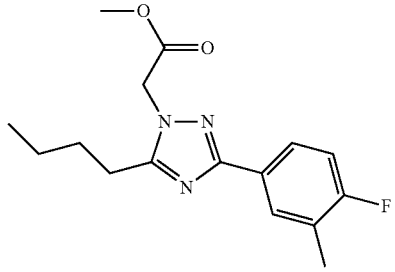 [SMILES: CCCCc1nc(-c2ccc(F)c(C)c2)nn1CC(=O)OC] | 306 | method U | 1.33 |
| 6.02.05.28 | 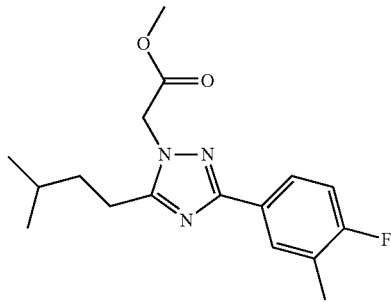 [SMILES: COC(=O)Cn1nc(-c2ccc(F)c(C)c2)nc1CCC(C)C] | 320 | method T | 0.92 |
| 6.02.05.29 | 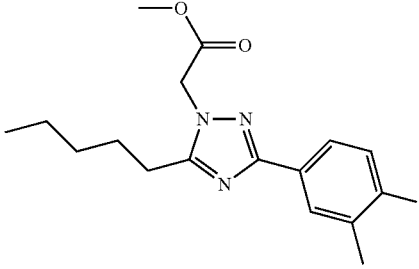 | 320 | method T | 0.88 |
| 6.02.05.30 | 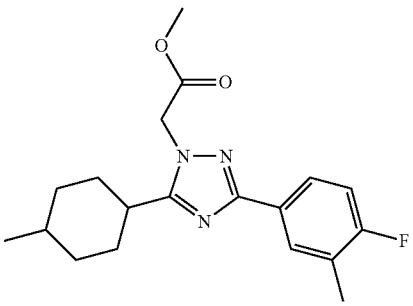 [SMILES: COC(=O)Cn1nc(-c2ccc(F)c(C)c2)nc1C1CCC(C)CC1] | 346 | method T | 1.05 |
| 6.02.05.31 | 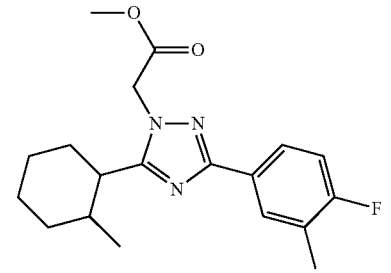 [SMILES: COC(=O)Cn1nc(-c2ccc(F)c(C)c2)nc1C1CCCCC1C] | 346 | method T | 1.06 |

-continued

| Examples | Product | MS m/z [M + H]⁺ | HPLC Method | Rt min |
|---|---|---|---|---|
| 6.02.05.32 | | 331 | method W | 0.71 |
| 6.02.05.33 | | 331 | method W | 0.83 |
| 6.02.05.34 | | 368 | method Y | 1.47 |
| 6.02.05.35 | | 346 | method E | 0.95 |
| 6.02.05.36 | | 296/298 | method B | 1.07 |

-continued

| Examples | Product | MS m/z [M + H]+ | HPLC Method | Rt min |
|---|---|---|---|---|
| 6.02.05.37 | | 358 | method T | 0.94 |
| 6.02.05.38 | | 346 | method B | 1.39 |
| 6.02.05.39 | | 324 | method B | 1.37 |
| 6.02.05.40 | | 290 | method B | 1.24 |
| 6.02.05.41 | | 360 | | |

-continued

| Examples | Product | MS m/z [M + H]⁺ | HPLC Method | Rt min |
|---|---|---|---|---|
| 6.02.05.42 | | 312 | method L | 0.79 |
| 6.02.05.43 | | 326 | method L | 0.83 |

6.02.06.1 (3,5-bis-(4-fluoro-phenyl)-(1,2,4)triazol-1-yl)-acetic acid

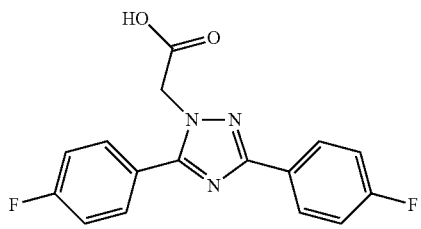 [SMILES: O=C(O)Cn1nc(-c2ccc(F)cc2)nc1-c1ccc(F)cc1]

30.8 g of (3,5-bis-(4-fluoro-phenyl)-(1,2,4)triazol-1-yl)-acetic acid methyl ester was dissolved in 250 mL dioxane and a solution of 2.4 g LiOH in 250 mL of water was added. The mixture was stirred for 24 h at RT. The mixture was acidified with HCl-solution. The precipitate was filtered to give 29 g of the desired product. $R_t$: 1.28 min (method B), (M+H)⁺: 316

6.02.06.02 (3-(4-methoxy-phenyl)-5-phenyl-(1,2,4)triazol-1-yl)-acetic acid

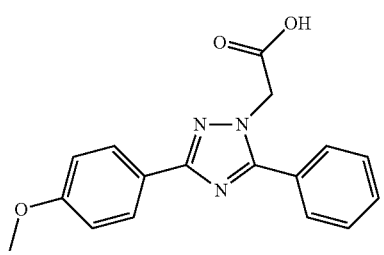 [SMILES: COc1ccc(-c2nc(-c3ccccc3)n(CC(=O)O)n2)cc1]

30.8 g of (3-(4-methoxy-phenyl)-5-phenyl-(1,2,4)triazol-1-yl)-acetic acid methyl ester was dissolved in 140 mL dioxane and a solution of 0.8 g LiOH in 140 mL of water was added. The mixture was stirred for 4 h at RT. The mixture was acidified with HCl-solution and the precipitate was filtered to give 9.0 g of the desired product as mixture of isomers. These isomers were seperated by HPLC chiral (method 1; solvent MeOH: DCM=1:1, concentration: 90 mg/mL). $R_t$: 1.26 min (method A) and 1.24 min (M+H)⁺: 310

By using the same synthesis strategy the following compounds were obtained:

| Examples | Product | MS m/z [M + H]+ | HPLC Method | Rt min |
|---|---|---|---|---|
| 6.02.06.03 | (triazole with two 4-methoxyphenyl groups, CH2COOH) | 340 | method A | 1.41 |
| 6.02.06.04 | (triazole with 3,4-dimethoxyphenyl and phenyl, CH2COOH) | 340 | method B | 1.18 |
| 6.02.06.05 | (triazole with cyclohexyl and 4-methoxyphenyl, CH2COOH) | 316 | method B | 1.27 |
| 6.02.06.06 | (triazole with two phenyl groups, CH2COOH) | 280 | method B | 1.23 |
| 6.02.06.07 | (triazole with two 3-fluorophenyl groups, CH2COOH) | 316 | method B | 1.34 |
| 6.02.06.08 | (triazole with 4-fluorophenyl and 3-methoxyphenyl, CH2COOH) | 328 | method B | 1.30 |

| Examples | Product | MS m/z [M + H]+ | HPLC Method | Rt min |
|---|---|---|---|---|
| 6.02.06.09 | | 328 | method B | 1.27 |
| 6.02.06.10 | | 304 | method B | 1.36 |
| 6.02.06.11 | | 328 | method B | 1.26 |
| 6.02.06.12 | | 328 | method B | 1.31 |
| 6.02.06.13 | | 290 | method B | 1.29 |
| 6.02.06.14 | | 315 | method B | 1.31 |

| Examples | Product | MS m/z [M + H]+ | HPLC Method | Rt min |
|---|---|---|---|---|
| 6.02.06.15 | | 372/374 | method B | 1.47 |
| 6.02.06.16 | | 312 | method B | 1.38 |
| 6.02.06.17 | | 260 | method B | 1.45 |
| 6.02.06.18 | | 312 | method B | 1.35 |
| 6.02.06.19 | | 346 | method V | 1.31 |

-continued

| Examples | Product | MS m/z [M + H]+ | HPLC Method | Rt min |
|---|---|---|---|---|
| 6.02.06.20 | [structure: 3-(4-fluoro-3-methylphenyl)-5-propyl-1H-1,2,4-triazol-1-yl acetic acid] | 278 | method U | 1.31 |
| 6.02.06.21 | [structure: 3-(4-fluoro-3-methylphenyl)-5-isopropyl-1H-1,2,4-triazol-1-yl acetic acid] | 278 | method U | 1.29 |
| 6.02.06.22 | [structure: 5-ethyl-3-(4-fluoro-3-methylphenyl)-1H-1,2,4-triazol-1-yl acetic acid] | 264 | method V | 0.93 |
| 6.02.06.23 | [structure: 3-(4-fluoro-3-methylphenyl)-5-methyl-1H-1,2,4-triazol-1-yl acetic acid] | 250 | method V | 0.87 |
| 6.02.06.24 | [structure: 5-sec-butyl-3-(4-fluoro-3-methylphenyl)-1H-1,2,4-triazol-1-yl acetic acid] | 292 | method T | 0.85 |

| Examples | Product | MS m/z [M + H]+ | HPLC Method | Rt min |
|---|---|---|---|---|
| 6.02.06.25 | 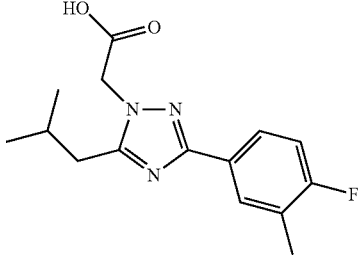 [SMILES: Cc1cc(-c2nc(CC(C)C)n(CC(=O)O)n2)ccc1F] | 292 | method U | 1.39 |
| 6.02.06.26 | 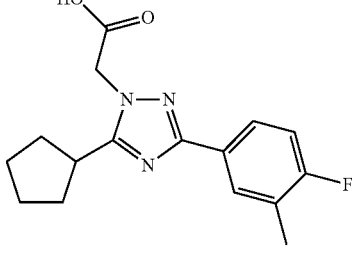 | 304 | method F | 1.29 |
| 6.02.06.27 | 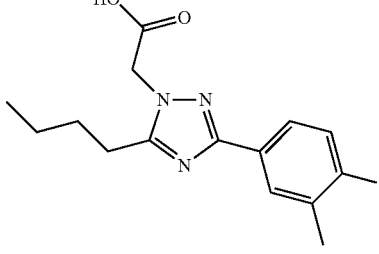 | 292 | method U | 1.24 |
| 6.02.06.28 | 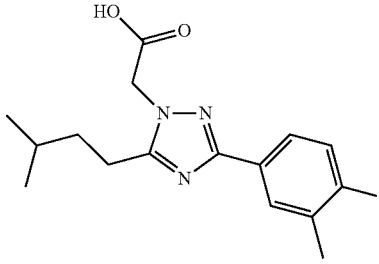 | 306 | method T | 0.88 |
| 6.02.06.29 | 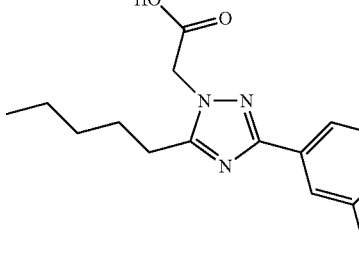 | 306 | method T | 0.84 |

-continued

| Examples | Product | MS m/z [M + H]+ | HPLC Method | Rt min |
|---|---|---|---|---|
| 6.02.06.30 | (4-methylcyclohexyl)-5-yl, 3-(4-fluoro-3-methylphenyl)-1,2,4-triazol-1-yl acetic acid | 332 | method T | 0.98 |
| 6.02.06.31 | (2-methylcyclohexyl)-5-yl, 3-(4-fluoro-3-methylphenyl)-1,2,4-triazol-1-yl acetic acid | 332 | method T | 0.98 |
| 6.02.06.32 | 5-(4-fluorophenyl)-3-(5-fluoropyridin-2-yl)-1,2,4-triazol-1-yl acetic acid | 317 | method W | 0.65 |
| 6.02.06.33 | 3-(4-fluorophenyl)-5-(5-fluoropyridin-2-yl)-1,2,4-triazol-1-yl acetic acid | 317 | method W | 0.79 |
| 6.02.06.34 | 5-(4,4-difluorocyclohexyl)-3-(4-fluoro-3-methylphenyl)-1,2,4-triazol-1-yl acetic acid | 354 | method E | 0.87 |
| 6.02.06.35 | 5-(3-methylcyclohexyl)-3-(4-fluoro-3-methylphenyl)-1,2,4-triazol-1-yl acetic acid | 332 | method F | 1.42 |

| Examples | Product | MS m/z [M + H]+ | HPLC Method | Rt min |
|---|---|---|---|---|
| 6.02.06.36 | 3-bromo-5-phenyl-1,2,4-triazol-1-yl acetic acid | 282/284 | method B | 0.98 |
| 6.02.06.37 | 3,5-bis(4-fluoro-3-methylphenyl)-1,2,4-triazol-1-yl acetic acid | 344 | method T | 0.90 |
| 6.02.06.38 | 3-(4-fluoro-3-methoxyphenyl)-5-(4-fluorophenyl)-1,2,4-triazol-1-yl acetic acid | 346 | method T | 0.87 |
| 6.02.06.39 | 3-(4-methoxyphenyl)-5-phenyl-1,2,4-triazol-1-yl acetic acid | 310 | method B | 1.25 |
| 6.02.06.40 | 5-isopropyl-3-(3-methoxyphenyl)-1,2,4-triazol-1-yl acetic acid | 276 | method B | 1.14 |
| 6.02.06.41 | 3-(4-difluoromethoxyphenyl)-5-phenyl-1,2,4-triazol-1-yl acetic acid | 346 | method L | 0.80 |

-continued

| Examples | Product | MS m/z [M + H]+ | HPLC Method | Rt min |
|---|---|---|---|---|
| 6.02.06.42 | [structure: 3-(4-difluoromethoxyphenyl)-5-ethyl-1,2,4-triazol-1-yl acetic acid] | 298 | method L | 0.72 |
| 6.02.06.43 | [structure: 3-(4-difluoromethoxyphenyl)-5-propyl-1,2,4-triazol-1-yl acetic acid] | 312 | method L | 0.79 |

6.02.07.01 (3,5-Bis-(4-fluoro-phenyl)-(1,2,4)triazol-1-yl)-acetyl chloride

[structure]

1.2 g of ((3,5-bis-(4-fluoro-phenyl)-(1,2,4)triazol-1-yl)-acetic acid in 15 mL thionylchloride was stirred 30 min at 60° C. The solvent was removed to give 1.3 g of the desired product.

(M+H)+: 334

By using the same synthesis strategy as for (3,5-Bis-(4-fluoro-phenyl)-(1,2,4)triazol-1-yl)-acetyl chloride the following compounds were obtained:

| Examples | Product | MS m/z [M + H]+ |
|---|---|---|
| 6.02.07.02 | [structure: 3,5-bis(4-methoxyphenyl)triazol-1-yl acetyl chloride] | 358 |
| 6.02.07.03 | [structure: 5-(3,4-dimethoxyphenyl)-3-phenyl-triazol-1-yl acetyl chloride] | 358 |
| 6.02.07.04 | [structure: 5-cyclohexyl-3-(4-methoxyphenyl)-triazol-1-yl acetyl chloride] | 334 |

-continued

| Examples | Product | MS m/z [M+H]+ |
|---|---|---|
| 6.02.07.05 | | 298 |

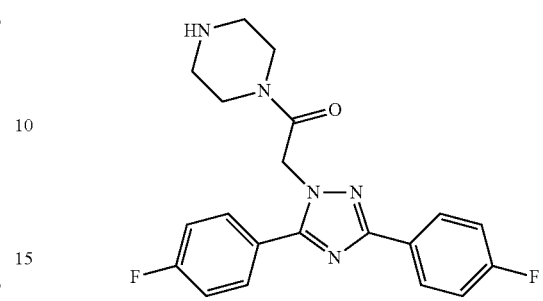

6.02.08.01 4-(2-(3,5-bis-(4-fluoro-phenyl)-(1,2,4)triazol-1-yl)-acetyl)-piperazine-1-carboxylic acid tert-butyl ester

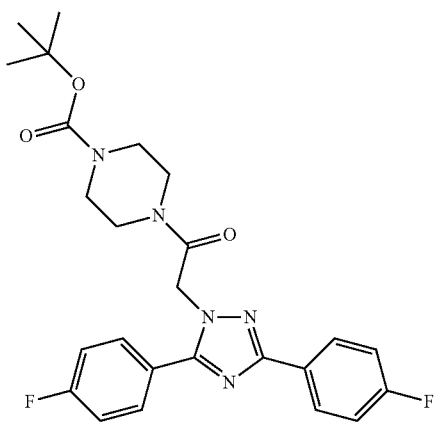 [SMILES: CC(C)(C)OC(=O)N1CCN(C(=O)Cn2nc(-c3ccc(F)cc3)nc2-c2ccc(F)cc2)CC1]

1.8 g piperazine-1-carboxylic acid tert-butyl ester was added to 3.2 g (3,5-Bis-(4-fluoro-phenyl)-(1,2,4)triazol-1-yl)-acetyl chloride and 1 g triethylamine in 50 mL dichlormethane. The reaction was stirred 1 day at RT, evaporated and purified by chromatography on silica gel (petrolether/diethylether:1/1) to yield 3.1 g of the desired compound.

$R_t$: 1.42 min (method B), (M+H)+: 484

6.02.08.02 2-(3,5-Bis-(4-fluoro-phenyl)-(1,2,4)triazol-1-yl)-1-piperazin-1-yl-ethanone 3.1 g 4-(2-(3,5-bis-(4-fluoro-phenyl)-(1,2,4)triazol-1-yl)-acetyl)-piperazine-1-carboxylic acid tert-butyl ester was dissolved in 20 ml dichlormethane and 20 mL trifluor acetic acid was added. The reaction was stirred 24 h at RT and the solvent was evaporated. 10% potassiumcarbonate solution was added to the residue. The precipitate was filtered and crystallized with a mixture of acetonitrile and isopropylether to give 2.3 g of the desired compound. (M+H)+: 384

6.02.09.01 2-(3-bromo-5-phenyl-(1,2,4)triazol-1-yl)-1-(4-pyrimidin-2-yl-piperazin-1-yl)-ethanone

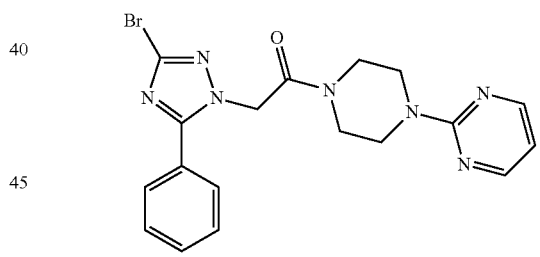

11 g 5-bromo-3-phenyl-1H-(1,2,4)triazole, 13.2 g 2-bromo-1-(4-pyrimidin-2-yl-piperazin-1-yl)-ethanon and 28.2 g potassiumcarbonat in 300 mL acetone was stirred overnight at RT. The reaction was filtered and the filtrate was evaporated. The residue was purified by HPLC to give 1.45 g of the desired product. $R_t$: 1.08 min (method B), (M+H)+: 428/430

By using the same synthesis strategy as for 2-(3-bromo-5-phenyl-(1,2,4)triazol-1-yl)-1-(4-pyrimidin-2-yl-piperazin-1-yl)-ethanone the following compounds were obtained:

| Examples | Product | MS m/z [M + H]+ | HPLC Method | Rt min |
|---|---|---|---|---|
| 6.02.09.02 | 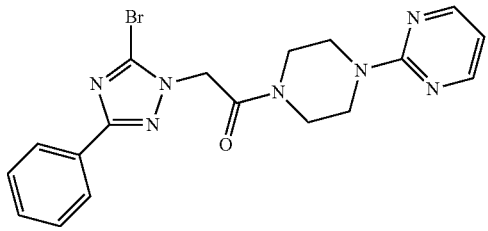 [SMILES: O=C(Cn1nc(-c2ccccc2)nc1Br)N1CCN(c2ncccn2)CC1] | 428/430 | method H | 1.18 |
| 6.02.09.03 | 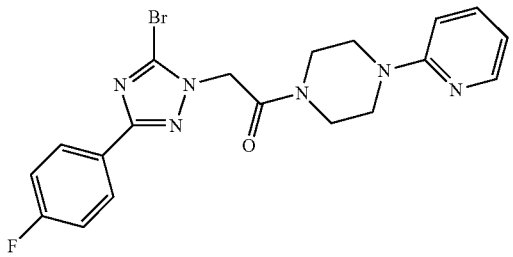 [SMILES: O=C(Cn1nc(-c2ccc(F)cc2)nc1Br)N1CCN(c2ccccn2)CC1] | 445/447 | method | 0.88 |

6.02.09.04 2-(3-bromo-5-phenyl-(1,2,4)triazol-1-yl)-1-(4-(6-methoxy-pyrimidin-4-yl)-piperazin-1-yl-ethanone

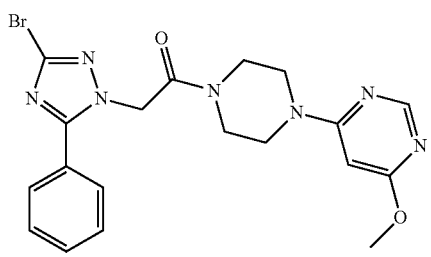 [SMILES: COc1cc(N2CCN(C(=O)Cn3nc(Br)nc3-c3ccccc3)CC2)ncn1]

2 g (5-bromo-3-phenyl-(1,2,4)triazol-1-yl)-acetic acid was dissolved in 10 mL DMF. 7.3 g PFTU and 0.92 g DIPEA were added to this solution and the mixture was stirred for 10 min at RT. 3.3 g 4-methoxy-6-piperazin-1-yl-pyrimidine hydrochloride and 0.92 g DIPEA dissolved in 10 mL DMF were added and the reaction was stirred 3 h at RT. Then, 10% potassiumhydrogencarbonate and $CH_2Cl_2$ were added, the organic phase was separated and the solvent was removed. The residue was purified by HPLC $R_t$: 0.95 min (method B), (M+H)+: 458/460

7. Synthesis of Target Compounds 7.01.01. 2-(3,5-Bis-(4-fluoro-phenyl)-(1,2,4)triazol-1-yl)-1-(4-pyrimidin-2-yl-piperazin-1-yl)-ethanone

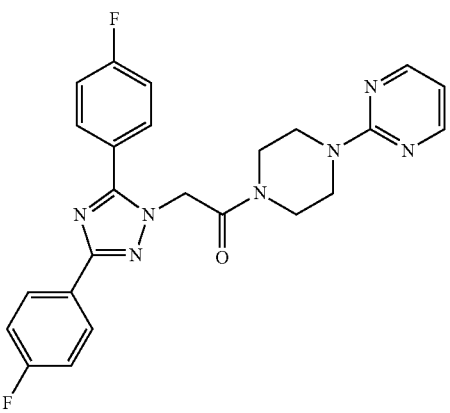 [SMILES: O=C(Cn1nc(-c2ccc(F)cc2)nc1-c1ccc(F)cc1)N1CCN(c2ncccn2)CC1]

100 mg 3,5-bis-(4-fluoro-phenyl)-1H-(1,2,4)triazole, 111 mg 2-bromo-1-(4-pyrimidin-2-yl-piperazin-1-yl)-ethanon and 237 mg potassiumcarbonat in 5 mL acetone was stirred 24 h at RT. The reaction was filtered and the filtrate was evaporated. The residue was crystallized with acetonitrile to yield 124 mg of the desired compound.

$R_t$: 1.48 min (method A), (M+H)+: 462

By using the same synthesis strategy as for 2-(3,5-Bis-(4-fluoro-phenyl)-(1,2,4)triazol-1-yl)-1-(4-pyrimidin-2-yl-piperazin-1-yl)-ethanone the following compounds were obtained:

| Examples | Product | MS m/z [M + H]+ | HPLC Method | Rt min |
|---|---|---|---|---|
| 7.01.02 | | 461 | method A | 1.34 |
| 7.01.03 | | 539 | method B | 1.35 |
| 7.01.04 | | 479 | method B | 1.29 |
| 7.01.05 | | 479 | method B | 1.42 |

| Examples | Product | MS m/z [M + H]+ | HPLC Method | Rt min |
|---|---|---|---|---|
| 7.01.06 | 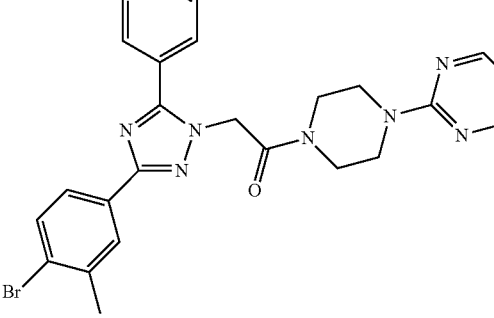 | 518/520 | method B | 1.47 |
| 7.01.07 | 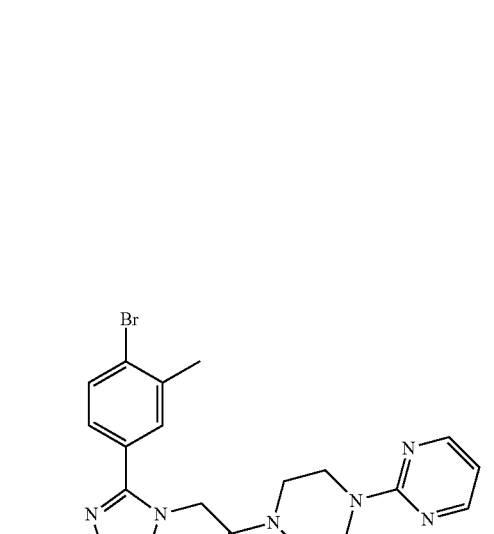 | 518/520 | method B | 1.44 |

7.02.01. 2-(4-(2-(3,5-Bis-(4-fluoro-phenyl)-(1,2,4)triazol-1-yl)-acetyl)-pipera zin-1-yl)-nicotinonitrile

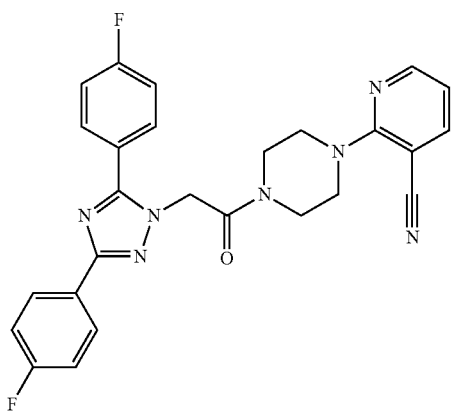 [SMILES: N#Cc1cccnc1N1CCN(C(=O)Cn2nc(-c3ccc(F)cc3)nc2-c2ccc(F)cc2)CC1]

126 mg 2-piperazin-1-yl-nicotinonitrile was added to 216 mg (3,5-Bis-(4-fluoro-phenyl)-(1,2,4)triazol-1-yl)-acetyl chloride and 150 µL triethylamine in 10 mL dichlormethane. The reaction was stirred 1 day at RT, the solvent was evaporated and the residue was purified by HPLC to give 93 mg of the desired product. (M+H)+: 486

By using the same synthesis strategy as for 2-(3,5-Bis-(4-fluoro-phenyl)-(1,2,4)triazol-1-yl)-1-(4-pyrimidin-2-yl-piperazin-1-yl)-ethanone the following compounds were obtained:

| Examples | Product | MS m/z [M + H]+ | HPLC Method | Rt min |
|---|---|---|---|---|
| 7.02.02 | | 529 | method B | 1.49 |
| 7.02.03 | | 491 | method B | 1.46 |
| 7.02.04 | | 475 | method B | 1.20 |
| 7.02.05 | | 475 | method B | 1.17 |

| Examples | Product | MS m/z [M + H]+ | HPLC Method | Rt min |
|---|---|---|---|---|
| 7.02.06 | | 475 | method B | 1.16 |
| 7.02.07 | | 529 | method B | 1.47 |
| 7.02.08 | | 486 | method B | 1.36 |
| 7.02.09 | | 486 | method A | 1.29 |

-continued

| Examples | Product | MS m/z [M + H]+ | HPLC Method | Rt min |
|---|---|---|---|---|
| 7.02.10 | | 485 | method B | 1.10 |
| 7.02.11 | | 499 | method A | 1.32 |
| 7.02.12 | | 519 | method A | 1.50 |
| 7.02.13 | | 510 | method A | 1.53 |

| Examples | Product | MS m/z [M + H]+ | HPLC Method | Rt min |
|---|---|---|---|---|
| 7.02.14 |  | 553 | method A | 1.60 |
| 7.02.15 |  | 515 | method A | 1.57 |
| 7.02.16 |  | 510 | method A | 1.53 |

-continued

| Examples | Product | MS m/z [M + H]⁺ | HPLC Method | Rt min |
|---|---|---|---|---|
| 7.02.17 | | 528 | method B | 1.14 |
| 7.02.18 | | 485 | method B | 1.02 |
| 7.02.19 | | 510 | method B | 1.25 |
| 7.02.20 | | 499 | method B | 1.05 |

| Examples | Product | MS m/z [M + H]+ | HPLC Method | Rt min |
|---|---|---|---|---|
| 7.02.21 | | 499 | method B | 1.04 |
| 7.02.22 | | 499 | method B | 1.04 |
| 7.02.23 | | 553 | method B | 1.40 |
| 7.02.24 | | 462 | method B | 1.32 |

-continued

| Examples | Product | MS m/z [M + H]+ | HPLC Method | Rt min |
|---|---|---|---|---|
| 7.02.25 | | 461 | method B | 1.16 |
| 7.02.26 | | 475 | method B | 1.19 |
| 7.02.27 | | 425 | method B | 1.07 |
| 7.02.28 | | 439 | method B | 1.15 |

7.03.01. 2-(3,5-Bis-(4-fluoro-phenyl)-(1,2,4)triazol-1-yl)-1-(4-(4-methoxy-pyridin-2-yl)-piperazin-1-yl)-ethanone

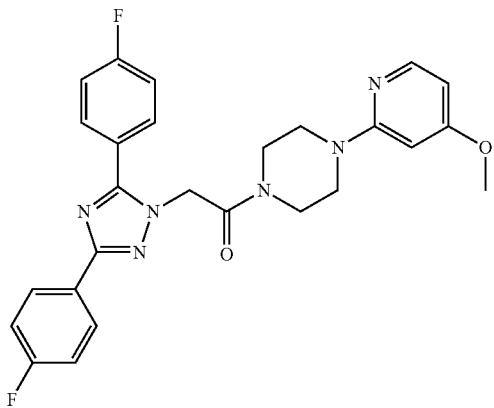 [SMILES: COc1ccnc(N2CCN(C(=O)Cn3nc(-c4ccc(F)cc4)nc3-c3ccc(F)cc3)CC2)c1]

32 mg (3,5-bis-(4-fluoro-phenyl)-(1,2,4)triazol-1-yl)-acetic acid was dissolved in 2 mL DMF. 39 mg TBTU and 53 µL DIPEA were added to this solution and the mixture was stirred for a few minutes at RT. Then 24 mg 1-(4-methoxy-pyridin-2-yl)-piperazine was added. The mixture was stirred 1 h at RT. The reaction-solution was evaporated and the residue was purified by HPLC to give 30 mg of the desired compound. $R_t$: 1.68 (method C), (M+H)$^+$: 491

By using the same synthesis strategy as for 2-(3,5-Bis-(4-fluoro-phenyl)-(1,2,4)triazol-1-yl)-1-(4-(4-methoxy-pyridin-2-yl)-piperazin-1-yl)-ethanone the following compounds were obtained:

| Examples | Product | MS m/z [M + H]$^+$ | HPLC Method | Rt min |
|---|---|---|---|---|
| 7.03.02 | (structure) | 532 | method G | 1.70 |
| 7.03.03 | (structure) | 530 | method G | 1.70 |

| Examples | Product | MS m/z [M + H]+ | HPLC Method | Rt min |
|---|---|---|---|---|
| 7.03.04 | | 540 | method D | 2.39 |
| 7.03.05 | | 478 | method G | 1.66 |
| 7.03.06 | | 485 | method G | 1.59 |
| 7.03.07 | | 490 | method G | 1.53 |

-continued

| Examples | Product | MS m/z [M + H]+ | HPLC Method | Rt min |
|---|---|---|---|---|
| 7.03.08 | | 487 | method G | 1.57 |
| 7.03.09 | | 496 | method G | 1.47 |
| 7.03.10 | | 492 | method G | 1.34 |
| 7.03.11 | | 505 | method Q | 1.76 |

-continued

| Examples | Product | MS m/z [M + H]+ | HPLC Method | Rt min |
|---|---|---|---|---|
| 7.03.12 | | 462 | method G | 1.13 |
| 7.03.13 | | 522 | method G | 1.68 |
| 7.03.14 | | 463 | method D | 2.22 |
| 7.03.15 | | 501 | method G | 1.64 |

-continued

| Examples | Product | MS m/z [M + H]⁺ | HPLC Method | Rt min |
|---|---|---|---|---|
| 7.03.16 | | 505 | method Q | 1.65 |
| 7.03.17 | | 504 | method J | 1.47 |
| 7.03.18 | | 492 | method Q | 2.02 |
| 7.03.19 | | 492 | method Q | 1.67 |

| Examples | Product | MS m/z [M + H]+ | HPLC Method | Rt min |
|---|---|---|---|---|
| 7.03.20 | | 539 | method D | 2.41 |
| 7.03.21 | | 530 | method D | 2.43 |
| 7.03.22 | | 505 | method Q | 1.72 |
| 7.03.23 | | 504 | method J | 1.47 |

-continued
| Examples | Product | MS m/z [M + H]+ | HPLC Method | Rt min |
|---|---|---|---|---|
| 7.03.24 | 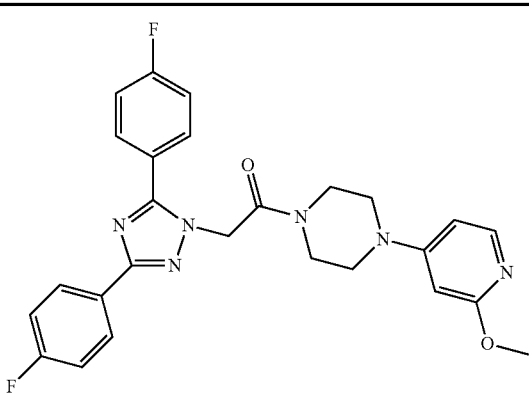 | 491 | method C | 1.68 |
| 7.03.25 | 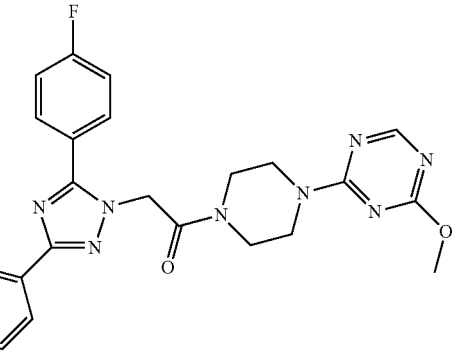 | 492 | method K | 1.68 |
| 7.03.26 | 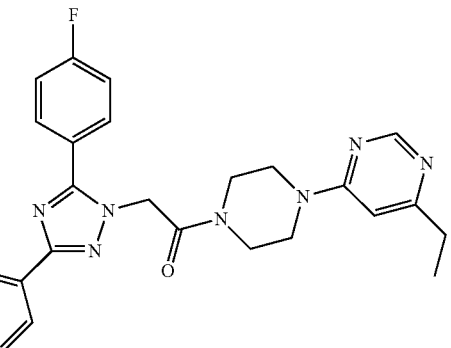 | 490 | method K | 2.49 |
| 7.03.27 | 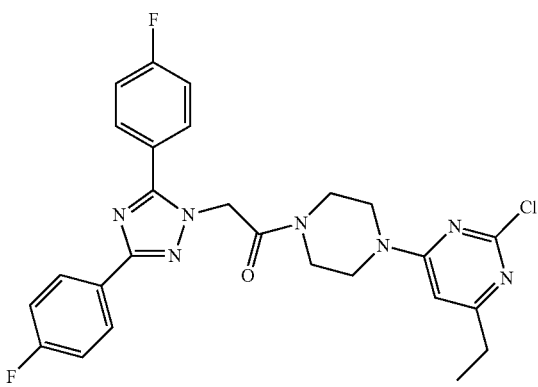 [SMILES: CCc1cc(N2CCN(C(=O)Cn3nc(-c4ccc(F)cc4)nc3-c3ccc(F)cc3)CC2)nc(Cl)n1] | 524 | method C | 2.19 |

| Examples | Product | MS m/z [M + H]+ | HPLC Method | Rt min |
|---|---|---|---|---|
| 7.03.28 | 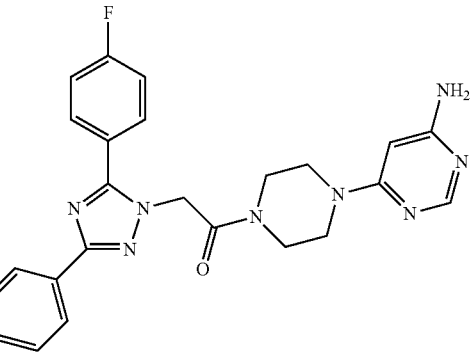 | 477 | Method N | 1.69 |

7.04.001 2-(3,5-Bis-(4-fluoro-phenyl)-(1,2,4)triazol-1-yl)-1-(4-(5-methoxy-pyrimidin-2-yl)-piperazin-1-yl)-ethanone

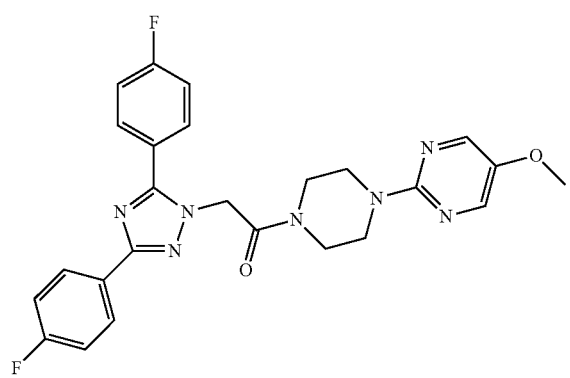 [SMILES: COc1cnc(N2CCN(C(=O)Cn3nc(-c4ccc(F)cc4)nc3-c3ccc(F)cc3)CC2)nc1]

100 mg (3,5-bis-(4-fluoro-phenyl)-(1,2,4)triazol-1-yl)-acetic acid was dissolved in 2 mL DMF. 163 mg PFTU and 0.5 mL DIPEA were added to this solution and the mixture was stirred for 7 min at RT. Then, 88 mg 5-Methoxy-2-piperazin-1-yl-pyrimidine hydrochloride and 0.11 mL DIPEA dissolved in 1.5 mL DMF were added and the reaction was stirred 3 h at RT. Then, a saturated sodiumhydrogencarbonate solution and $CH_2Cl_2$ were added, the organic phase was separated and the solvent was removed. The residue was purified by HPLC and crystallized with diethylether to give 32 mg of the desired compound. $R_t$: 0.82 min (method E), (M+H)+: 492

By using the same synthesis strategy as for 2-(3,5-Bis-(4-fluoro-phenyl)-(1,2,4)triazol-1-yl)-1-(4-(5-methoxy-pyrimidin-2-yl)-piperazin-1-yl)-ethanone the following compounds were obtained:

| Examples | Product | MS m/z [M + H]+ | HPLC Method | Rt min |
|---|---|---|---|---|
| 7.04.002 | 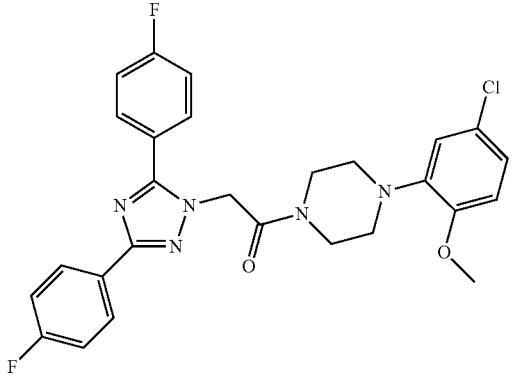 [SMILES: COc1ccc(Cl)cc1N1CCN(C(=O)Cn2nc(-c3ccc(F)cc3)nc2-c2ccc(F)cc2)CC1] | 524 | method D | 2.13 |

-continued

| Examples | Product | MS m/z [M + H]+ | HPLC Method | Rt min |
|---|---|---|---|---|
| 7.04.003 | | 462 | method D | 1.73 |
| 7.04.004 | | 461 | method D | 1.72 |
| 7.04.005 | | 511 | method D | 2.09 |
| 7.04.006 | | 511 | method D | 1.84 |

-continued

| Examples | Product | MS m/z [M + H]+ | HPLC Method | Rt min |
|---|---|---|---|---|
| 7.04.007 | | 485 | method D | 2.06 |
| 7.04.008 | | 462 | method D | 2.02 |
| 7.04.009 | | 496 | method D | 2.02 |
| 7.04.010 | | 476 | method D | 2.02 |

-continued

| Examples | Product | MS m/z [M + H]+ | HPLC Method | Rt min |
|---|---|---|---|---|
| 7.04.011 | | 486 | method D | 2.04 |
| 7.04.012 | | 495 | method D | 2.12 |
| 7.04.013 | | 478 | method D | 2.10 |
| 7.04.014 | | 490 | method D | 2.09 |

-continued

| Examples | Product | MS m/z [M + H]+ | HPLC Method | Rt min |
|---|---|---|---|---|
| 7.04.015 | | 495 | method B | 1.20 |
| 7.04.016 | | 492 | method B | 1.25 |
| 7.04.017 | | 492 | method B | 1.16 |
| 7.04.018 | | 426 | method B | 1.27 |

-continued

| Examples | Product | MS m/z [M + H]+ | HPLC Method | Rt min |
|---|---|---|---|---|
| 7.04.019 | | 456 | method B | 1.17 |
| 7.04.020 | | 480 | method B | 1.36 |
| 7.04.021 | | 493 | method B | 1.21 |
| 7.04.022 | | 479 | method B | 1.21 |

-continued

| Examples | Product | MS m/z [M + H]+ | HPLC Method | Rt min |
|---|---|---|---|---|
| 7.04.023 | | 462 | method B | 1.36 |
| 7.04.024 | | 475 | method B | 1.20 |
| 7.04.025 | | 487 | method B | 1.17 |
| 7.04.026 | | 474 | method B | 1.35 |

-continued

| Examples | Product | MS m/z [M + H]+ | HPLC Method | Rt min |
|---|---|---|---|---|
| 7.04.027 | | 487 | method B | 1.15 |
| 7.04.028 | | 474 | method B | 1.32 |
| 7.04.029 | | 449 | method B | 1.23 |
| 7.04.030 | | 463 | method B | 1.24 |

-continued

| Examples | Product | MS m/z [M + H]⁺ | HPLC Method | Rt min |
|---|---|---|---|---|
| 7.04.031 | | 450 | method B | 1.38 |
| 7.04.032 | | 487 | method B | 1.15 |
| 7.04.033 | | 474 | method B | 1.30 |
| 7.04.034 | | 504 | method B | 1.20 |

-continued

| Examples | Product | MS m/z [M + H]+ | HPLC Method | Rt min |
|---|---|---|---|---|
| 7.04.035 | | 473 | method B | 1.12 |
| 7.04.036 | | 552/554 | method B | 1.48 |
| 7.04.037 | | 474 | method B | 1.11 |
| 7.04.038 | | 508 | method B | 1.47 |

-continued

| Examples | Product | MS m/z [M + H]+ | HPLC Method | Rt min |
|---|---|---|---|---|
| 7.04.039 | | 503 | method B | 1.14 |
| 7.04.040 | | 474 | method B | 1.35 |
| 7.04.041 | | 487 | method B | 1.19 |
| 7.04.042 | | 504 | method B | 1.24 |

-continued

| Examples | Product | MS m/z [M + H]+ | HPLC Method | Rt min |
|---|---|---|---|---|
| 7.04.043 | | 474 | method B | 1.16 |
| 7.04.044 | | 552/554 | method B | 1.51 |
| 7.04.045 | | 508 | method B | 1.49 |
| 7.04.046 | | 436 | method B | 1.36 |

-continued

| Examples | Product | MS m/z [M + H]+ | HPLC Method | Rt min |
|---|---|---|---|---|
| 7.04.047 | | 435 | method B | 1.19 |
| 7.04.048 | | 449 | method B | 1.20 |
| 7.04.049 | | 473 | method B | 1.13 |
| 7.04.050 | | 473 | method B | 1.15 |

| Examples | Product | MS m/z [M + H]+ | HPLC Method | Rt min |
|---|---|---|---|---|
| 7.04.051 | (structure) | 462 | method B | 1.37 |
| 7.04.052 | (structure) | 475 | method B | 1.22 |
| 7.04.053 | (structure) | 461 | method B | 1.21 |
| 7.04.054 | (structure) | 455 | method B | 1.09 |

| Examples | Product | MS m/z [M + H]+ | HPLC Method | Rt min |
|---|---|---|---|---|
| 7.04.055 | 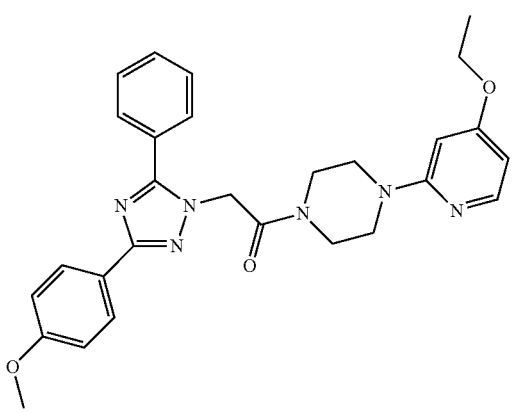 [SMILES: CCOc1ccnc(N2CCN(C(=O)Cn3nc(-c4ccc(OC)cc4)nc3-c3ccccc3)CC2)c1] | 499 | method B | 1.18 |
| 7.04.056 | 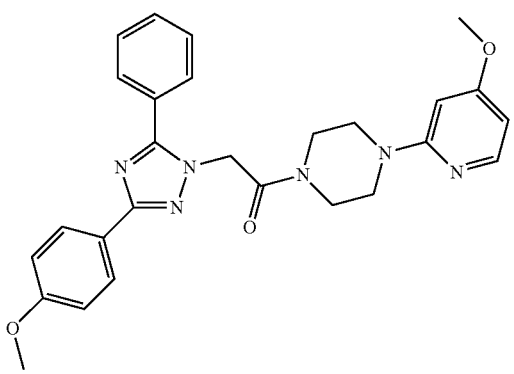 [SMILES: COc1ccc(-c2nc(-c3ccccc3)n(CC(=O)N3CCN(c4cc(OC)ccn4)CC3)n2)cc1] | 485 | method B | 1.13 |
| 7.04.057 | 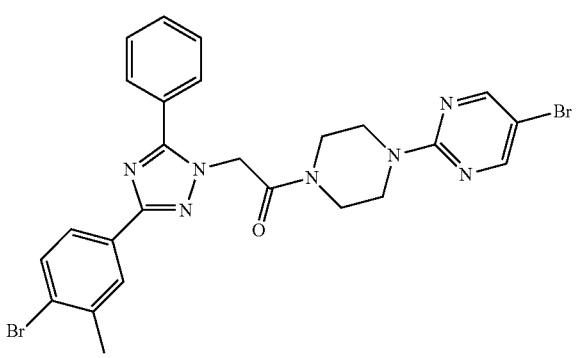 [SMILES: Cc1cc(-c2nc(-c3ccccc3)n(CC(=O)N3CCN(c4ncc(Br)cn4)CC3)n2)ccc1Br] | 598 | method B | 1.72 |
| 7.04.058 | 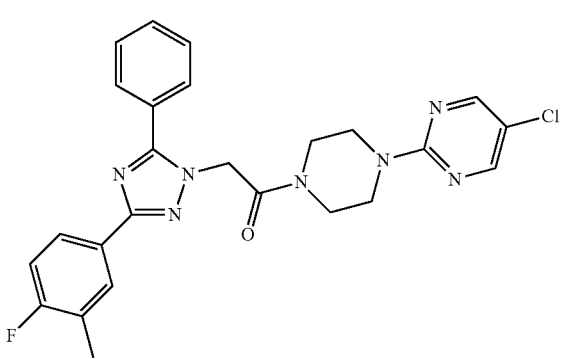 [SMILES: Cc1cc(-c2nc(-c3ccccc3)n(CC(=O)N3CCN(c4ncc(Cl)cn4)CC3)n2)ccc1F] | 492 | method B | 1.53 |

| Examples | Product | MS m/z [M + H]+ | HPLC Method | Rt min |
|---|---|---|---|---|
| 7.04.059 | | 458 | method B | 1.21 |
| 7.04.060 | | 488 | method B | 1.21 |
| 7.04.061 | | 457 | method B | 1.20 |
| 7.04.062 | | 471 | method B | 1.22 |

-continued

| Examples | Product | MS m/z [M + H]+ | HPLC Method | Rt min |
|---|---|---|---|---|
| 7.04.063 | | 487 | method B | 1.23 |
| 7.04.064 | | 488 | method B | 1.22 |
| 7.04.065 | | 494 | method B | 1.39 |
| 7.04.066 | | 464 | method B | 1.46 |

-continued

| Examples | Product | MS m/z [M + H]⁺ | HPLC Method | Rt min |
|---|---|---|---|---|
| 7.04.067 | | 477 | method B | 1.30 |
| 7.04.068 | | 493 | method B | 1.31 |
| 7.04.069 | | 498/500 | method B | 1.59 |
| 7.04.070 | | 542/544 | method B | 1.61 |

-continued
| Examples | Product | MS m/z [M + H]+ | HPLC Method | Rt min |
|---|---|---|---|---|
| 7.04.071 | 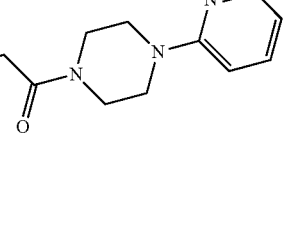 | 463 | method B | 1.30 |
| 7.04.072 | 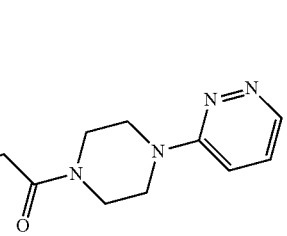 | 464 | method B | 1.31 |
| 7.04.073 |  | 458 | method S | 0.42 |
| 7.04.074 | 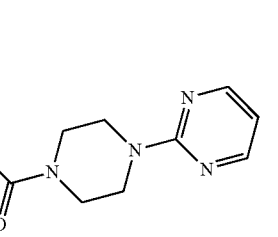 | 488 | method S | 0.40 |

-continued

| Examples | Product | MS m/z [M + H]+ | HPLC Method | Rt min |
|---|---|---|---|---|
| 7.04.075 | | 471 | method S | 0.38 |
| 7.04.076 | | 457 | method S | 0.37 |
| 7.04.077 | | 492 | method T | 0.81 |
| 7.04.078 | | 492 | method T | 0.68 |

-continued
| Examples | Product | MS m/z [M + H]+ | HPLC Method | Rt min |
|---|---|---|---|---|
| 7.04.079 | 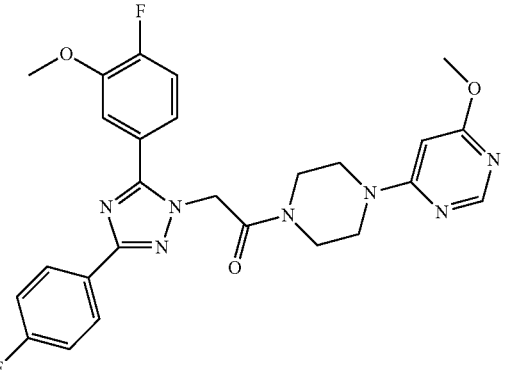 | 522 | method T | 0.75 |
| 7.04.080 | 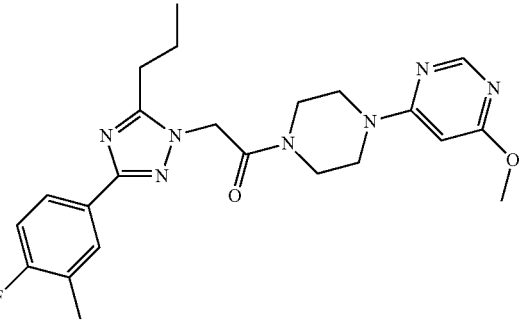 | 454 | method B | 1.23 |
| 7.04.081 | 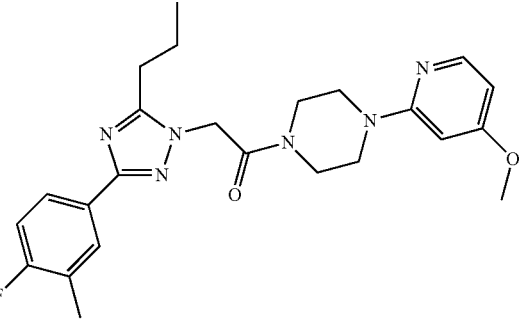 | 453 | method B | 1.20 |
| 7.04.082 | 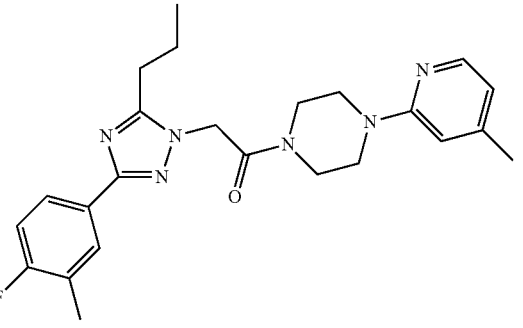 | 437 | method B | 1.19 |

-continued

| Examples | Product | MS m/z [M + H]+ | HPLC Method | Rt min |
|---|---|---|---|---|
| 7.04.083 | | 423 | method B | 1.18 |
| 7.04.084 | | 425 | method B | 1.25 |
| 7.04.085 | | 424 | method B | 1.32 |
| 7.04.086 | | 454 | method T | 0.74 |
| 7.04.087 | | 423 | method T | 0.67 |

-continued

| Examples | Product | MS m/z [M + H]+ | HPLC Method | Rt min |
|---|---|---|---|---|
| 7.04.088 | | 453 | method T | 0.69 |
| 7.04.089 | | 424 | method T | 0.81 |
| 7.04.090 | | 437 | method T | 0.69 |
| 7.04.091 | | 409 | method T | 0.63 |
| 7.04.092 | | 410 | method T | 0.78 |

-continued

| Examples | Product | MS m/z [M + H]+ | HPLC Method | Rt min |
|---|---|---|---|---|
| 7.04.093 | | 440 | method T | 0.71 |
| 7.04.094 | | 439 | method T | 0.66 |
| 7.04.095 | | 395 | method S | 0.36 |
| 7.04.096 | | 425 | method S | 0.37 |
| 7.04.097 | | 396 | method S | 0.39 |

-continued
| Examples | Product | MS m/z [M + H]+ | HPLC Method | Rt min |
|---|---|---|---|---|
| 7.04.098 | 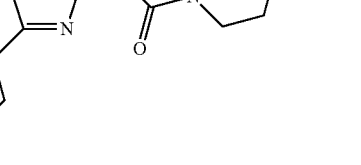 | 409 | method S | 0.37 |
| 7.04.099 |  | 451 | method T | 0.82 |
| 7.04.100 | 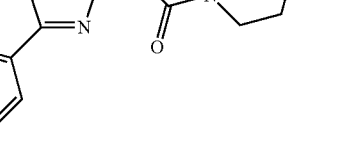 | 467 | method T | 0.82 |
| 7.04.101 | 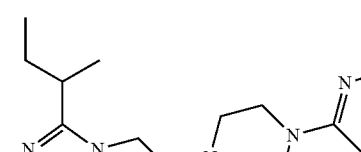 | 438 | method T | 0.93 |
| 7.04.102 | 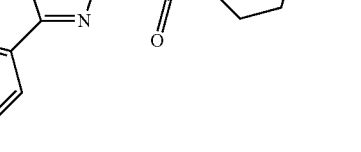 | 437 | method T | 0.83 |

| Examples | Product | MS m/z [M + H]+ | HPLC Method | Rt min |
|---|---|---|---|---|
| 7.04.103 | | 468 | method T | 0.89 |
| 7.04.104 | | 438 | method T | 0.82 |
| 7.04.105 | | 451 | method T | 0.73 |
| 7.04.106 | | 437 | method T | 0.72 |

| Examples | Product | MS m/z [M + H]+ | HPLC Method | Rt min |
|---|---|---|---|---|
| 7.04.107 | | 467 | method T | 0.73 |
| 7.04.108 | | 438 | method T | 0.85 |
| 7.04.109 | | 468 | method T | 0.79 |
| 7.04.110 | | 479 | method T | 0.77 |

-continued

| Examples | Product | MS m/z [M + H]⁺ | HPLC Method | Rt min |
|---|---|---|---|---|
| 7.04.111 | | 450 | method T | 0.88 |
| 7.04.112 | | 480 | method T | 0.84 |
| 7.04.113 | | 449 | method T | 0.76 |
| 7.04.114 | | 463 | method T | 0.77 |

-continued

| Examples | Product | MS m/z [M + H]+ | HPLC Method | Rt min |
|---|---|---|---|---|
| 7.04.115 | | 451 | method T | 0.75 |
| 7.04.116 | | 437 | method T | 0.74 |
| 7.04.117 | | 438 | method T | 0.87 |
| 7.04.118 | | 467 | method T | 0.75 |

-continued

| Examples | Product | MS m/z [M + H]+ | HPLC Method | Rt min |
|---|---|---|---|---|
| 7.04.119 | | 468 | method T | 0.82 |
| 7.04.120 | | 481 | method T | 0.81 |
| 7.04.121 | | 465 | method T | 0.81 |
| 7.04.122 | | 452 | method T | 0.92 |

-continued
| Examples | Product | MS m/z [M + H]+ | HPLC Method | Rt min |
|---|---|---|---|---|
| 7.04.123 | 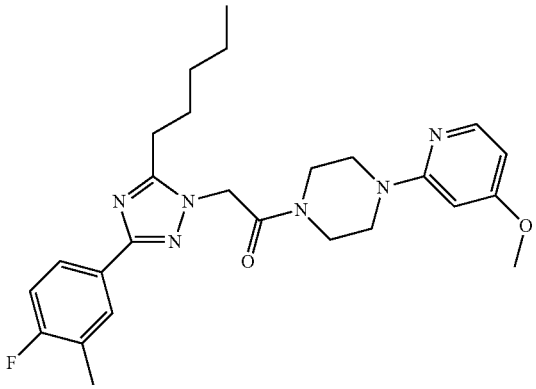 [SMILES: CCCCCc1nc(-c2ccc(F)c(C)c2)nn1CC(=O)N1CCN(c2cc(OC)ccn2)CC1] | 481 | method T | 0.79 |
| 7.04.124 | 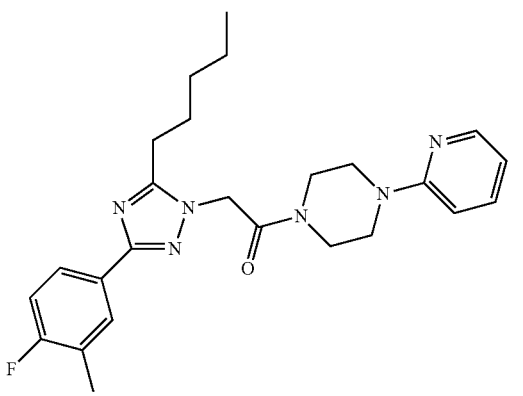 [SMILES: CCCCCc1nc(-c2ccc(F)c(C)c2)nn1CC(=O)N1CCN(c2ccccn2)CC1] | 451 | method T | 0.78 |
| 7.04.125 | 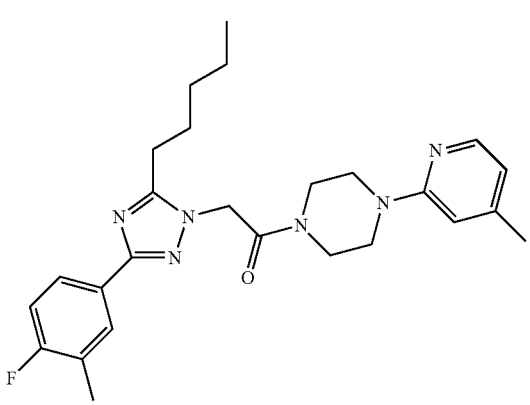 [SMILES: CCCCCc1nc(-c2ccc(F)c(C)c2)nn1CC(=O)N1CCN(c2cc(C)ccn2)CC1] | 465 | method T | 0.79 |
| 7.04.126 | 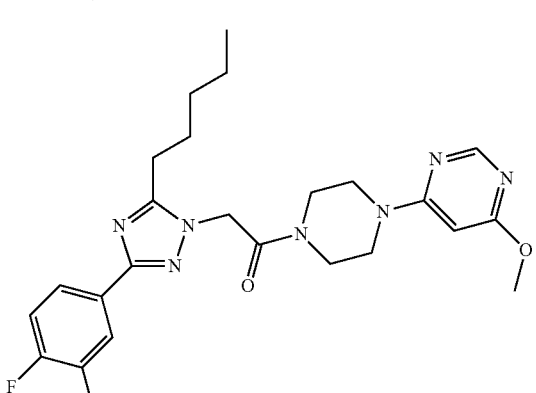 | 482 | method T | 0.85 |

-continued
| Examples | Product | MS m/z [M + H]+ | HPLC Method | Rt min |
|---|---|---|---|---|
| 7.04.127 | 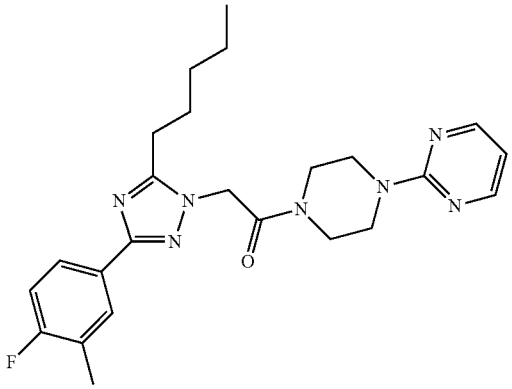 [SMILES: CCCCCc1nc(-c2ccc(F)c(C)c2)nn1CC(=O)N1CCN(c2ncccn2)CC1] | 452 | method T | 0.90 |
| 7.04.128 | 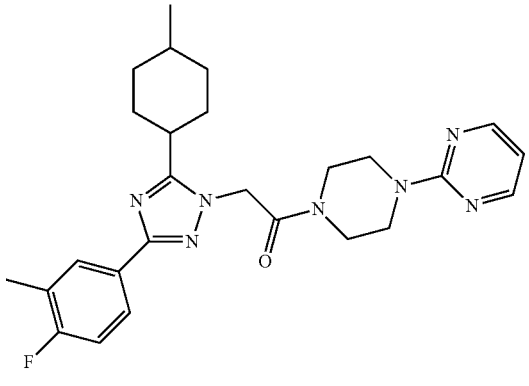 [SMILES: Cc1cc(-c2nc(C3CCC(C)CC3)n(CC(=O)N3CCN(c4ncccn4)CC3)n2)ccc1F] | 478 | method T | 1.01 |
| 7.04.129 | 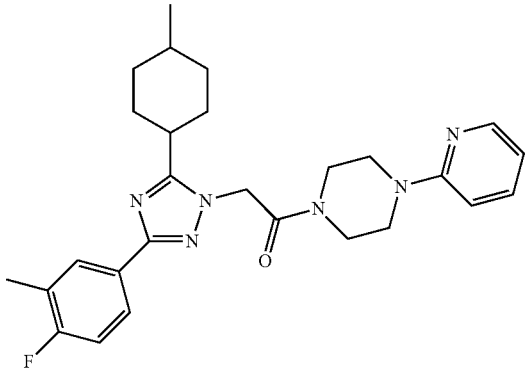 [SMILES: Cc1cc(-c2nc(C3CCC(C)CC3)n(CC(=O)N3CCN(c4ccccn4)CC3)n2)ccc1F] | 477 | method T | 0.94 |
| 7.04.130 | 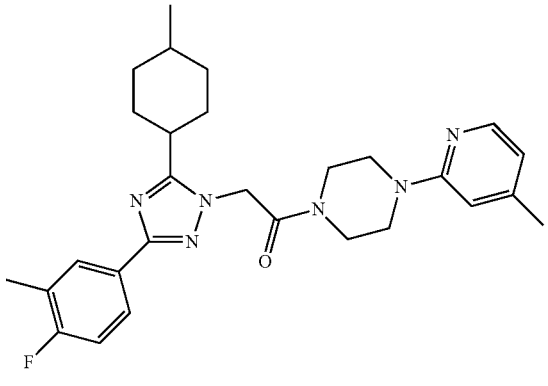 | 491 | method T | 0.93 |

-continued

| Examples | Product | MS m/z [M + H]+ | HPLC Method | Rt min |
|---|---|---|---|---|
| 7.04.131 | | 507 | method T | 0.94 |
| 7.04.132 | | 508 | method E | 0.94 |
| 7.04.133 | | 477 | method T | 0.94 |
| 7.04.134 | | 491 | method T | 0.93 |

-continued

| Examples | Product | MS m/z [M + H]+ | HPLC Method | Rt min |
|---|---|---|---|---|
| 7.04.135 | | 478 | method T | 1.04 |
| 7.04.136 | | 507 | method T | 0.91 |
| 7.04.137 | | 508 | method T | 1.00 |
| 7.04.138 | | 476 | method T | 0.62 |

-continued

| Examples | Product | MS m/z [M + H]+ | HPLC Method | Rt min |
|---|---|---|---|---|
| 7.04.139 | | 462 | method T | 0.61 |
| 7.04.140 | | 463 | method T | 0.74 |
| 7.04.141 | | 493 | method T | 0.86 |
| 7.04.142 | | 492 | method W | 0.60 |

-continued
| Examples | Product | MS m/z [M + H]+ | HPLC Method | Rt min |
|---|---|---|---|---|
| 7.04.143 | 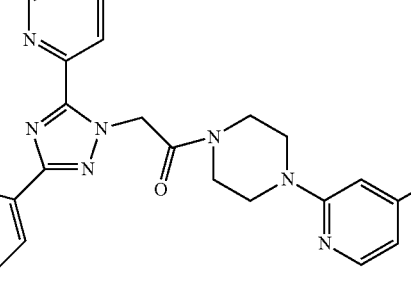 | 476 | method T | 0.72 |
| 7.04.144 | 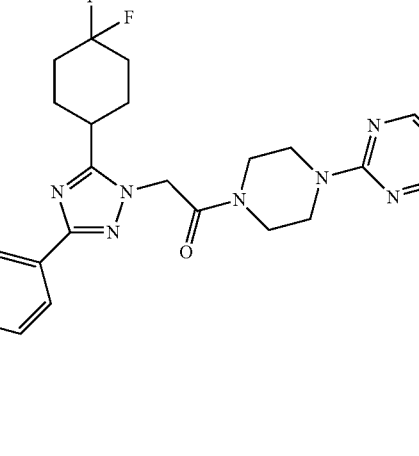 | 500 | method E | 0.89 |
| 7.04.145 | 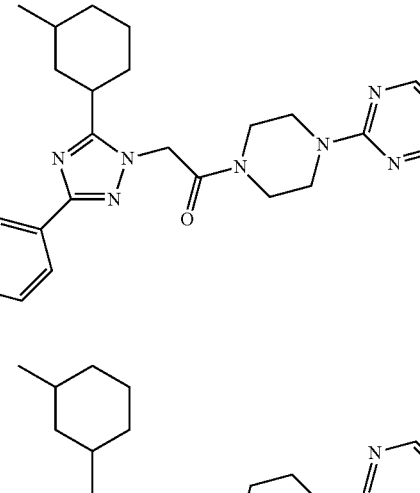 | 478 | method E | 0.93 |
| 7.04.146 | 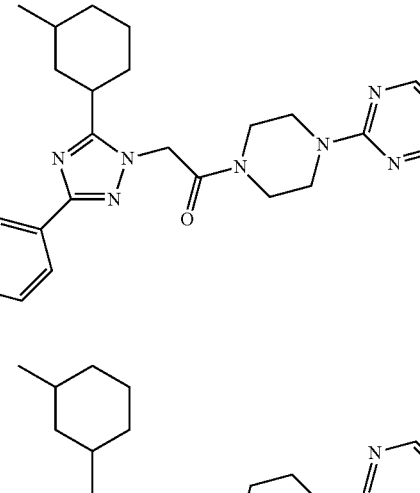 | 491 | method E | 0.83 |

-continued
| Examples | Product | MS m/z [M + H]+ | HPLC Method | Rt min |
|---|---|---|---|---|
| 7.04.147 | 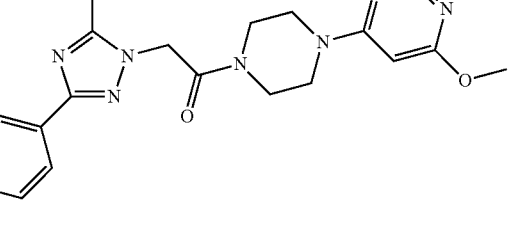 | 508 | method E | 0.90 |
| 7.04.148 | 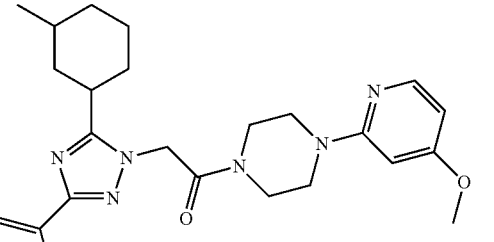 | 507 | method E | 0.83 |
| 7.04.149 |  | 477 | method E | 0.84 |
| 7.04.150 | 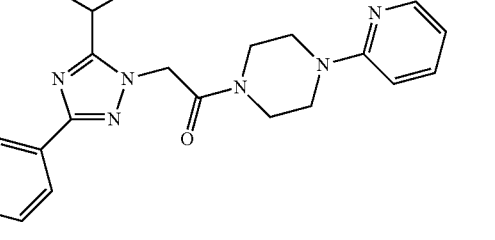 | 472 | method B | 1.40 |

| Examples | Product | MS m/z [M + H]+ | HPLC Method | Rt min |
|---|---|---|---|---|
| 7.04.151 | 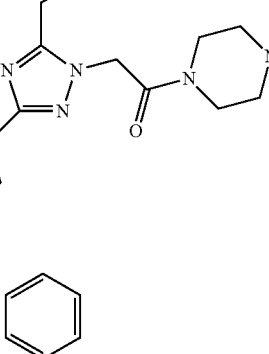 | 485 | method B | 1.24 |
| 7.04.152 | 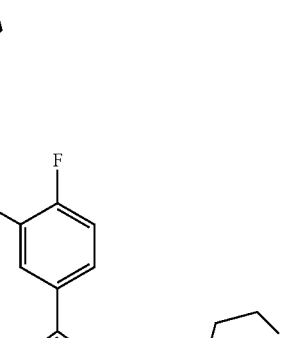 | 486 | method B | 1.17 |
| 7.04.153 | 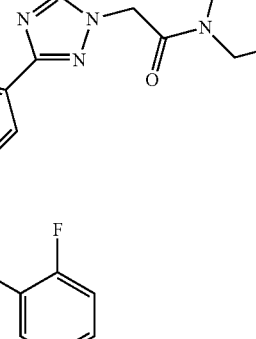 | 490 | method T | 0.96 |
| 7.04.154 | 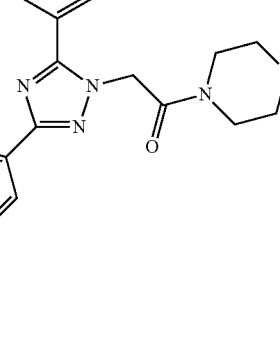 | 489 | method T | 0.86 |

-continued

| Examples | Product | MS m/z [M + H]+ | HPLC Method | Rt min |
|---|---|---|---|---|
| 7.04.155 | | 520 | method T | 0.92 |
| 7.04.156 | | 492 | method T | 0.91 |
| 7.04.157 | | 491 | method T | 0.79 |
| 7.04.158 | | 522 | method T | 0.85 |

| Examples | Product | MS m/z [M + H]+ | HPLC Method | Rt min |
|---|---|---|---|---|
| 7.04.159 | | 485 | method B | 1.41 |
| 7.04.160 | | 469 | method B | 1.11 |
| 7.04.161 | | 422 | method B | 1.22 |
| 7.04.162 | | 522 | method P | 0.79 |

-continued

| Examples | Product | MS m/z [M + H]+ | HPLC Method | Rt min |
|---|---|---|---|---|
| 7.04.163 | | 444 | method P | 0.79 |
| 7.04.164 | | 491 | method P | 0.73 |
| 7.04.165 | | 492 | method P | 0.85 |
| 7.04.166 | | 491 | method P | 0.74 |

-continued
| Examples | Product | MS m/z [M + H]+ | HPLC Method | Rt min |
|---|---|---|---|---|
| 7.04.167 | 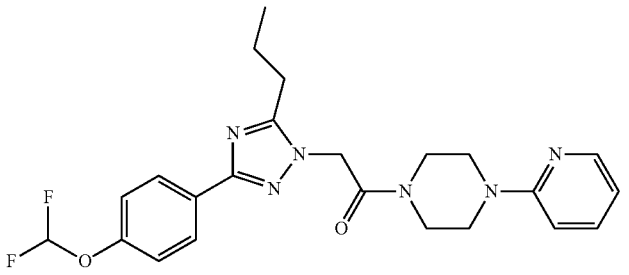 [SMILES: CCCc1nc(-c2ccc(OC(F)F)cc2)nn1CC(=O)N1CCN(c2ccccn2)CC1] | 457 | method P | 0.67 |
| 7.04.168 | 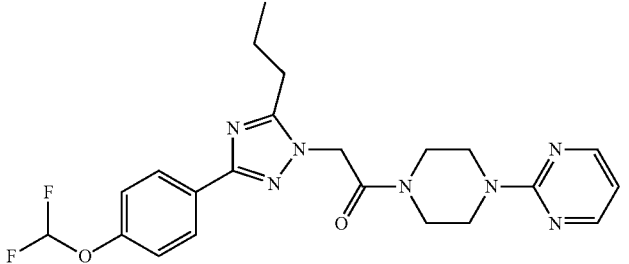 [SMILES: CCCc1nc(-c2ccc(OC(F)F)cc2)nn1CC(=O)N1CCN(c2ncccn2)CC1] | 458 | method P | 0.84 |
| 7.04.169 | 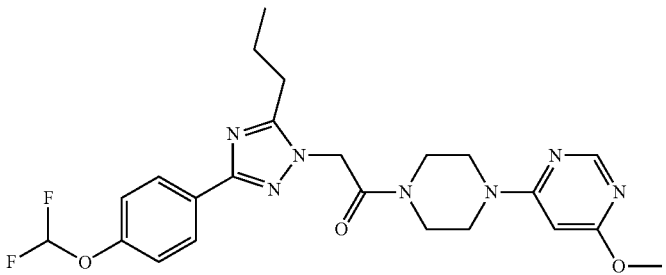 [SMILES: CCCc1nc(-c2ccc(OC(F)F)cc2)nn1CC(=O)N1CCN(c2cc(OC)ncn2)CC1] | 488 | method P | 0.77 |

7.05.01. 2-(3,5-Bis-(4-fluoro-phenyl)-(1,2,4)triazol-1-yl)-1-(4-(4-ethoxy-pyridin-2-yl)-piperazin-1-yl)-ethanone

7.06.01. 2-(3,5-Bis-(4-fluoro-phenyl)-(1,2,4)triazol-1-yl)-1-(4-(6-dimethylamino-pyrimidin-4-yl)-piperazin-1-yl)-ethanone

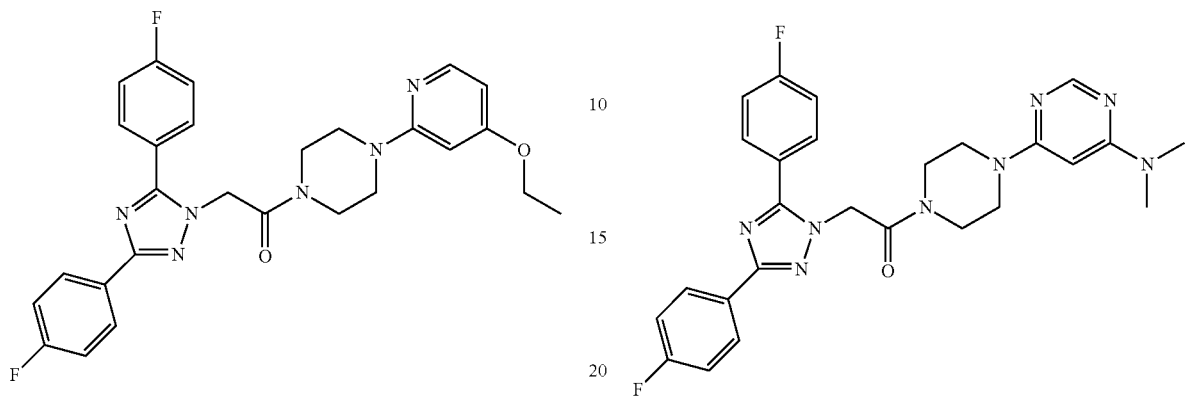

17 mg BINAP and 24 mg tris-(dibenzylidenacetone)palladium(0) were added to 255 mg casiumcarbonate, 65 mg 2-brom-4-ethoxy-pyridine and 100 mg 2-(3,5-Bis-(4-fluoro-phenyl)-(1,2,4)triazol-1-yl)-1-piperazin-1-yl-ethanone in 10 mL toluole under nitrogen atmosphere. The reaction was refluxed for 4 days. The mixture was filtered and the filtrate was evaporated. The residue was purified by HPLC. $R_t$: 1.22 min (method B), (M+H)$^+$: 505

40 mg 2-(3,5-Bis-(4-fluoro-phenyl)-(1,2,4)triazol-1-yl)-1-(4-(6-chloro-pyrimidin-4-yl)-piperazin-1-yl)-ethanone and 2 mL 2 M dimethylamine solution in THF were stirred 30 min at 170° C. under microwave condition. The mixture was purified by HPLC to give 19.1 mg of the desired product. $R_t$: 1.88 min (method I), (M+H)$^+$: 505

By using the same synthesis strategy as for 2-(3,5-Bis-(4-fluoro-phenyl)-(1,2,4)triazol-1-yl)-1-(4-(4-ethoxy-pyridin-2-yl)-piperazin-1-yl)-ethanone the following compounds was obtained:

By using the same synthesis strategy as for 2-(3,5-Bis-(4-fluoro-phenyl)-(1,2,4)triazol-1-yl)-1-(4-(6-dimethylamino-pyrimidin-4-yl)-piperazin-1-yl)-ethanone the following compounds were obtained:

| Examples | Product | MS m/z [M + H]$^+$ | HPLC Method | Rt min |
|---|---|---|---|---|
| 7.05.02 | (structure) | 489 | method B | 1.22 |

| Examples | Product | MS m/z [M + H]⁺ | HPLC Method | Rt min |
|---|---|---|---|---|
| 7.06.02 | | 506 | method K | 2.56 |
| 7.06.03 | | 536 | method K | 2.49 |
| 7.06.04 | | 520 | method K | 2.62 |

7.07.01. 2-(3,5-bis-(4-fluoro-phenyl)-(1,2,4)triazol-1-yl)-1-(4-(6-(2-hydroxy-ethoxy)-pyrimidin-4-yl)-piperazin-1-yl)-ethanone

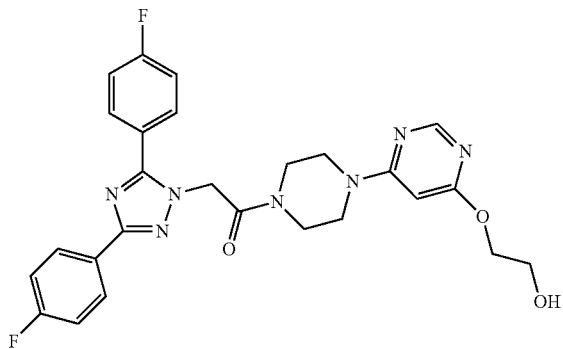 [SMILES: O=C(Cn1nc(-c2ccc(F)cc2)nc1-c1ccc(F)cc1)N1CCN(c2cc(OCCO)ncn2)CC1]

50 mg 2-(3,5-Bis-(4-fluoro-phenyl)-(1,2,4)triazol-1-yl)-1-(4-(6-chloro-pyrimidin-4-yl)-piperazin-1-yl)-ethanone and 3 mL ethane-1,2-diol were added to 10 mg potassiumcarbonate in 3 mL ethanol. The reaction was stirred 30 min at 150° C. under microwave conditions. The solvent was removed and the precipate was purified by HPLC to give 29 mg of the desired product. $R_t$: 1.87 min (method C), $(M+H)^+$: 522

By using the same synthesis strategy as for 2-(3,5-bis-(4-fluoro-phenyl)-(1,2,4)triazol-1-yl)-1-(4-(6-(methyl-(tetrahydro-furan-3-ylmethyl)-amino)-pyrimidin-4-yl)-piperazin-1-yl)-ethanone the following compounds was obtained:

| Examples | Product | MS m/z [M + H]$^+$ | HPLC Method | Rt min |
|---|---|---|---|---|
| 7.07.02 | | 549 | method C | 1.70 |

7.08.01. 2-(3,5-bis-(4-fluoro-phenyl)-(1,2,4)triazol-1-yl)-1-(4-(6-(methyl-(tetrahydro-furan-3-ylmethyl)-amino)-pyrimidin-4-yl)-piperazin-1-yl)-ethanone

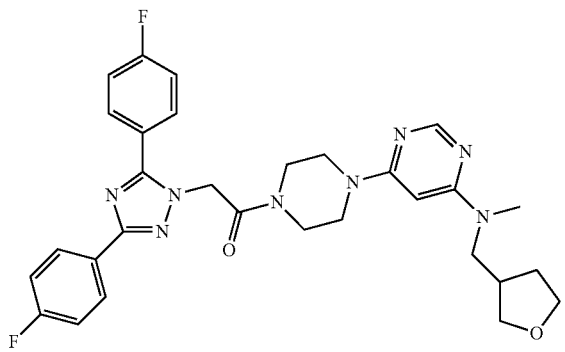 [SMILES: CN(CC1CCOC1)c1cc(N2CCN(C(=O)Cn3nc(-c4ccc(F)cc4)nc3-c3ccc(F)cc3)CC2)ncn1]

58 mg methyl-(tetrahydro-furan-3-ylmethyl)-amine was added to 50 mg 2-(3,5-Bis-(4-fluoro-phenyl)-(1,2,4)triazol-1-yl)-1-(4-(6-chloro-pyrimidin-4-yl)-piperazin-1-yl)-ethanone and 35 µl DIPEA in 1 mL DMSO. The reaction was stirred 3 h at 80° C. The mixture was purified by HPLC to give 44 mg of the desired product. $R_t$: 2.13 min (method M), $(M+H)^+$: 575

By using the same synthesis strategy as for 2-(3,5-bis-(4-fluoro-phenyl)-(1,2,4)triazol-1-yl)-1-(4-(6-(methyl-(tetrahydro-furan-3-ylmethyl)-amino)-pyrimidin-4-yl)-piperazin-1-yl)-ethanone the following compounds were obtained:

| Examples | Product | MS m/z [M + H]⁺ | HPLC Method | Rt min |
|---|---|---|---|---|
| 7.08.02 | 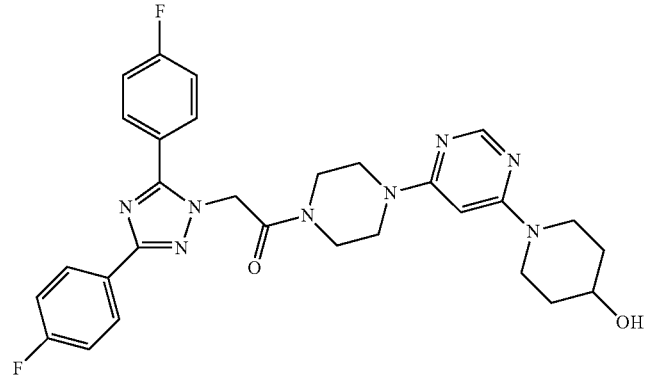 [SMILES: O=C(Cn1nc(-c2ccc(F)cc2)nc1-c1ccc(F)cc1)N1CCN(c2cc(N3CCC(O)CC3)ncn2)CC1] | 561 | method M | 1.98 |
| 7.08.03 | 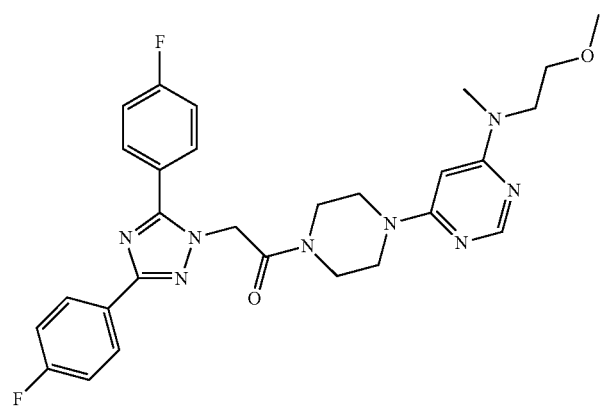 [SMILES: COCCN(C)c1cc(N2CCN(C(=O)Cn3nc(-c4ccc(F)cc4)nc3-c3ccc(F)cc3)CC2)ncn1] | 549 | method M | 2.13 |

-continued

| Examples | Product | MS m/z [M + H]+ | HPLC Method | Rt min |
|---|---|---|---|---|
| 7.08.04 | | 517 | method M | 2.11 |
| 7.08.05 | | 561 | method M | 2.03 |
| 7.08.06 | | 575 | method M | 2.18 |
| 7.08.07 | | 519 | method M | 2.15 |

-continued
| Examples | Product | MS m/z [M + H]+ | HPLC Method | Rt min |
|---|---|---|---|---|
| 7.08.08 | 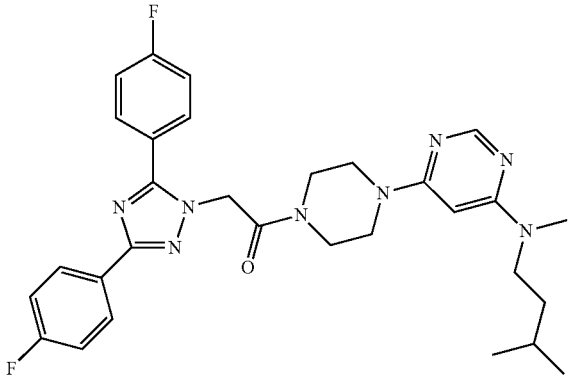 [SMILES: CC(C)CCN(C)c1cc(N2CCN(C(=O)Cn3nc(-c4ccc(F)cc4)nc3-c3ccc(F)cc3)CC2)ncn1] | 561 | method M | 2.49 |
| 7.08.09 | 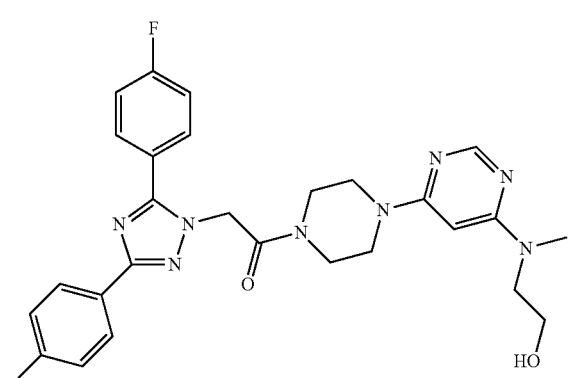 | 535 | method M | 1.97 |
| 7.08.10 | 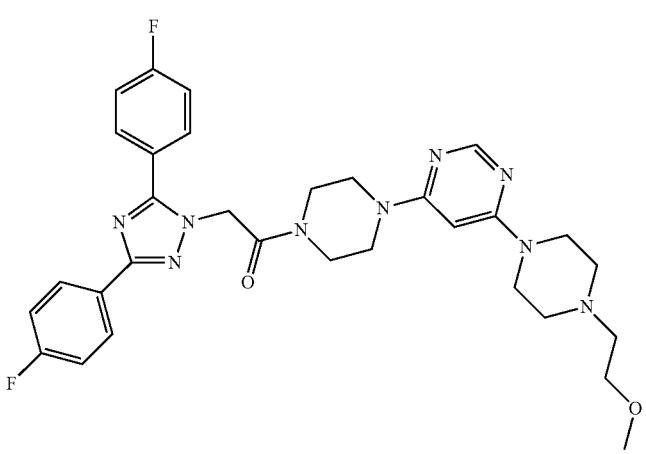 [SMILES: COCCN1CCN(c2cc(N3CCN(C(=O)Cn4nc(-c5ccc(F)cc5)nc4-c4ccc(F)cc4)CC3)ncn2)CC1] | 604 | method M | 2.07 |

-continued

| Examples | Product | MS m/z [M + H]+ | HPLC Method | Rt min |
|---|---|---|---|---|
| 7.08.11 | | 563 | method M | 2.18 |
| 7.08.12 | | 505 | method M | 2.08 |
| 7.08.13 | | 531 | method M | 2.18 |
| 7.08.14 | | 574 | method M | 1.97 |

-continued
| Examples | Product | MS m/z [M + H]+ | HPLC Method | Rt min |
|---|---|---|---|---|
| 7.08.15 | 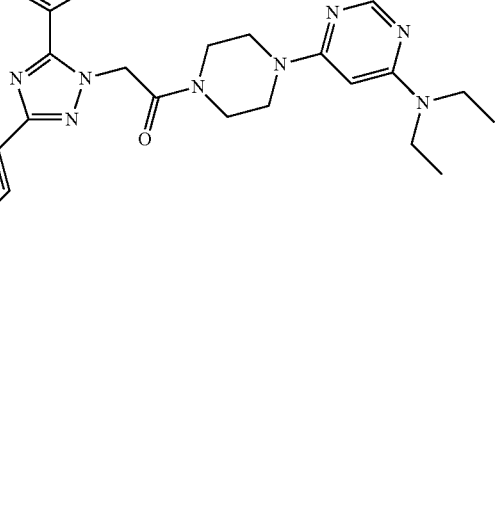 | 533 | method M | 2.29 |
| 7.08.16 | 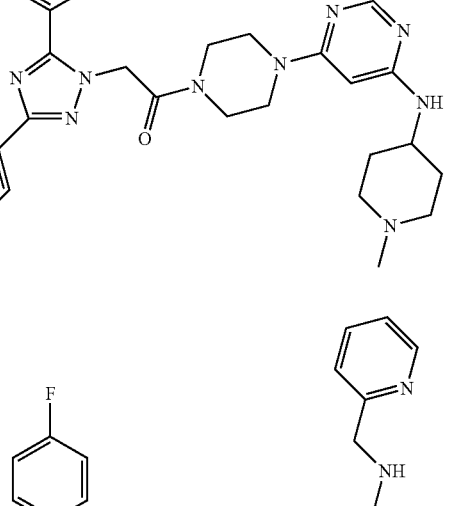 | 574 | method M | 2.03 |
| 7.08.17 | 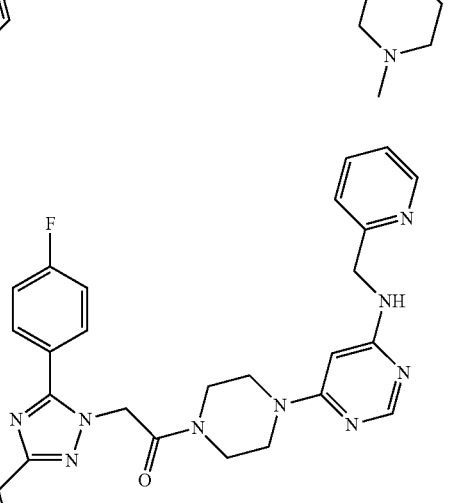 | 568 | method M | 2.04 |

| Examples | Product | MS m/z [M + H]+ | HPLC Method | Rt min |
|---|---|---|---|---|
| 7.08.18 | 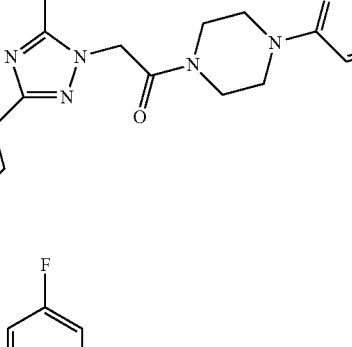 | 531 | method M | 2.24 |
| 7.08.19 | 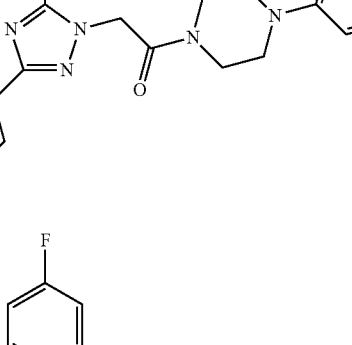 | 519 | method M | 2.20 |
| 7.08.20 | 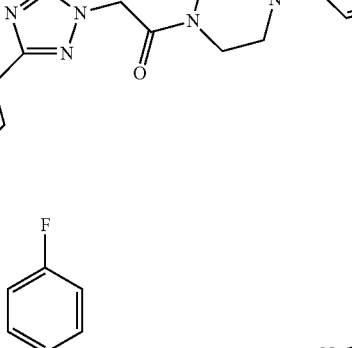 | 531 | method M | 2.20 |
| 7.08.21 | 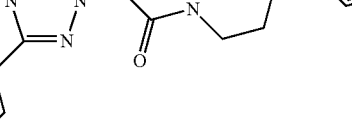 | 535 | method M | 2.03 |

-continued

| Examples | Product | MS m/z [M + H]⁺ | HPLC Method | Rt min |
|---|---|---|---|---|
| 7.08.22 | | 517 | method M | 2.09 |
| 7.08.23 | | 560 | method M | 2.04 |
| 7.08.24 | | 491 | method M | 2.00 |

7.09.01. 2-(3,5-Bis-(4-fluoro-phenyl)-(1,2,4)triazol-1-yl]-1-(4-(6-(4-methoxy-butoxy)-pyrimidin-4-yl)-piperazin-1-yl)-ethanone

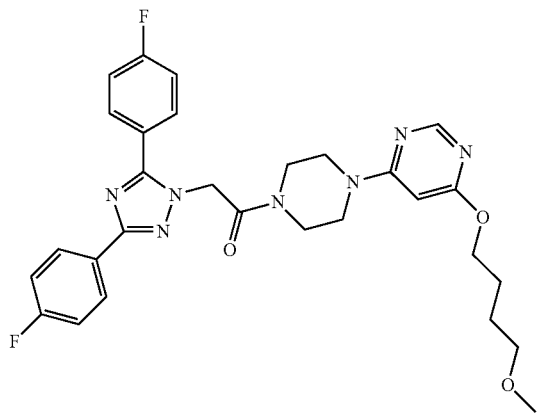 [SMILES: COCCCCOc1cc(N2CCN(C(=O)Cn3nc(-c4ccc(F)cc4)nc3-c3ccc(F)cc3)CC2)ncn1]

50 mg 2-(3,5-Bis-(4-fluoro-phenyl)-(1,2,4)triazol-1-yl)-1-(4-(6-chloro-pyrimidin-4-yl)-piperazin-1-yl)-ethanone and 53 mg 4-methoxy-1-butanol were added to 14 mg potassium-carbonate in 2 mL n-methyl-2-pyrrolidinone. The reaction was sonicated for a few minutes and stirred 30 min at 200° C. The reaction was purified by HPLC to give 29 mg desired product. $R_t$: 1.82 min (method N), (M+H)$^+$: 564

By using the same synthesis strategy as for 2-(3,5-Bis-(4-fluoro-phenyl)-(1,2,4)triazol-1-yl]-1-(4-(6-(4-methoxy-butoxy)-pyrimidin-4-yl)-piperazin-1-yl)-ethanone the following compounds were obtained:

| Examples | Product | MS m/z [M + H]$^+$ | HPLC Method | Rt min |
|---|---|---|---|---|
| 7.09.02 | | 562 | method O | 1.62 |
| 7.09.03 | | 562 | method J | 1.86 |

| Examples | Product | MS m/z [M + H]+ | HPLC Method | Rt min |
|---|---|---|---|---|
| 7.09.04 | 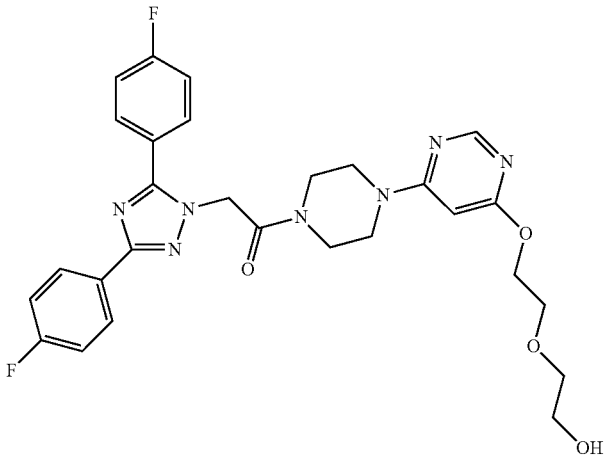 [SMILES: O=C(Cn1nc(-c2ccc(F)cc2)nc1-c1ccc(F)cc1)N1CCN(c2cc(OCCOCCO)ncn2)CC1] | 566 | method J | 1.70 |
| 7.09.05 | 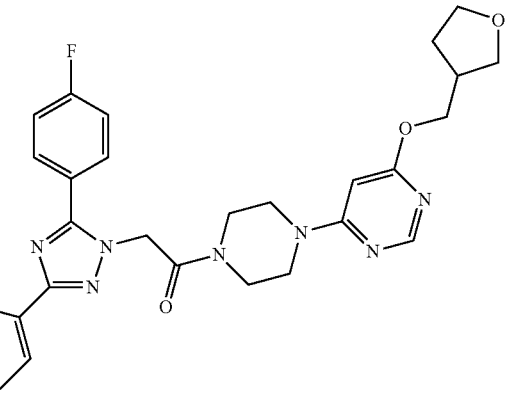 | 562 | method J | 1.84 |
| 7.09.06 | 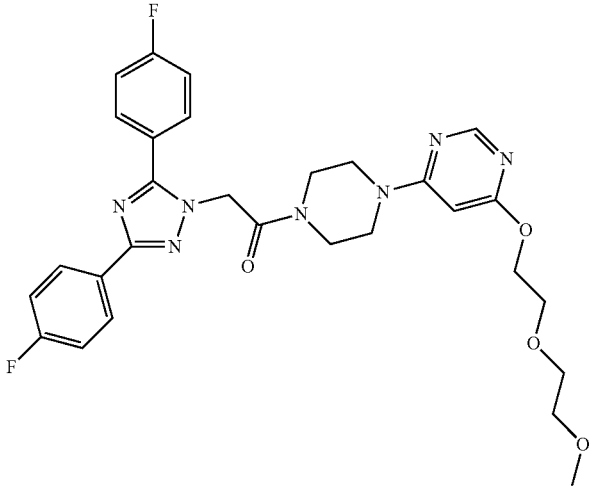 [SMILES: COCCOCCOc1cc(N2CCN(C(=O)Cn3nc(-c4ccc(F)cc4)nc3-c3ccc(F)cc3)CC2)ncn1] | 580 | method J | 1.81 |

-continued

| Examples | Product | MS m/z [M + H]+ | HPLC Method | Rt min |
|---|---|---|---|---|
| 7.09.07 | | 591 | method J | 1.48 |
| 7.09.08 | | 603 | method J | 1.80 |
| 7.09.09 | | 562 | method J | 1.92 |

| Examples | Product | MS m/z [M + H]+ | HPLC Method | Rt min |
|---|---|---|---|---|
| 7.09.10 | 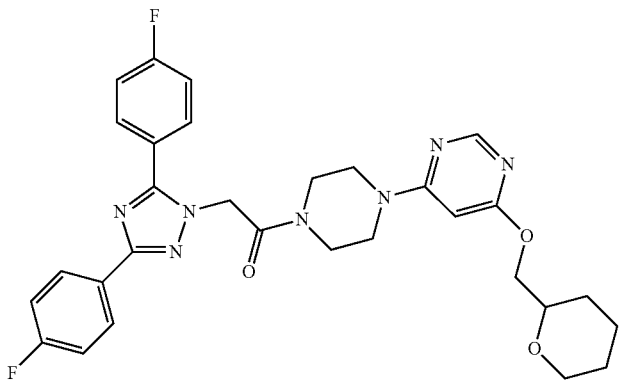 [SMILES: O=C(Cn1nc(-c2ccc(F)cc2)nc1-c1ccc(F)cc1)N1CCN(c2cc(OCC3CCCCO3)ncn2)CC1] | 576 | method J | 1.97 |
| 7.09.11 | 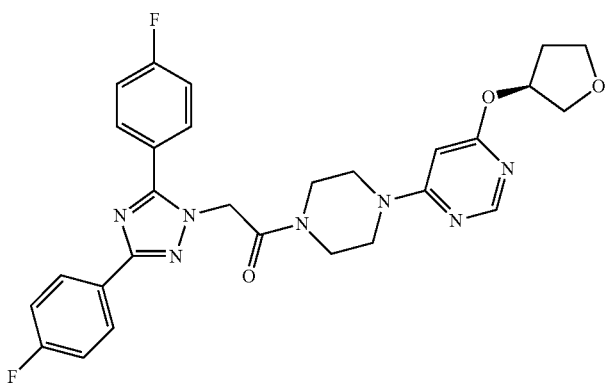 [SMILES: O=C(Cn1nc(-c2ccc(F)cc2)nc1-c1ccc(F)cc1)N1CCN(c2cc(O[C@H]3CCOC3)ncn2)CC1] | 548 | method J | 1.86 |
| 7.09.12 | 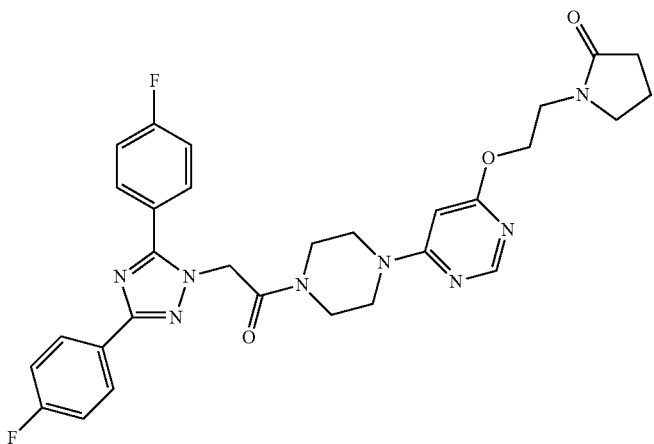 [SMILES: O=C1CCCN1CCOc1cc(N2CCN(C(=O)Cn3nc(-c4ccc(F)cc4)nc3-c3ccc(F)cc3)CC2)ncn1] | 589 | method J | 1.77 |

-continued

| Examples | Product | MS m/z [M + H]+ | HPLC Method | Rt min |
|---|---|---|---|---|
| 7.09.13 | | 569 | method J | 1.73 |
| 7.09.14 | | 550 | method J | 1.88 |
| 7.09.15 | | 564 | method J | 1.76 |

-continued

| Examples | Product | MS m/z [M + H]⁺ | HPLC Method | Rt min |
|---|---|---|---|---|
| 7.09.16 | | 610 | method J | 1.72 |
| 7.09.17 | | 572 | method J | 1.50 |
| 7.09.18 | | 590 | method J | 1.70 |

-continued

| Examples | Product | MS m/z [M + H]+ | HPLC Method | Rt min |
|---|---|---|---|---|
| 7.09.19 | | 605 | method J | 1.47 |
| 7.09.20 | | 536 | method J | 1.67 |
| 7.09.21 | | 562 | method J | 1.88 |

-continued

| Examples | Product | MS m/z [M + H]+ | HPLC Method | Rt min |
|---|---|---|---|---|
| 7.09.22 | | 569 | method J | 1.62 |
| 7.09.23 | | 562 | method J | 1.87 |
| 7.09.24 | | 575 | method J | 1.70 |

-continued
| Examples | Product | MS m/z [M + H]+ | HPLC Method | Rt min |
|---|---|---|---|---|
| 7.09.25 | 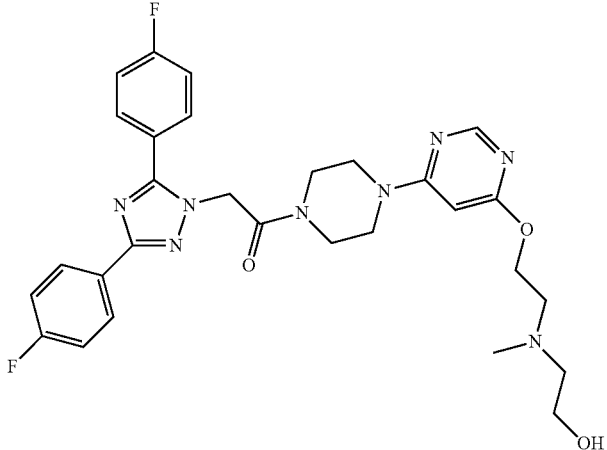 [SMILES: CN(CCO)CCOc1cc(N2CCN(C(=O)Cn3nc(-c4ccc(F)cc4)nc3-c3ccc(F)cc3)CC2)ncn1] | 579 | method J | 1.48 |
| 7.09.26 | 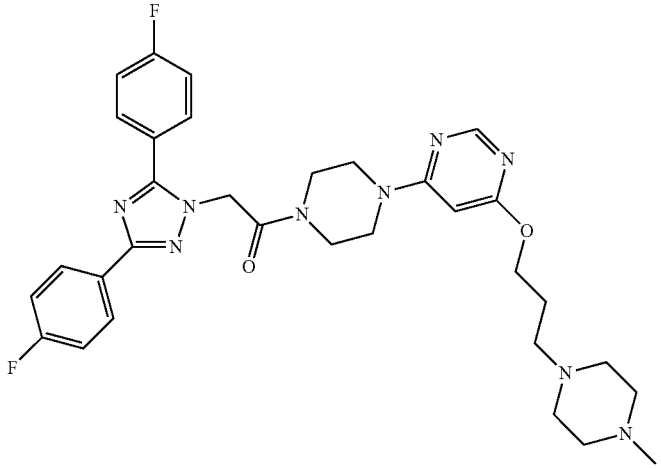 [SMILES: CN1CCN(CCCOc2cc(N3CCN(C(=O)Cn4nc(-c5ccc(F)cc5)nc4-c4ccc(F)cc4)CC3)ncn2)CC1] | 618 | method J | 1.42 |
| 7.09.27 | 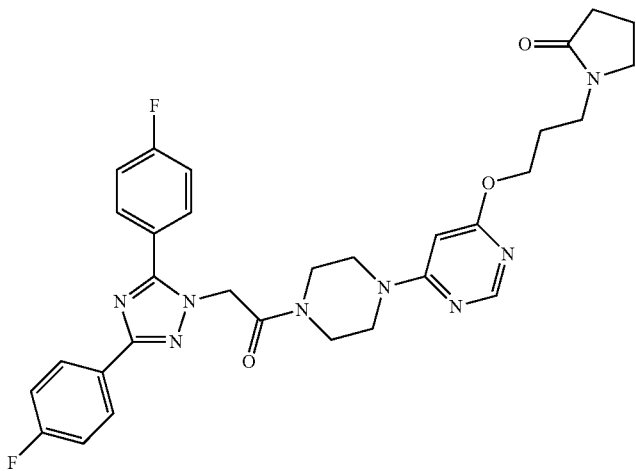 [SMILES: O=C1CCCN1CCCOc1cc(N2CCN(C(=O)Cn3nc(-c4ccc(F)cc4)nc3-c3ccc(F)cc3)CC2)ncn1] | 603 | method J | 1.74 |

| Examples | Product | MS m/z [M + H]+ | HPLC Method | Rt min |
|---|---|---|---|---|
| 7.09.28 | | 604 | method J | 1.46 |
| 7.09.29 | | 576 | method J | 1.87 |
| 7.09.30 | | 550 | method J | 1.87 |

7.10.01. 2-(3-(4-fluoro-3-methyl-phenyl)-5-phenyl-(1,2,4)triazol-1-yl)-1-(4-pyrimidin-2-yl-piperazin-1-yl)-ethanone

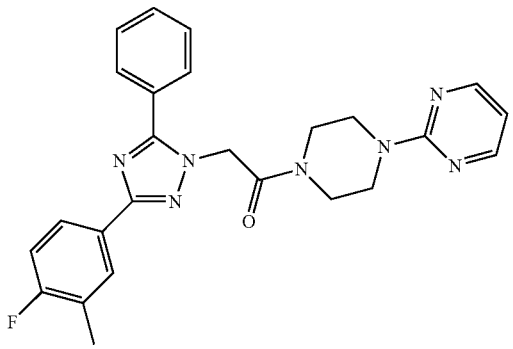 [SMILES: Cc1cc(-c2nc(-c3ccccc3)n(CC(=O)N3CCN(c4ncccn4)CC3)n2)ccc1F]

15 mg tetrakis(triphenylphosphine)palladium(0) was added to 100 mg 2-(3-bromo-5-phenyl-(1,2,4)triazol-1-yl)-1-(4-pyrimidin-2-yl-piperazin-1-yl)-ethanone, 500 μL 2 mol/L aqueous sodiumdicarbonate solution and 43 mg 4-fluoro-3-methylphenylboronic acid in 10 mL dioxane under nitrogen. The reaction was stirred over night at 120° C. The reaction was filltered and evaporated. The residue was purified by HPLC to give 32 mg of the desired product.

$R_t$: 1.38 min (method B), (M+H)$^+$: 458

By using the same synthesis strategy as for 2-(3-(4-fluoro-3-methyl-phenyl)-5-phenyl-(1,2,4)triazol-1-yl)-1-(4-pyrimidin-2-yl-piperazin-1-yl)-ethanone the following compounds were obtained:

| Examples | Product | MS m/z [M + H]$^+$ | HPLC Method | Rt min |
|---|---|---|---|---|
| 7.10.02 | 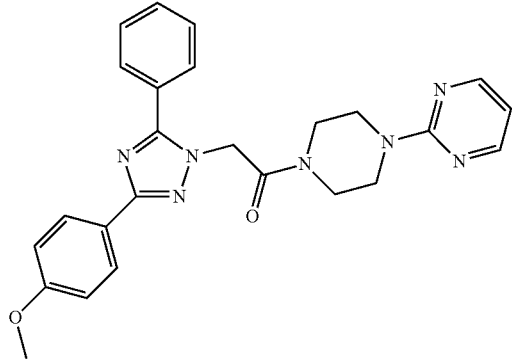 [SMILES: COc1ccc(-c2nc(-c3ccccc3)n(CC(=O)N3CCN(c4ncccn4)CC3)n2)cc1] | 456 | method B | 1.28 |
| 7.10.03 | 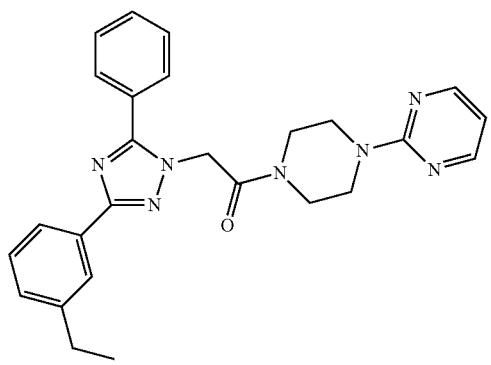 [SMILES: CCc1cccc(-c2nc(-c3ccccc3)n(CC(=O)N3CCN(c4ncccn4)CC3)n2)c1] | 454 | method B | 1.40 |

-continued

| Examples | Product | MS m/z [M + H]+ | HPLC Method | Rt min |
|---|---|---|---|---|
| 7.10.04 | | 470 | method B | 1.36 |
| 7.10.05 | | 440 | method B | 1.34 |
| 7.10.06 | | 451 | method B | 1.24 |
| 7.10.07 | | 444 | method B | 1.33 |

-continued

| Examples | Product | MS m/z [M + H]⁺ | HPLC Method | Rt min |
|---|---|---|---|---|
| 7.10.08 | | 470 | method B | 1.25 |
| 7.10.09 | | 486 | method B | 1.32 |
| 7.10.10 | | 456 | method B | 1.27 |
| 7.10.11 | | 554 | method B | 1.40 |

| Examples | Product | MS m/z [M + H]+ | HPLC Method | Rt min |
|---|---|---|---|---|
| 7.10.12 | 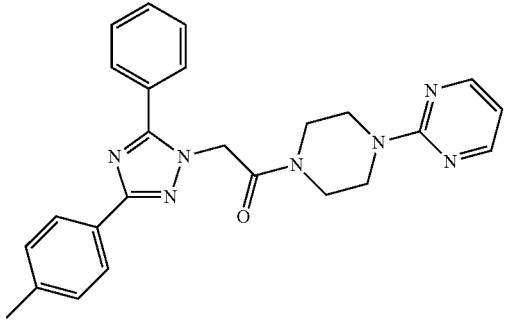 [SMILES: Cc1ccc(-c2nc(-c3ccccc3)n(CC(=O)N3CCN(c4ncccn4)CC3)n2)cc1] | 440 | method B | 1.33 |
| 7.10.13 | 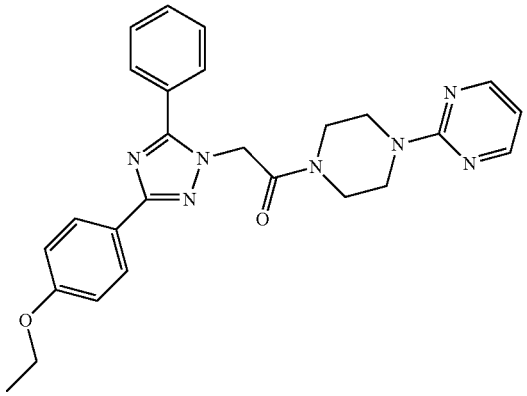 [SMILES: CCOc1ccc(-c2nc(-c3ccccc3)n(CC(=O)N3CCN(c4ncccn4)CC3)n2)cc1] | 470 | method B | 1.35 |
| 7.10.14 | 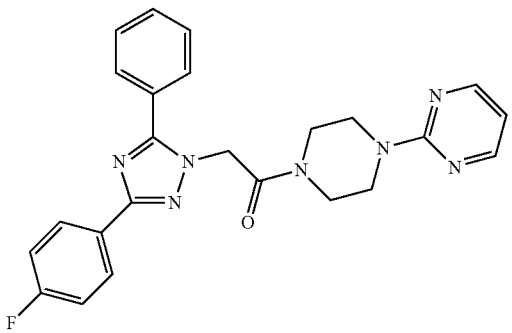 [SMILES: O=C(Cn1nc(-c2ccc(F)cc2)nc1-c1ccccc1)N1CCN(c2ncccn2)CC1] | 444 | method B | 1.31 |
| 7.10.15 | 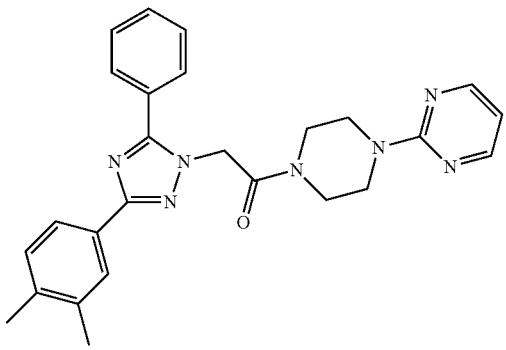 [SMILES: Cc1ccc(-c2nc(-c3ccccc3)n(CC(=O)N3CCN(c4ncccn4)CC3)n2)cc1C] | 454 | method B | 1.41 |

-continued

| Examples | Product | MS m/z [M + H]⁺ | HPLC Method | Rt min |
|---|---|---|---|---|
| 7.10.16 | | 454 | method B | 1.42 |
| 7.10.17 | | 470 | method B | 1.36 |
| 7.10.18 | | 484 | method B | 1.39 |
| 7.10.19 | | 440 | method B | 1.33 |

| Examples | Product | MS m/z [M + H]+ | HPLC Method | Rt min |
|---|---|---|---|---|
| 7.10.20 | | 468 | method B | 1.44 |
| 7.10.21 | | 465 | method B | 1.20 |
| 7.10.22 | | 440 | method B | 1.34 |
| 7.10.23 | | 416 | method B | 1.27 |

| Examples | Product | MS m/z [M + H]+ | HPLC Method | Rt min |
|---|---|---|---|---|
| 7.10.24 | | 470 | method B | 1.27 |
| 7.10.25 | | 451 | method B | 1.27 |
| 7.10.26 | | 430 | method B | 1.34 |
| 7.10.27 | | 390 | method B | 1.19 |

-continued
| Examples | Product | MS m/z [M + H]+ | HPLC Method | Rt min |
|---|---|---|---|---|
| 7.10.28 | 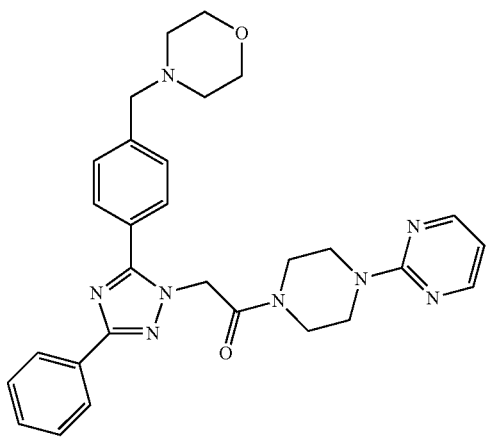 [SMILES: O=C(Cn1nc(-c2ccccc2)nc1-c1ccc(CN2CCOCC2)cc1)N1CCN(c2ncccn2)CC1] | 525 | method B | 1.12 |
| 7.10.29 | 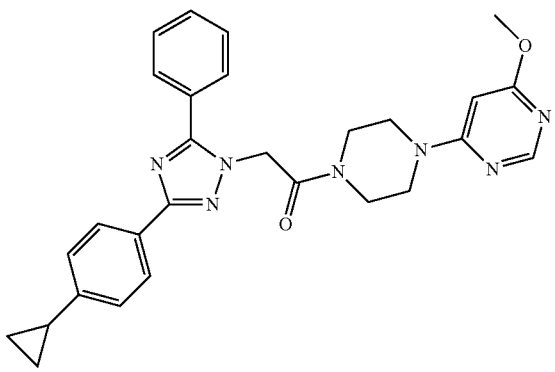 [SMILES: COc1cc(N2CCN(C(=O)Cn3nc(-c4ccc(C5CC5)cc4)nc3-c3ccccc3)CC2)ncn1] | 496 | method B | 1.31 |
| 7.10.30 | 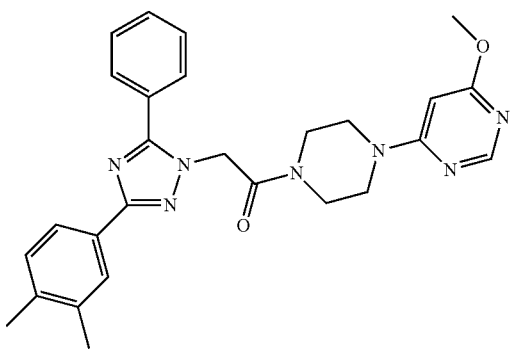 [SMILES: COc1cc(N2CCN(C(=O)Cn3nc(-c4ccc(C)c(C)c4)nc3-c3ccccc3)CC2)ncn1] | 484 | method B | 1.29 |

| Examples | Product | MS m/z [M + H]+ | HPLC Method | Rt min |
|---|---|---|---|---|
| 7.10.31 | | 542 | method B | 1.37 |
| 7.10.32 | | 474 | method B | 1.23 |
| 7.10.33 | | 492 | method B | 1.27 |
| 7.10.34 | | 498 | method B | 1.36 |

| Examples | Product | MS m/z [M + H]+ | HPLC Method | Rt min |
|---|---|---|---|---|
| 7.10.35 | | 470 | method B | 1.24 |
| 7.10.36 | | 484 | method B | 1.31 |
| 7.10.37 | | 508 | method B | 1.34 |
| 7.10.38 | | 497 | method B | 1.36 |

-continued
| Examples | Product | MS m/z [M + H]+ | HPLC Method | Rt min |
|---|---|---|---|---|
| 7.10.39 | 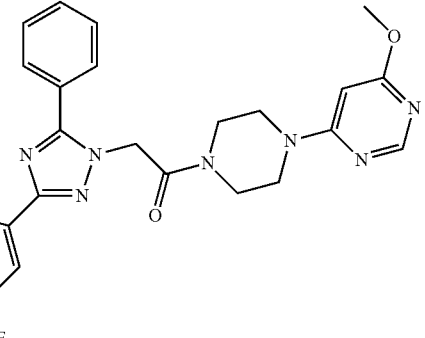 | 510 | method B | 1.36 |
| 7.10.40 | 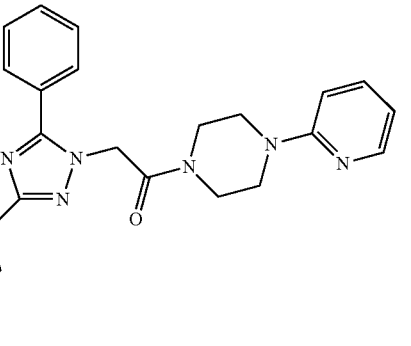 | 443 | method B | 1.11 |
| 7.10.41 | 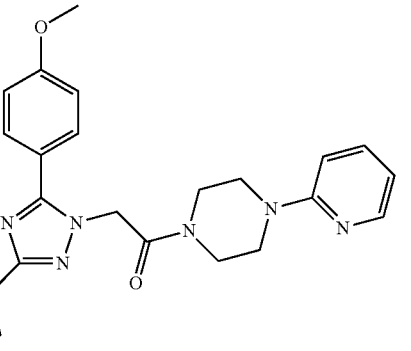 | 473 | method B | 1.13 |
| 7.10.42 | 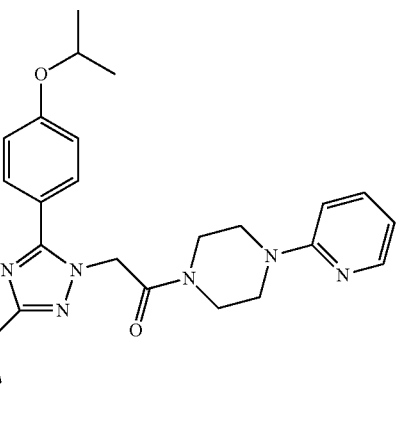 | 473 | method B | 1.13 |

-continued

| Examples | Product | MS m/z [M + H]+ | HPLC Method | Rt min |
|---|---|---|---|---|
| 7.10.43 | 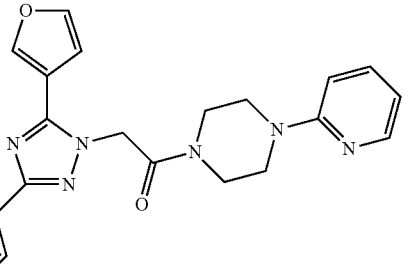 | 473 | method B | 1.13 |

7.11.01. 2-(3-(4-fluoro-phenyl)-5-phenylethynyl-(1,2,4)triazol-1-yl)-1-(4-pyridin-2-yl-piperazin-1-yl)-ethanone

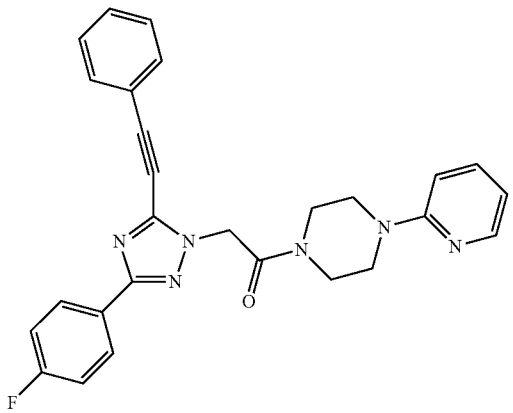 [SMILES: O=C(Cn1nc(-c2ccc(F)cc2)nc1C#Cc1ccccc1)N1CCN(c2ccccn2)CC1]

20 mg triphenylphosphinpalladium(II)chloride and 5 mg cupper(I)iodide were added to 100 mg 2-(5-bromo-3-(4-fluoro-phenyl)-(1,2,4)triazol-1-yl]-1-(4-pyridin-2-yl-piperazin-1-yl)-ethanone, 250 µl triethylamine and 45 mg ethynylbenzene acid in 5 mL tetrahydrofuran. The reaction was stirred 2 h at 70° C. The reaction was filltered and evaporated. The residue was purified by HPLC to give 5 mg desired product. $R_t$: 1.24 min (method B), (M+H)+: 467

By using the same synthesis strategy as for 2-(3-(4-fluoro-phenyl)-5-phenylethynyl-(1,2,4)triazol-1-yl)-1-(4-pyridin-2-yl-piperazin-1-yl)-ethanone the following compounds were obtained:

| Examples | Product | MS m/z [M + H]+ | HPLC Method | Rt min |
|---|---|---|---|---|
| 7.11.02 | 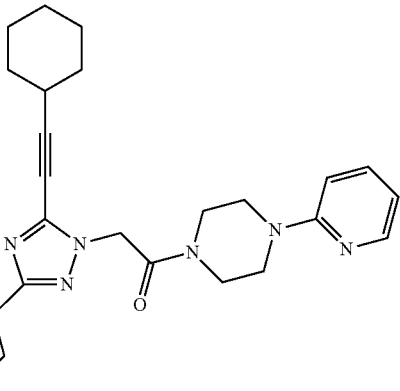 | 473 | method B | 1.31 |

The invention claimed is:

1. A compound of formula I

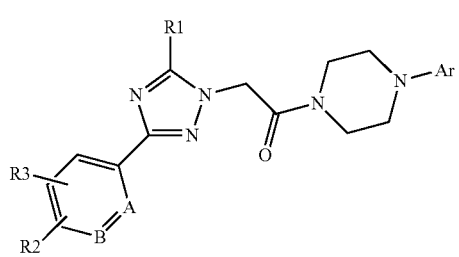

in which

A and B independently represent CH or N;

R[1] represents phenylethynyl, $C_{3-6}$cycloalkylethynyl, $C_{2-5}$alkenyl, $C_{5-7}$cycloalkenyl, aryl, heteroaryl, $C_{1-8}$alkyl, $C_{3-7}$cycloalkyl or —O—$C_{1-8}$alkyl which latter five groups are optionally substituted with one or more substituents selected from halogen, cyano, $C_{1-3}$alkyl, $C_{3-6}$cycloalkyl, —O—$C_{1-3}$alkyl, —CH$_2$—O—CH$_3$, —CH$_2$-morpholine and —CH$_2$CN which latter six substituents are optionally substituted with one or more fluorine atoms;

R[2] and R[3] independently represent —H, halogen, —CN, —COO—$C_{1-4}$alkyl, $C_{1-5}$alkyl, $C_{3-5}$cycloalkyl or —O—$C_{1-5}$alkyl which latter four groups are optionally substituted with one or more fluorine atoms;

Ar represents;

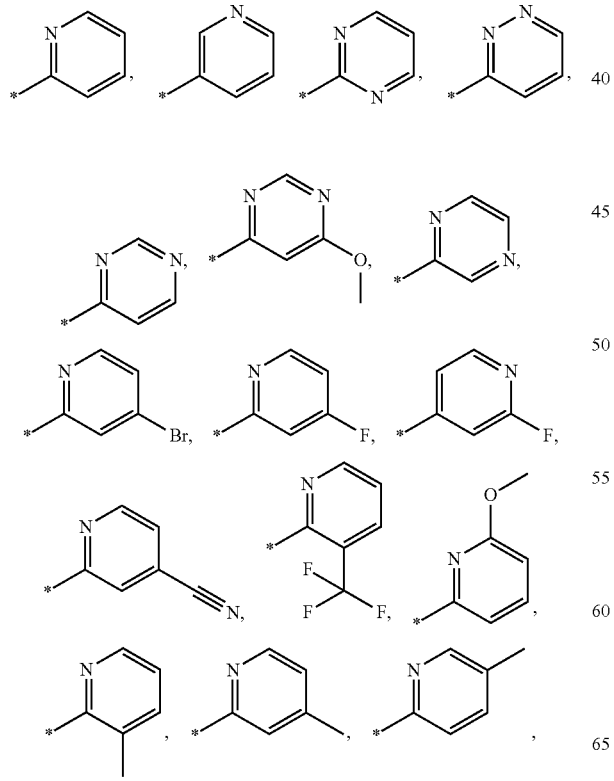

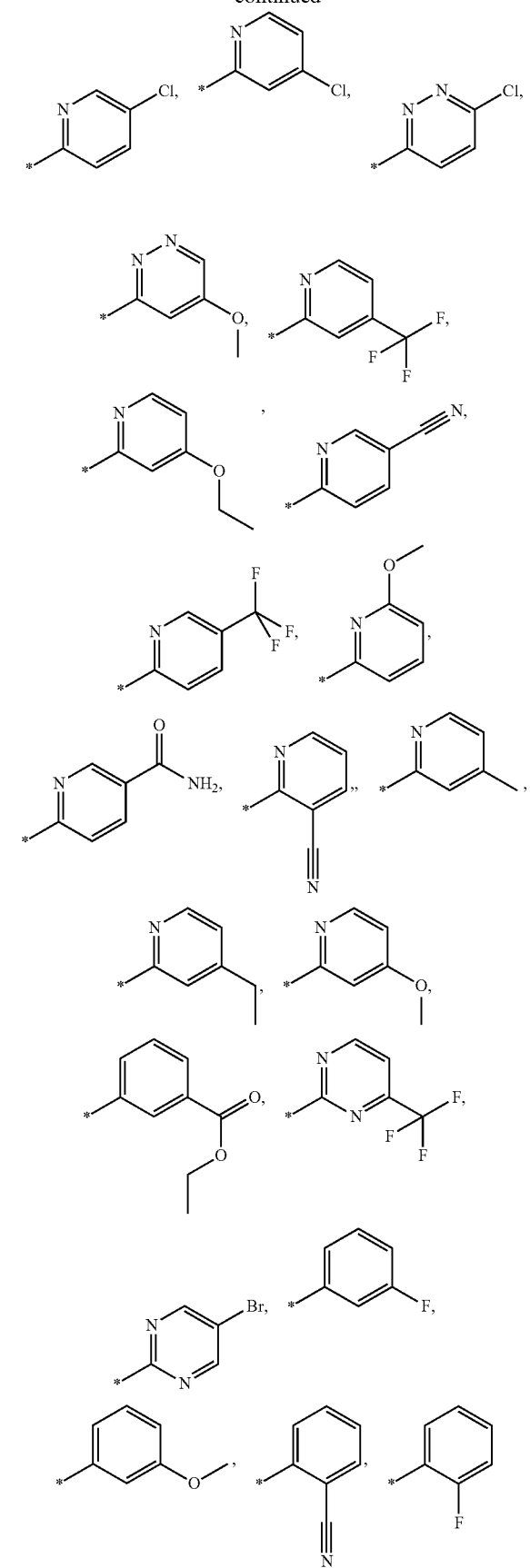

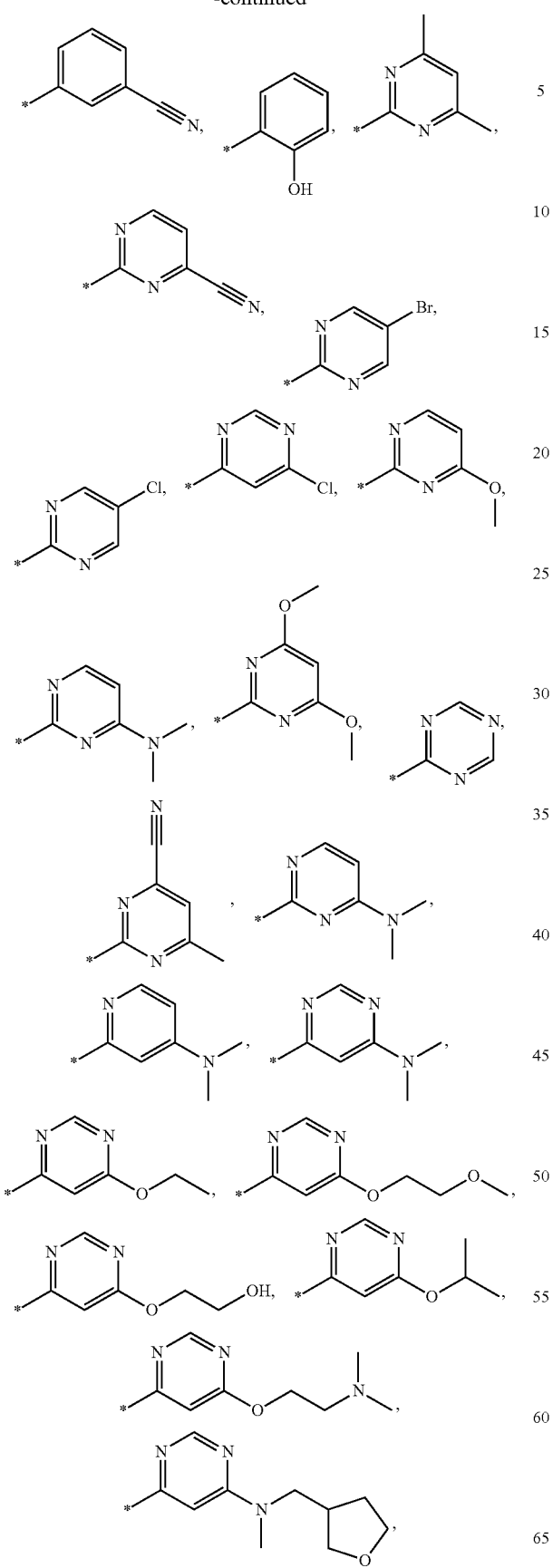
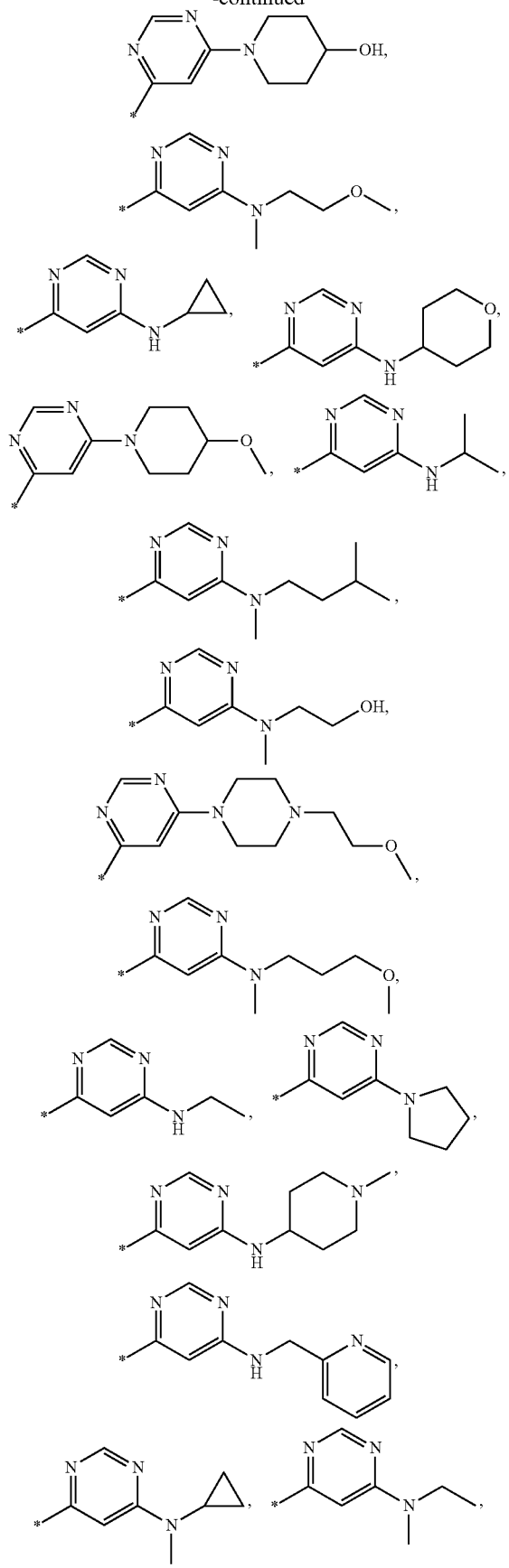

309
-continued
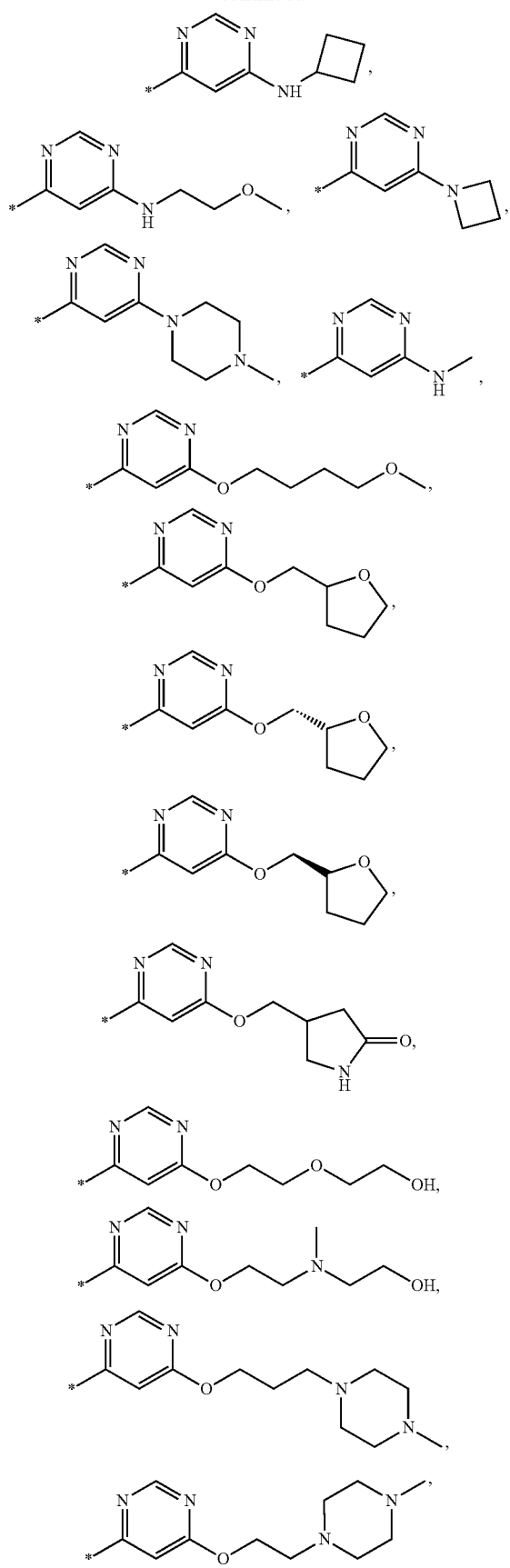
310
-continued
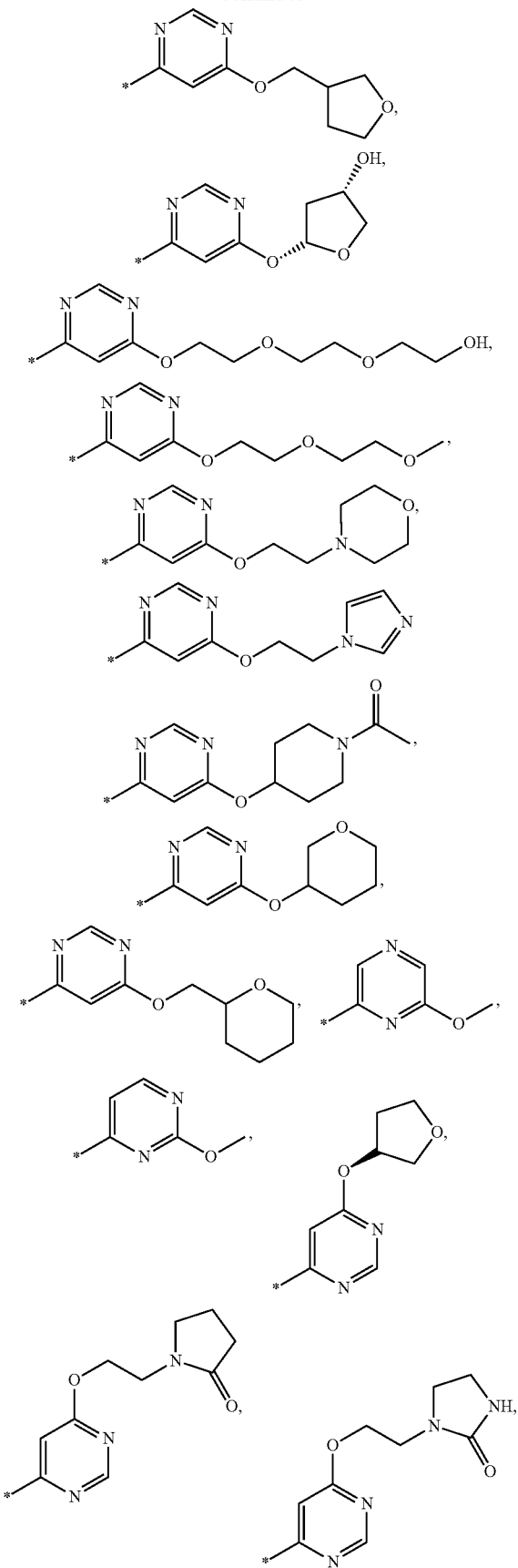

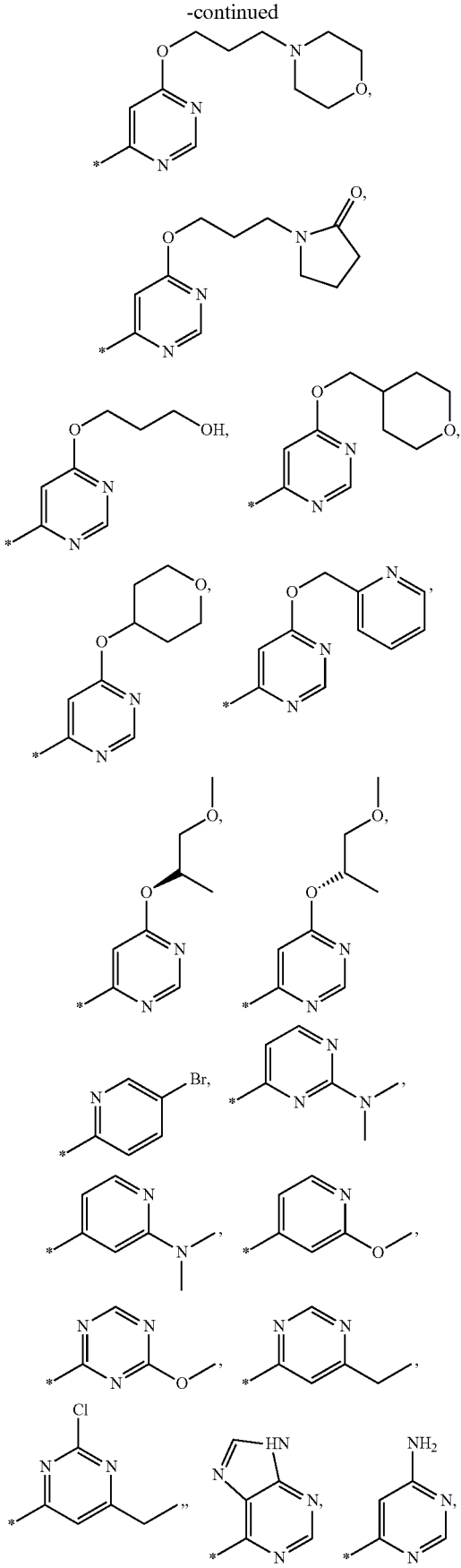

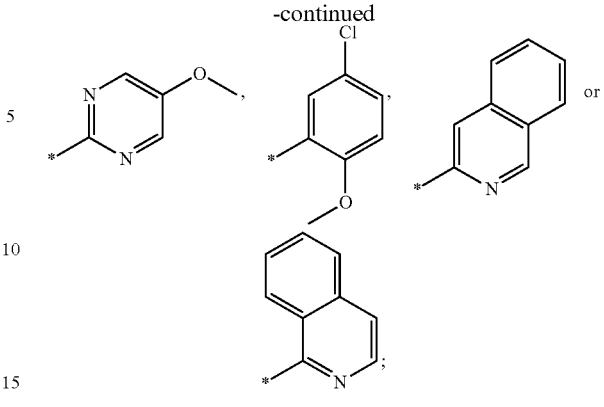

or a physiologically acceptable salt thereof.

2. The compound according to claim 1, wherein
R¹ represents phenylethynyl, cyclohexylethynyl, $C_{2-4}$alkenyl, $C_{5-6}$cycloalkenyl, phenyl, furyl, $C_{1-5}$alkyl or $C_{3-6}$cycloalkyl which latter four groups are optionally substituted with one or more substituents selected from fluoro, chloro, cyano, —$CH_2$-morpholine, —$CH_2$—O—$CH_3$, —$CH_2CN$, $C_{1-3}$alkyl, $C_{3-6}$cycloalkyl and —O—$C_{1-3}$alkyl which latter three substituents are optionally substituted with one or more fluorine atoms.

3. The compound according to claim 1, wherein
A represents N or CH;
B represents CH.

4. The compound according to claim 3, wherein the group

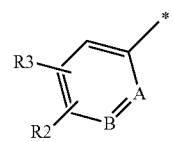

represents
phenyl or 2-pyridyl which latter two groups are optionally substituted with one or two substituents selected from fluoro, chloro, bromo, —CN and $C_{1-3}$alkyl optionally substituted with one or more fluorine atoms.

5. The compound according to claim 1, namely a compound of formula I

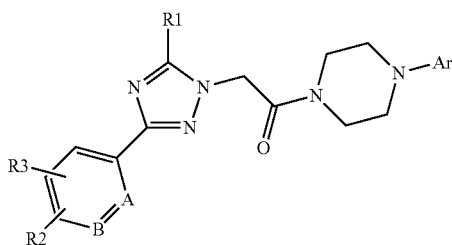

in which
R¹ represents phenylethynyl, cyclohexylethynyl, $C_{2-4}$alkenyl, $C_{5-6}$cycloalkenyl, phenyl, furyl, $C_{1-5}$alkyl or $C_{3-6}$cycloalkyl which latter four groups are optionally substituted with one or more substituents selected from fluoro, chloro, cyano, —$CH_2$-morpholine, —$CH_2$—$CH_3$, —$CH_2CN$, $C_{1-3}$alkyl, $C_{3-6}$cycloalkyl and —O—C$_{1-3}$alkyl which latter three substituents are optionally substituted with one or more fluorine atoms; and the group

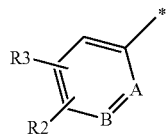

represents phenyl or 2-pyridyl which latter two groups are optionally substituted with one or two substituents selected from fluoro, chloro, bromo, —CN and C$_{1-3}$alkyl optionally substituted with one or more fluorine atoms;

or a physiologically acceptable salt thereof.

6. The compound according to claim 5, wherein

R$^1$ represents phenyl, methyl, ethyl, propyl, iso-propyl, n-butyl, n-pentyl, cyclopentyl, cyclohexyl,

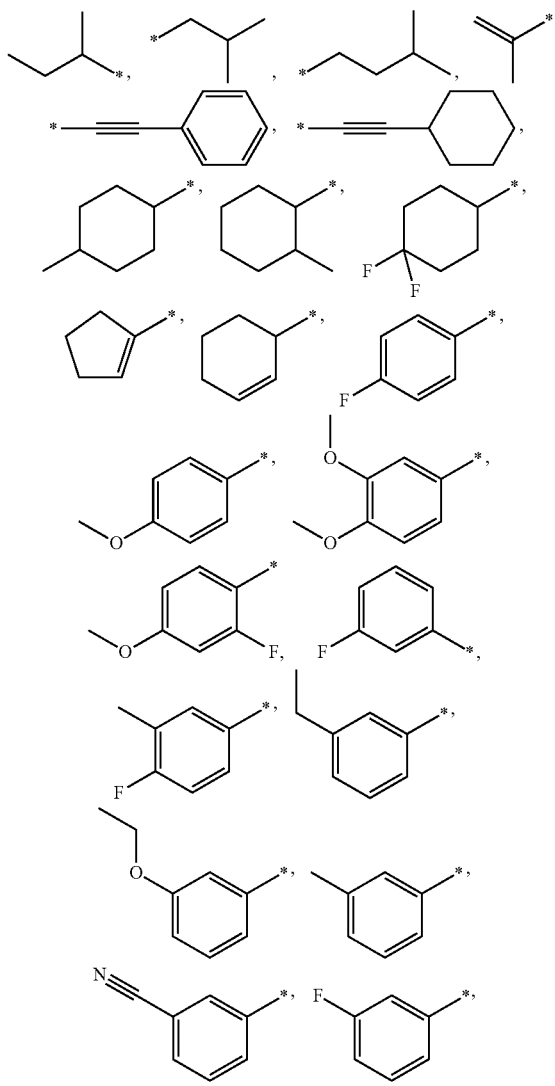

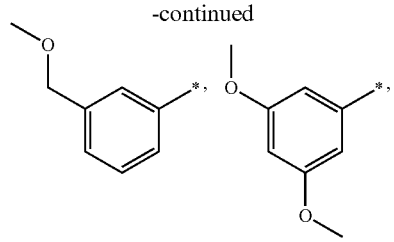

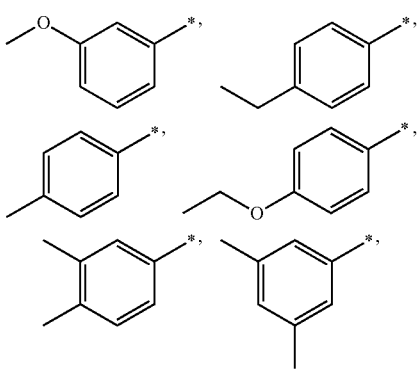

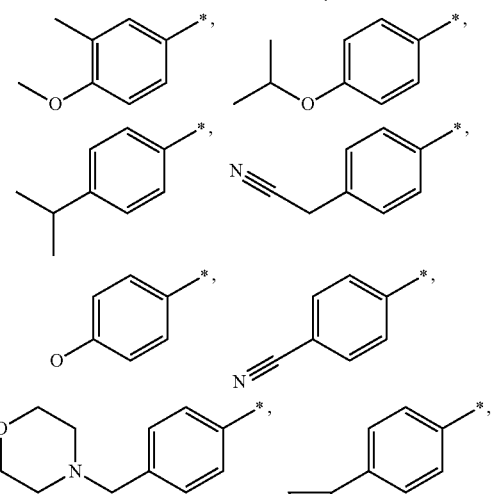

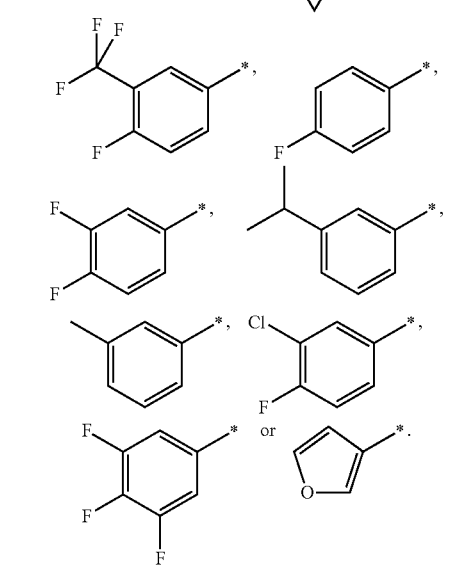

7. The compound according to claim 6, wherein the group
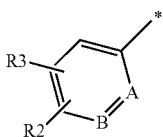
represents
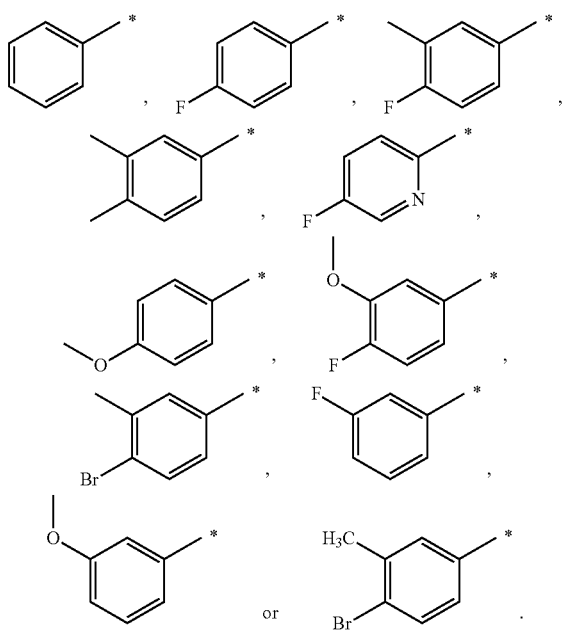
or
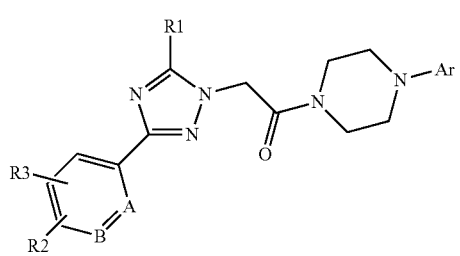
.
8. The compound according to claim 1, namely a compound of formula I
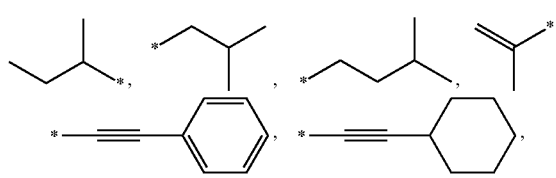
in which
R¹ represents phenyl, methyl, ethyl, propyl, iso-propyl, n-butyl, n-pentyl, cyclopentyl, cyclohexyl,
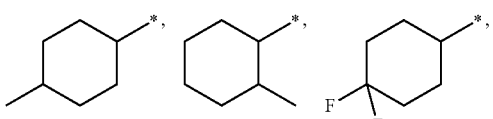
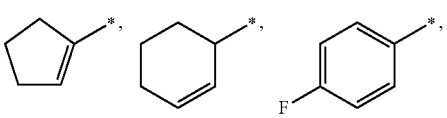
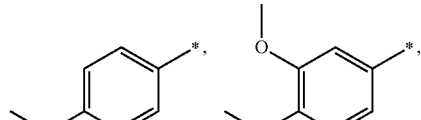
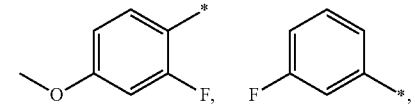
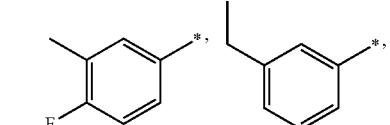
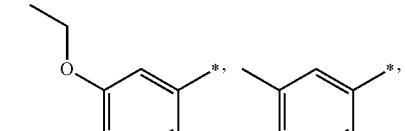
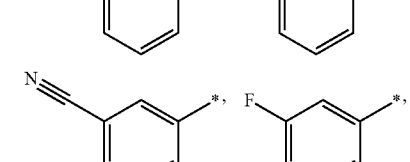
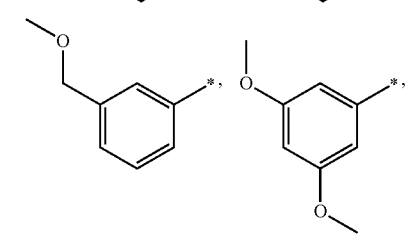
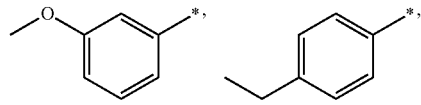
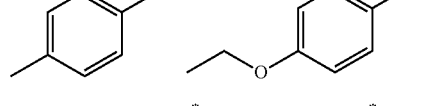
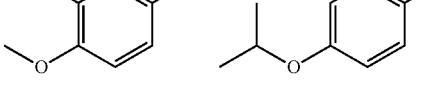

317
-continued
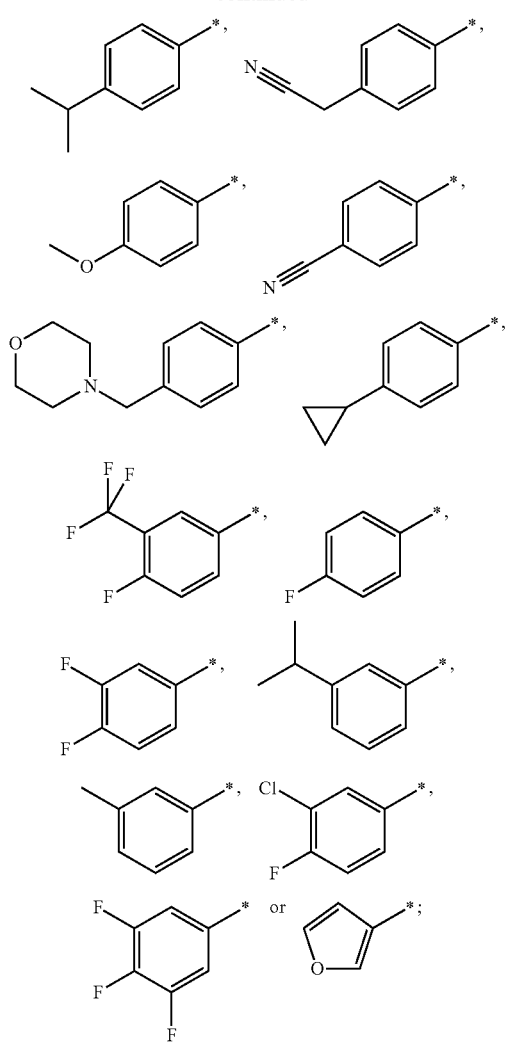
Ar represents
318
-continued
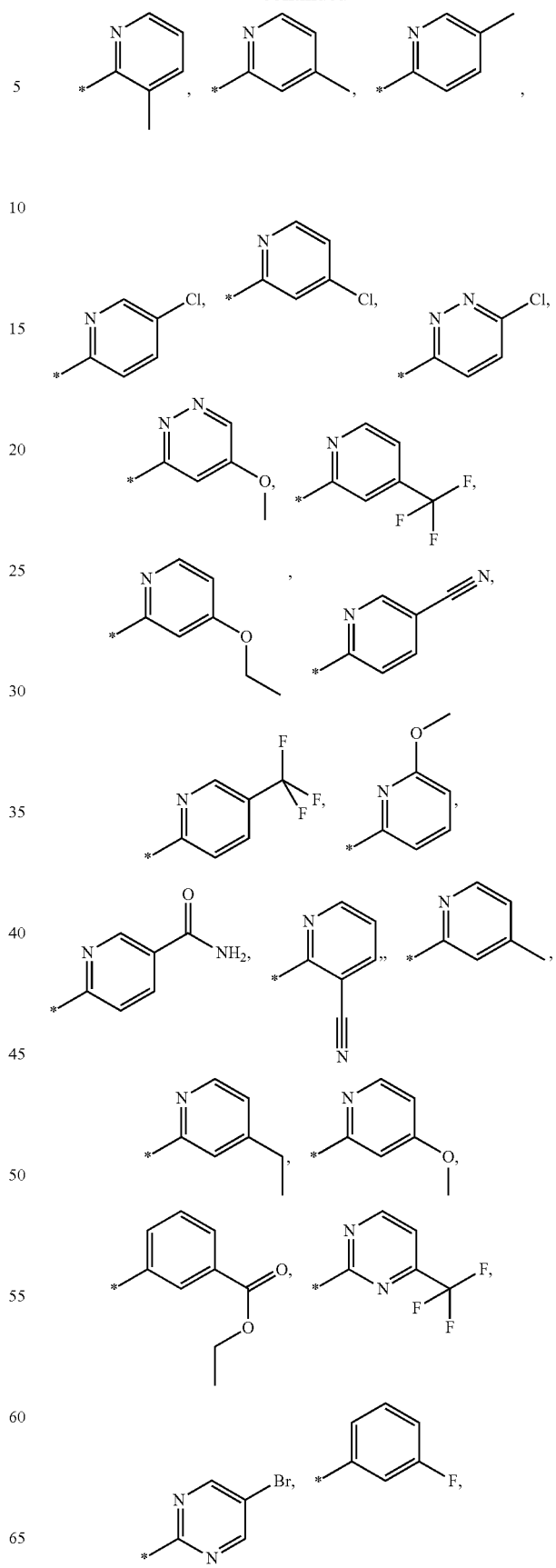

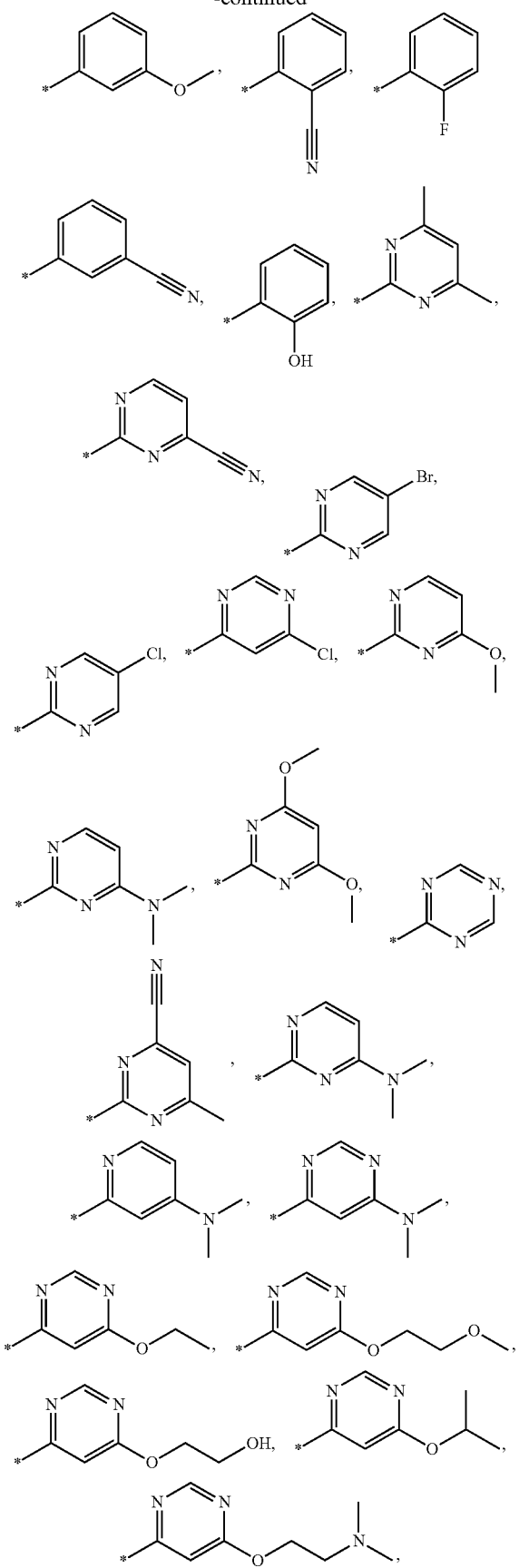
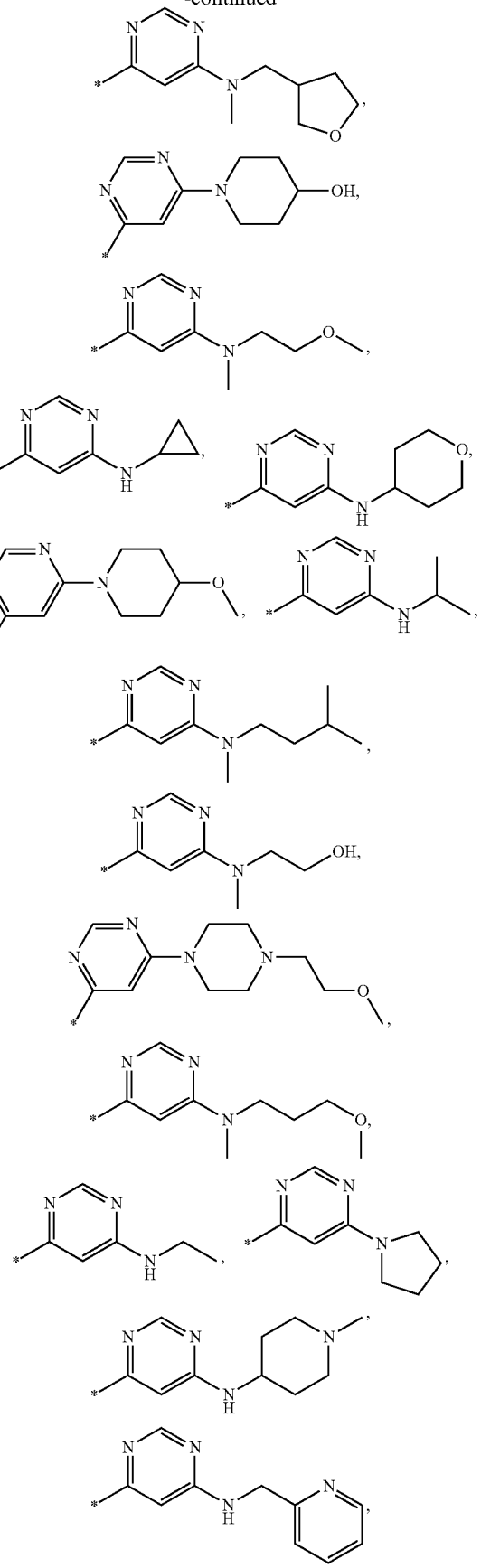

321
-continued
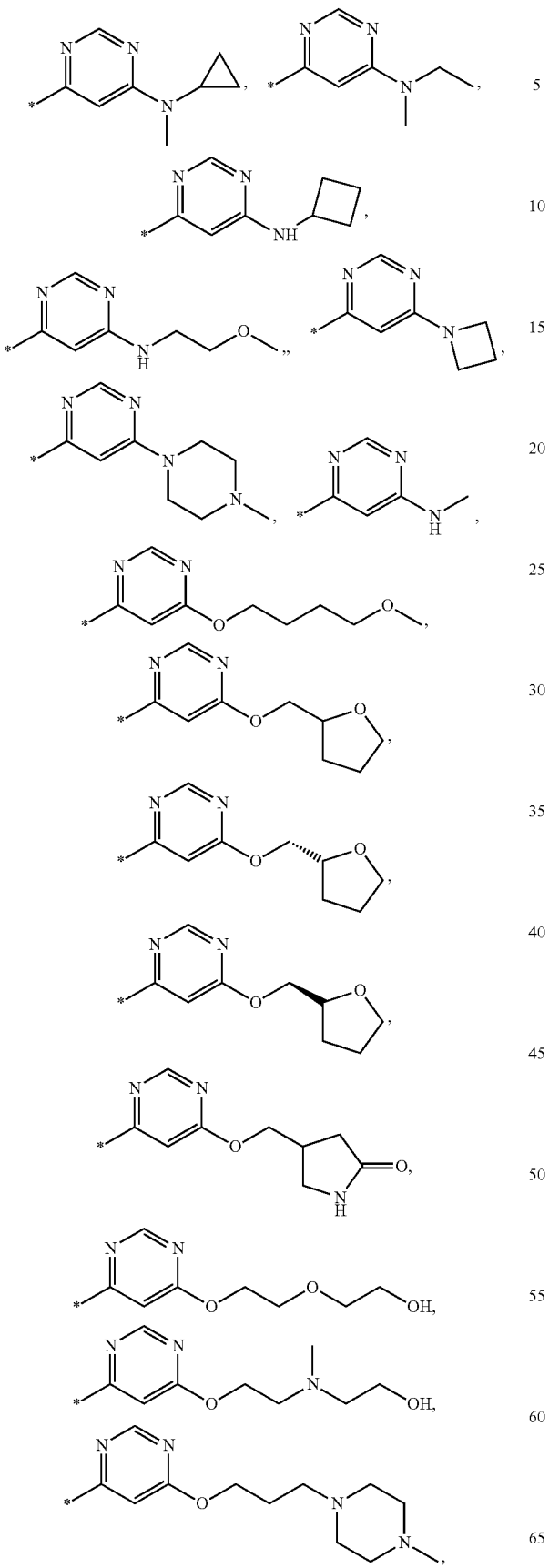
322
-continued
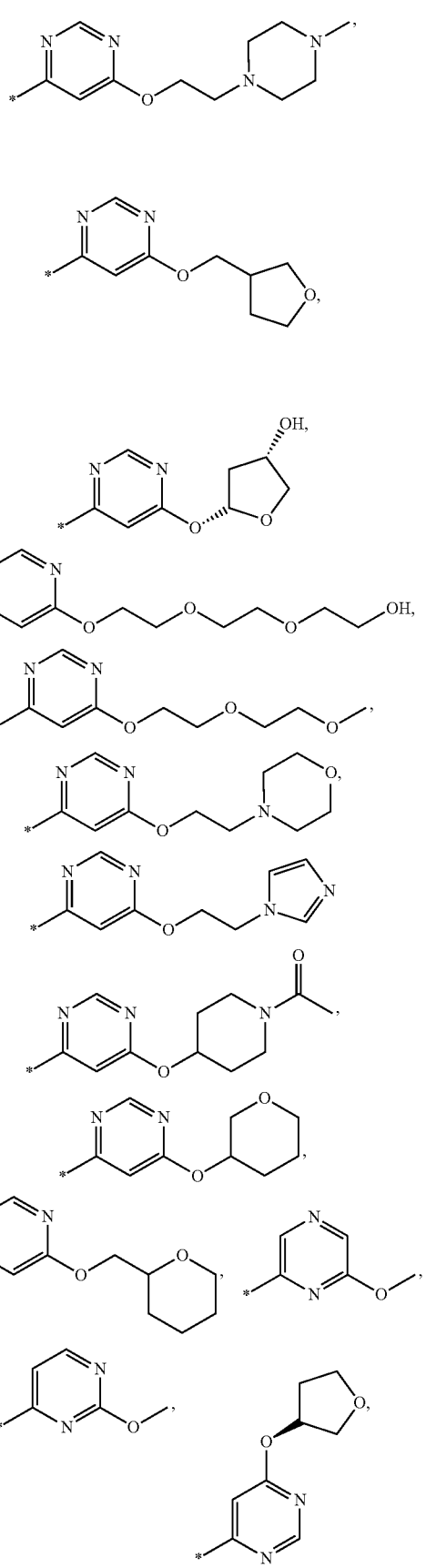

323
-continued
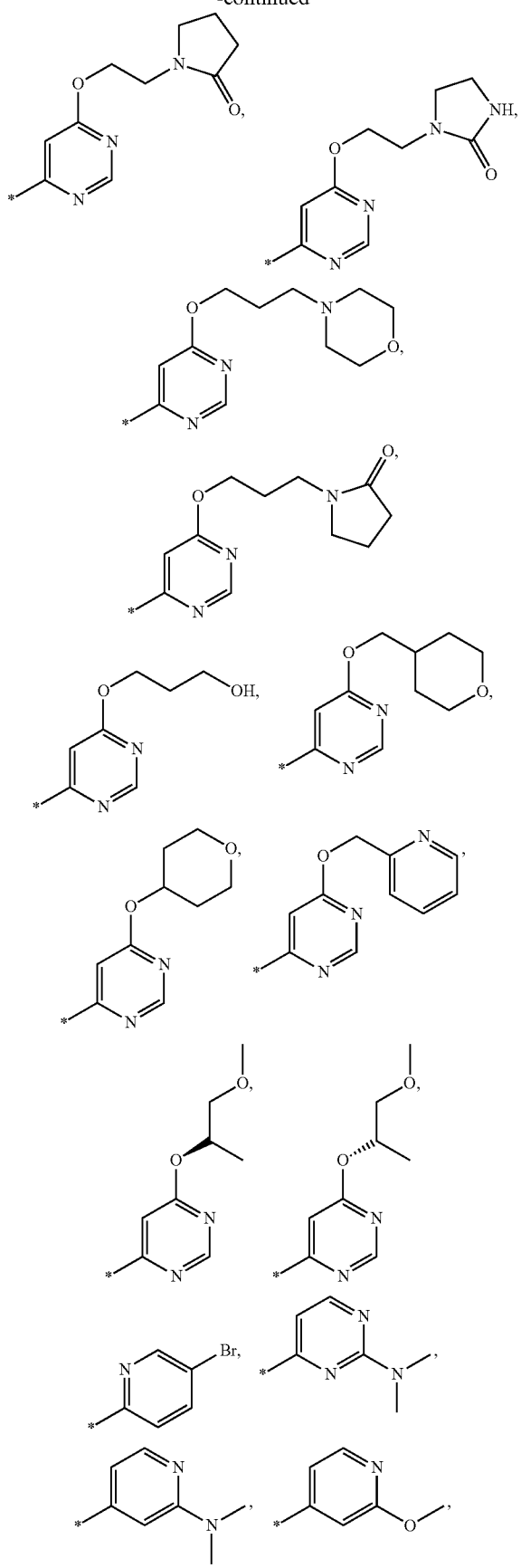
324
-continued
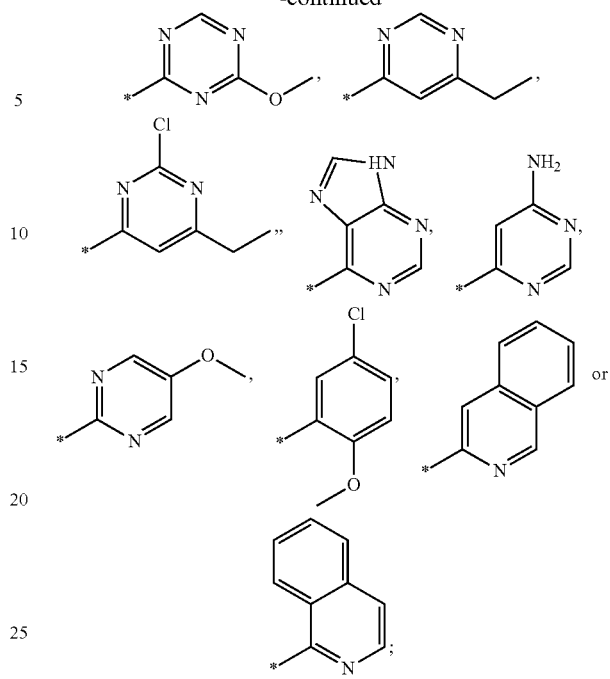
the group
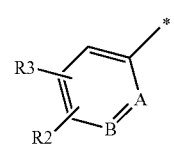
represents
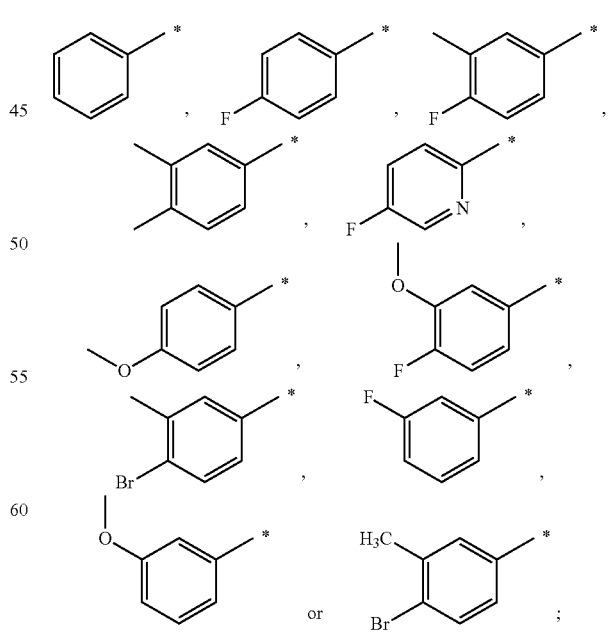
or a physiologically acceptable salt thereof.

9. A compound selected from
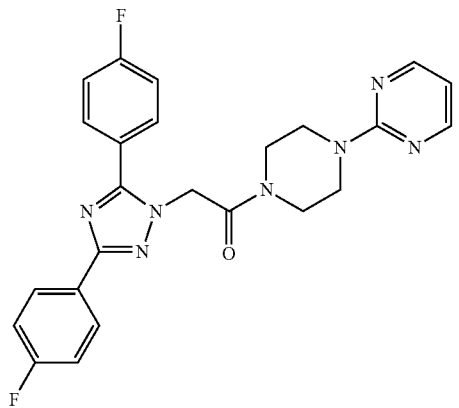
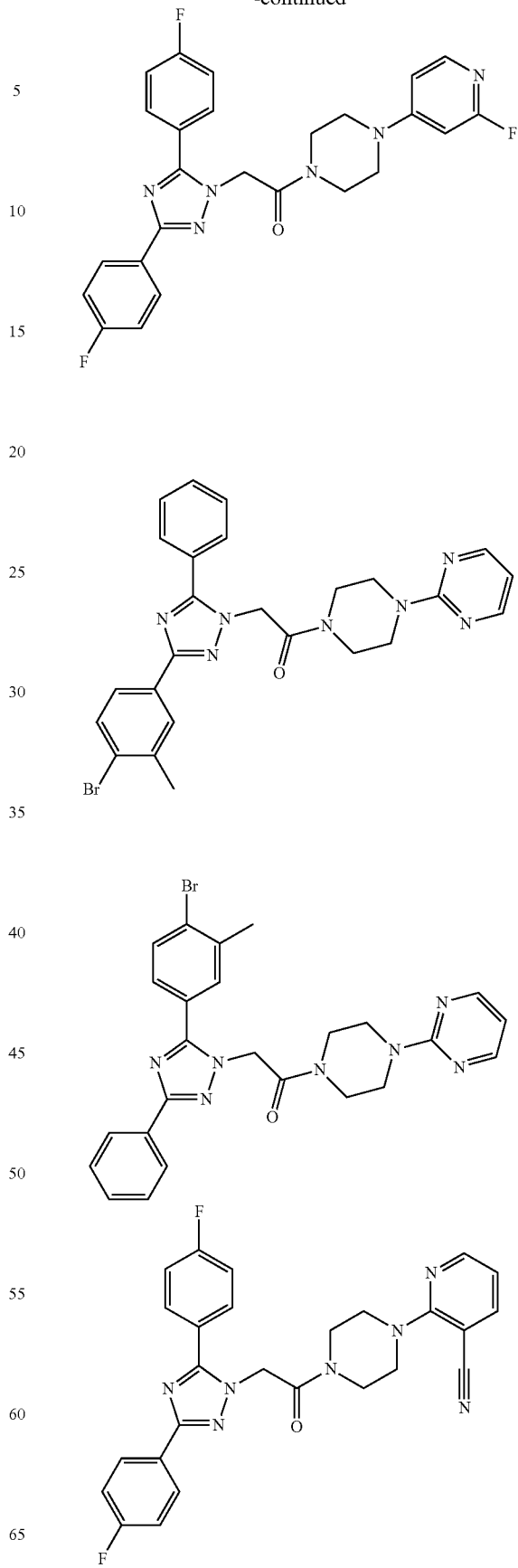

327
-continued
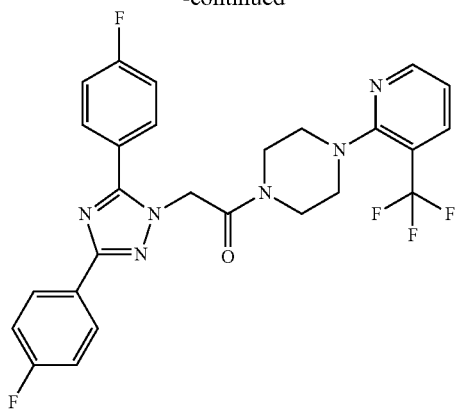
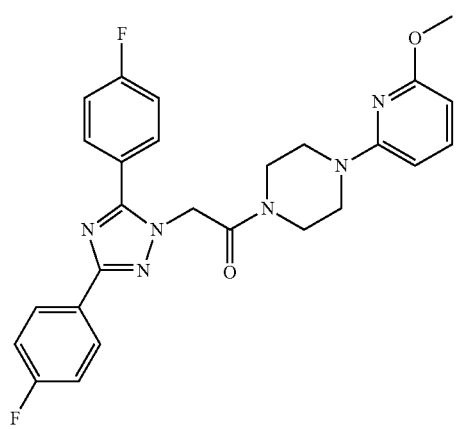
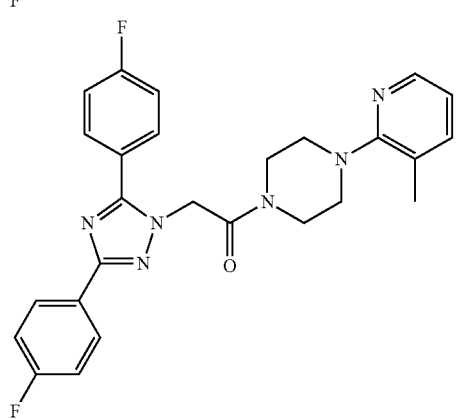
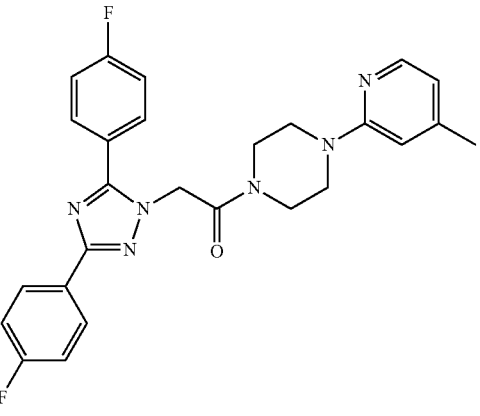
328
-continued
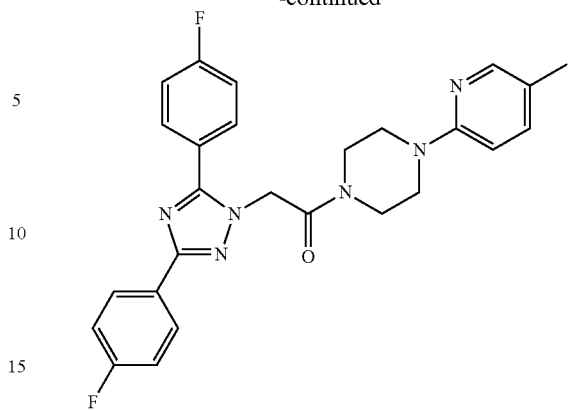
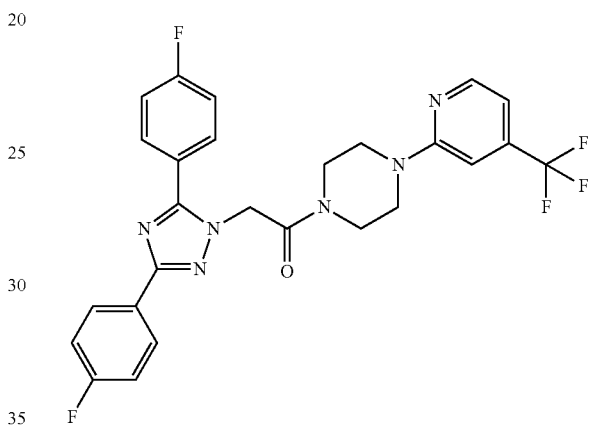
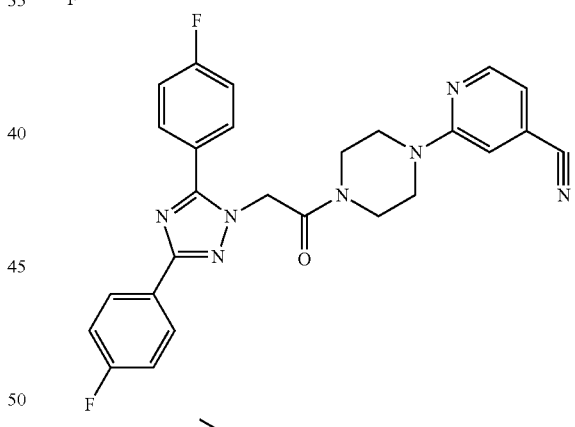
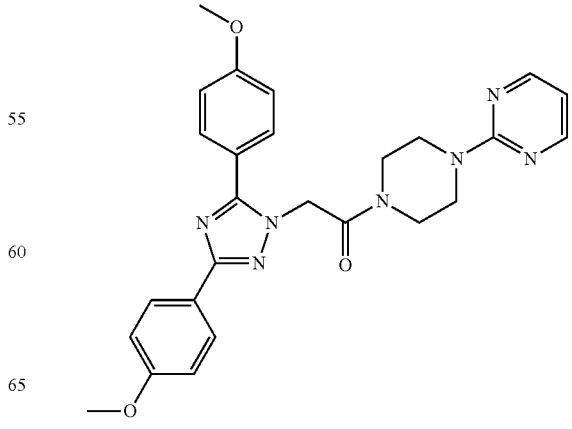

329
-continued
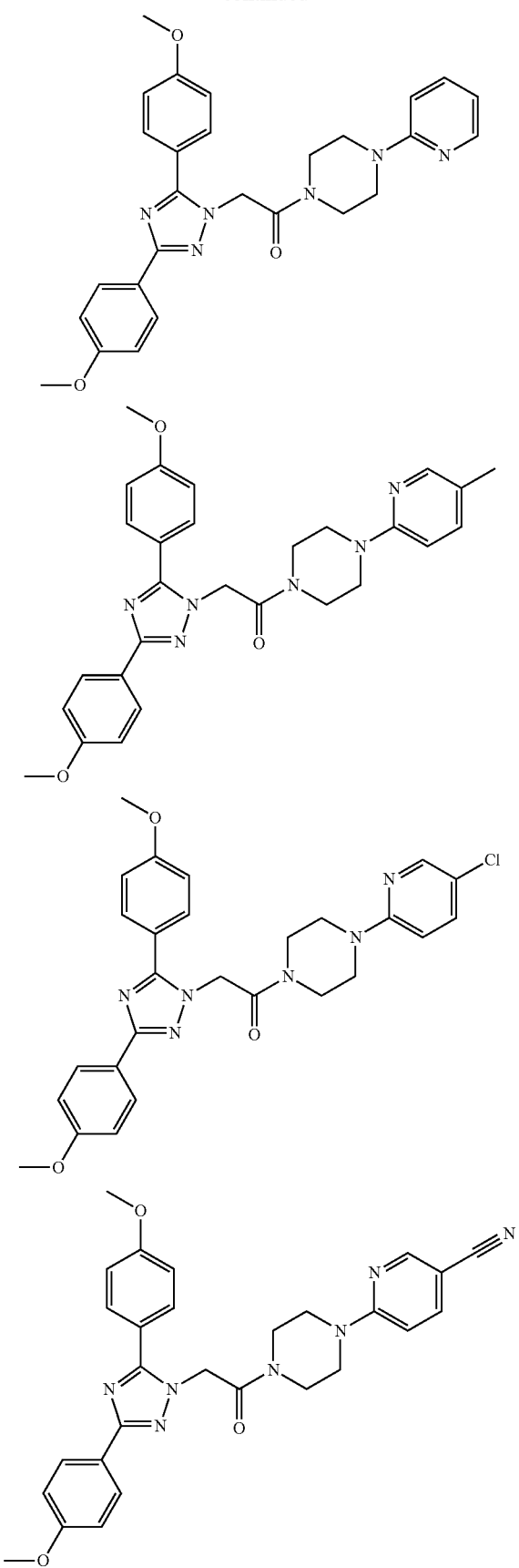
330
-continued
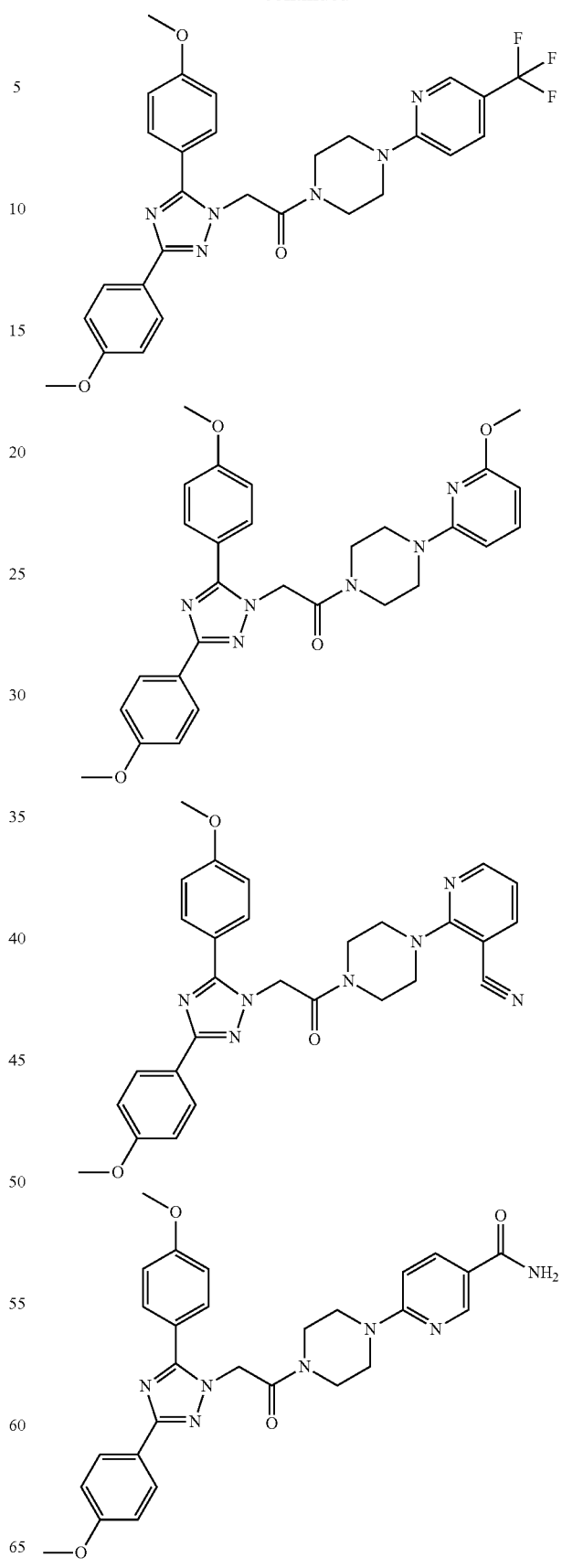

331
-continued
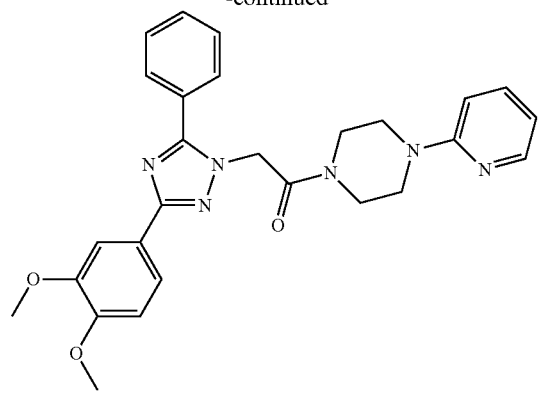
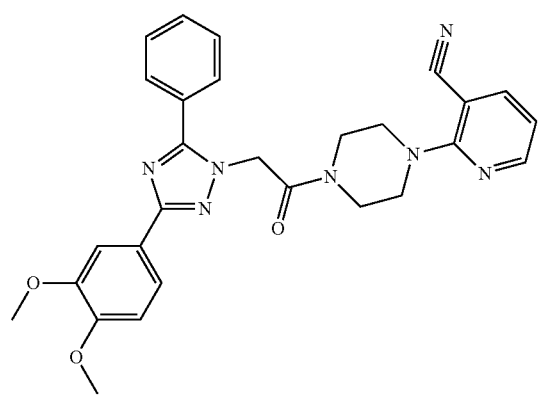
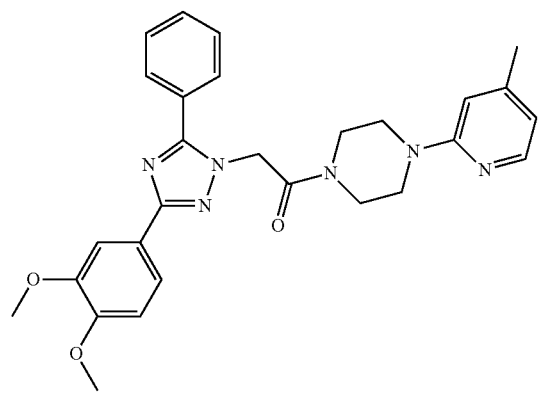
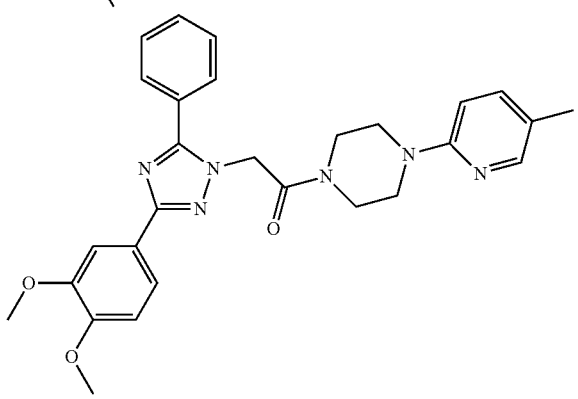
332
-continued
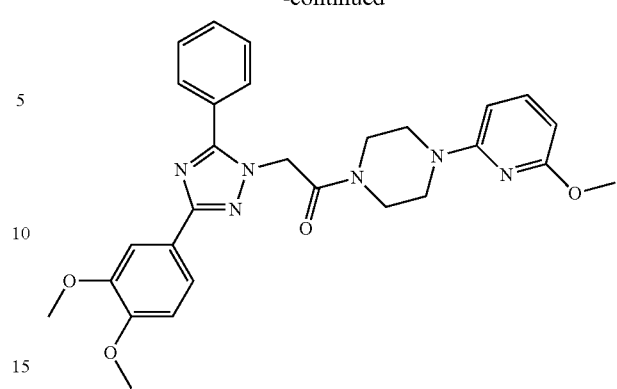
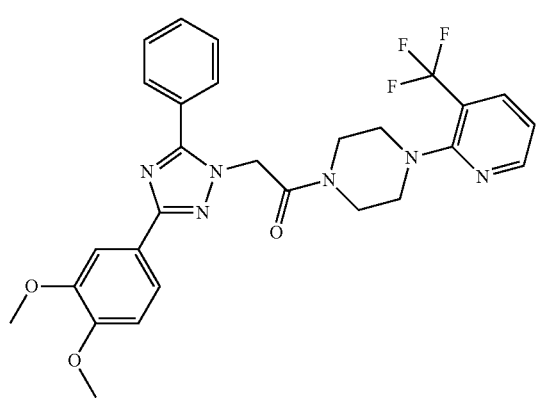
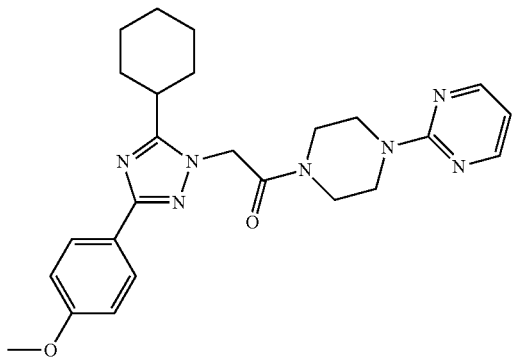
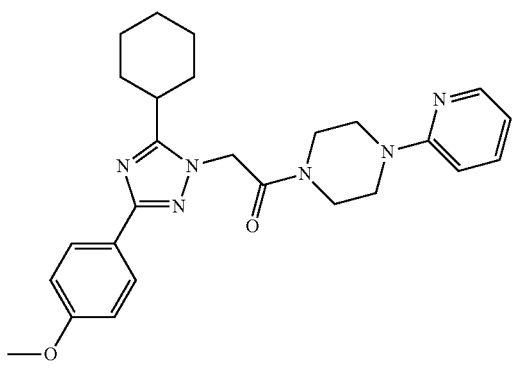

333
-continued
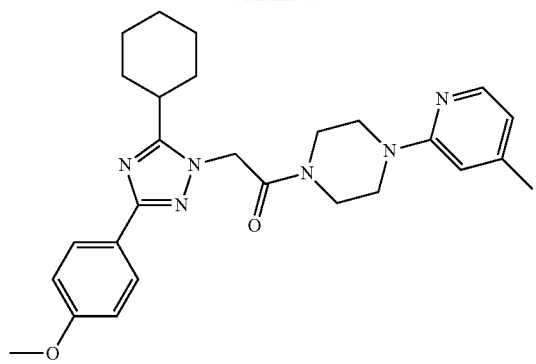
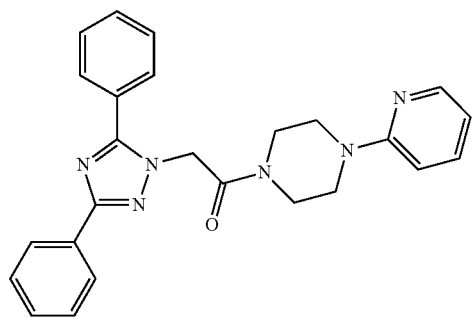
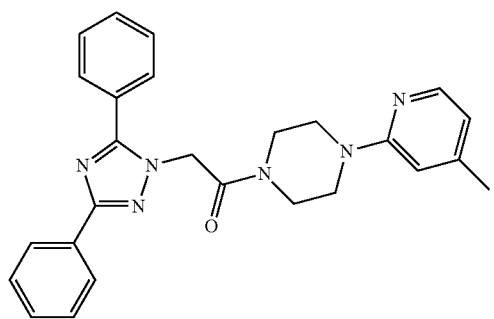
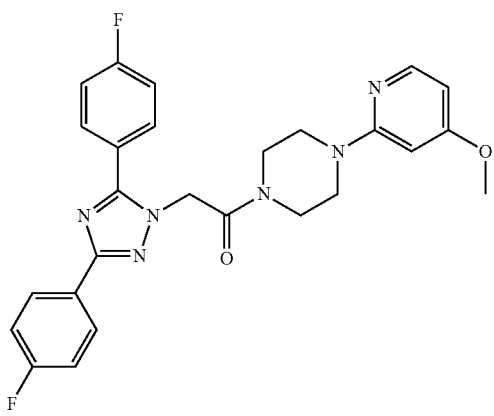
334
-continued
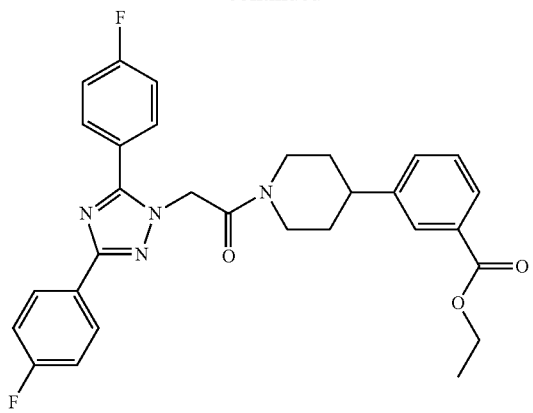
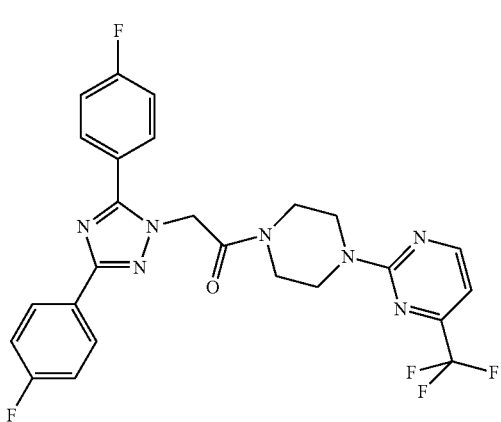
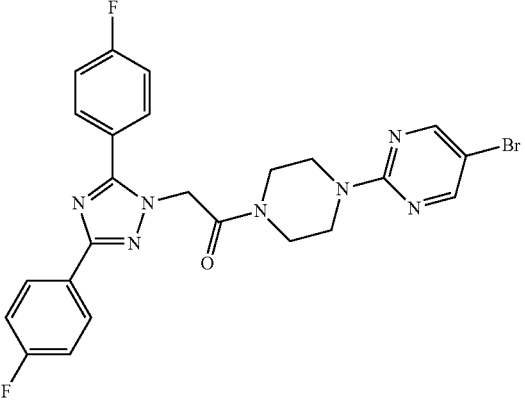
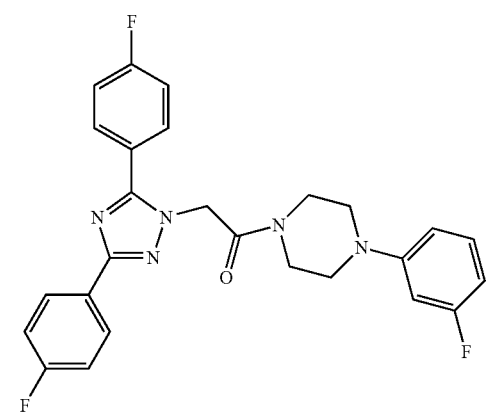

335
-continued
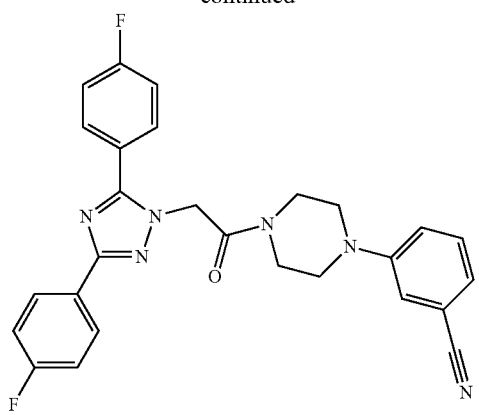
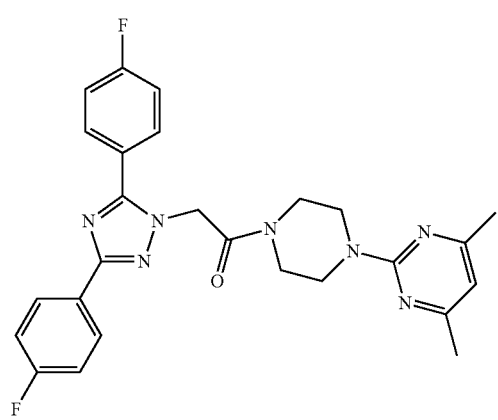
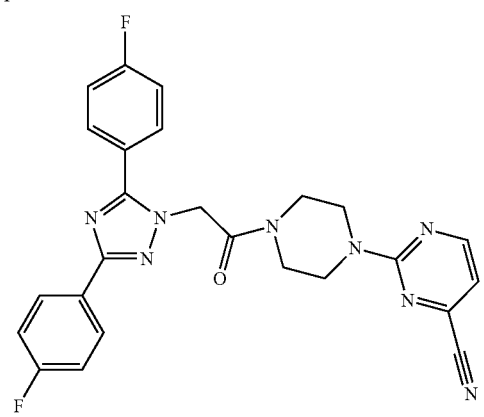
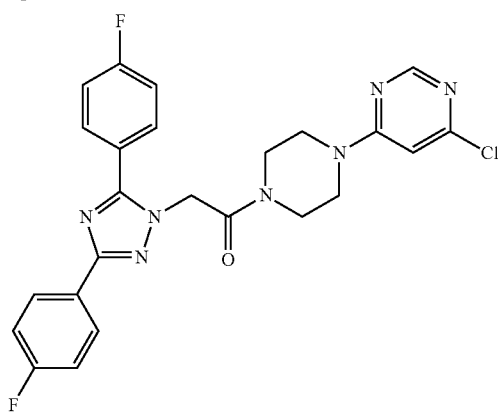
336
-continued
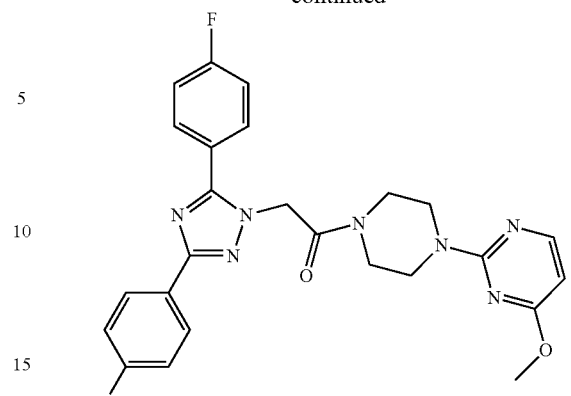
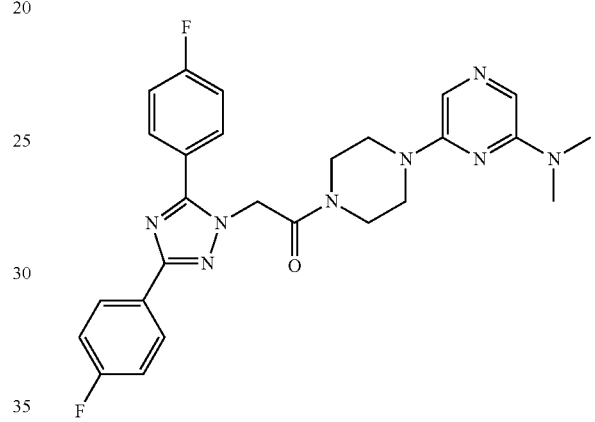
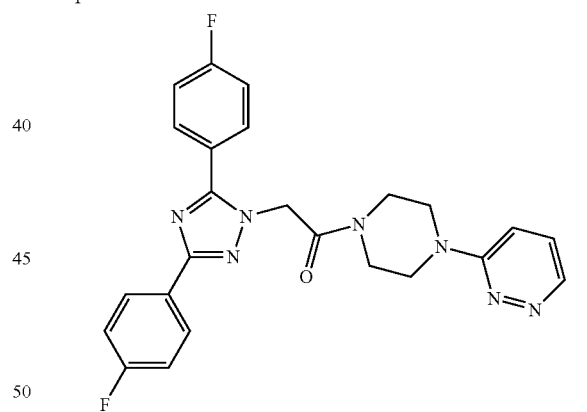
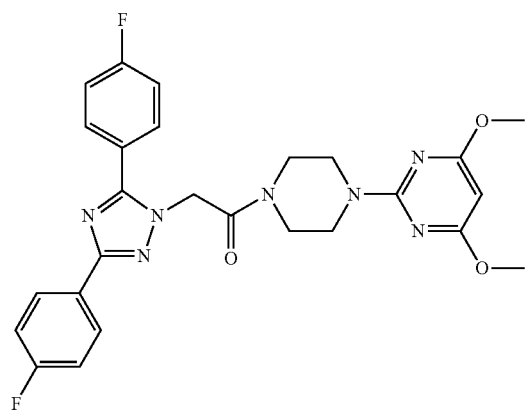

337
-continued
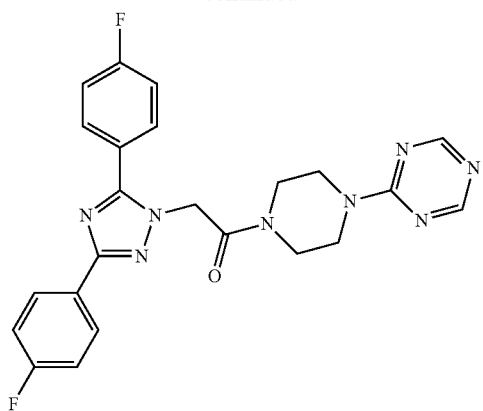
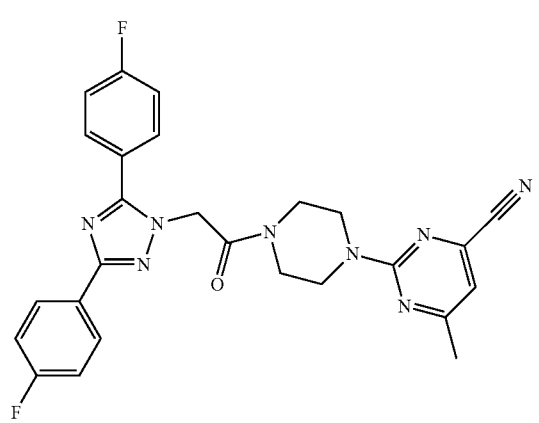
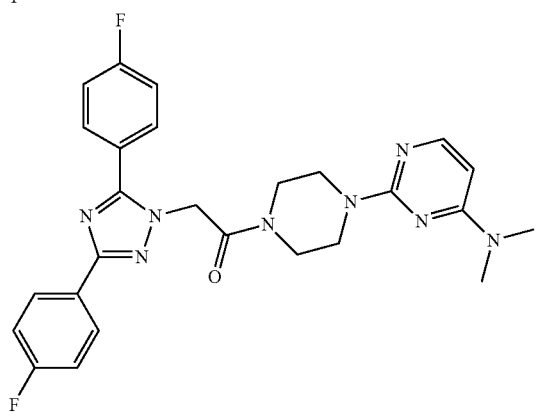
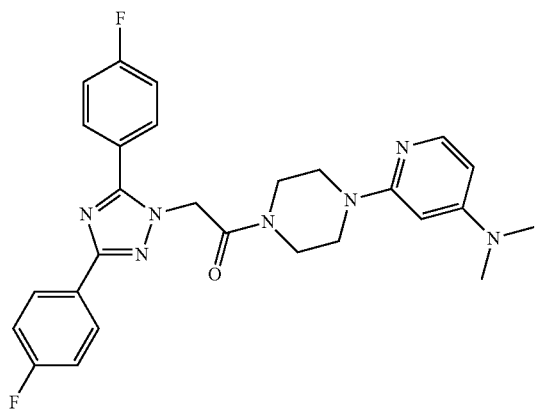
338
-continued
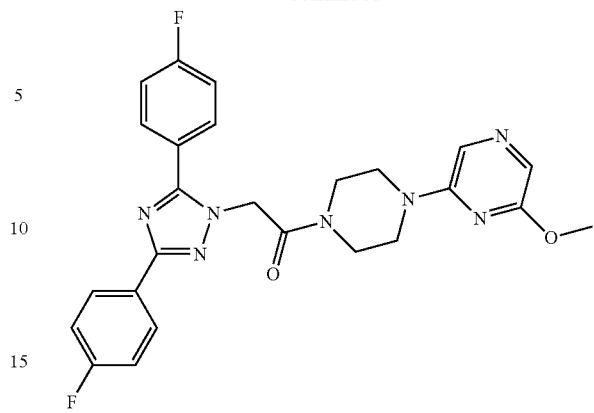
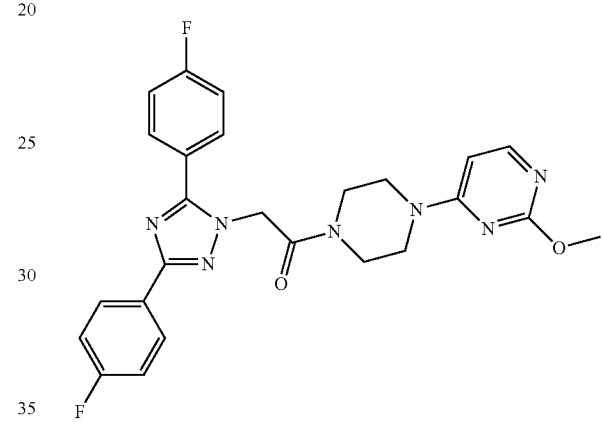
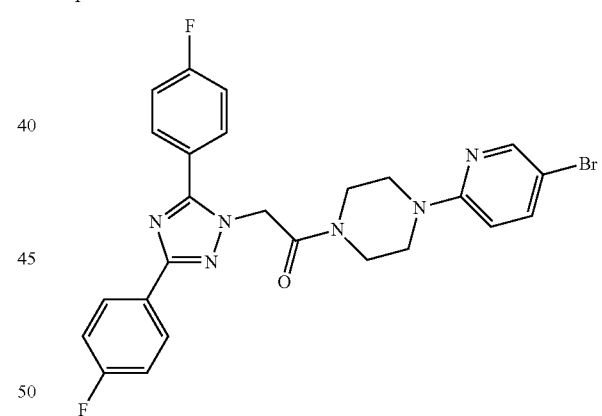
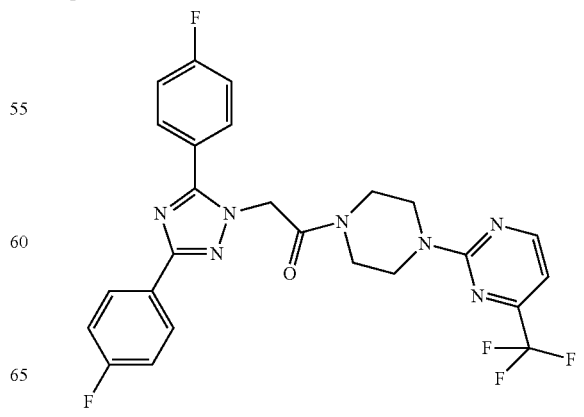

339
-continued
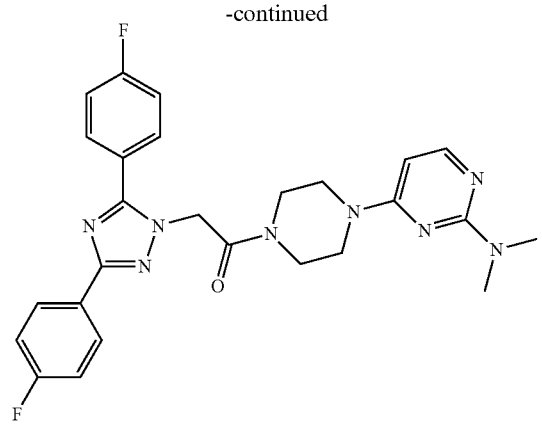
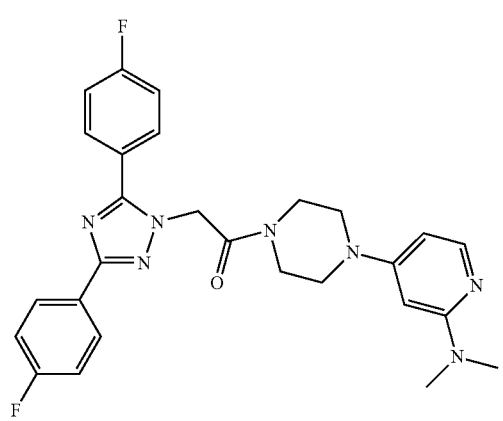
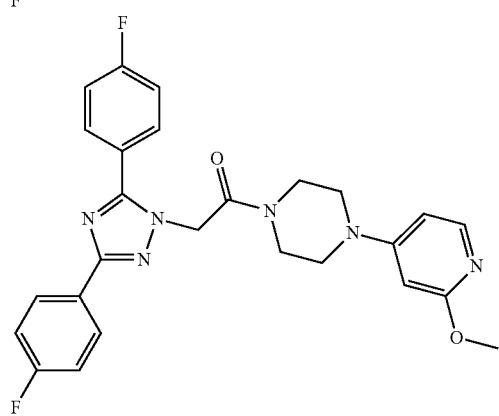
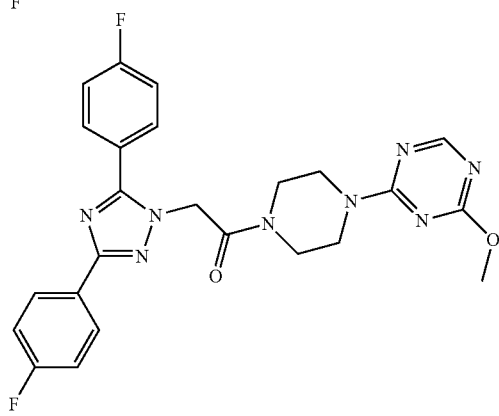
340
-continued
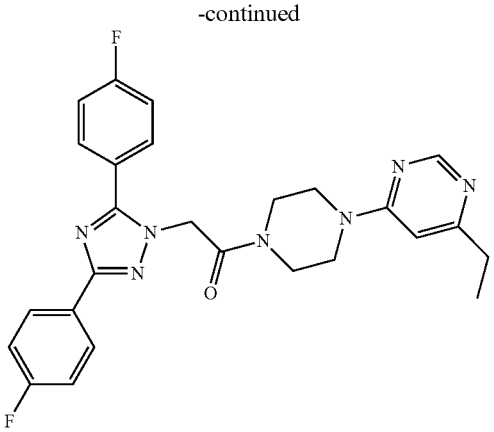
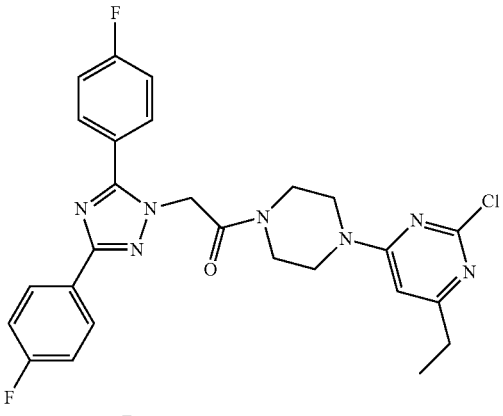
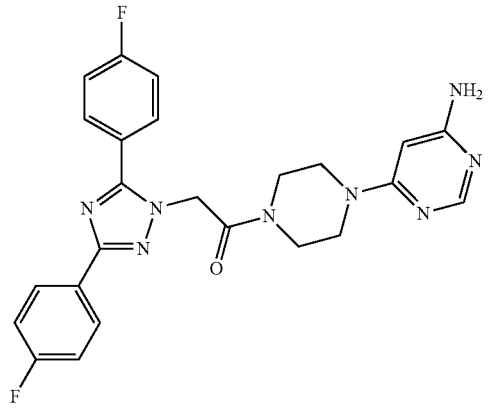
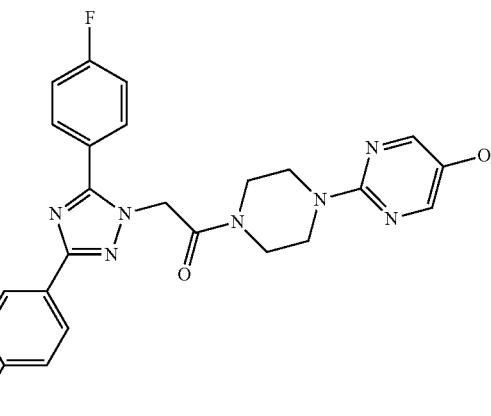

341
-continued
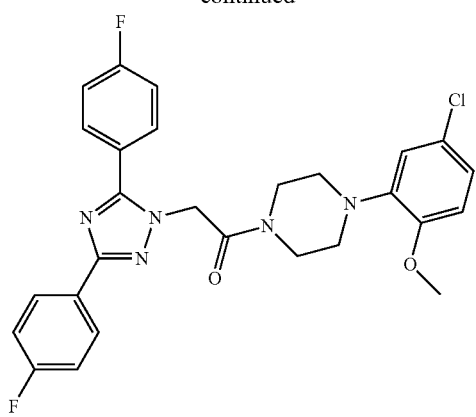
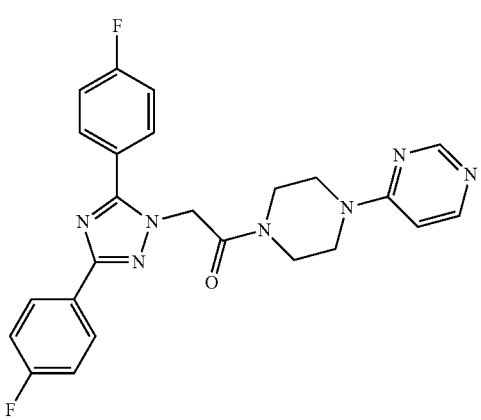
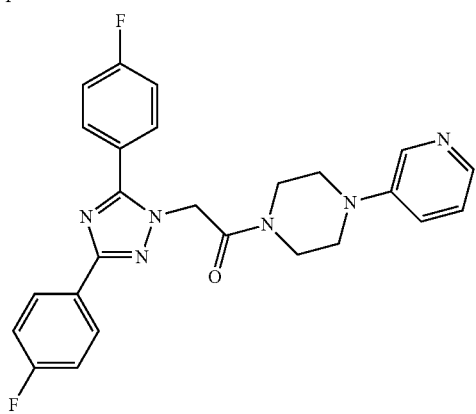
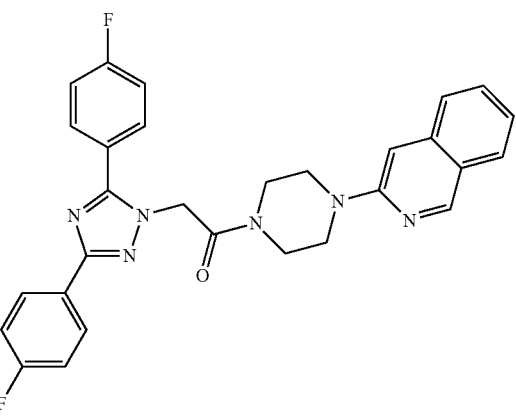
342
-continued
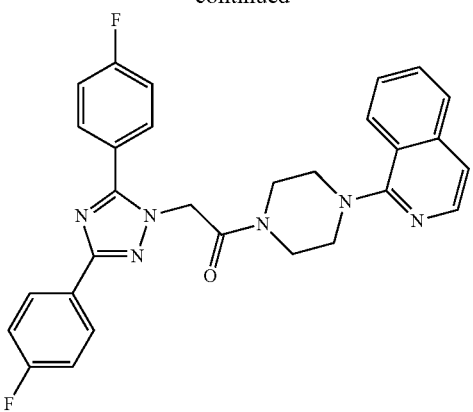
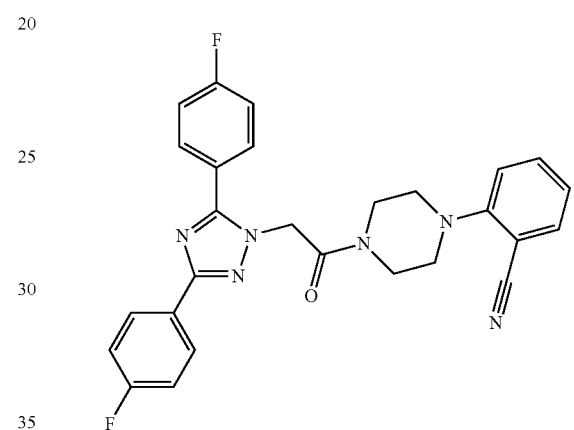
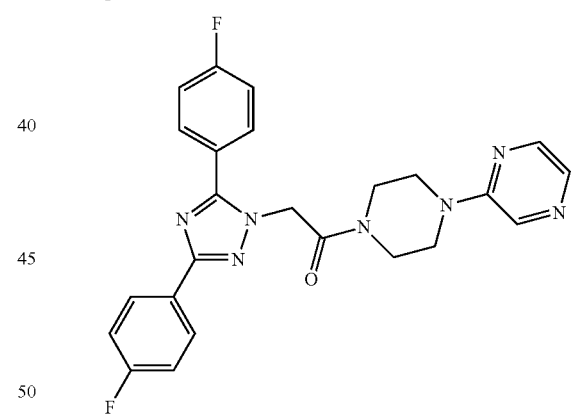
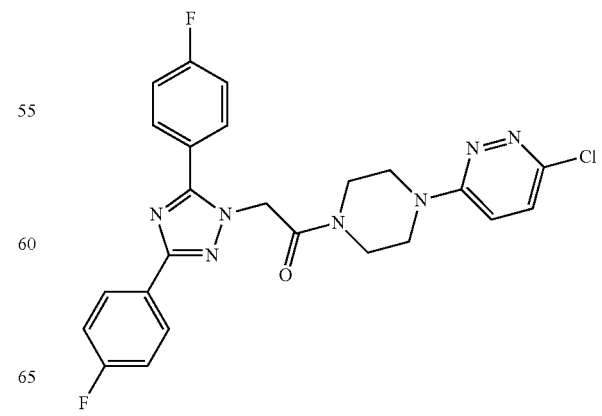

343
-continued
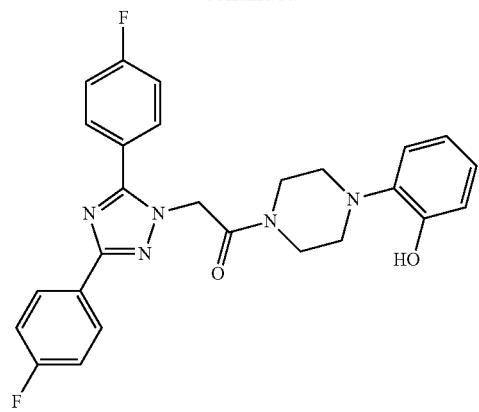
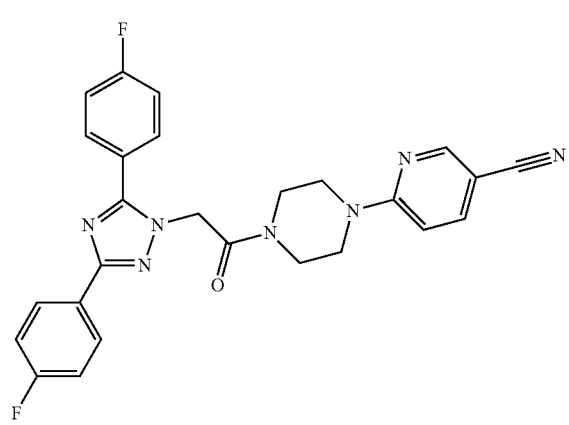
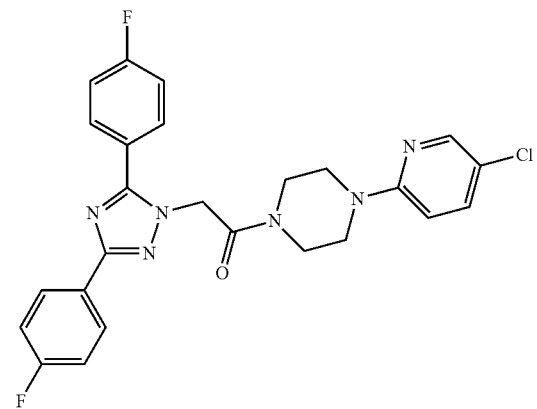
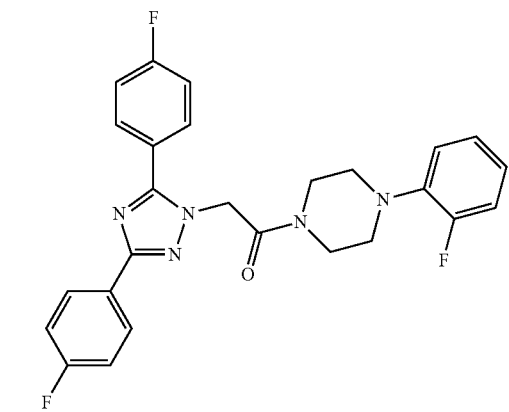
344
-continued
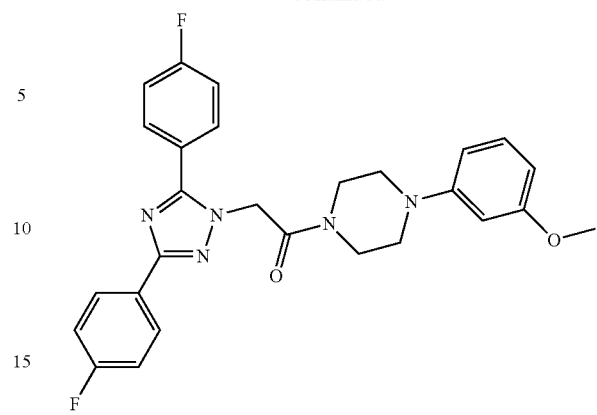
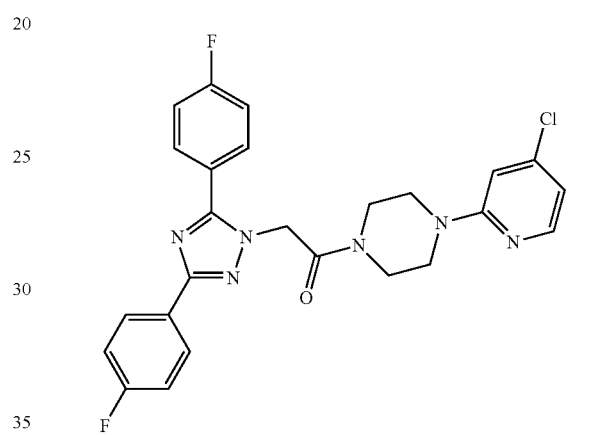
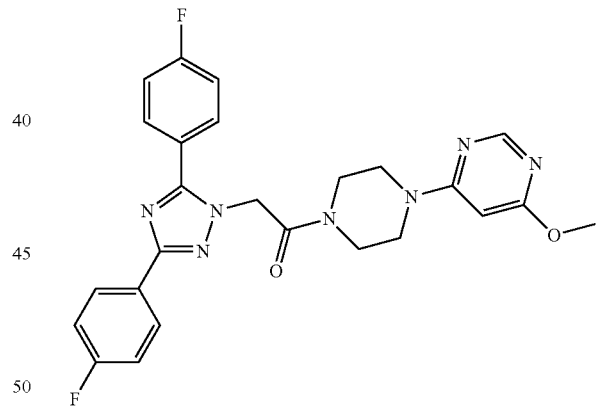
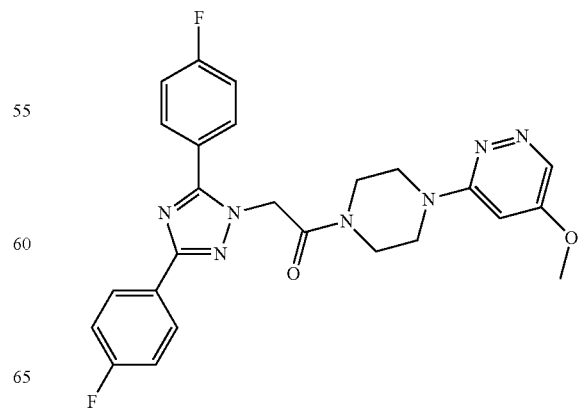

345
-continued
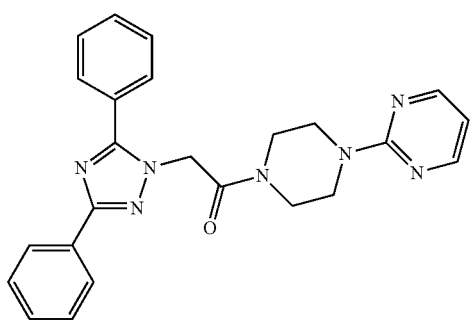
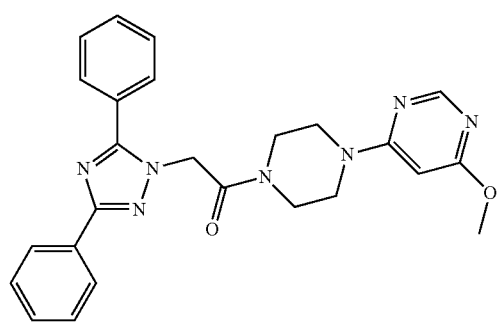
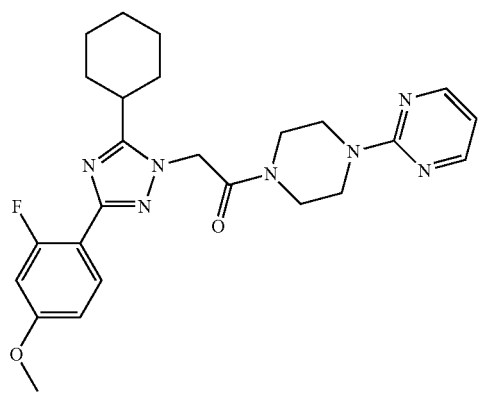
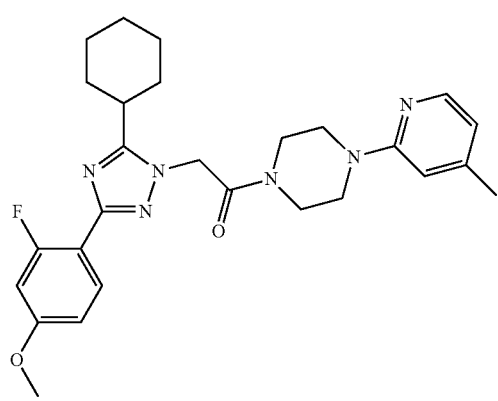
346
-continued
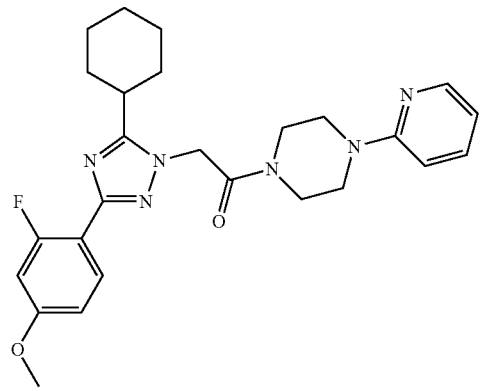
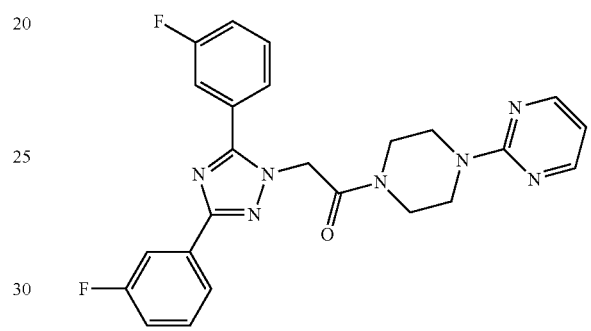
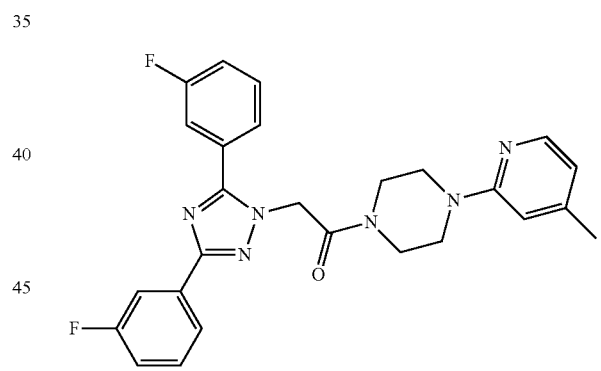
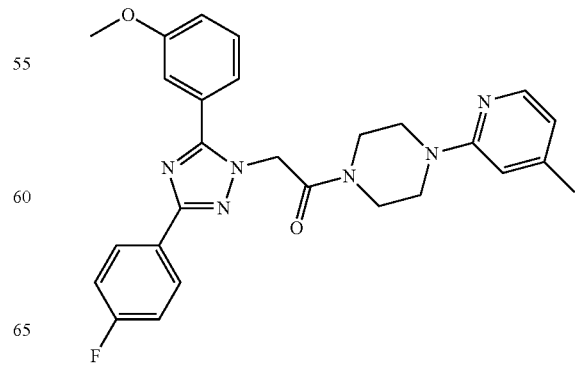

347
-continued
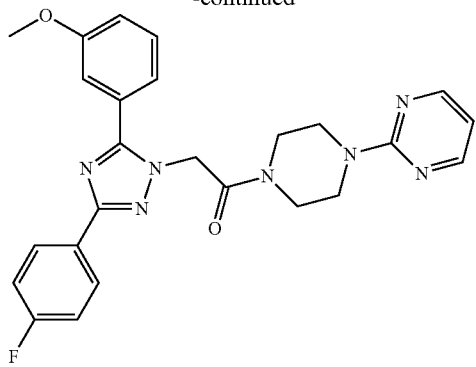
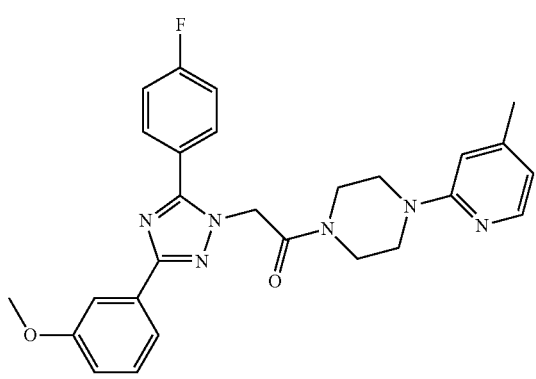
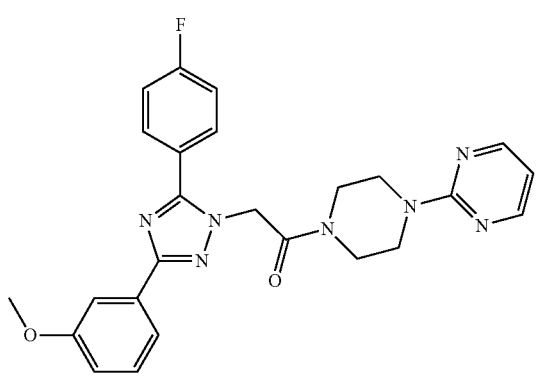
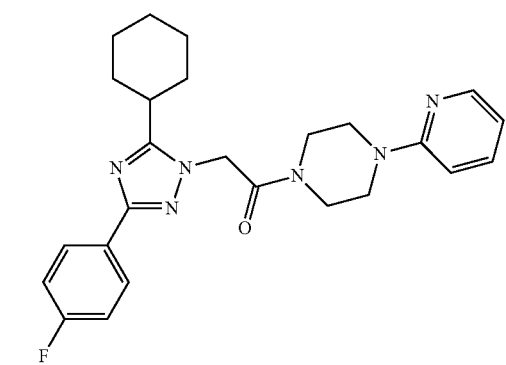
348
-continued
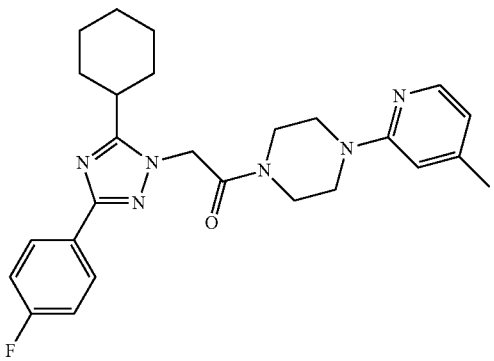
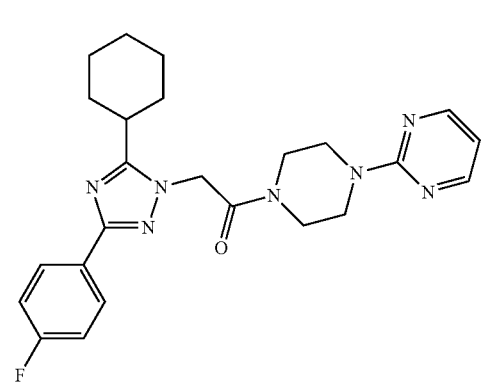
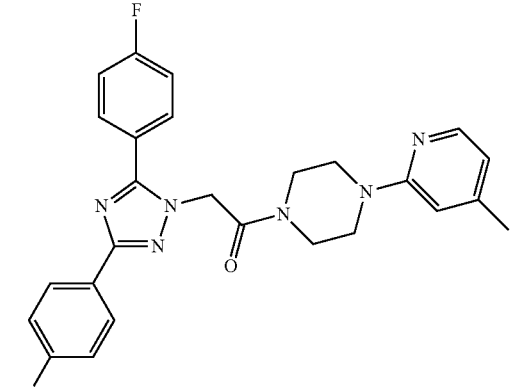
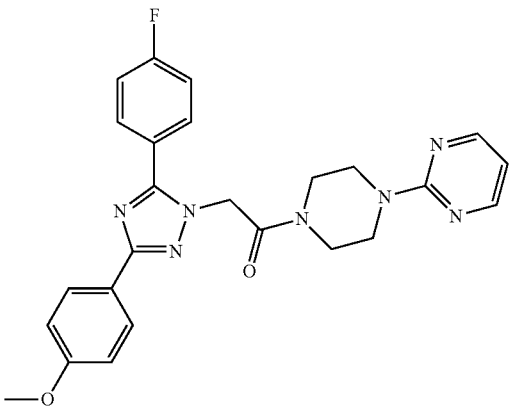

349
-continued
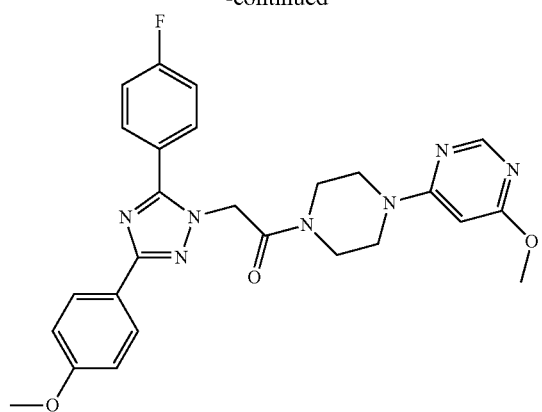
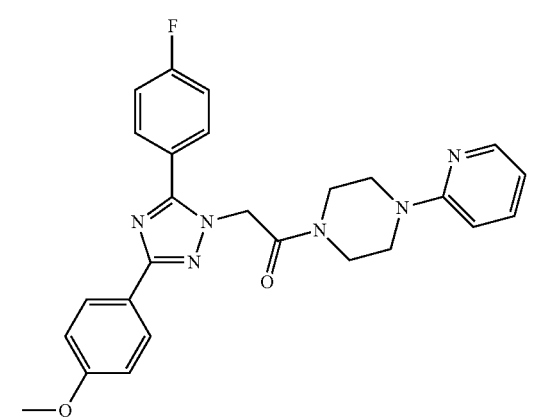
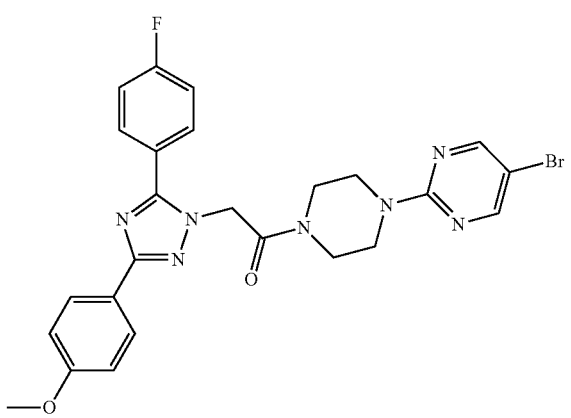
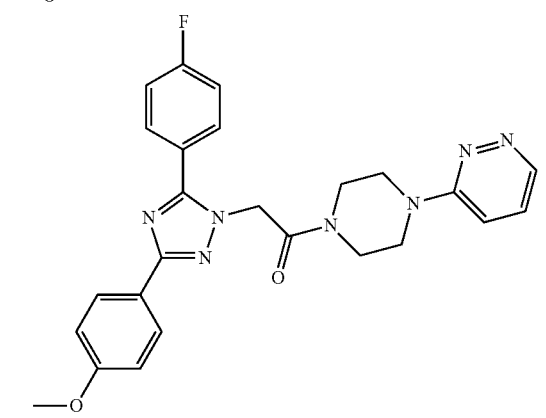
350
-continued
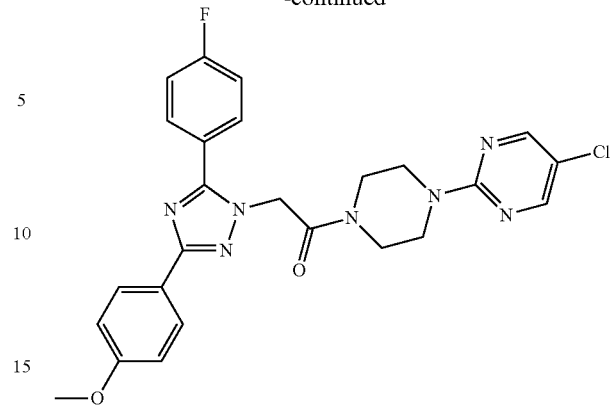
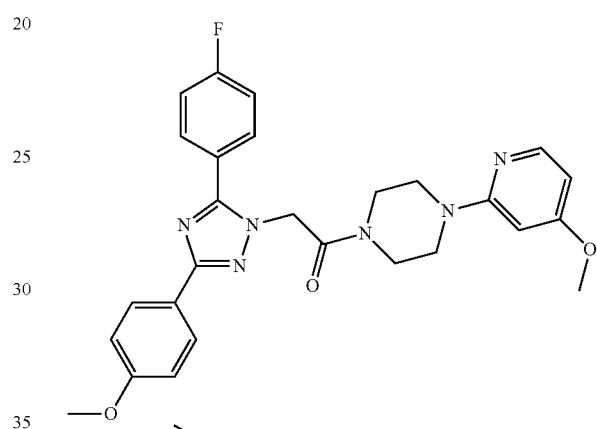
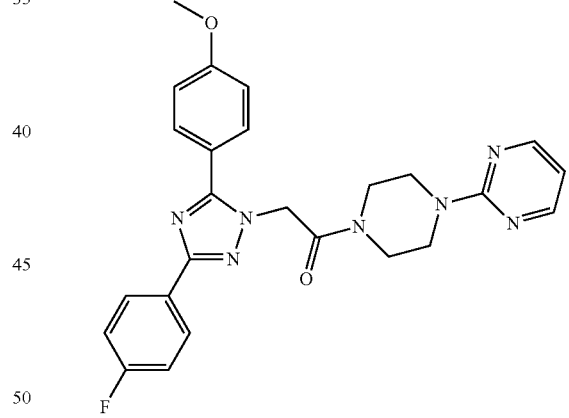
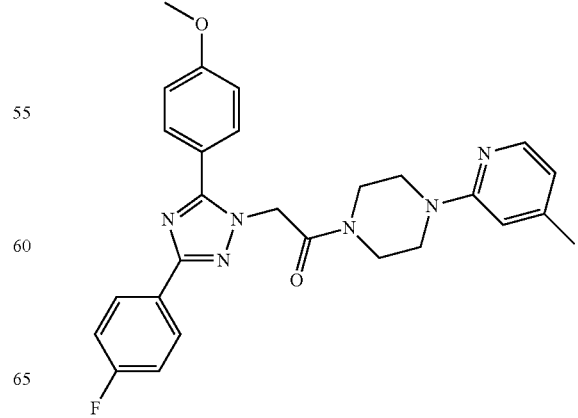

351
-continued
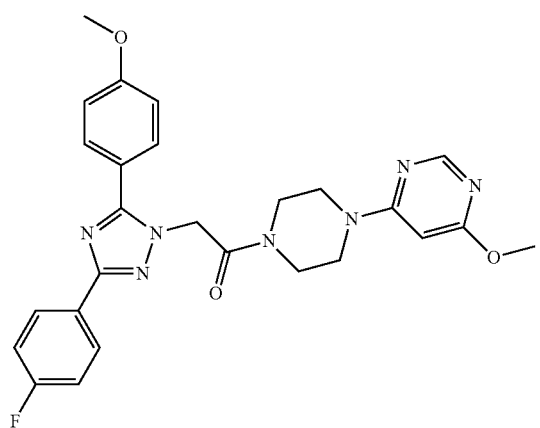
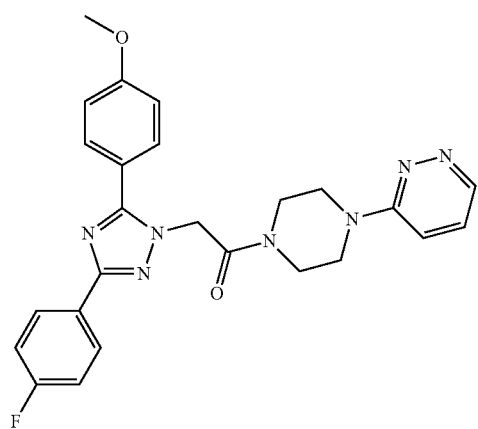
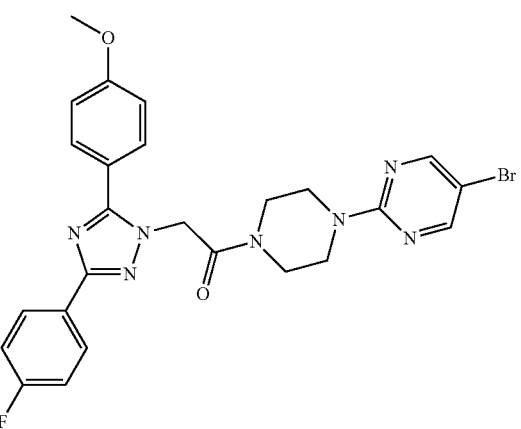
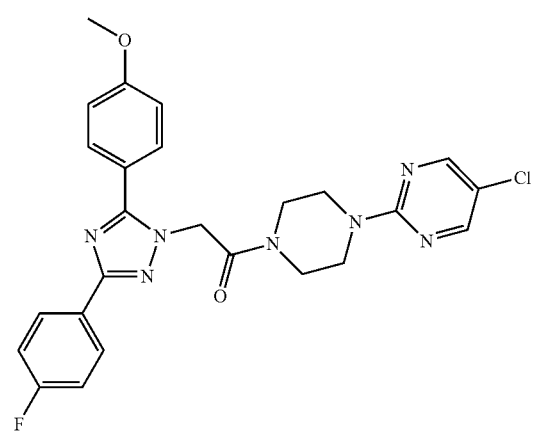
352
-continued
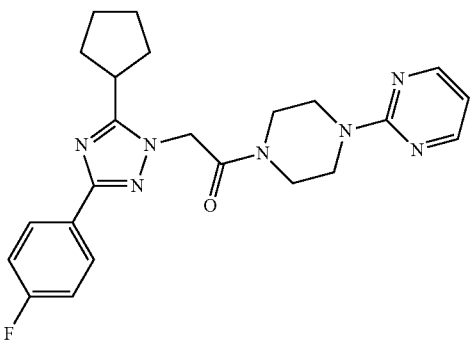
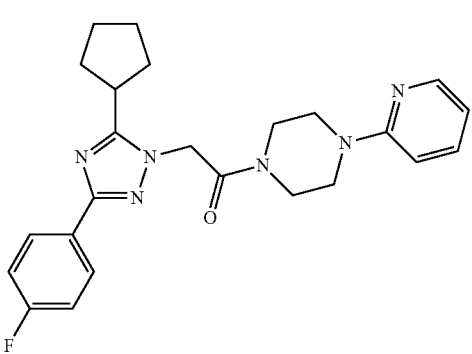
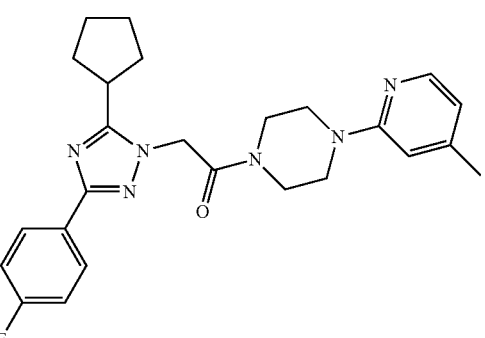
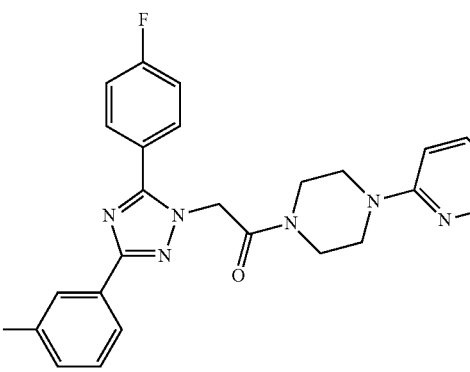

353
-continued
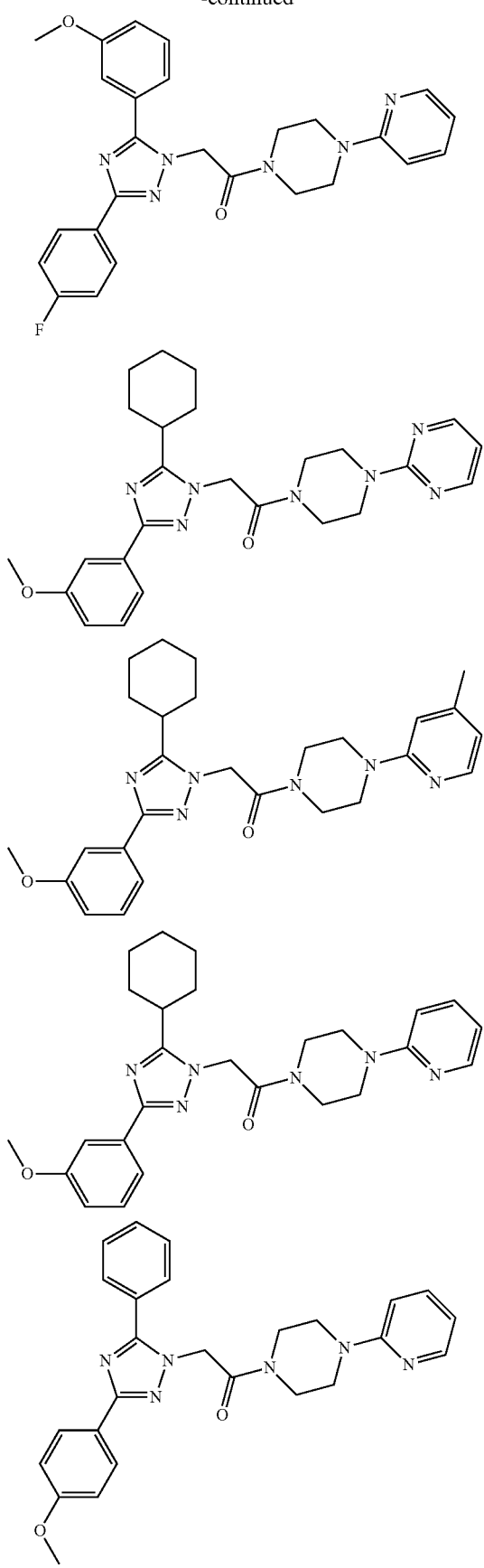
354
-continued
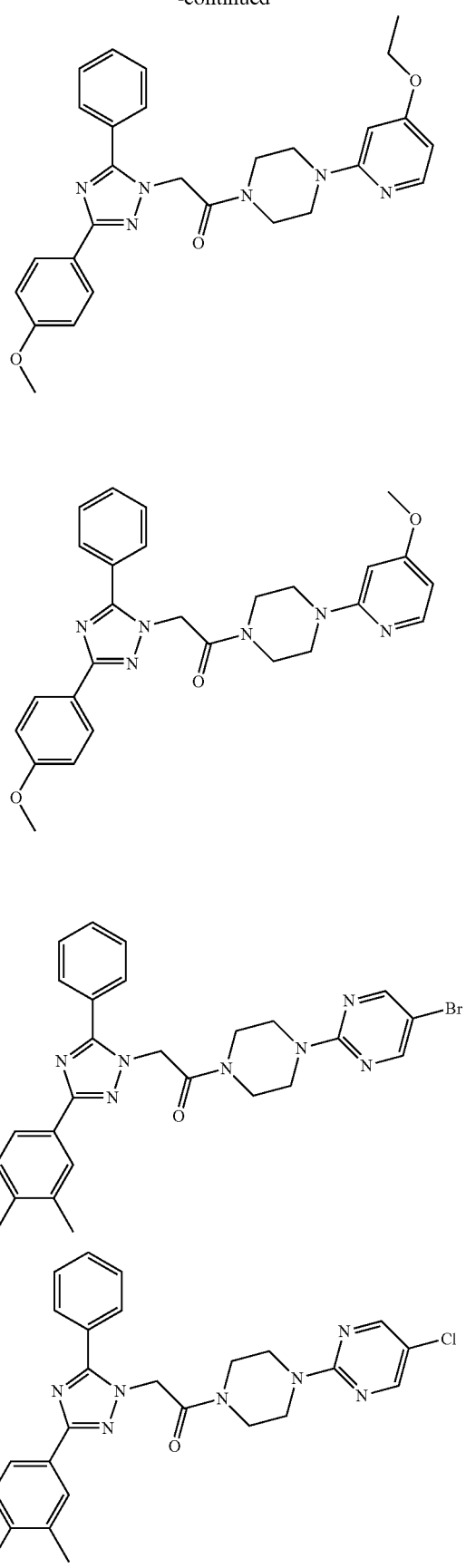

355
-continued
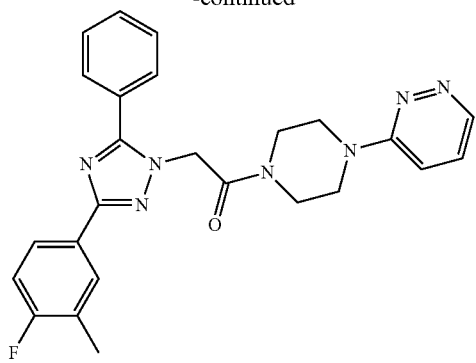
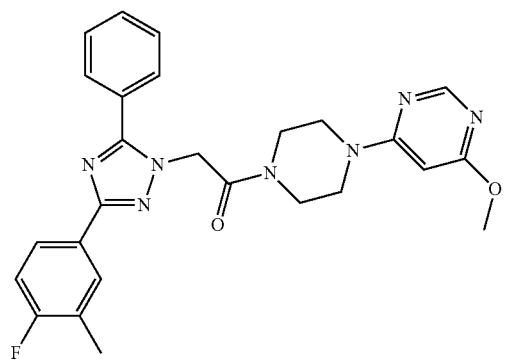
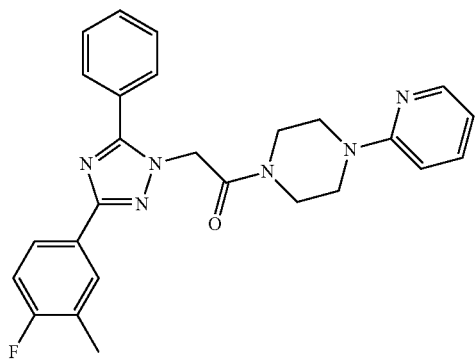
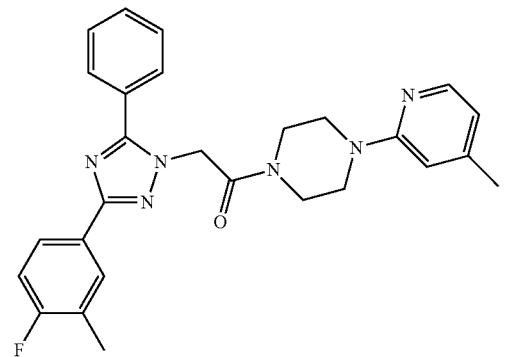
356
-continued
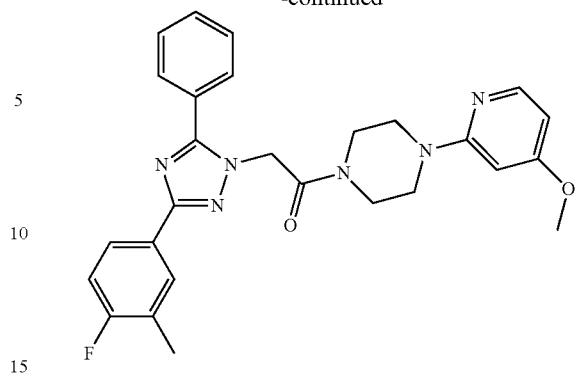
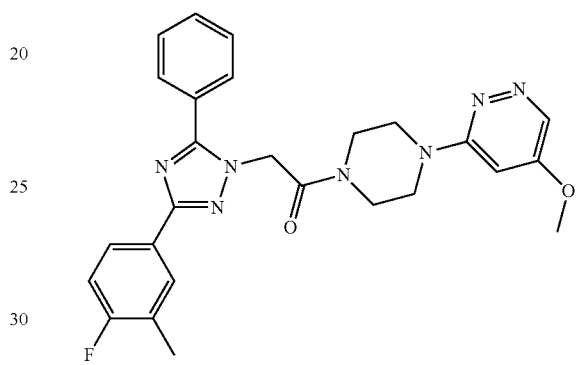
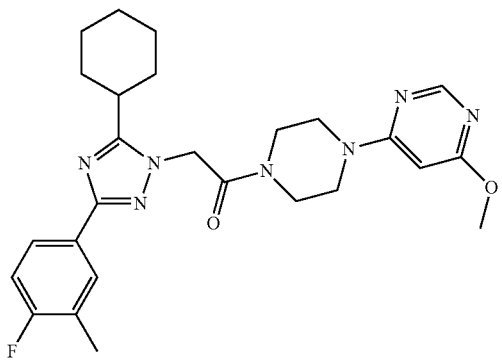
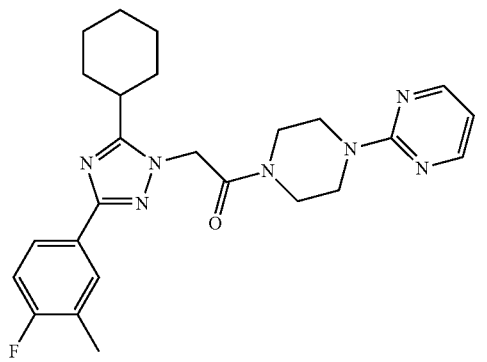

357                                    358
-continued                             -continued
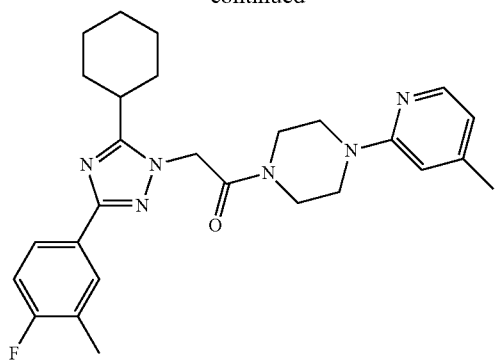 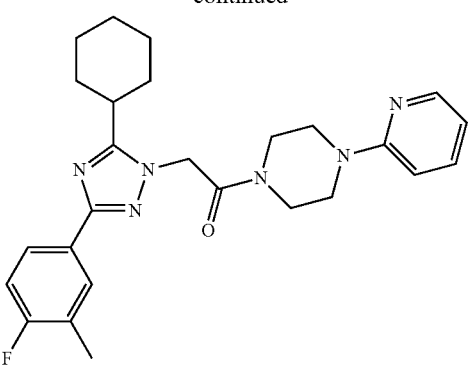
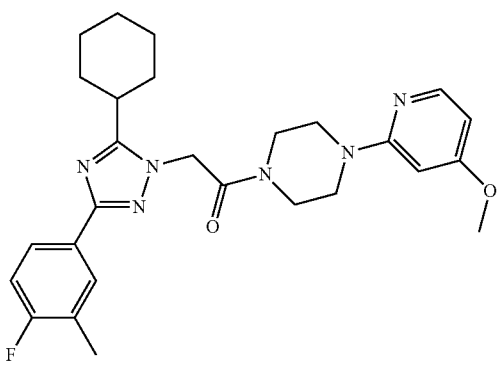 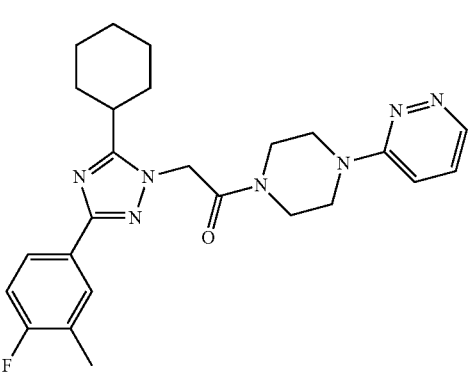
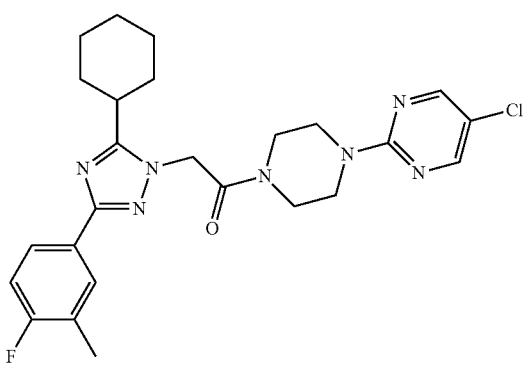 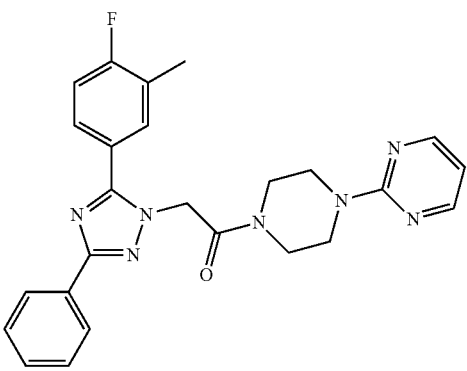
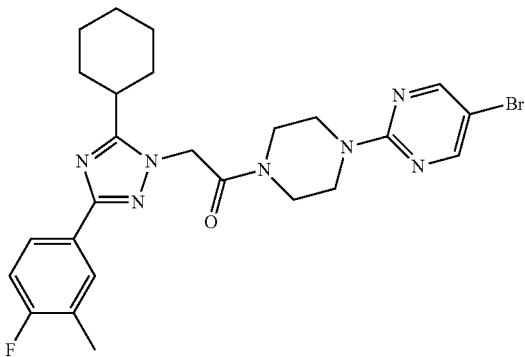 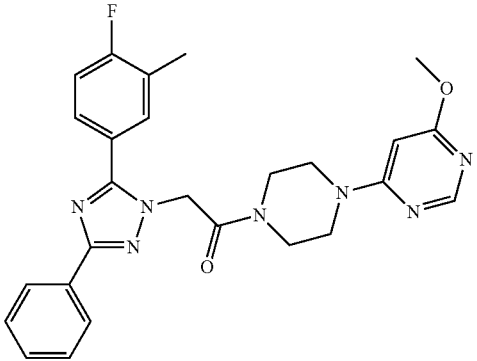

359
-continued
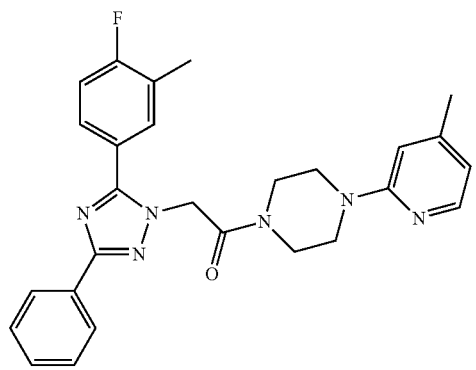
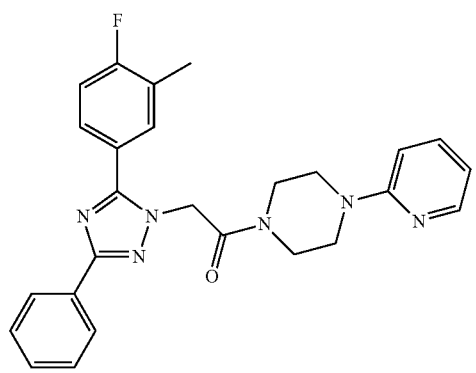
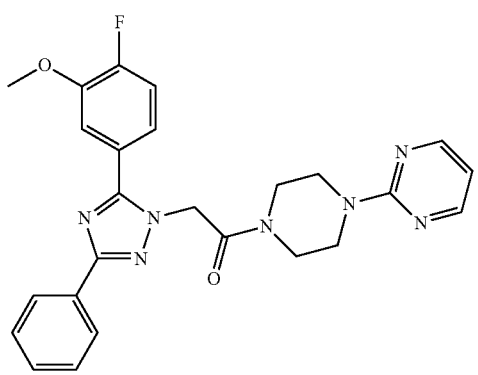
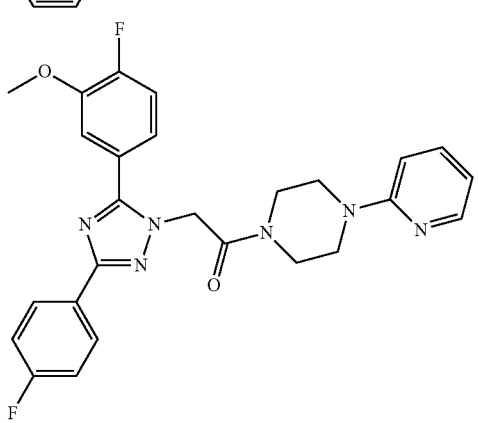
360
-continued
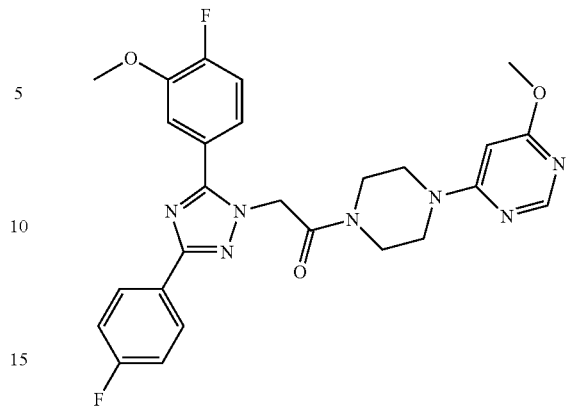
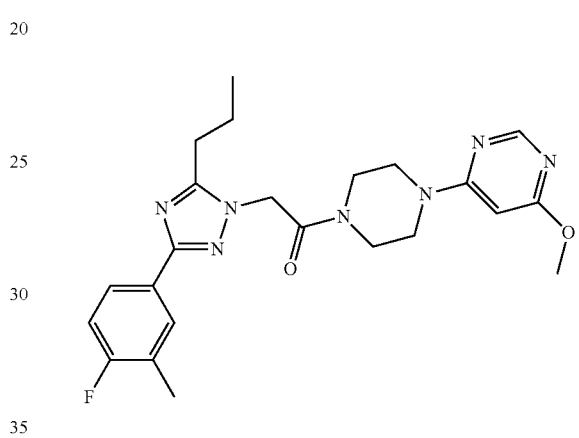
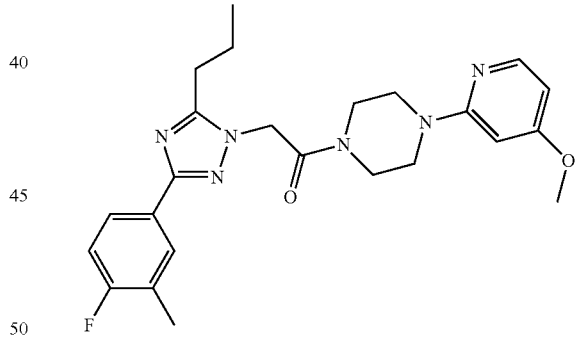
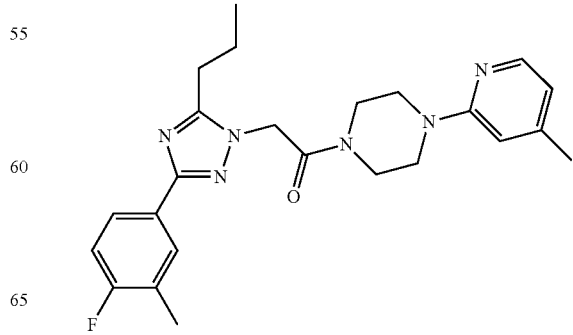

361
-continued
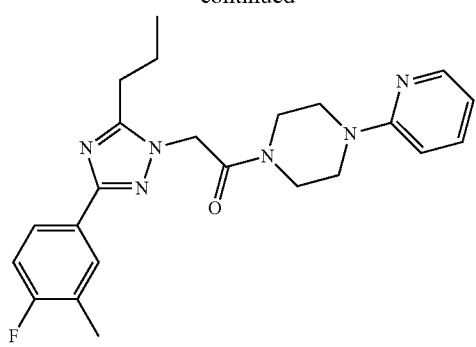
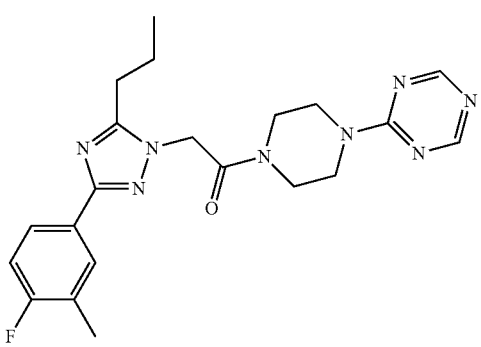
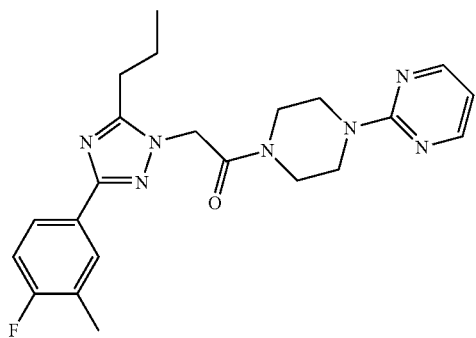
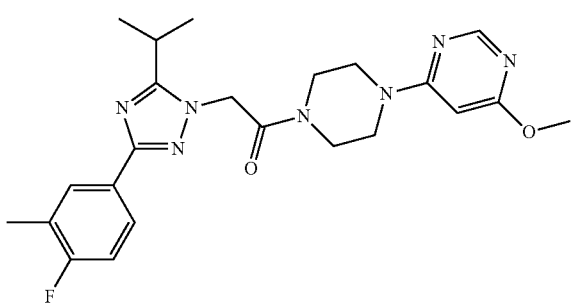
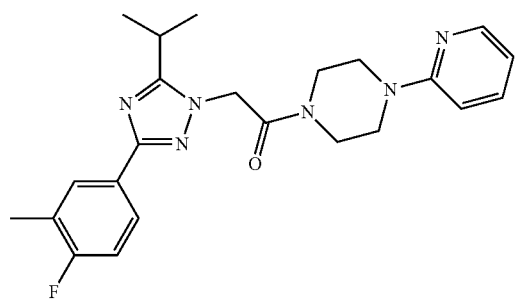
362
-continued
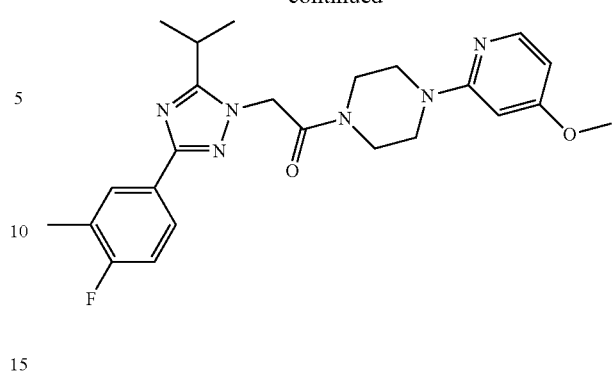
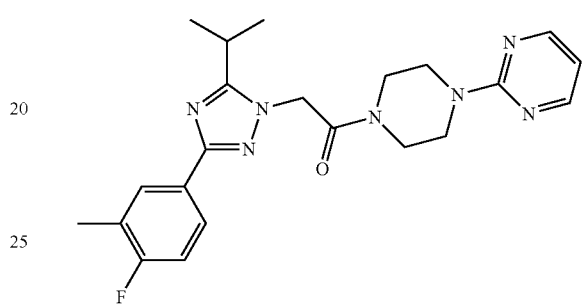
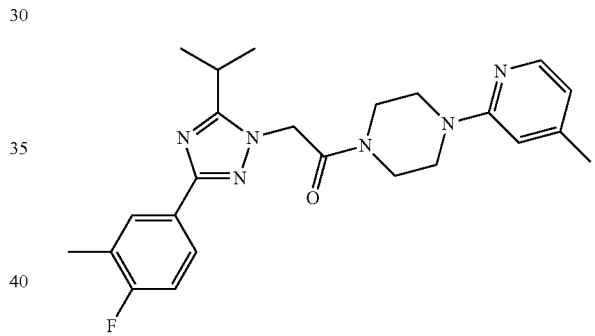
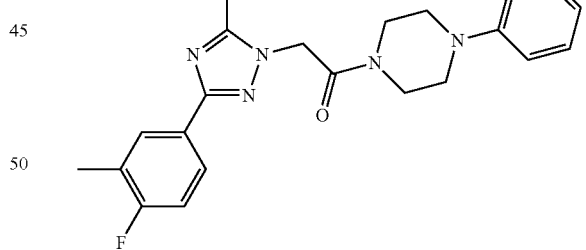
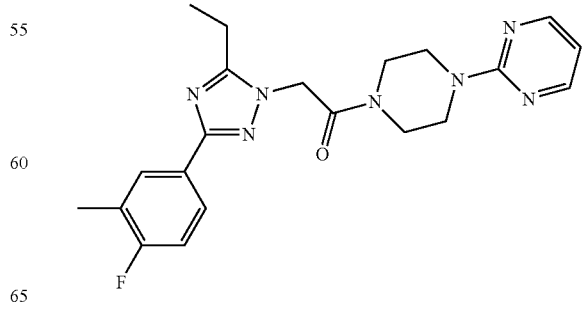

363
-continued
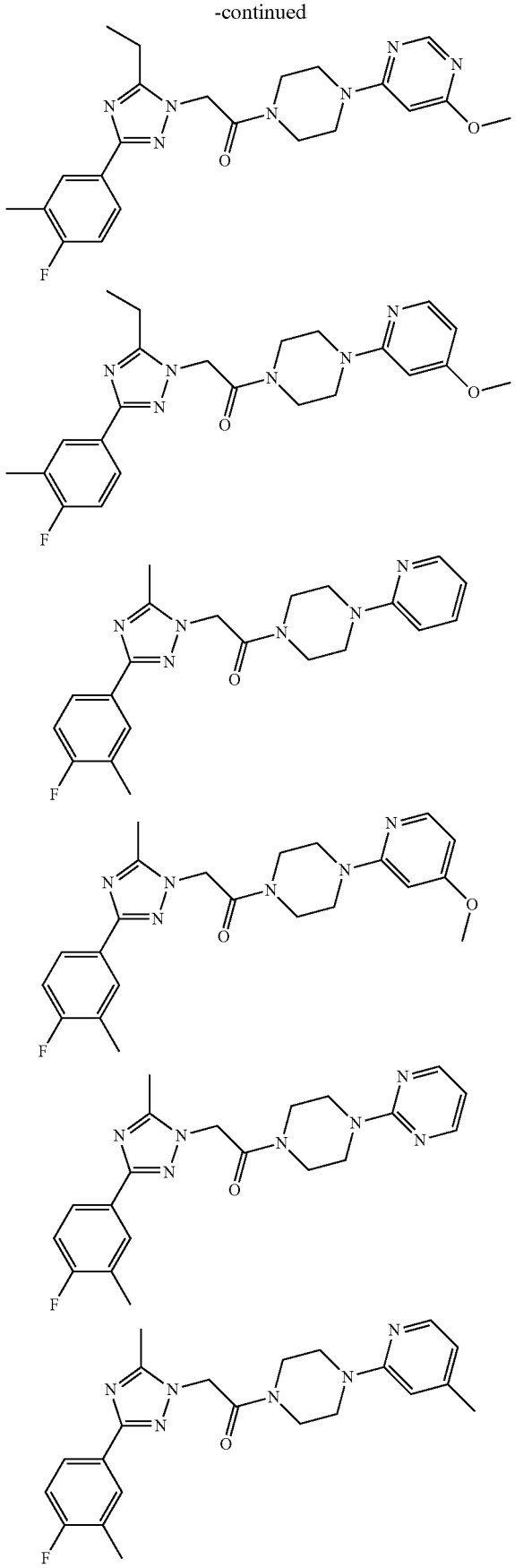
364
-continued
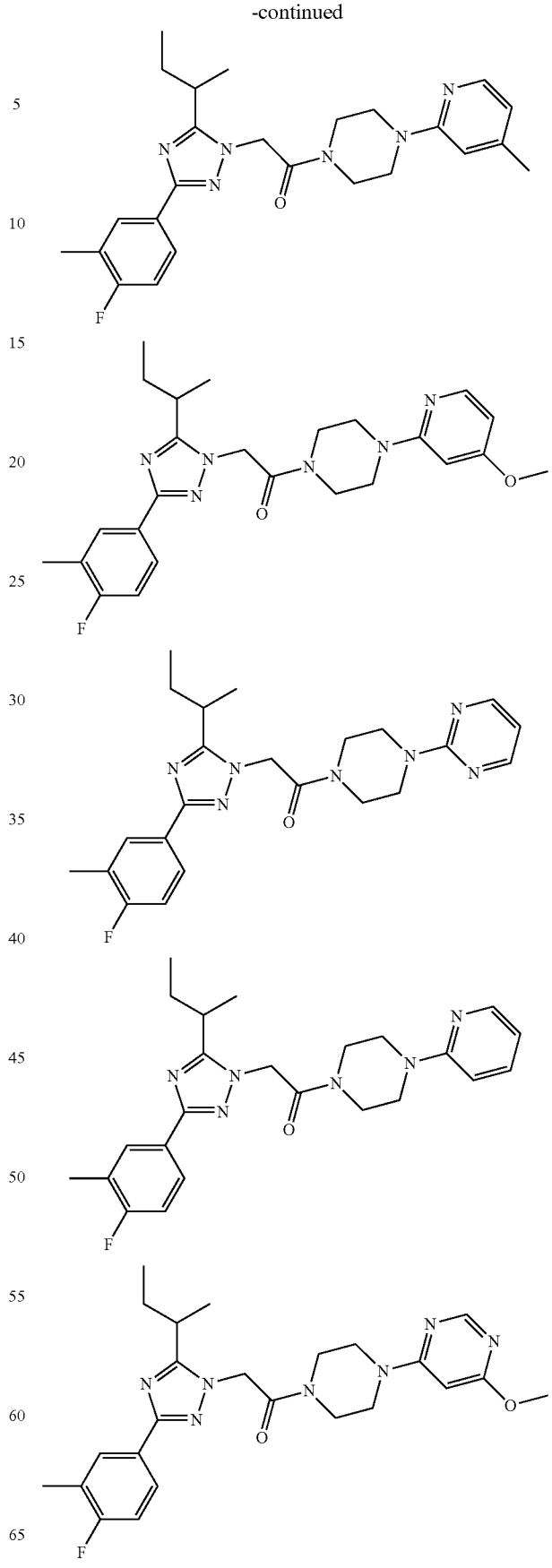

365
-continued
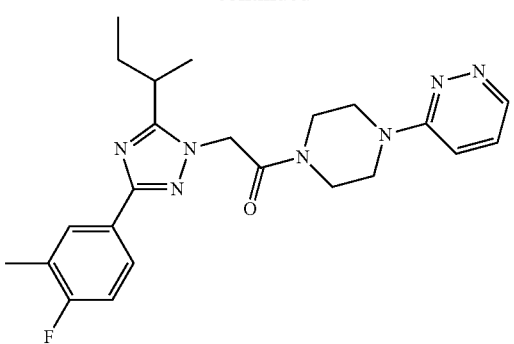
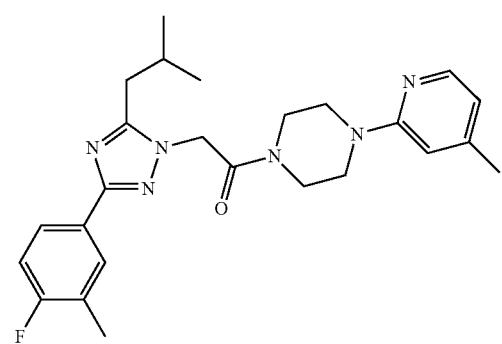
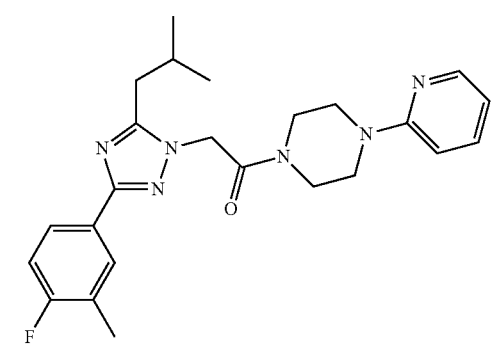
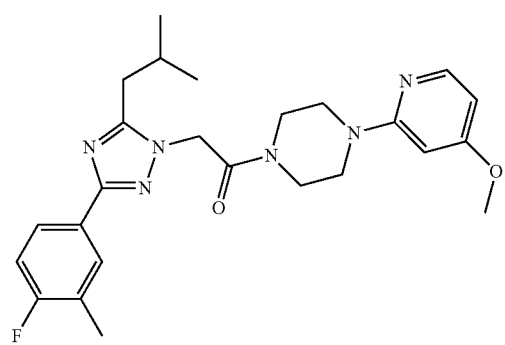
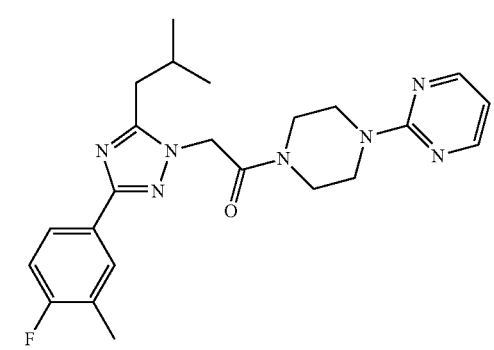
366
-continued
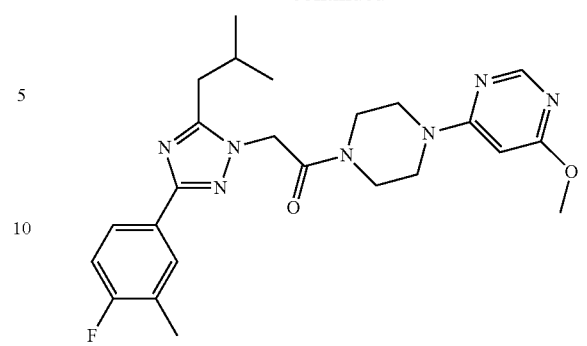
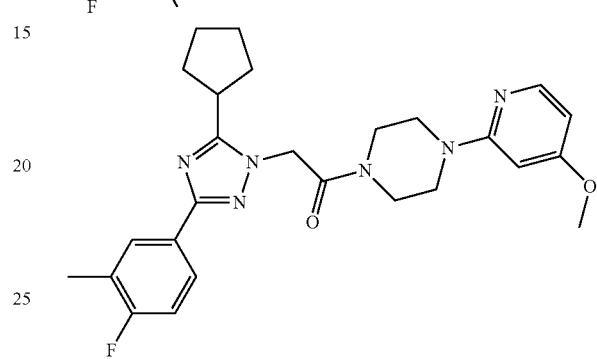
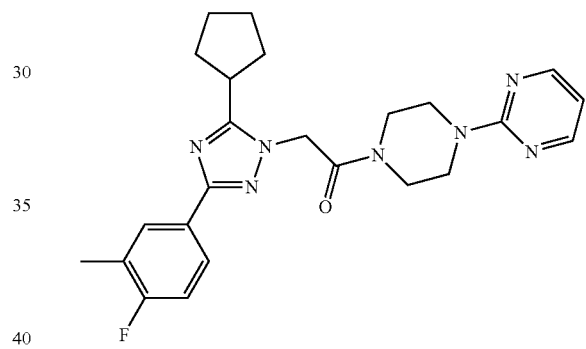
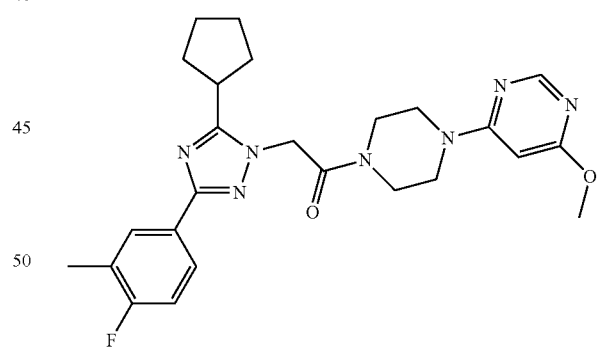
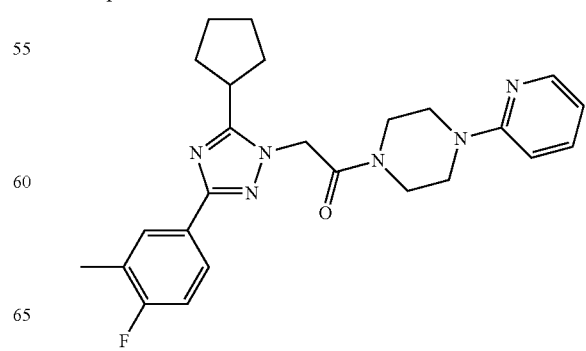

367  368
-continued  -continued
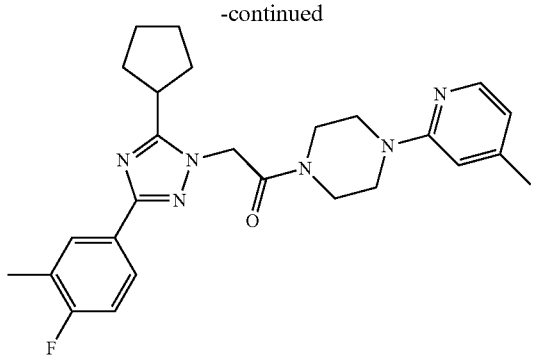
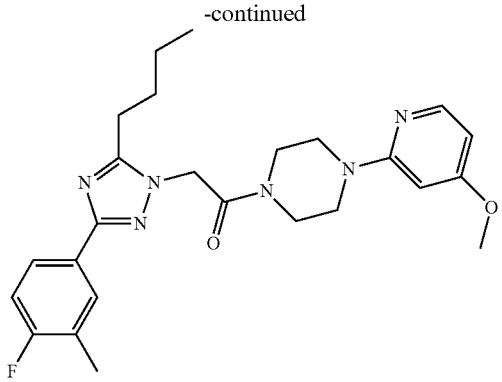
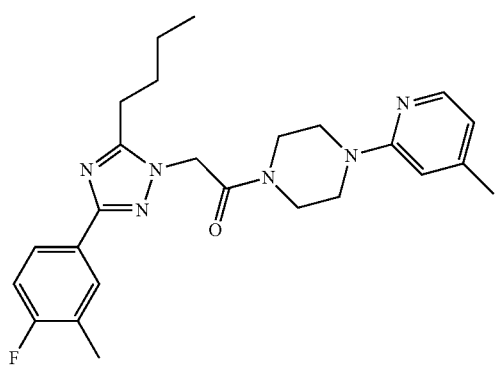
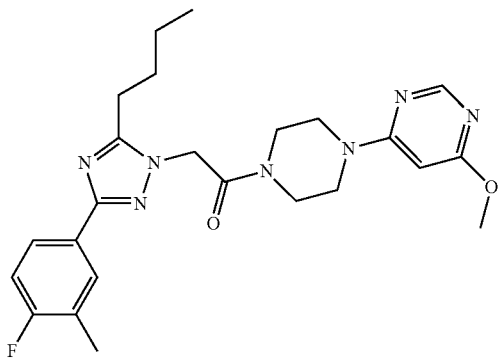
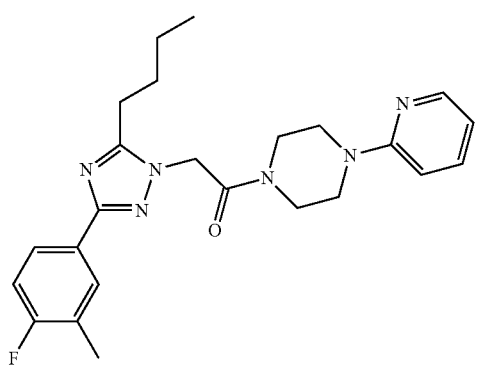
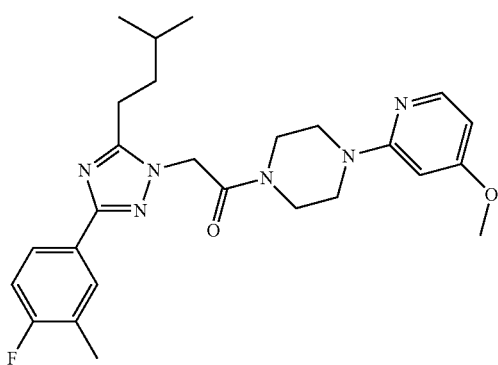
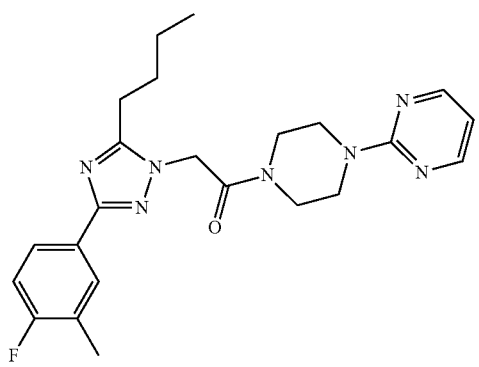
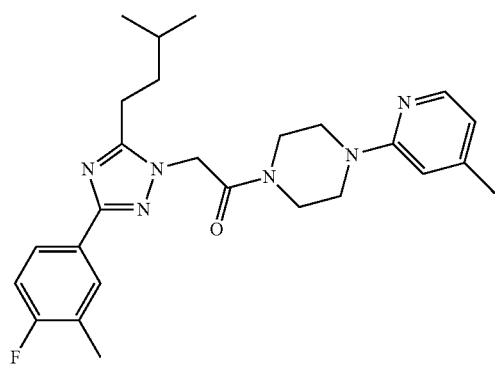

369
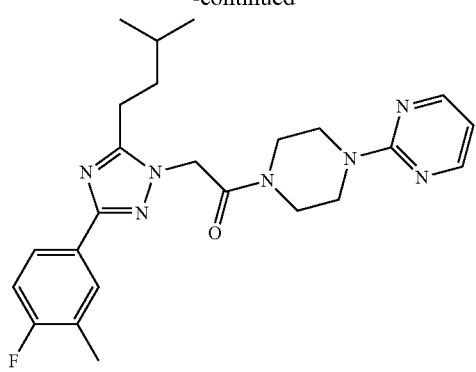
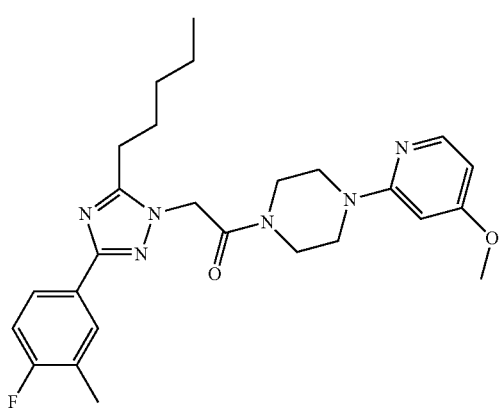
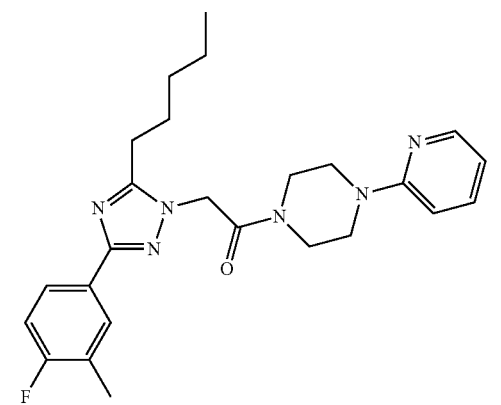
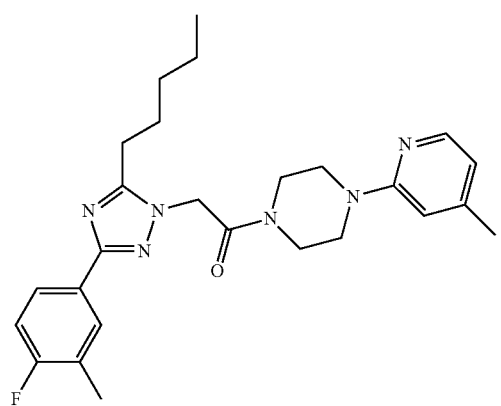
370
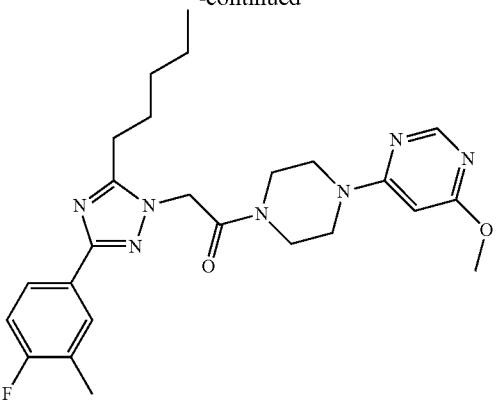
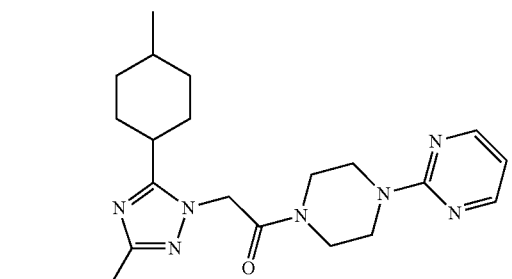
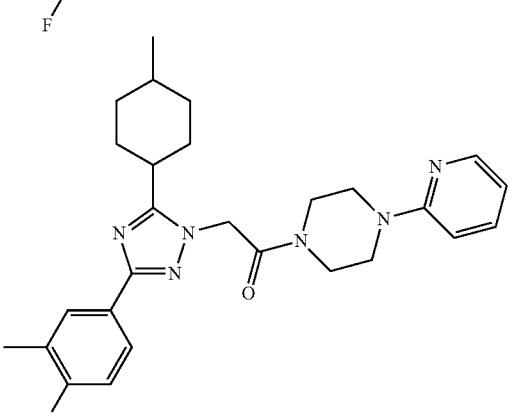

371
-continued
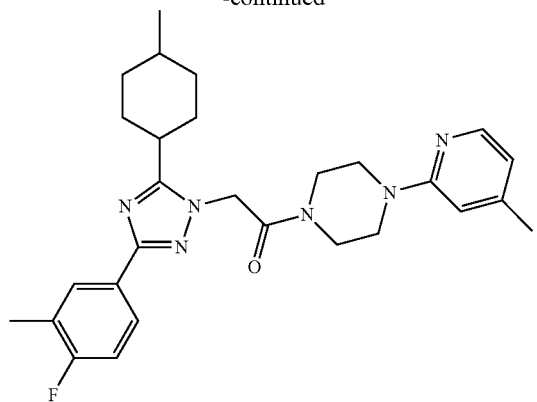
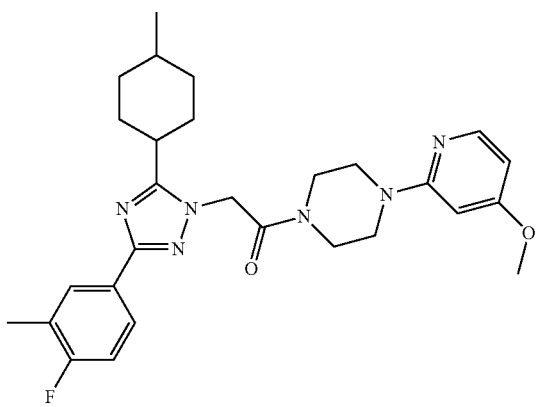
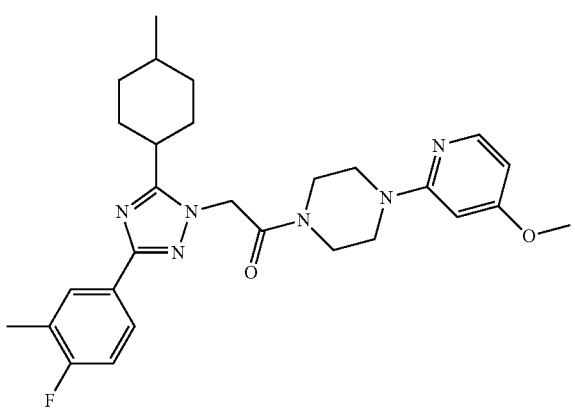
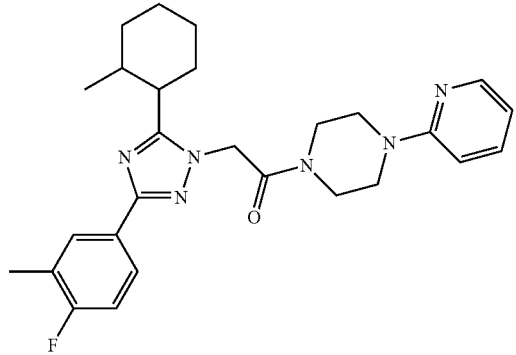
372
-continued
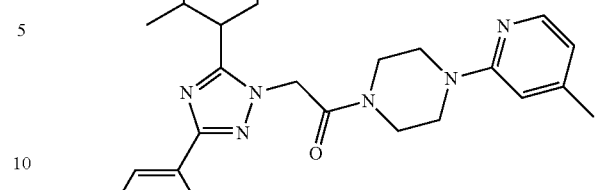
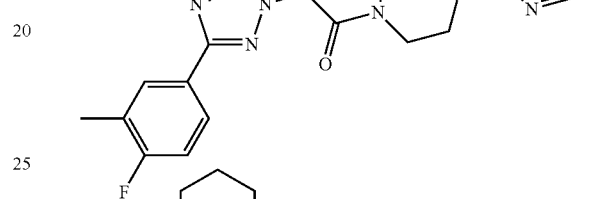
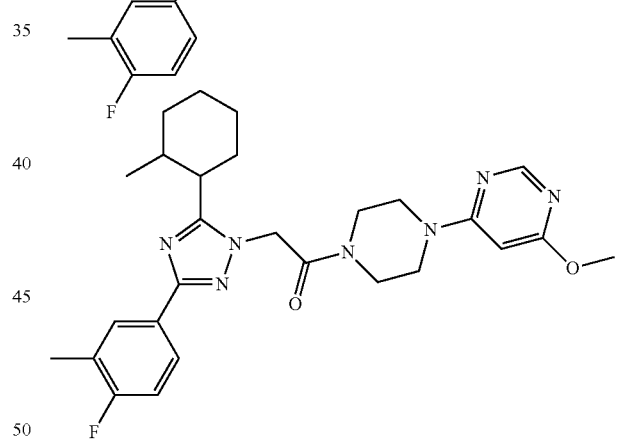
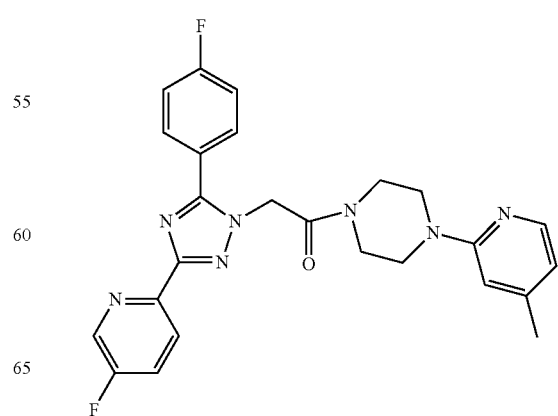

373
-continued
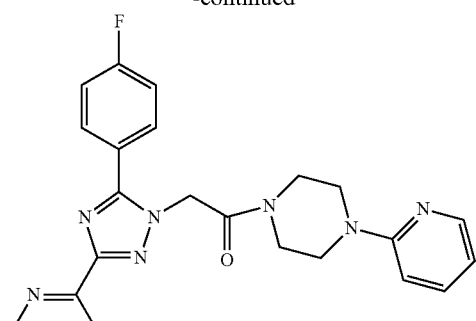
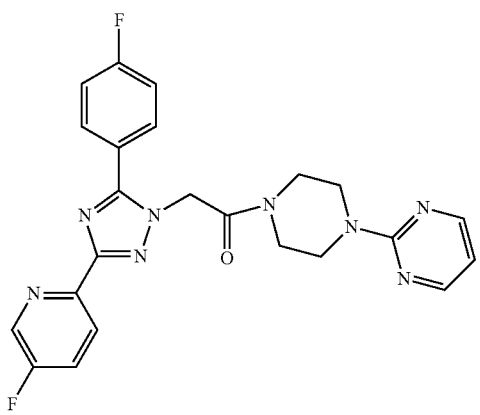
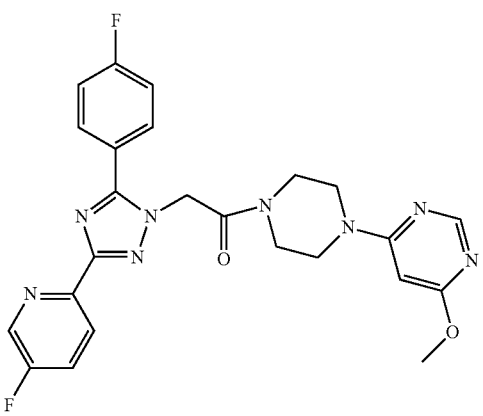
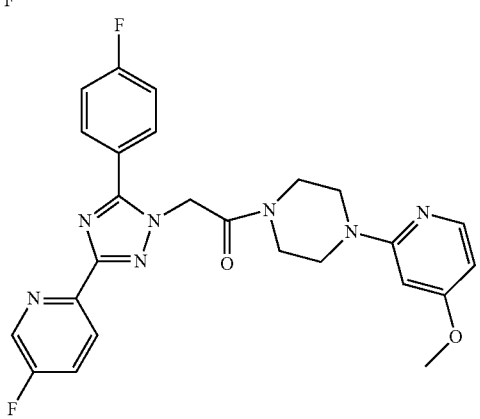
374
-continued
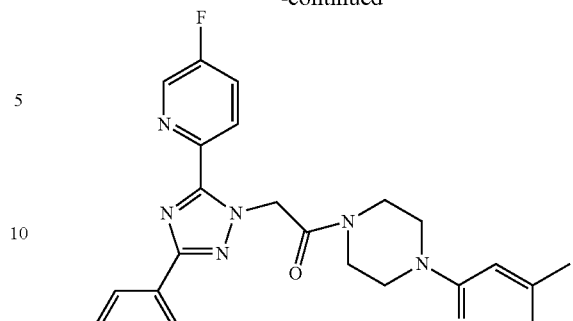
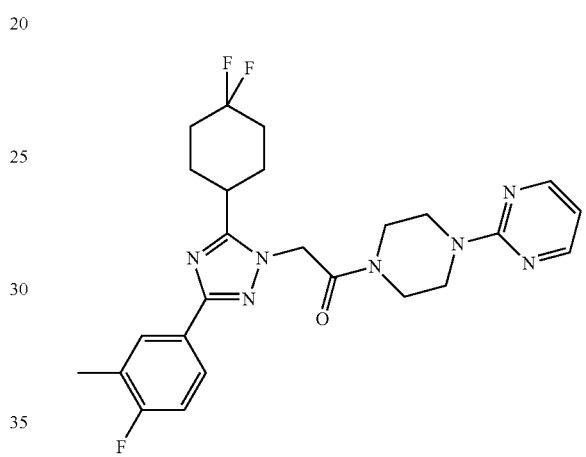
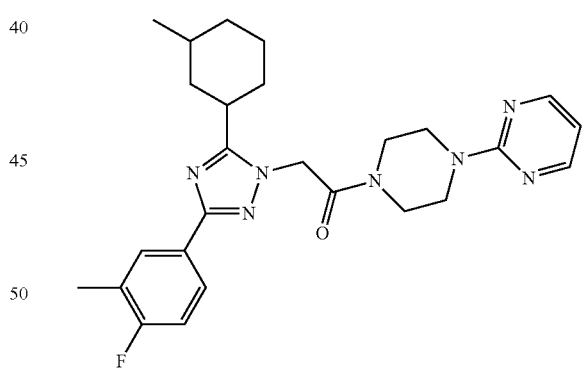
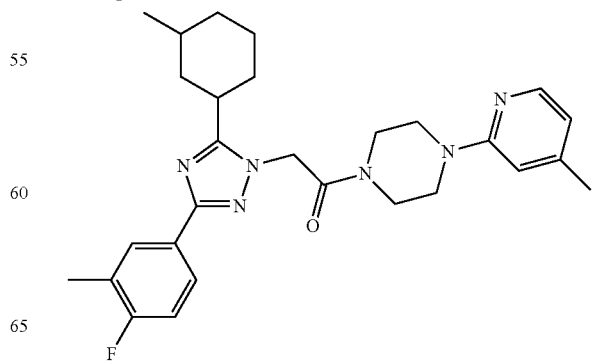

375
-continued
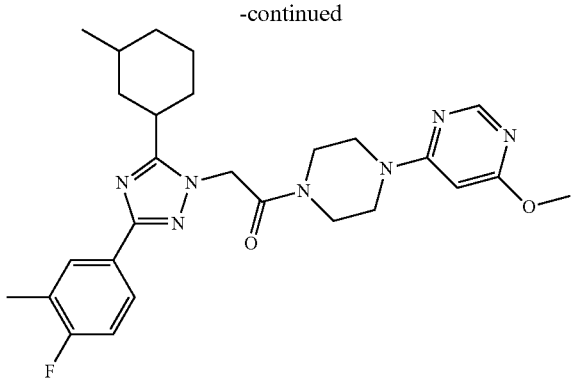
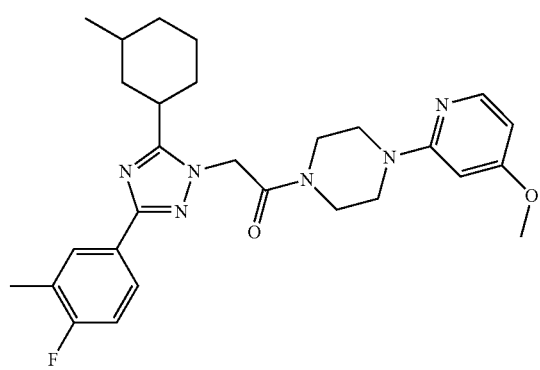
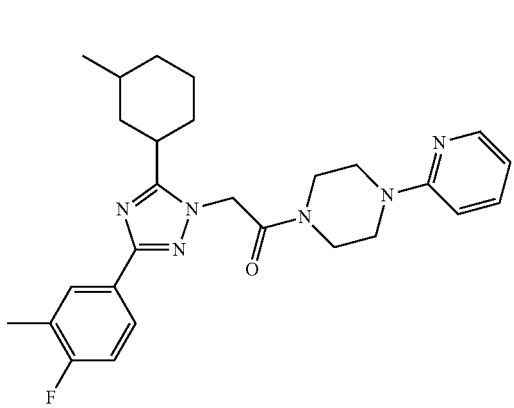
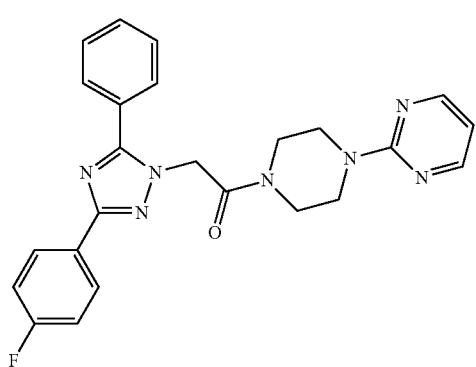
376
-continued
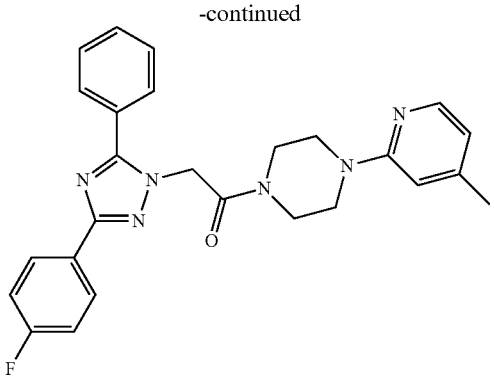
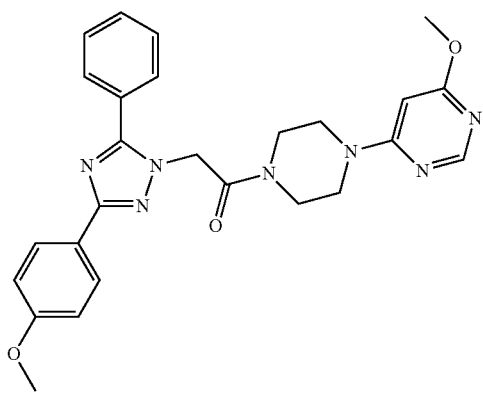
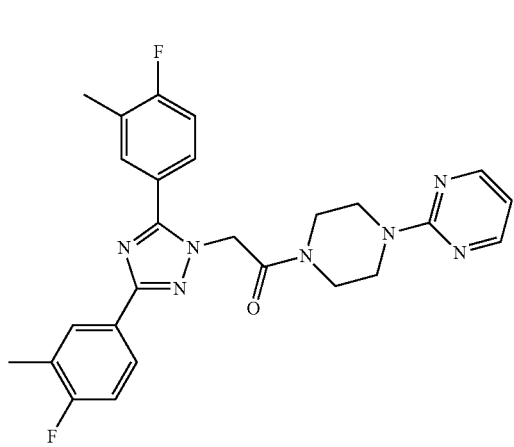
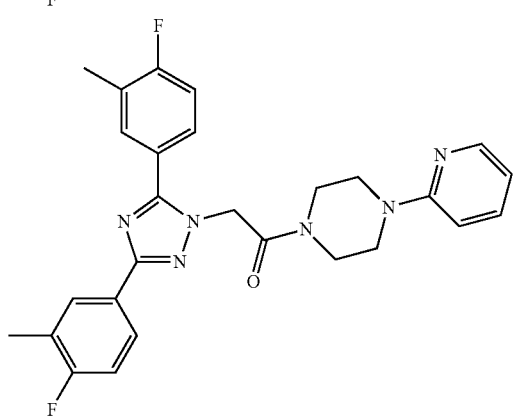

377
-continued
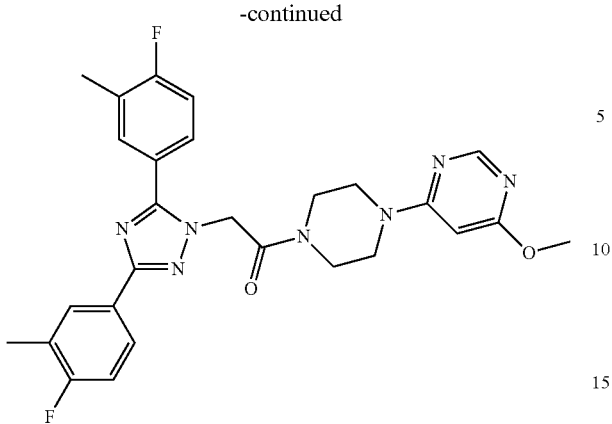
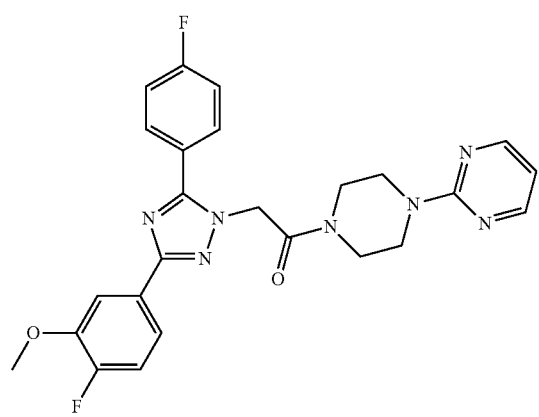
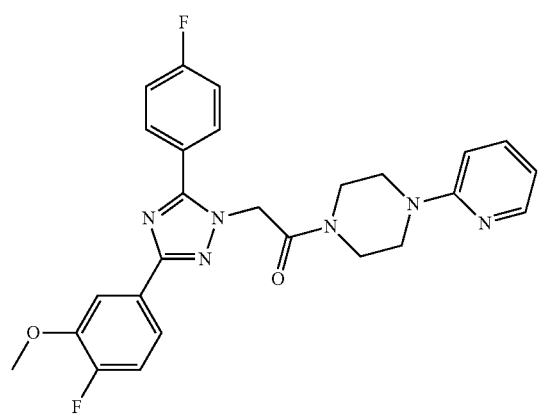
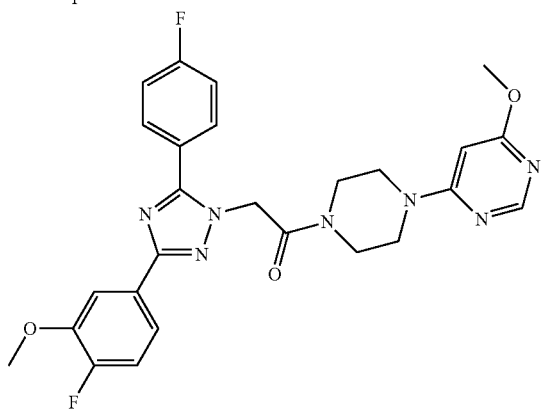
378
-continued
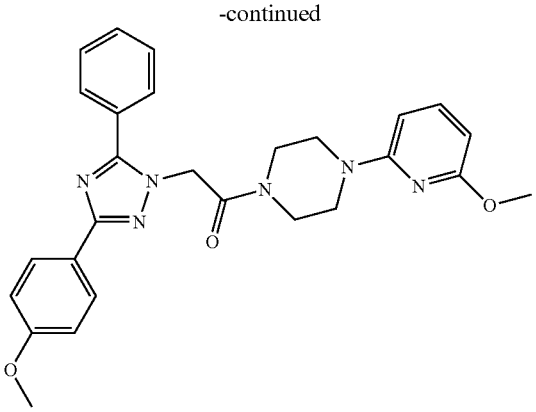
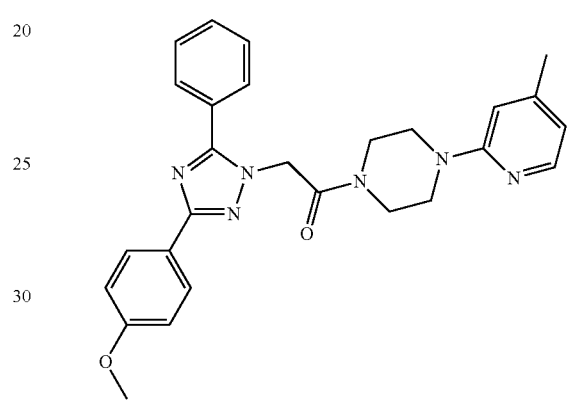
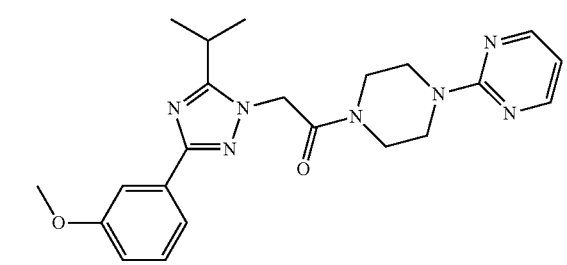
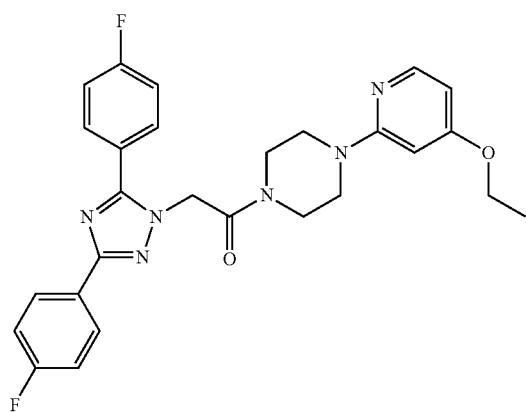

379
-continued
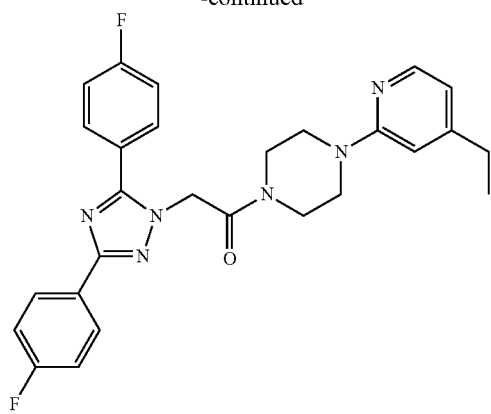
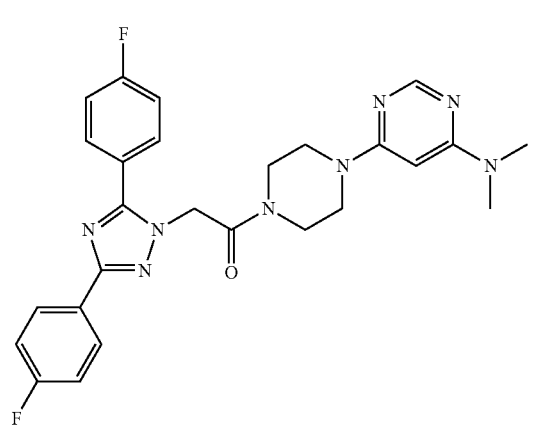
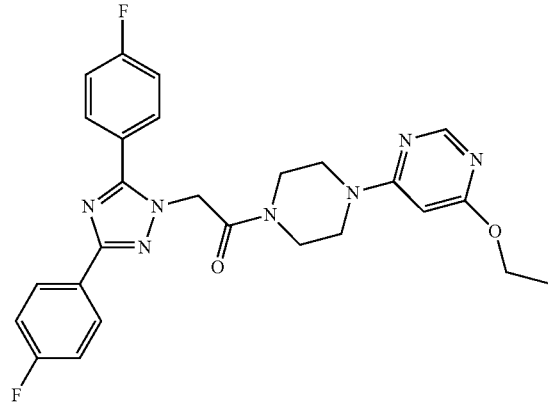
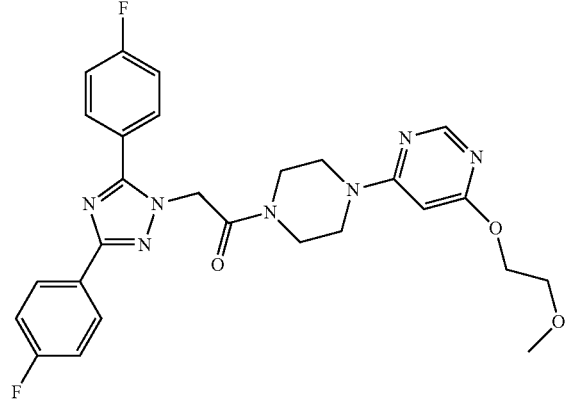
380
-continued
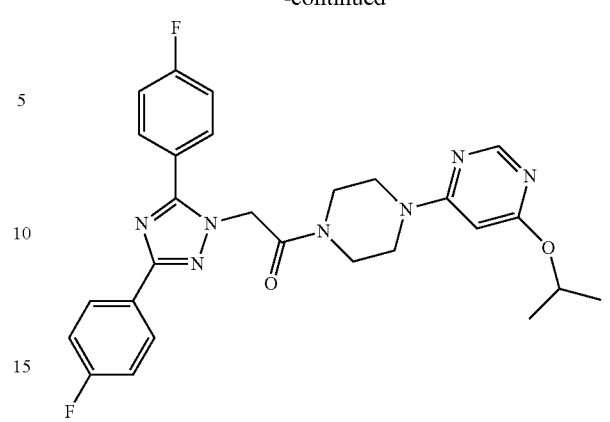
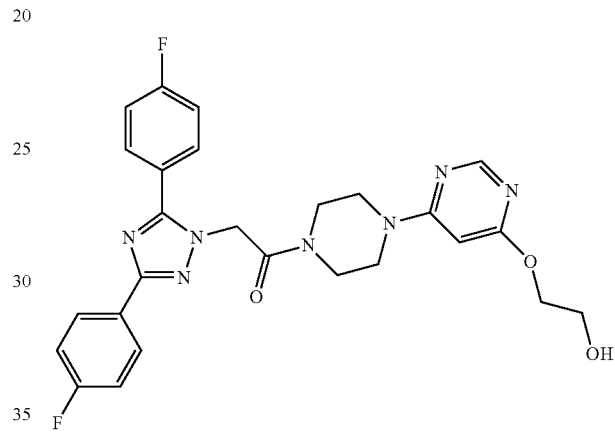
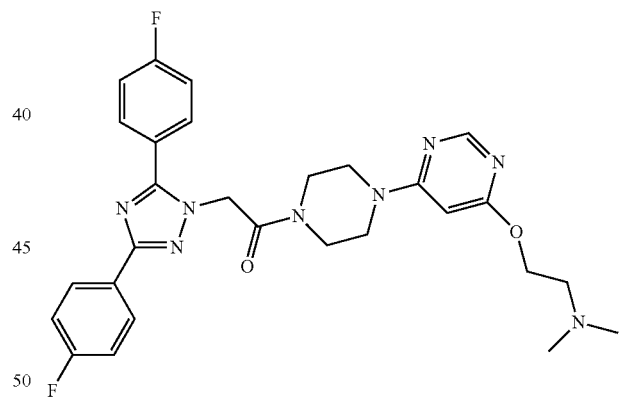
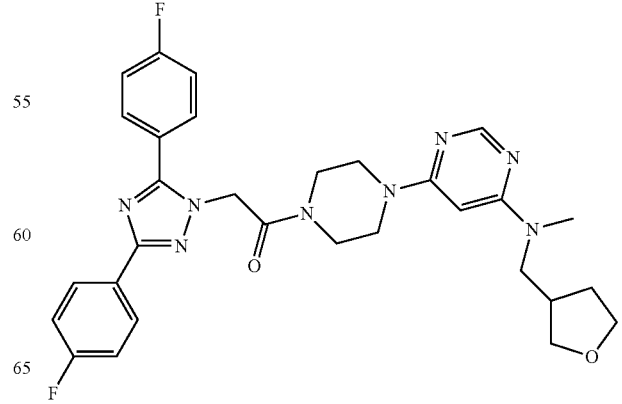

381
-continued
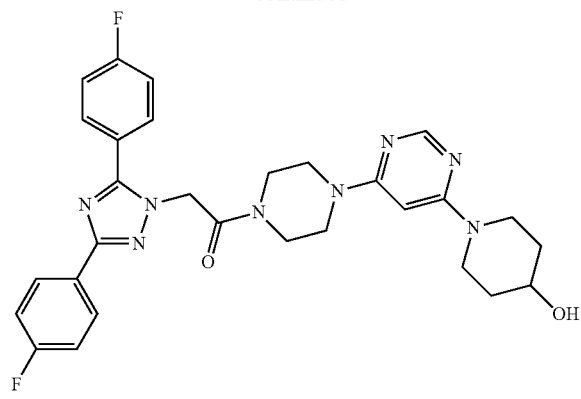
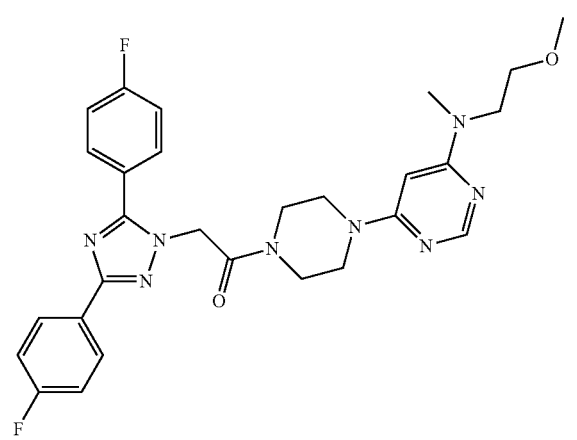
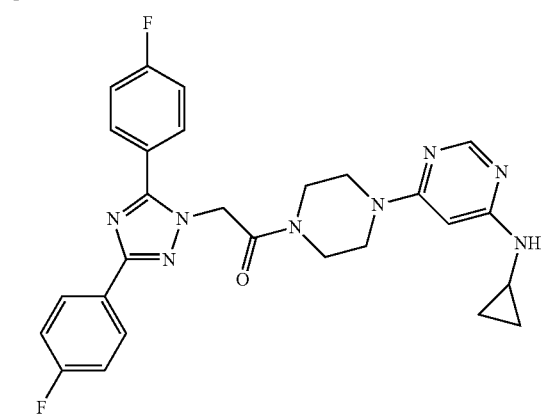
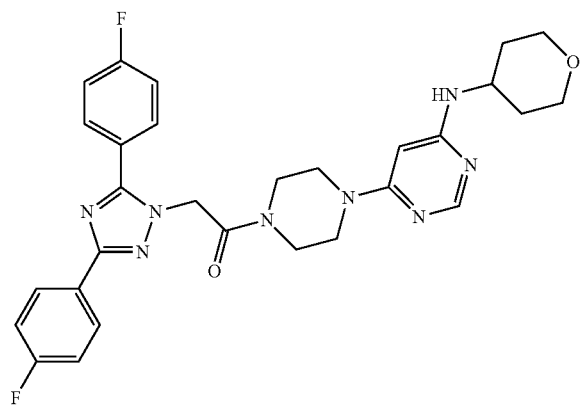
382
-continued
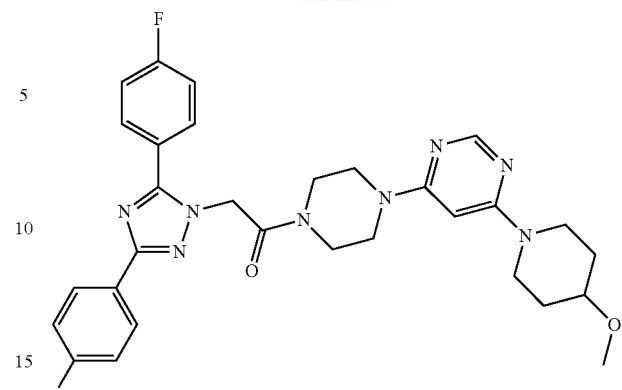
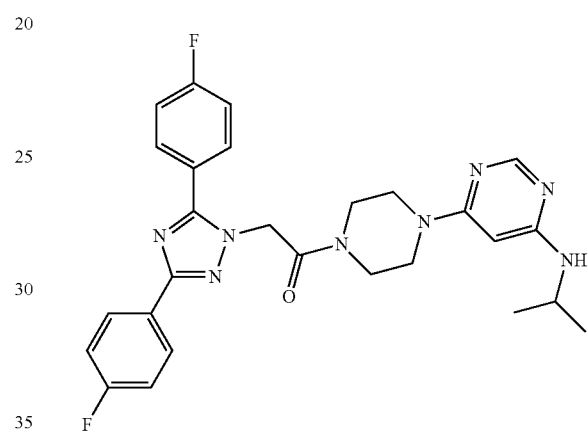
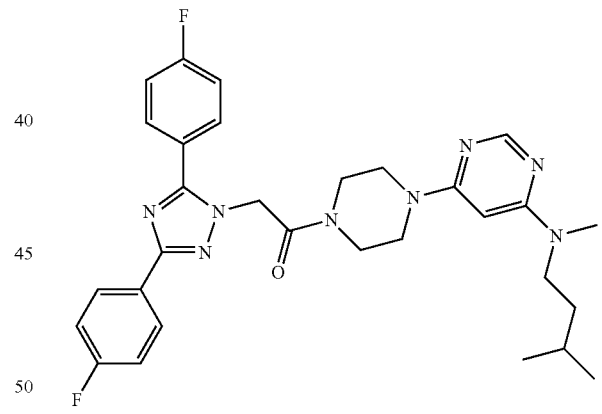
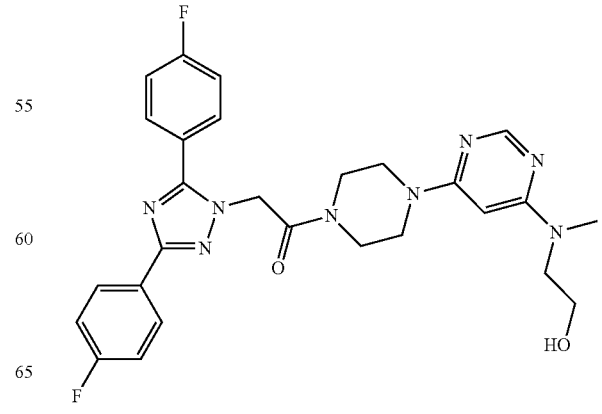

383
-continued
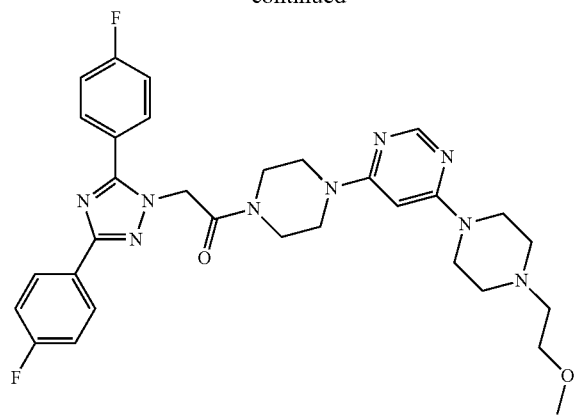
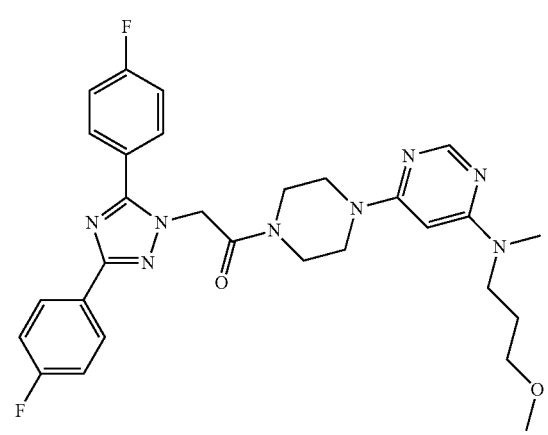
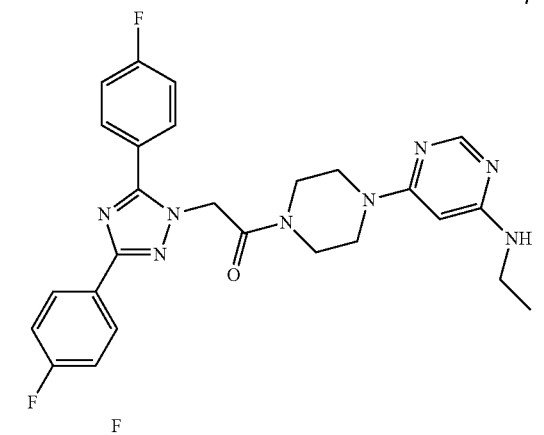
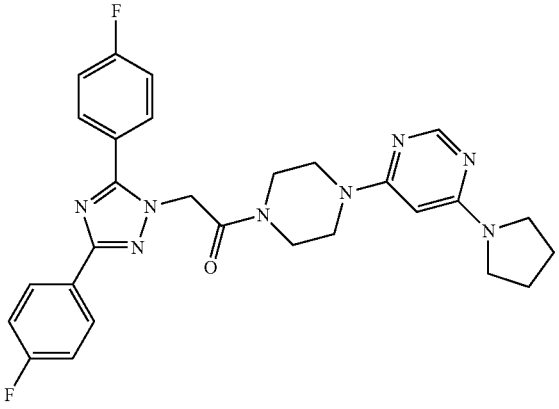
384
-continued
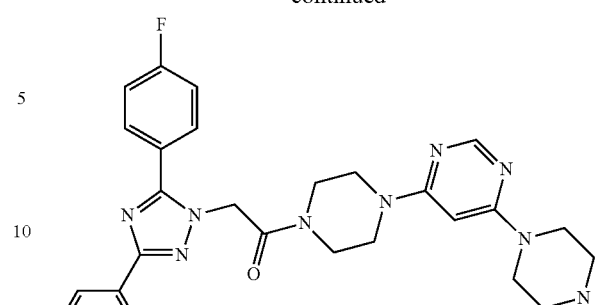
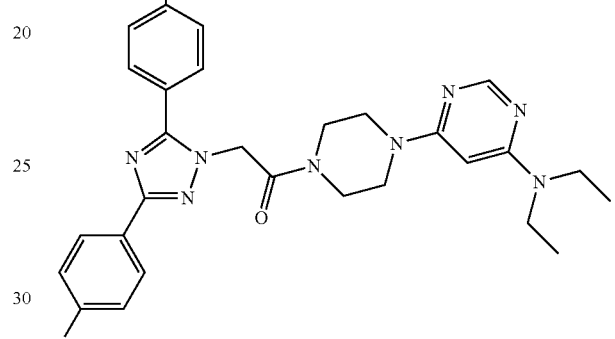
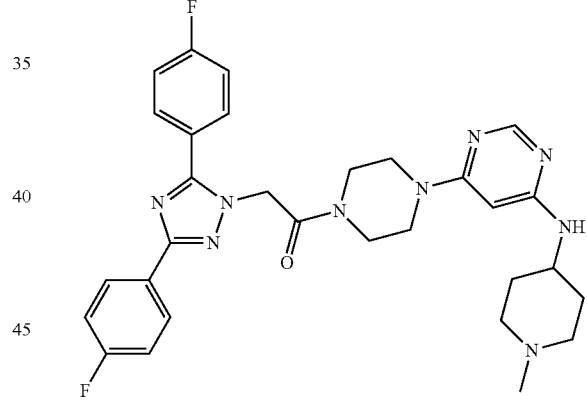
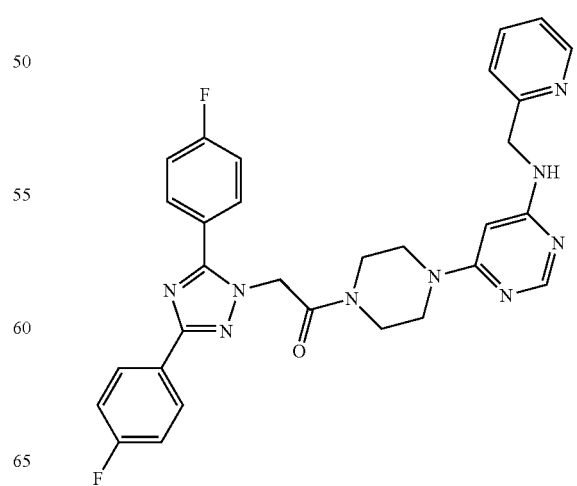

385
-continued
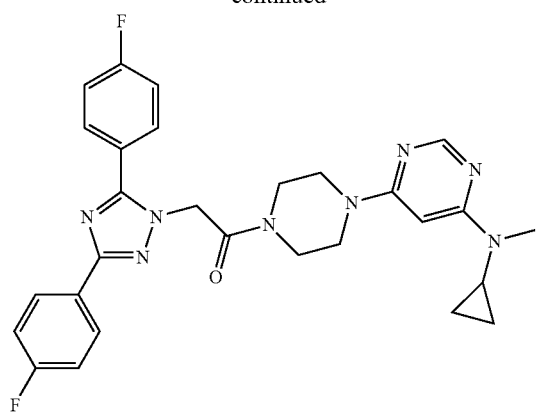
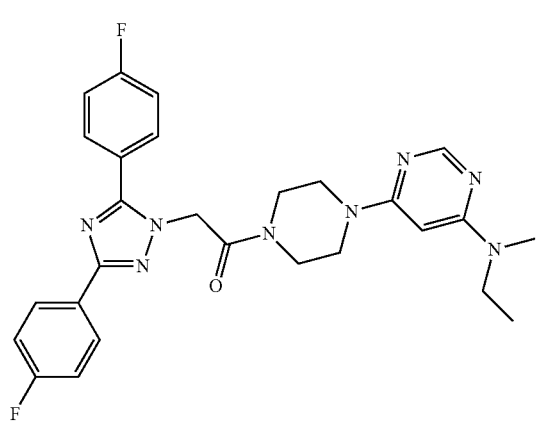
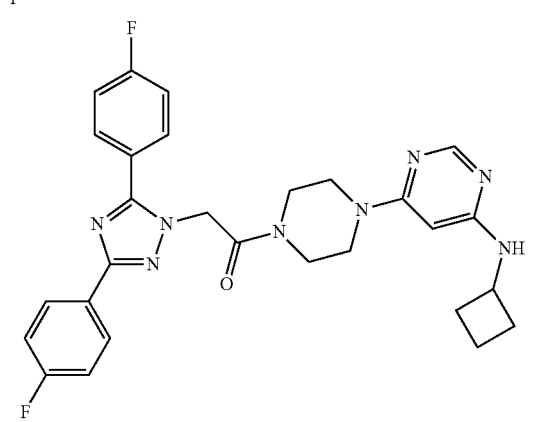
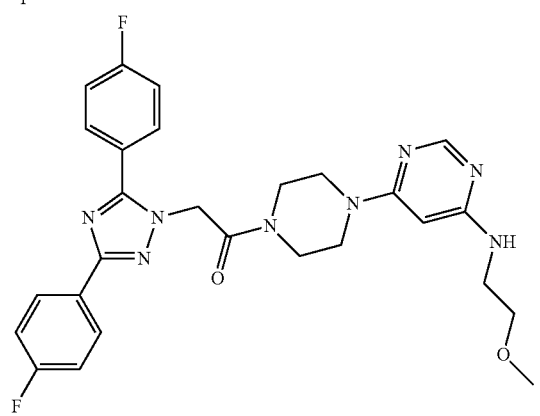
386
-continued
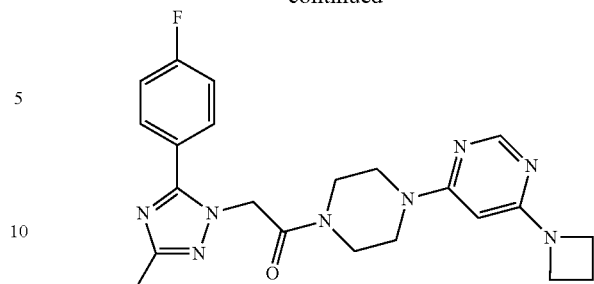
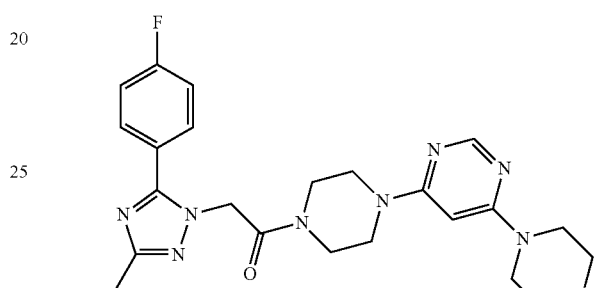
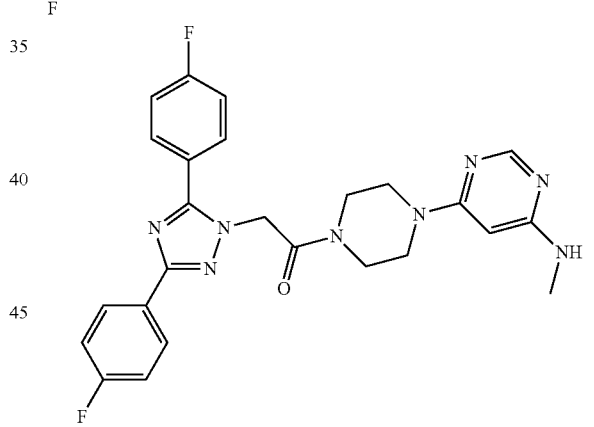
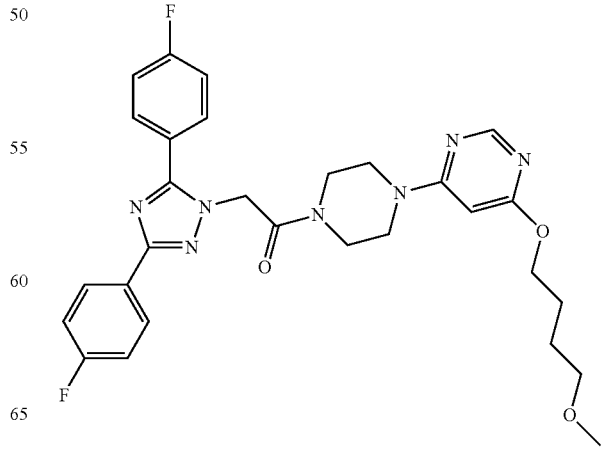

387
-continued
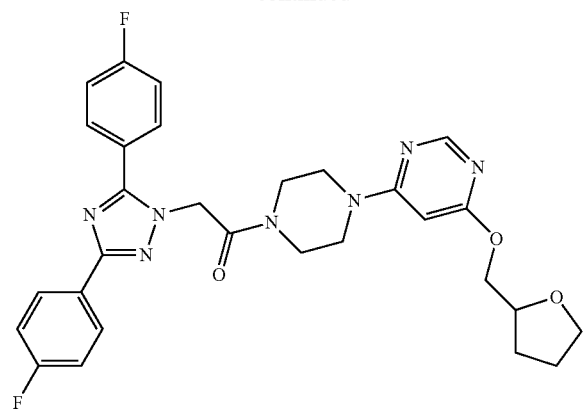
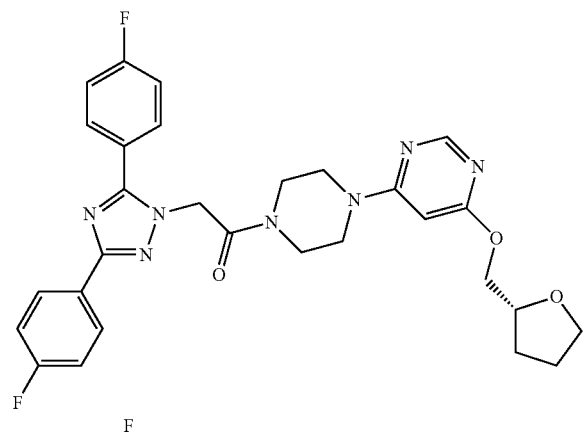
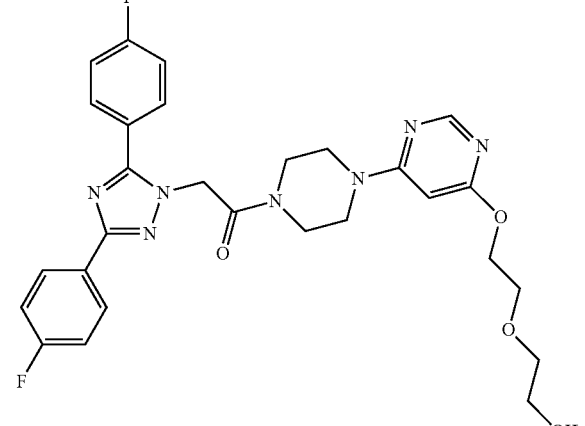
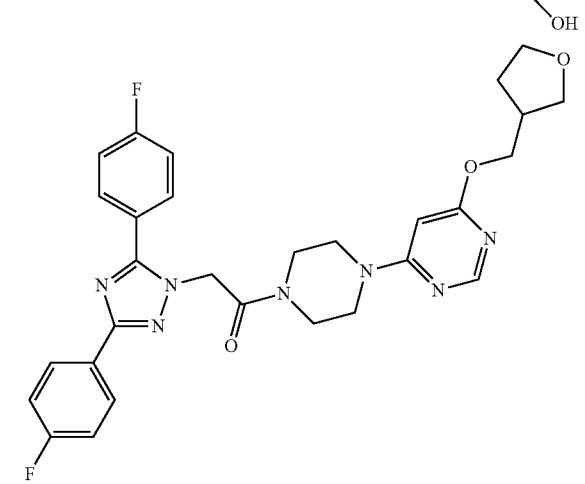
388
-continued
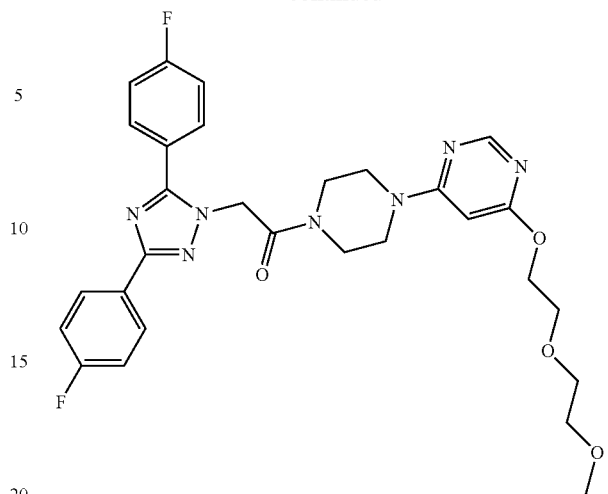
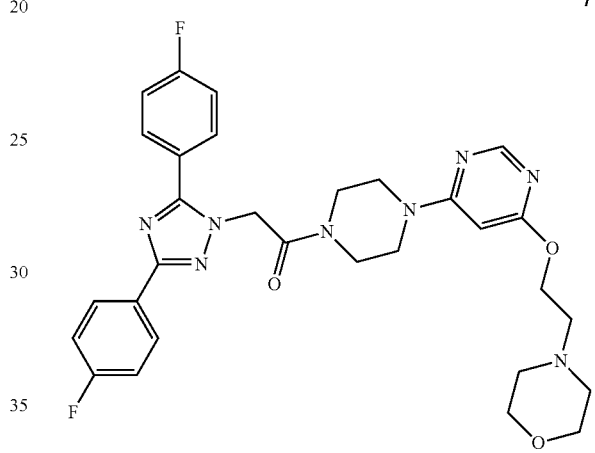
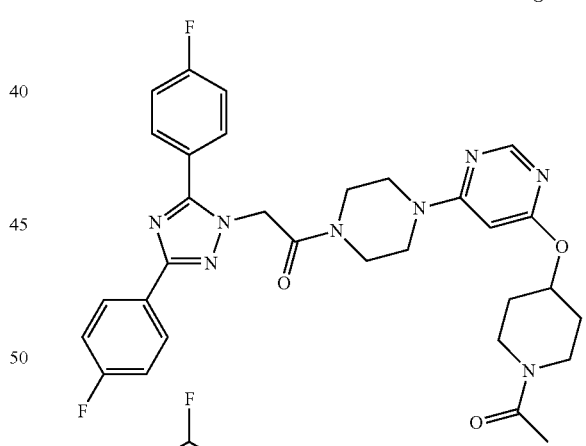
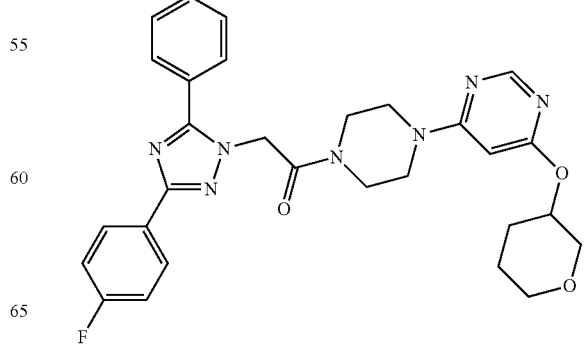

389
-continued
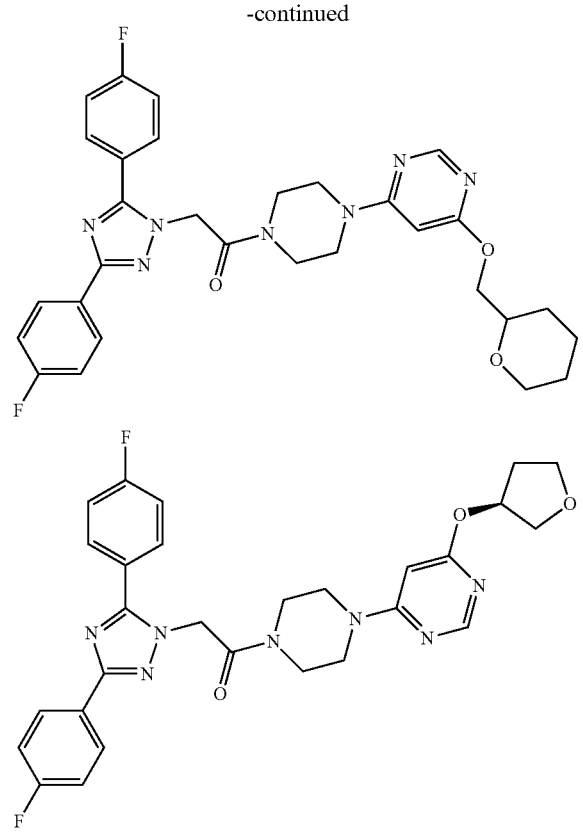
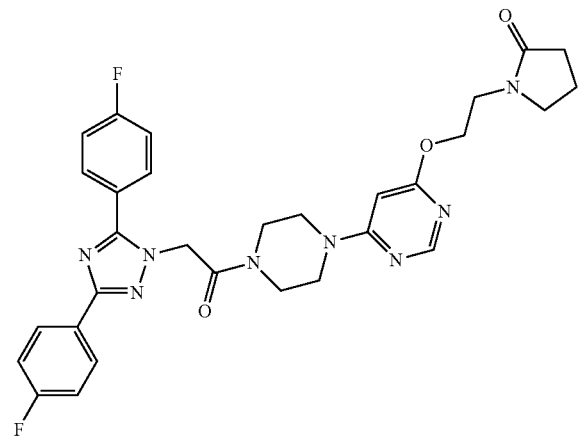
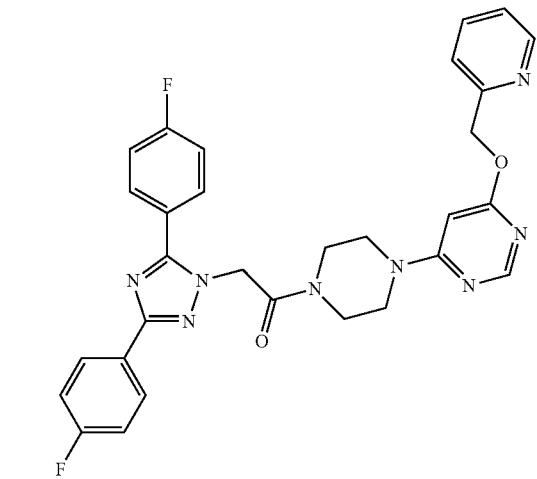
390
-continued
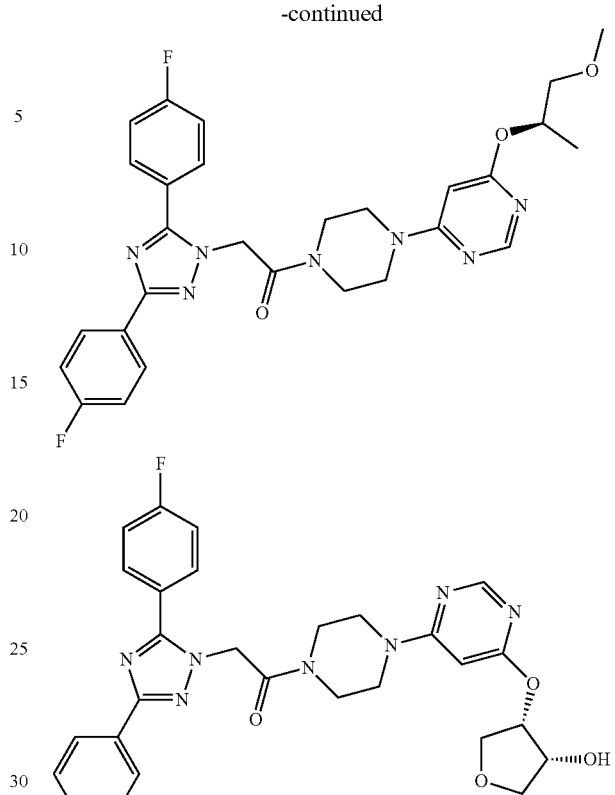
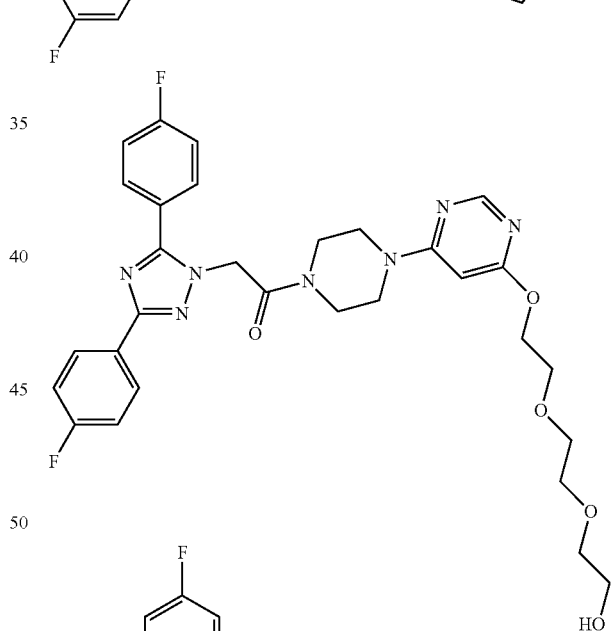
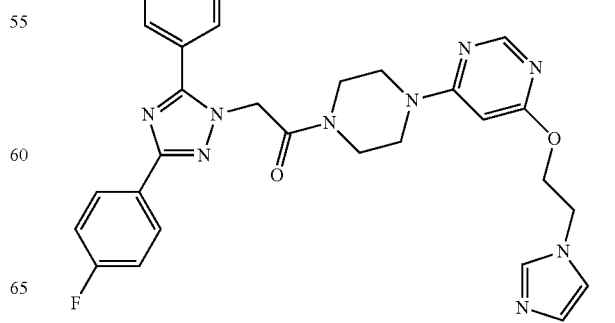

391
-continued
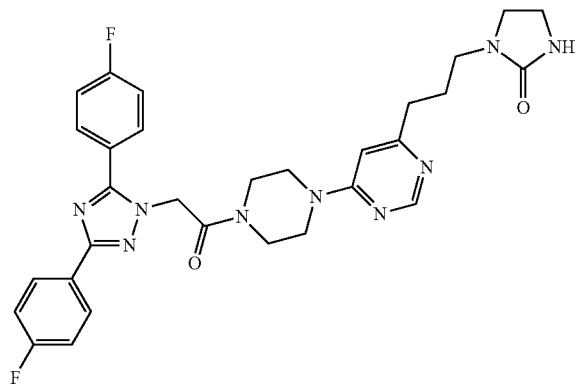
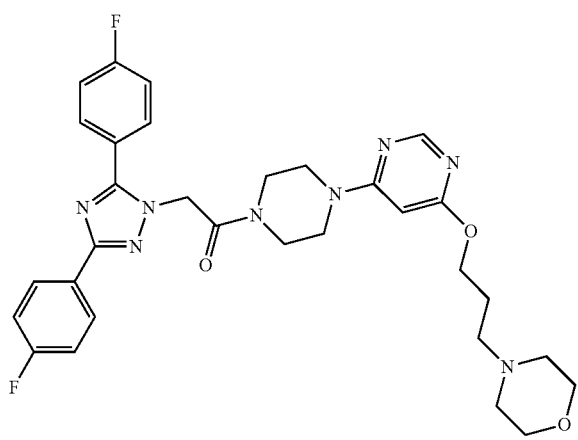
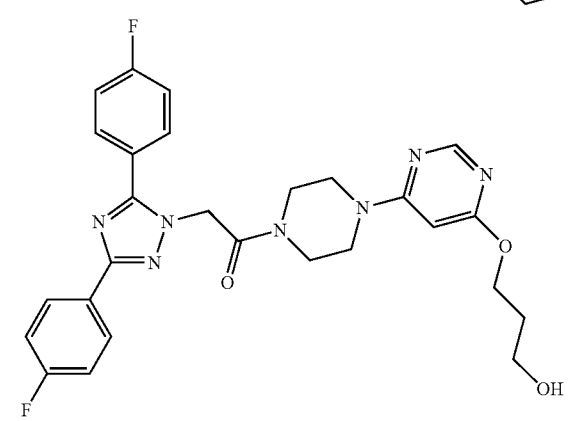
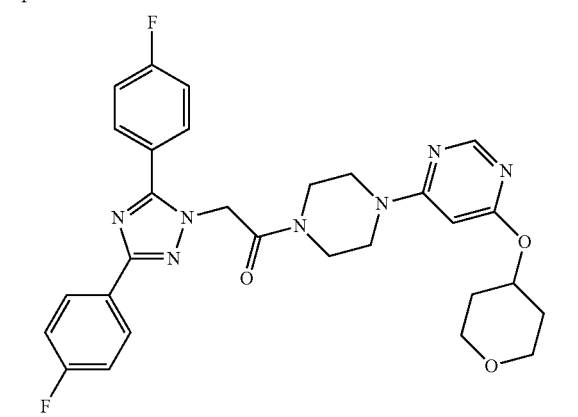
392
-continued
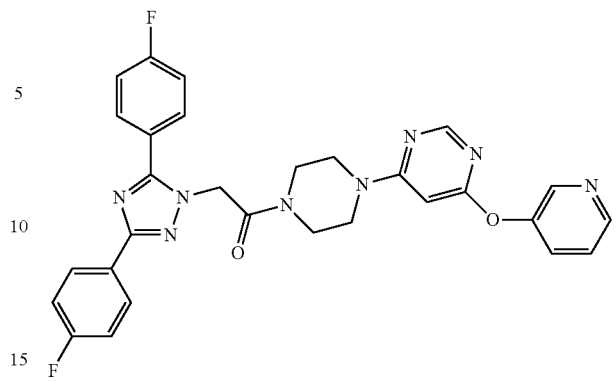
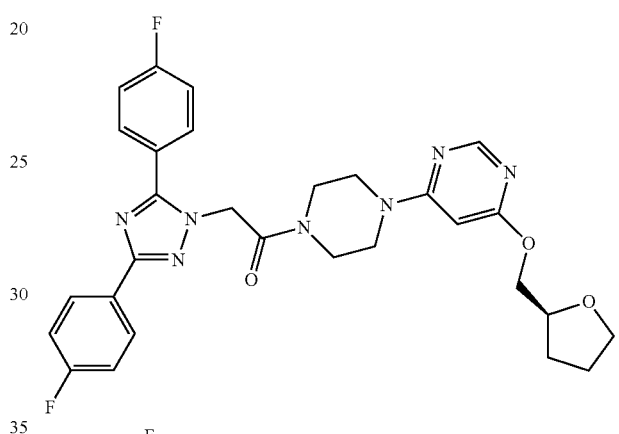
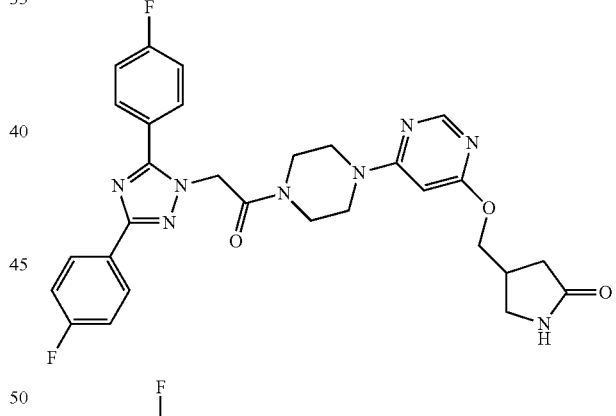
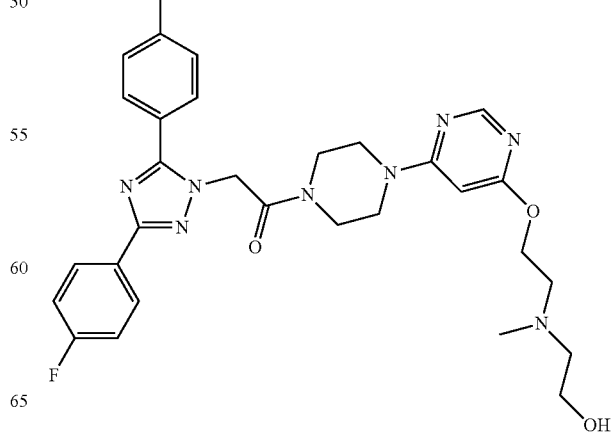

393
-continued
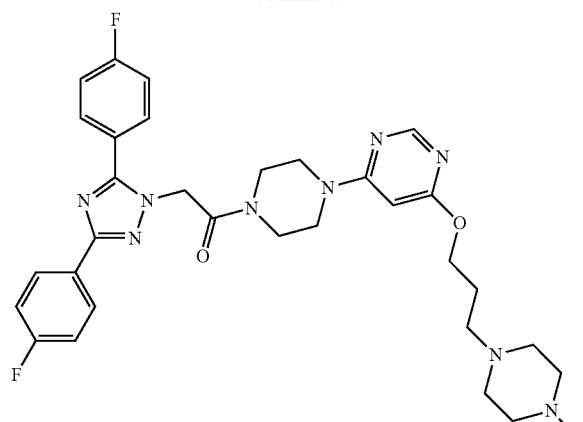
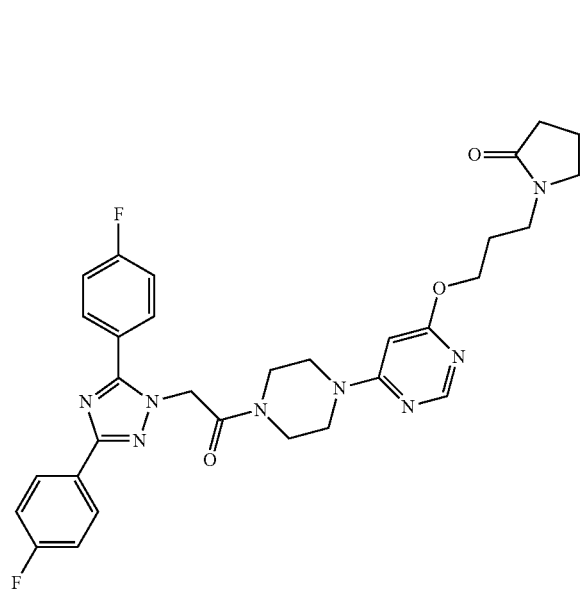
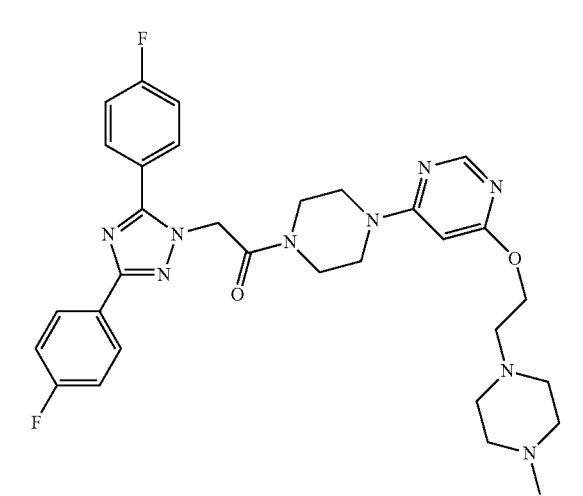
394
-continued
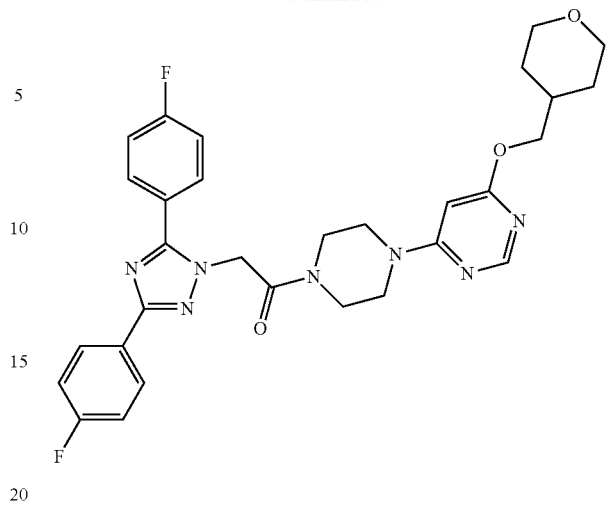
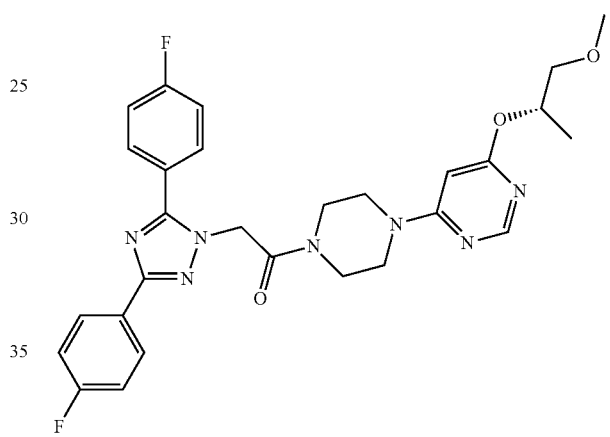
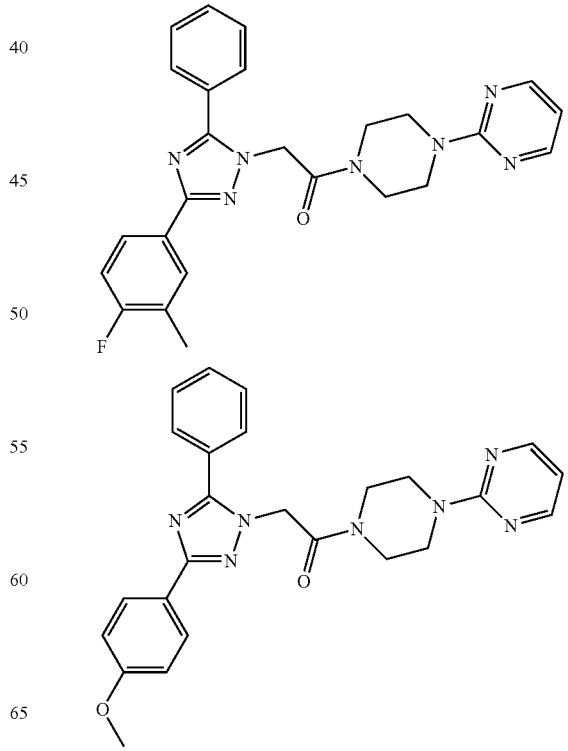

395
-continued
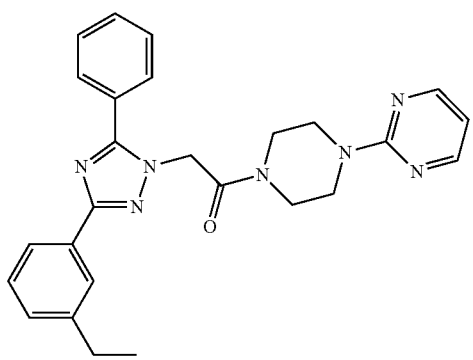
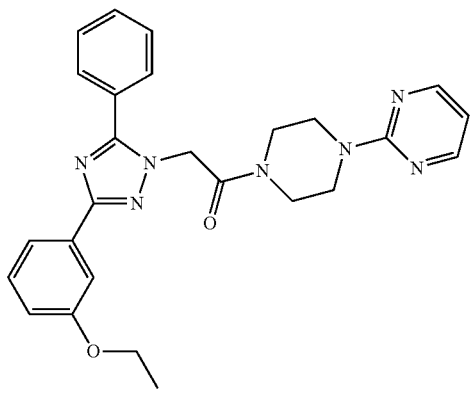
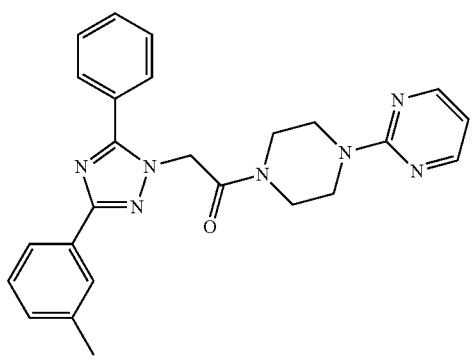
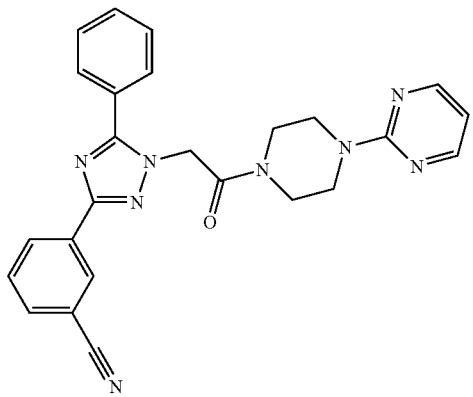
396
-continued
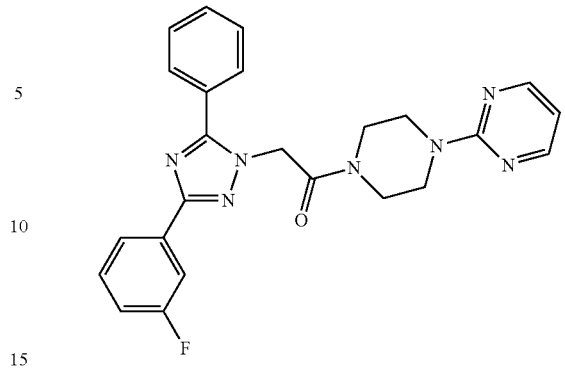
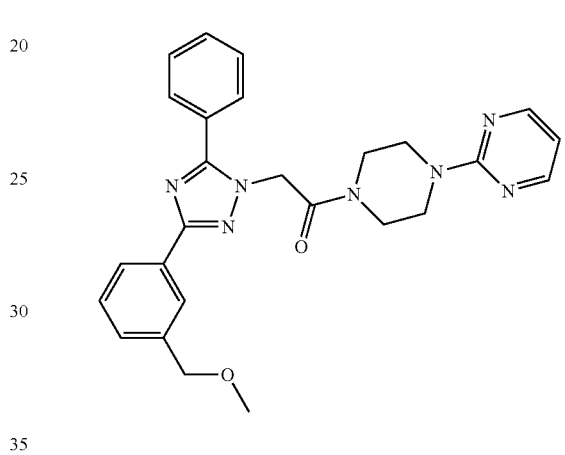
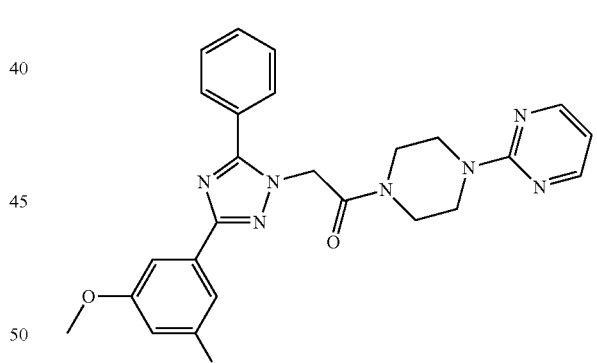
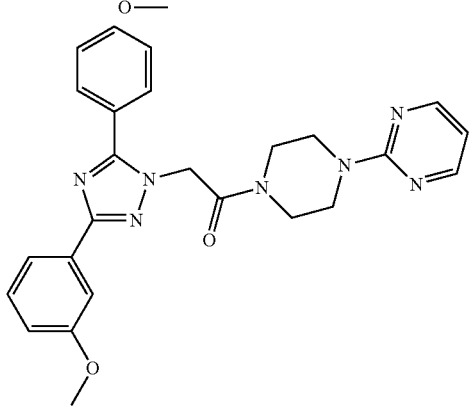

397
-continued
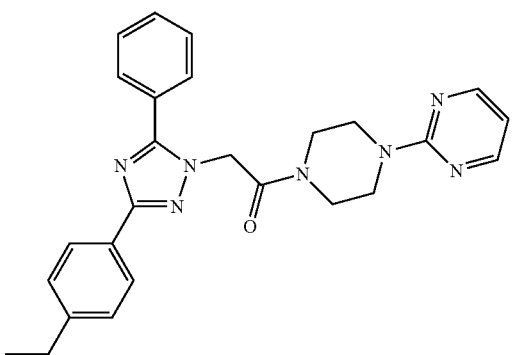
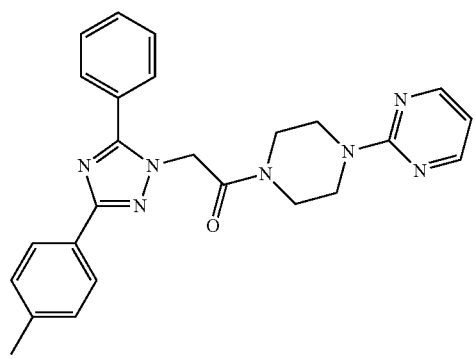
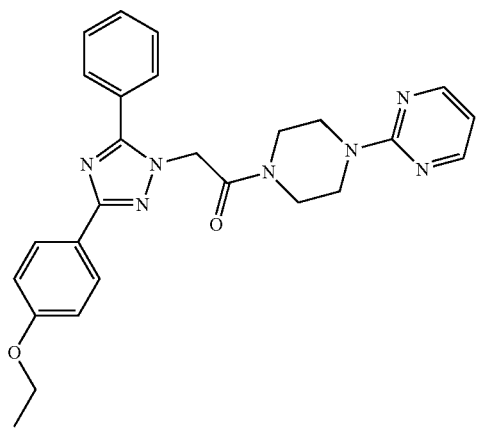
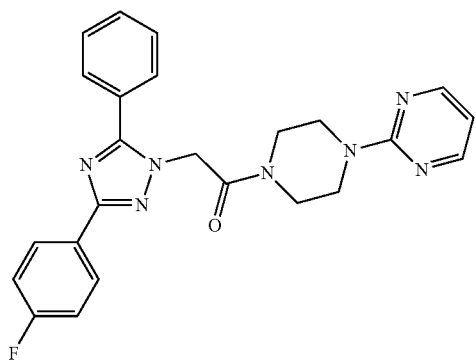
398
-continued
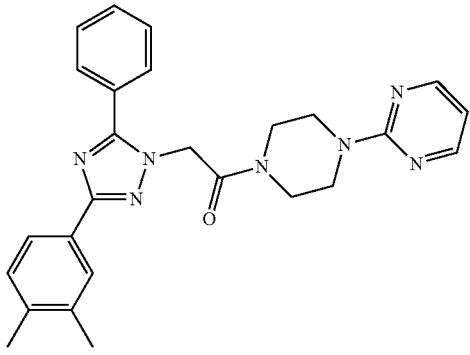
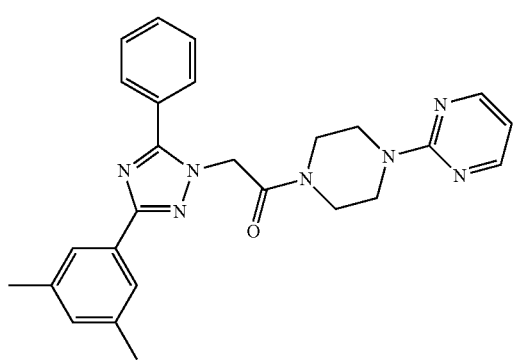
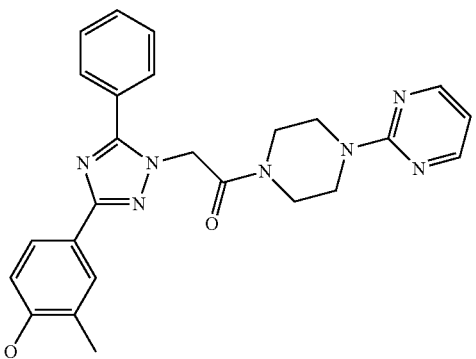
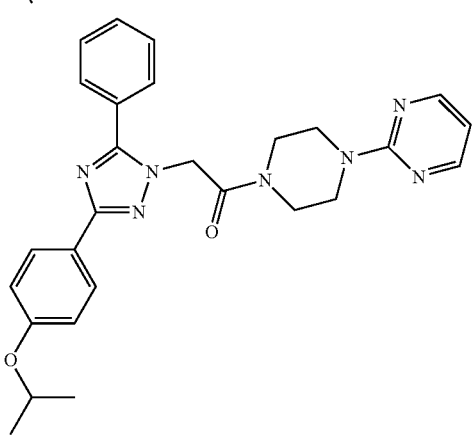

399
-continued
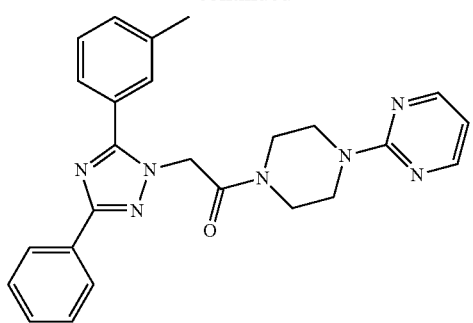
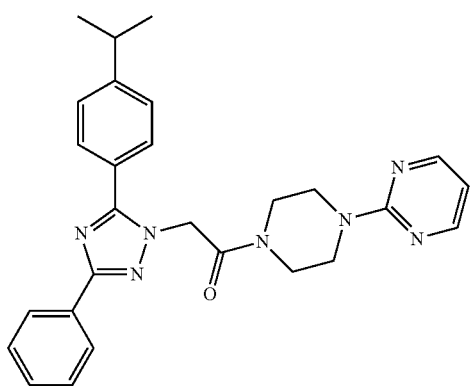
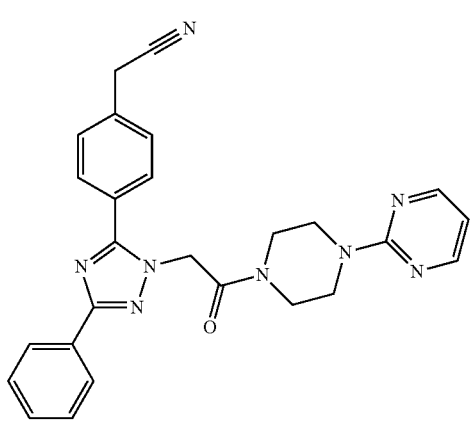
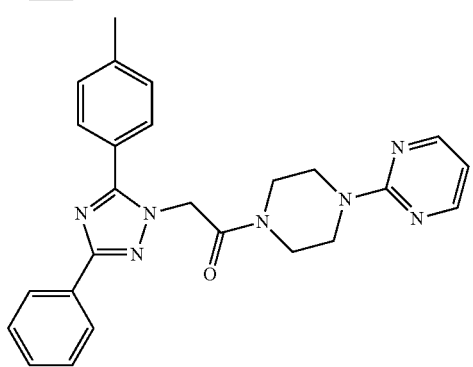
400
-continued
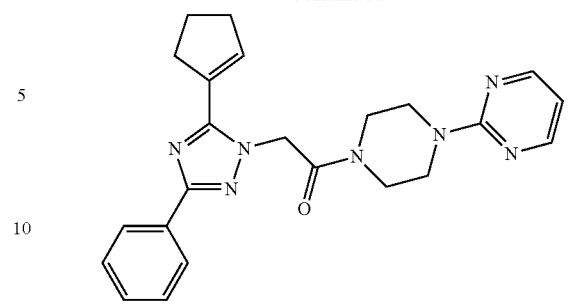
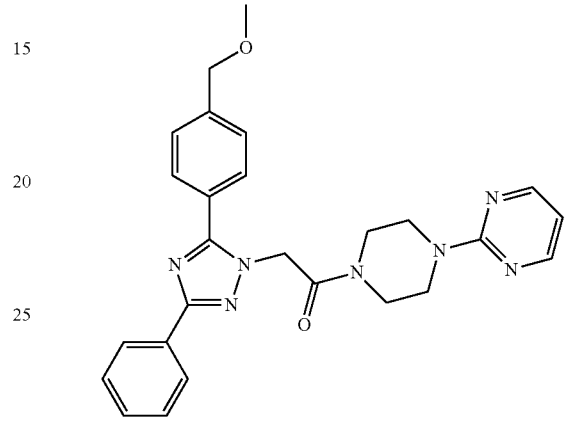
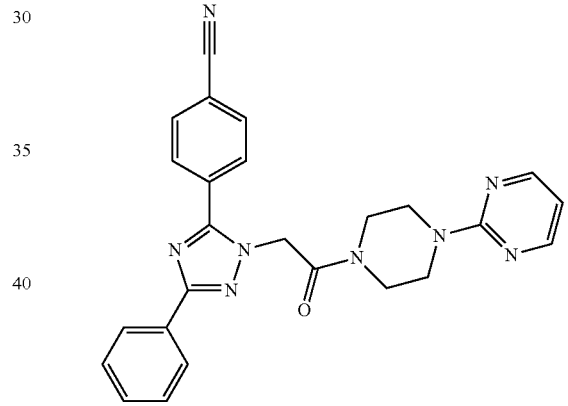
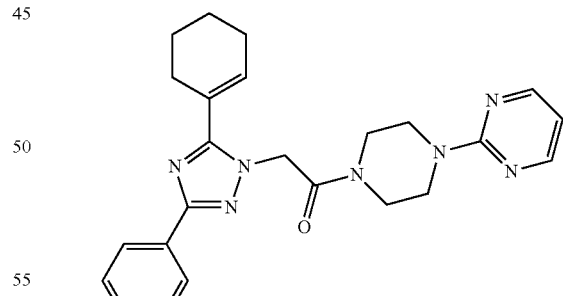
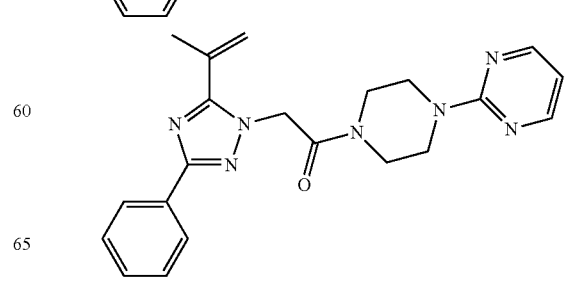

| 401 | 402 |
|---|---|
| -continued | -continued |
| 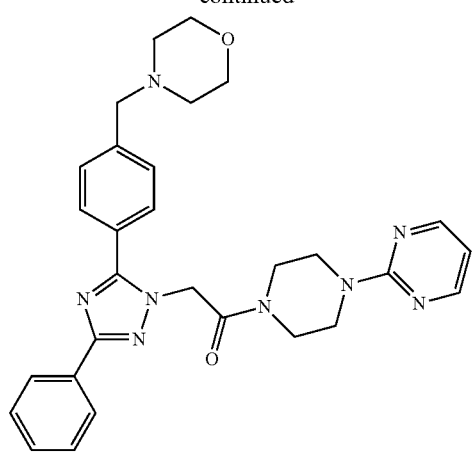 | 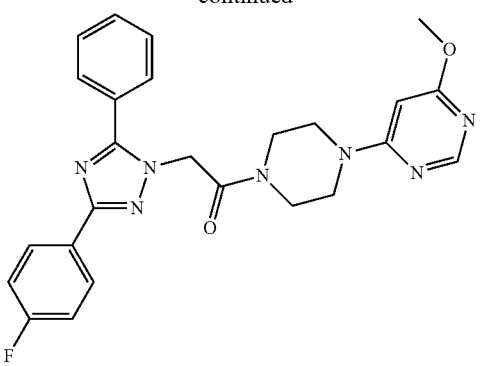 |
| 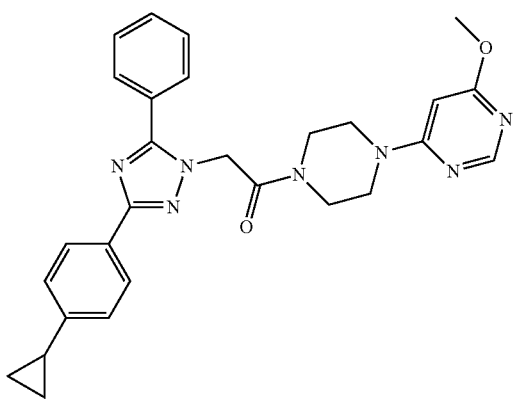 | 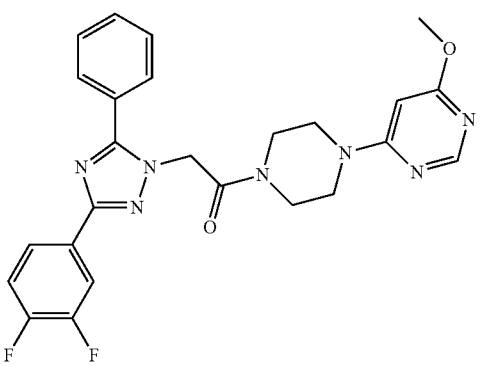 |
| 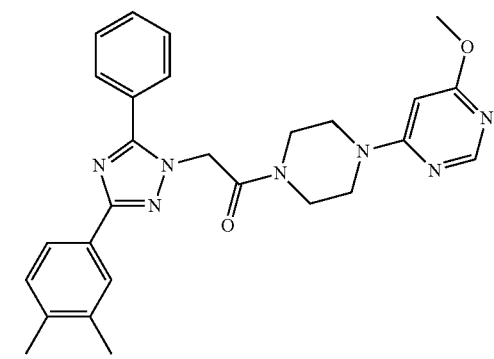 | 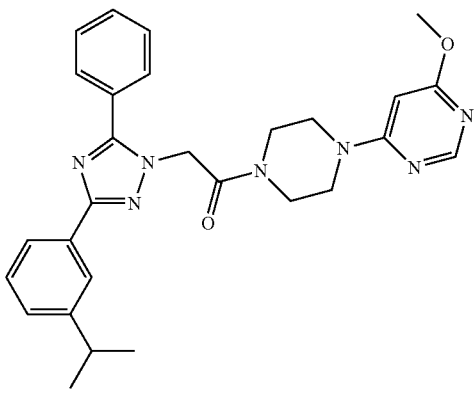 |
| 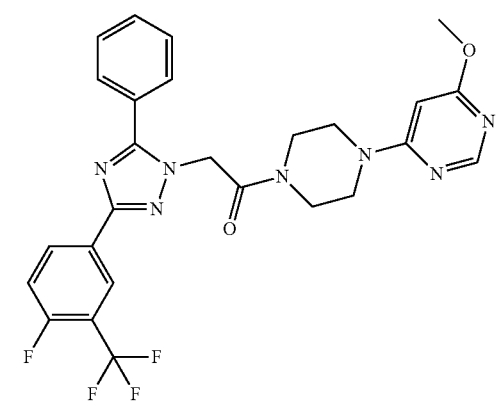 | 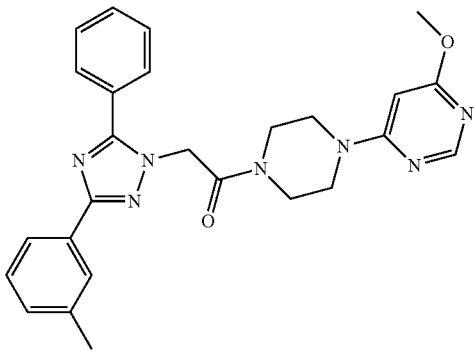 |

403
-continued
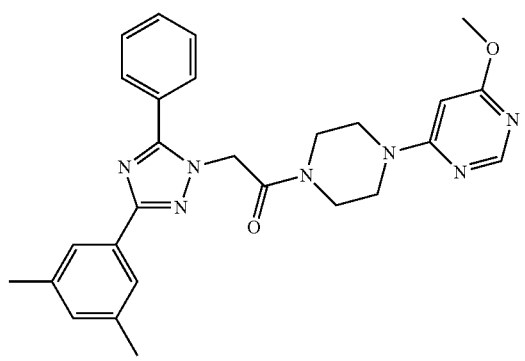
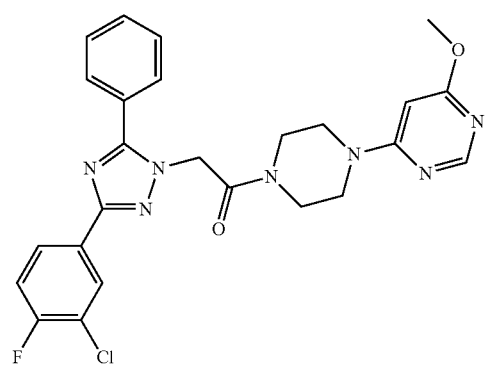
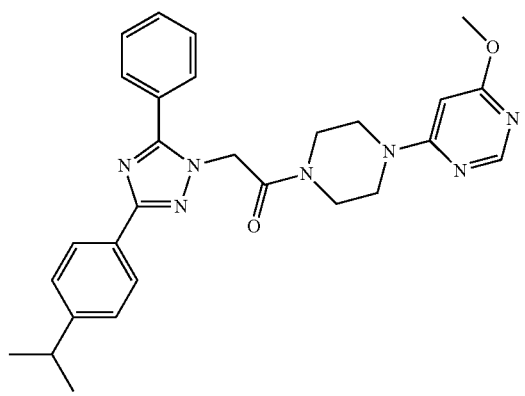
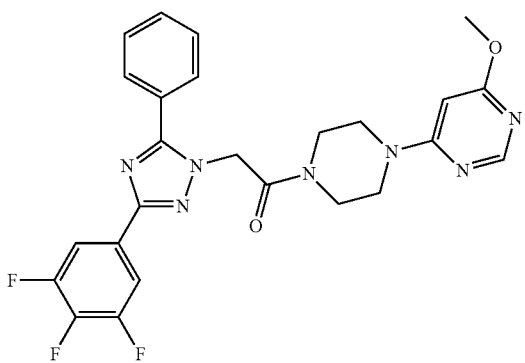
404
-continued
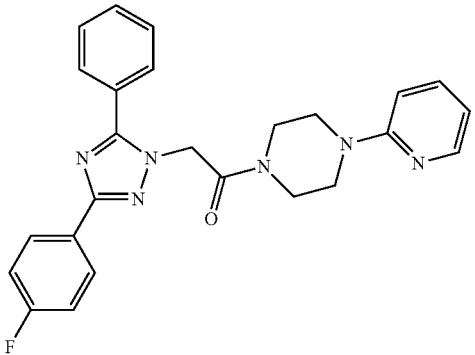
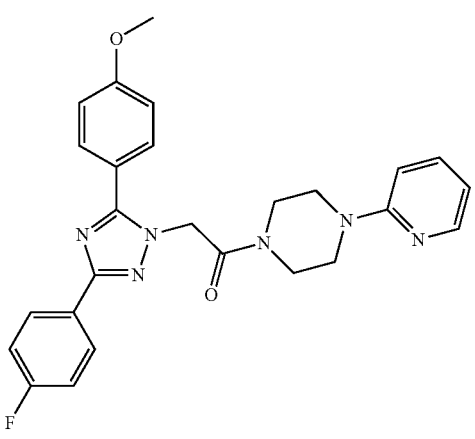
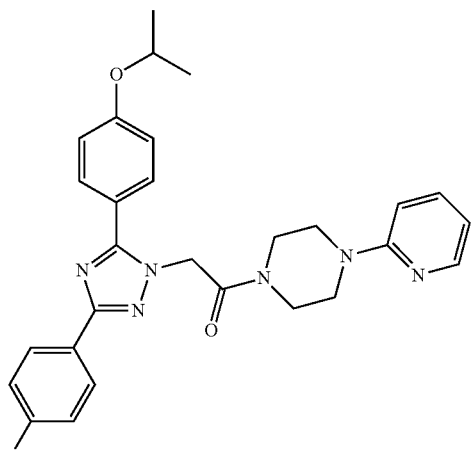
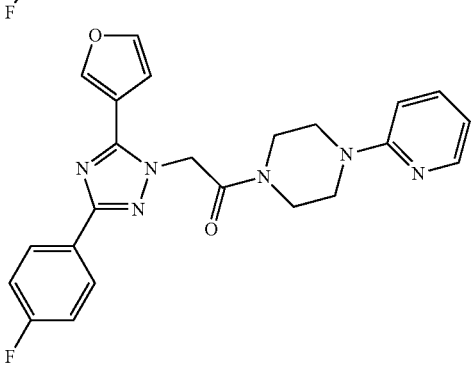

405
-continued
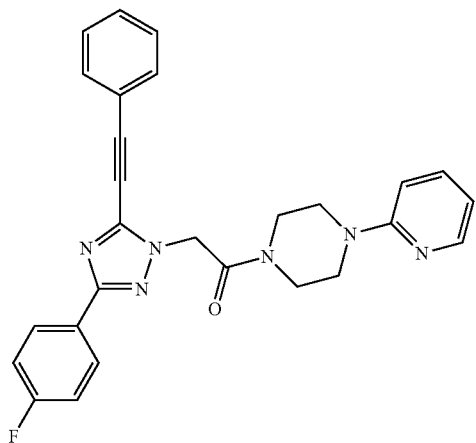
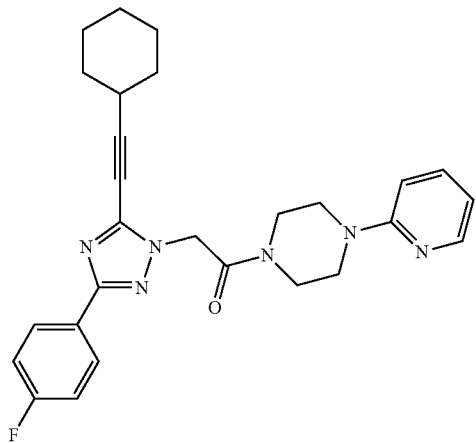
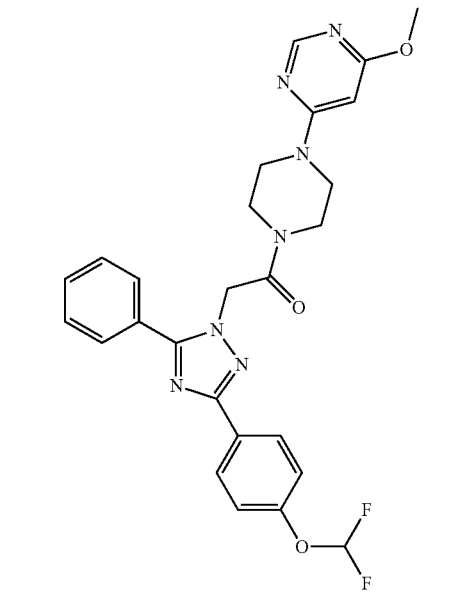
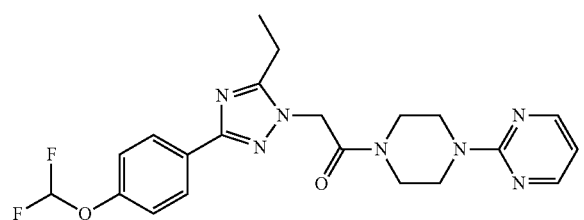
406
-continued
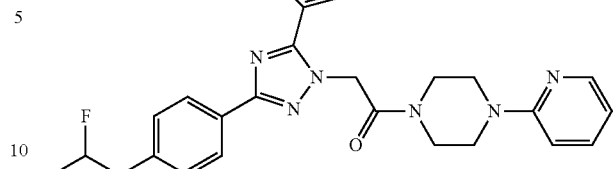
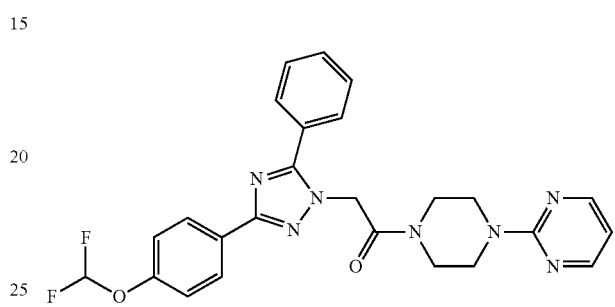
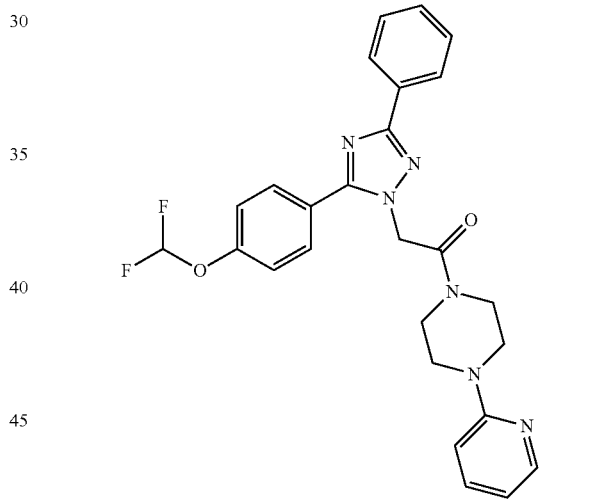
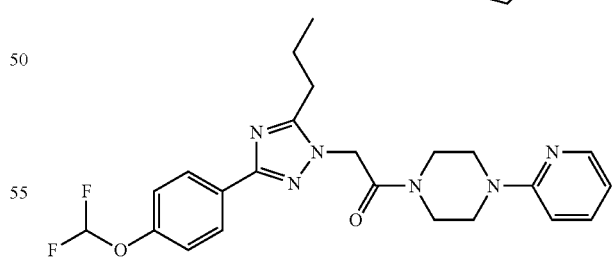
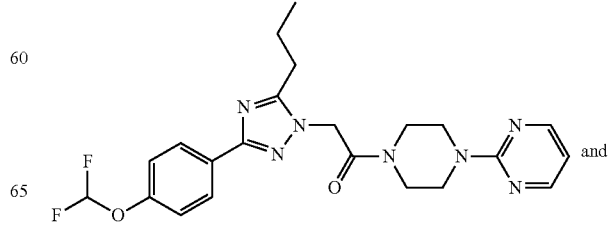 and

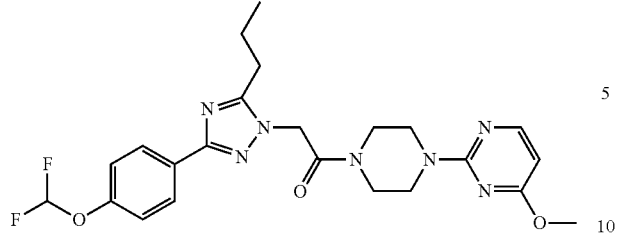
or a physiologically acceptable salt thereof.
10. A pharmaceutical composition comprising a therapeutically effective amount of a compound according to claim 1 or a pharmaceutically acceptable salt thereof in admixture with a pharmaceutically acceptable adjuvant, diluent and/or carrier.
* * * * *